(12) United States Patent
Larsen et al.

(10) Patent No.: US 7,585,839 B2
(45) Date of Patent: Sep. 8, 2009

(54) MEDICAL USES OF INTERCELLULAR COMMUNICATION FACILITATING COMPOUNDS

(75) Inventors: Bjarne Due Larsen, Roskilde (DK); Jorgen Soberg Petersen, Hellebaek (DK); Eddi Meier, Vaerlose (DK); Anne Louise Kjolbye, Hellebaek (DK); Niklas Rye Jorgensen, Frederiksberg C (DK); Morten Schak Neilsen, Ballerup (DK); Neils-Henrik Holstein-Rathlou, Herlev (DK); James B. Martins, Iowa City, IA (US); Peter Holme Jensen, Copenhagen (DK)

(73) Assignee: Zealand Pharma A/S, Glostrup (DK)

( * ) Notice: Subject to any disclaimer, the term of this patent is extended or adjusted under 35 U.S.C. 154(b) by 641 days.

(21) Appl. No.: 10/646,294

(22) Filed: Aug. 22, 2003

(65) Prior Publication Data

US 2005/0113293 A1     May 26, 2005

Related U.S. Application Data

(63) Continuation of application No. PCT/US02/05773, filed on Feb. 22, 2002.

(60) Provisional application No. 60/314,470, filed on Aug. 23, 2001.

(30) Foreign Application Priority Data

Feb. 22, 2001   (WO) .................... PCT/DK01/00127

(51) Int. Cl.
    *A61K 38/12*    (2006.01)
(52) U.S. Cl. .......................... 514/9; 514/183
(58) Field of Classification Search .................. None
    See application file for complete search history.

(56) References Cited

U.S. PATENT DOCUMENTS

| 4,775,743 | A | 10/1988 | Mimura et al. |
| 5,817,316 | A | 10/1998 | Sodroski et al. |
| 6,815,426 | B2 * | 11/2004 | Scialdone et al. ............. 514/18 |
| 7,250,397 | B2 | 7/2007 | Larsen et al. |
| 2005/0075280 | A1 | 4/2005 | Larsen et al. |

FOREIGN PATENT DOCUMENTS

| DE | 197 07 854 A1 | 9/1998 |
| EP | 0 214 659 A | 3/1987 |
| WO | WO 96/21674 | 7/1996 |
| WO | WO 99/43309 | 9/1999 |
| WO | WO 01 62775 A2 | 8/2001 |

OTHER PUBLICATIONS

Y. Kohama, et al. "Effect of N-3-(4-Hydroxyphenyl) propionyl Pro-Pro-Gly-Ala-Gly on Calcium-Induced Arrhythmias", Chemical & Pharmaceutical Bulletin, vol. 36, No. 11, 1988, pp. 4597-4599.
S. Dhein, et al. "Therapeutic Potential of Antiarrhythmic Peptides", Drugs, vol. 49, No. 6, 1995, pp. 851-855.
B. Kundu "Synthesis, conformational features and biological activity of Pro-3 antiarrhythmic peptide", Collection of Czechoslovak Chemical Communications, vol. 54, No. 3, 1989, pp. 760-771.
B. Weinstein "Chemistry and Biochemistry of Amino Acids, Peptides and Proteins" 1982, Marcel Dekker Inc., New York and Basel, p. 357.
Stefan Dhein, et al. "Therapeutic Potential Of Antiarrhythmic Peptides Cellular Coupling As A New Antiarrhythmic Target", Drugs, Adis International Ltd. , vol. 49, No. 6, 1995, pp. 851-855.
International Search Report published Oct. 9, 2003 from WO 02/077017 A3.
Lazar et al., "Transforming Growth Factor α: Mutation of Aspartic Acid 47 and Leucine 48 Results in Different Biological Activities" *Molecular and Cellular Biology* 8:1247-1252, 1988.
Oas et al., "The amide $^{15}$N chemical shift tensors of four peptides determined from $^{13}$C dipole-coupled chemical shift powder patterns," *J. Am. Chem. Soc.* 109:5962-5966 (1987).
*Aldrich Catalog Handbook of Fine Chemicals*; CAS registry Nos. 1668-10-6 and 33208-99-0, 1998-1999.
Wako Pure Chemical Industries, Ltd., p. 528.

* cited by examiner

*Primary Examiner*—Christopher R. Tate
*Assistant Examiner*—Roy Teller
(74) *Attorney, Agent, or Firm*—Clark & Elbing LLP; Kristina Bieker-Brady

(57) ABSTRACT

Disclosed are novel peptides including antiarrhythmic peptides that have improved stability. Further disclosed are compositions that include such peptides and methods of using the compositions particularly as medicaments.

20 Claims, 15 Drawing Sheets

SEQUENCE LISTING

```
<160> NUMBER OF SEQ ID NOS: 114

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
```

```
<223> OTHER INFORMATION: 4Hyp

<400> SEQUENCE: 1

Gly Ala Gly Xaa Pro Tyr
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 4Hyp

<400> SEQUENCE: 2

Pro Xaa Gly Ala Gly
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Pro Leu Gly Pro
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Pro Gly Ala Gly
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 5

Ala Gly Xaa Pro Tyr
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)
<223> OTHER INFORMATION: Sar

<400> SEQUENCE: 6

Gly Xaa Pro Gly Ala Gly
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Sar

<400> SEQUENCE: 7

Gly Pro Xaa Gly Ala Gly
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Sar

<400> SEQUENCE: 8

Gly Xaa Xaa Gly Ala Gly
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr (3-I)

<400> SEQUENCE: 9

Gly Ala Gly Xaa Pro Tyr
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
```

-continued

```
<223> OTHER INFORMATION: Hyp
<220> FEATURE:
<221> NAME/KEY: MOD_RES
<222> LOCATION: (6)
<223> OTHER INFORMATION: Tyr (3-F)

<400> SEQUENCE: 10

Gly Ala Gly Xaa Pro Tyr
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr (3-Cl)

<400> SEQUENCE: 11

Gly Ala Gly Xaa Pro Tyr
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Tyr (3-Br)

<400> SEQUENCE: 12

Gly Ala Gly Xaa Pro Tyr
  1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp

<400> SEQUENCE: 13

Arg Ala Gly Xaa Pro Tyr
  1               5

<210> SEQ ID NO 14
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp

<400> SEQUENCE: 14

Val Ala Gly Xaa Pro Tyr
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp

<400> SEQUENCE: 15

Ala Ala Gly Xaa Pro Tyr
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp

<400> SEQUENCE: 16

Gly Ala Gly Xaa His Tyr
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp

<400> SEQUENCE: 17

Gly Ala Gly Xaa Pro Phe
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ala Gly Gly Pro Tyr
 1               5
```

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 19

Tyr Pro Xaa Gly Ala Gly
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Pro Pro Gly Ala Gly
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 4Hyp

<400> SEQUENCE: 21

Tyr Xaa Pro Gly Ala Gly
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: 4Hyp

<400> SEQUENCE: 22

Tyr Xaa Xaa Gly Ala Gly
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)
<223> OTHER INFORMATION: Sar
<220> FEATURE:
<221> NAME/KEY: MOD_RES
<222> LOCATION: (3)
<223> OTHER INFORMATION: 4Hyp

<400> SEQUENCE: 23

Tyr Xaa Xaa Gly Ala Gly
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (3)
<223> OTHER INFORMATION: Sar

<400> SEQUENCE: 24

Tyr Xaa Xaa Gly Ala Gly
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Sar

<400> SEQUENCE: 25

Tyr Pro Xaa Gly Ala Gly
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Sar

<400> SEQUENCE: 26

Tyr Xaa Pro Gly Ala Gly
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(3)
<223> OTHER INFORMATION: Sar

<400> SEQUENCE: 27

Tyr Xaa Xaa Gly Ala Gly
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Pro Gly Ala Gly
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: 4Hyp

<400> SEQUENCE: 29

Xaa Pro Gly Ala Gly
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Sar

<400> SEQUENCE: 30

Xaa Pro Gly Ala Gly
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Sar

<400> SEQUENCE: 31

Pro Xaa Gly Ala Gly
 1               5

<210> SEQ ID NO 32
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Sar
<220> FEATURE:
<221> NAME/KEY: MOD_RES
<222> LOCATION: (6)
<223> OTHER INFORMATION: Sar

<400> SEQUENCE: 32

Tyr Pro Pro Xaa Ala Xaa
 1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (4)
<223> OTHER INFORMATION: Sar

<400> SEQUENCE: 33

Tyr Pro Xaa Xaa Ala Gly
 1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Sar

<400> SEQUENCE: 34

Tyr Pro Pro Xaa Ala Gly
 1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (4)
<223> OTHER INFORMATION: Sar

<400> SEQUENCE: 35
```

```
Tyr Xaa Pro Xaa Ala Gly
 1               5
```

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Sar

<400> SEQUENCE: 36

```
Tyr Pro Xaa Xaa Ala Gly
 1               5
```

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (4)
<223> OTHER INFORMATION: Sar

<400> SEQUENCE: 37

```
Tyr Xaa Pro Xaa Ala Gly
 1               5
```

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Sar

<400> SEQUENCE: 38

```
Pro Pro Xaa Ala Gly
 1               5
```

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (6)
<223> OTHER INFORMATION: Sar

<400> SEQUENCE: 39

```
Tyr Pro Xaa Gly Ala Xaa
 1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Sar

<400> SEQUENCE: 40

Tyr Pro Pro Gly Ala Xaa
 1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 4Hyp
<220> FEATURE:
<221> NAME/KEY: MOD_RES
<222> LOCATION: (6)
<223> OTHER INFORMATION: Sar

<400> SEQUENCE: 41

Tyr Xaa Pro Gly Ala Xaa
 1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (6)
<223> OTHER INFORMATION: Sar

<400> SEQUENCE: 42

Tyr Pro Xaa Gly Ala Xaa
 1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Sar
<220> FEATURE:
```

```
<221> NAME/KEY: MOD_RES
<222> LOCATION: (6)
<223> OTHER INFORMATION: Sar

<400> SEQUENCE: 43

Tyr Xaa Pro Gly Ala Xaa
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Sar

<400> SEQUENCE: 44

Pro Pro Gly Ala Xaa
 1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp
<220> FEATURE:
<221> NAME/KEY: MOD_RES
<222> LOCATION: (5)
<223> OTHER INFORMATION: Aib

<400> SEQUENCE: 45

Tyr Pro Xaa Gly Xaa Gly
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Aib

<400> SEQUENCE: 46

Tyr Pro Pro Gly Xaa Gly
 1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: 4Hyp
```

```
<220> FEATURE:
<221> NAME/KEY: MOD_RES
<222> LOCATION: (5)
<223> OTHER INFORMATION: Aib

<400> SEQUENCE: 47

Tyr Xaa Pro Gly Xaa Gly
 1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (5)
<223> OTHER INFORMATION: Aib

<400> SEQUENCE: 48

Tyr Pro Xaa Gly Xaa Gly
 1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Sar
<220> FEATURE:
<221> NAME/KEY: MOD_RES
<222> LOCATION: (5)
<223> OTHER INFORMATION: Aib

<400> SEQUENCE: 49

Tyr Xaa Pro Gly Xaa Gly
 1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Aib

<400> SEQUENCE: 50

Pro Pro Gly Xaa Gly
 1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (4)
<223> OTHER INFORMATION: Sar
<220> FEATURE:
<221> NAME/KEY: MOD_RES
<222> LOCATION: (5)
<223> OTHER INFORMATION: Aib

<400> SEQUENCE: 51

Tyr Pro Pro Xaa Xaa Gly
 1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Aib
<220> FEATURE:
<221> NAME/KEY: MOD_RES
<222> LOCATION: (6)
<223> OTHER INFORMATION: Sar

<400> SEQUENCE: 52

Tyr Pro Pro Gly Xaa Xaa
 1               5

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ala Gly Asn
 1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ala Gly Gln
 1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ala Gly Asp
 1
```

```
<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Ala Gly Glu
  1

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 57

Tyr Pro Xaa Gly Ala Asn
  1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 58

Tyr Pro Xaa Gly Ala Asp
  1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 59

Tyr Pro Xaa Gly Ala Gly Asn
  1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
```

```
<223> OTHER INFORMATION: 4Hyp

<400> SEQUENCE: 60

Tyr Pro Xaa Gly Ala Gly Asp
 1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 61

Tyr Pro Xaa Gly Ala Gln
 1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 62

Tyr Pro Xaa Gly Ala Glu
 1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 63

Tyr Pro Xaa Gly Ala Gly Gln
 1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: 4Hyp

<400> SEQUENCE: 64

Tyr Pro Xaa Gly Ala Gly Glu
 1               5
```

```
<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Ala Ser Ala Gly Asn
  1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Gly Asn Tyr Gly Asn
  1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Gly Asn Tyr Ala Gly Asn
  1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Tyr Val Ser Gly Ala Gly Asn
  1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ser (O)
<220> FEATURE:
<221> NAME/KEY: MOD_RES
<222> LOCATION: (4)
<223> OTHER INFORMATION: 4Hyp

<400> SEQUENCE: 69

Xaa Tyr Pro Xaa Gly Ala Gly
  1               5
```

```
<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Thr(O)
<220> FEATURE:
<221> NAME/KEY: MOD_RES
<222> LOCATION: (4)
<223> OTHER INFORMATION: 4Hyp

<400> SEQUENCE: 70

Xaa Tyr Pro Xaa Gly Ala Gly
 1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 71

Cys Gly Xaa Pro Tyr Cys
 1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: 4Hyp

<400> SEQUENCE: 72

Cys Tyr Pro Xaa Gly Ala Gly Cys
 1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: 4Hyp

<400> SEQUENCE: 73

Cys Tyr Pro Xaa Gly Ala Cys
 1               5

<210> SEQ ID NO 74
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: 4Hyp

<400> SEQUENCE: 74

Cys Tyr Pro Xaa Gly Cys
  1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: 4Hyp

<400> SEQUENCE: 75

Cys Tyr Pro Xaa Cys
  1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dapa
<220> FEATURE:
<221> NAME/KEY: MOD_RES
<222> LOCATION: (4)
<223> OTHER INFORMATION: Hyp

<400> SEQUENCE: 76

Gly Xaa Gly Xaa Pro Tyr
  1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dab
<220> FEATURE:
<221> NAME/KEY: MOD_RES
<222> LOCATION: (4)
<223> OTHER INFORMATION: Hyp

<400> SEQUENCE: 77

Gly Xaa Gly Xaa Pro Tyr
  1               5

<210> SEQ ID NO 78
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dab
<220> FEATURE:
<221> NAME/KEY: MOD_RES
<222> LOCATION: (5)
<223> OTHER INFORMATION: Hyp

<400> SEQUENCE: 78

Gly Xaa Ala Gly Xaa Pro Tyr
 1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dapa
<220> FEATURE:
<221> NAME/KEY: MOD_RES
<222> LOCATION: (5)
<223> OTHER INFORMATION: Hyp

<400> SEQUENCE: 79

Gly Xaa Ala Gly Xaa Pro Tyr
 1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 80

Tyr Pro Xaa Gly Glu Gly
 1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 81

Tyr Pro Xaa Gly Asp Gly
 1               5

<210> SEQ ID NO 82
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 82

Tyr Pro Xaa Gly Ala Asp Gly
  1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 83

Tyr Pro Xaa Gly Ala Glu Gly
  1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ala Gly Asn Tyr
  1               5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Gly Asn Tyr
  1

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Tyr(3,5-di-I)
<220> FEATURE:
<221> NAME/KEY: MOD_RES
<222> LOCATION: (3)
<223> OTHER INFORMATION: Hyp
```

-continued

```
<400> SEQUENCE: 86

Tyr Pro Xaa Gly Ala Gly
 1               5

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: reduced Gly

<400> SEQUENCE: 87

Gly Gly Tyr Tyr
 1

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 88

Gly Pro Xaa Gly Ala Gly
 1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Hyp

<400> SEQUENCE: 89

Pro Xaa Gly Ala Gly
 1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys(Acm)
<220> FEATURE:
<221> NAME/KEY: MOD_RES
<222> LOCATION: (5)
<223> OTHER INFORMATION: Hyp
<220> FEATURE:
<221> NAME/KEY: MOD_RES
<222> LOCATION: (8)
<223> OTHER INFORMATION: Cys(Acm)
```

```
<400> SEQUENCE: 90

Cys Gly Ala Gly Xaa Pro Tyr Cys
 1               5

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys(Acm)
<220> FEATURE:
<221> NAME/KEY: MOD_RES
<222> LOCATION: (3)
<223> OTHER INFORMATION: Hyp
<220> FEATURE:
<221> NAME/KEY: MOD_RES
<222> LOCATION: (6)
<223> OTHER INFORMATION: Cys(Acm)

<400> SEQUENCE: 91

Cys Gly Xaa Pro Tyr Cys
 1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys(Acm)
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (8)
<223> OTHER INFORMATION: Cys(Acm)

<400> SEQUENCE: 92

Cys Tyr Pro Xaa Gly Ala Gly Cys
 1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys(Acm)
<220> FEATURE:
<221> NAME/KEY: MOD_RES
<222> LOCATION: (4)
<223> OTHER INFORMATION: Hyp
<220> FEATURE:
<221> NAME/KEY: MOD_RES
<222> LOCATION: (6)
<223> OTHER INFORMATION: Cys(Acm)
```

```
<400> SEQUENCE: 93

Cys Tyr Pro Xaa Gly Cys
 1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Hyp

<400> SEQUENCE: 94

Pro Tyr Asn Gly Ala Gly Xaa
 1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Hyp

<400> SEQUENCE: 95

Xaa Pro Tyr Asn Gly Ala Gly
 1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Sar
<220> FEATURE:
<221> NAME/KEY: MOD_RES
<222> LOCATION: (4)
<223> OTHER INFORMATION: Hyp

<400> SEQUENCE: 96

Gly Ala Xaa Xaa Pro Tyr
 1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)
<223> OTHER INFORMATION: Hyp

<400> SEQUENCE: 97

Gly Ala Gly Xaa Pro Tyr Gln
 1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp

<400> SEQUENCE: 98

Gly Ala Gly Xaa Pro Tyr Asn
 1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Ala Gly Pro Pro Tyr Asn
 1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Tyr(3-I, 5-I)
<220> FEATURE:
<221> NAME/KEY: MOD_RES
<222> LOCATION: (3)
<223> OTHER INFORMATION: 4Hyp

<400> SEQUENCE: 100

Tyr Pro Xaa Gly Ala Gly Asn
 1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Pro Pro Gly Ala Gly
 1               5
```

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Pro Gly Gly Ala Gly
 1               5

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Asn Tyr Ala
 1

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp

<400> SEQUENCE: 104

Gly Ala Gly Xaa Pro Tyr Lys Lys Lys Lys Lys Lys
 1               5                  10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Hyp

<400> SEQUENCE: 105

Pro Xaa Gly Ala Gly Lys Lys Lys Lys Lys Lys
 1               5                  10

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Tyr Asp Asn Gly
 1               5

<210> SEQ ID NO 107

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Ala Gly Pro Pro Tyr
  1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: des-Hyp

<400> SEQUENCE: 108

Gly Ala Gly Xaa Asn Tyr
  1               5

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Ala Asn Tyr
  1

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Asp Asn Tyr
  1

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Asp Asn Gly
  1

<210> SEQ ID NO 112
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Tyr(3,5-di-iodo)
<220> FEATURE:
<221> NAME/KEY: MOD_RES
<222> LOCATION: (3)
<223> OTHER INFORMATION: Hyp

<400> SEQUENCE: 112

Tyr Pro Xaa Gly Ala Gly
 1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Tyr(3,5-diiodo)
<220> FEATURE:
<221> NAME/KEY: MOD_RES
<222> LOCATION: (3)
<223> OTHER INFORMATION: 4Hyp

<400> SEQUENCE: 113

Tyr Pro Xaa Gly Ala Gly Asn
 1               5

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Lys Lys Lys Lys Lys Lys
 1               5
```

MEDICAL USES OF INTERCELLULAR COMMUNICATION FACILITATING COMPOUNDS

CROSS-REFERENCE TO RELATED APPLICATIONS

The present application is a continuation of PCT/US 02/05773 (WO 02/077017 A2) as filed on 22 Feb. 2002 which application claims the benefit of PCT/DK01/00127 as filed on 22 Feb. 2001 and U.S. Ser. No. 60/314,470 as filed on Aug. 23, 2001. The disclosures of the PCT/US02/05773; PCT/DK01/00127, U.S. Ser. No. 09/792,286, and 60/314,470 applications are each incorporated herein by reference.

FIELD OF THE INVENTION

The present invention relates to novel peptides including novel antiarrhythmic peptides of linear or cyclic structure having improved stability in vitro and/or in vivo, to compositions comprising said peptides, and to uses of said peptides for the preparation of medicaments. The present invention also relates to the use of compounds that facilitate the intercellular communication for the preparation of medicaments for the treatment of a range of diseases characterised in impaired intercellular gap junctional communication. The invention further relates to a method of treating diseases, such as bladder incontinence, disorders of alveolar tissue and bronchial tissue, impaired hearing due to diseases of the cochlea, endothelial lesions, diabetic retinopathy and diabetic neuropathy, ischemia of the central nervous system and spinal cord, dental tissue disorders including parodontal disease, kidney diseases such as impaired secernation from the juxtaglomarular apparatus leading to hypertension, and a method of preventing failures of bone marrow transplantation.

BACKGROUND OF THE INVENTION

Gap junctions are specialized regions of the cell membrane with clusters of hundreds to thousands of densely packed gap junction channels that directly connect the cytoplasmic compartment of two neighboring cells. The gap junction channels are composed of two hemichannels (connexons) provided by each of two neighboring cells. Each connexon consists of six proteins called connexins (Cx). The connexins are a large family of proteins all sharing the basic structure of four transmembrane domains, two extracellular loops, and a cytoplasmic loop. There is a high degree of conservation of the extracellular loops and transmembrane domains among species and connexin isoforms. The length of the C-terminus, however, varies considerably giving rise to the classification of the connexins on the basis of the molecular weight. The gap junction channel can switch between an open and a closed state by a twisting motion. In the open state ions and small molecules can pass through the pore. The conduction of the electrical impulse and intercellular diffusion of signaling molecules take place through the gap junctions and normally functioning gap junctions are therefore a prerequisite for normal intercellular communication. Normal intercellular communication is essential for cellular homeostasis, proliferation and differentiation.

The link between abnormalities in connexins and disease has been established in humans as will appear in the sections below. One example is Chagas' disease caused by the protozoan parasite *Trypanosoma cruzi*. This disease is a major cause of cardiac dysfunction in Latin America. An altered Cx43 distribution has been observed in cells infected by *Trypanosoma cruzi* and this alteration may be involved in the genesis of the conduction disturbances characterizing the disease[7].

In a multicellular organism, co-ordination between cells is of paramount importance. Among the various means of cellular cross talk, gap junctions provide the most direct pathway. Gap junctions are one type of junctional complex formed between adjacent cells and consist of aggregated channels that directly link the interiors (cytoplasm) of neighbouring cells. In the adult mammal, gap junctions are found in most cell types with one known exception being circulating blood elements.

Relatively little is known about the connexin gene structure. Results reported for mouse Cx43 revealed that Cx43 contains two exons and an intron located in the 5' untranslated region. Several putative transcription factor binding sites have been identified in the 5' proximal promotor. In vitro studies have shown that permeable channels could be produced by hemichannels composed of different pairs of connexins. For example, Cx43 can produce functional channels with Cx32, Cx37, Cx40 and Cx45 and endogenous Cx of oocytes (Cx38) but not with Cx26 oocytes. However, very little is known about their properties as well as about the regulation of permeability of these heterochannels. Cx are expressed in the vast majority of tissues and single cells are able to express several different Cx. Permeable gap junctions can be formed between cells, which express different types of Cx. Thus the gap junction intercellular communication (GJIC) in tissues appears to be very important for maintenance of tissue integrity. It appears that several genes are making the equivalent products in order to prevent the loss of GJIC due to a mutation in one of the genes.

The pore diameter of the gap junction channel formed has been reported to be in the range of 0.8-1.4 nm. Gap junctions are relatively non-selective and allow the passage of molecules up to about 1000 Daltons. Such substances are, i.a., ions, water, sugars, nucleotides, amino acids, fatty acids, small peptides, drugs, and carcinogens. Channel passage does not require ATP and appears to result from passive diffusion. This flux of materials between cells via gap junction channels is known as gap junctional intercellular communication (GJIC), which plays an important role in the regulation of cell metabolism, proliferation, and cell-to-cell signaling. One of the most significant physiological implications for GJIC is that gap junction coupled cells within a tissue are not individual, discrete entities, but are highly integrated with their neighbors. This property facilitates homeostasis and also permits the rapid, direct transfer of second messengers between cells to co-ordinate cellular responses within the tissue.

The process of GJIC is regulated by a variety of mechanisms that can be broadly divided into major categories. In one type of regulation the cellular quantity of gap junctions is controlled by influencing the expression, degradation, cellular trafficking of connexins to the plasma membrane, or assembly of connexins into functional gap junctions. Impaired GJIC caused by the down-regulation of connexin expression, e.g. in tumor cells, is an example of this mode of regulation. Another type of regulation does not generally involve any gross alteration of the cellular levels of gap junctions or connexins, but induces opening or closure (gating) of existing gap junctions. Extracellular soluble factors, such as mitogens (e.g. DDT), hormones (e.g. catecholamines), anaesthetics (e.g. halothane), intracellular biomolecules (e.g. cAMP), and cell stress (e.g. mechanical or metabolic stress) can result in this type of regulation. Additionally, GJIC is regulated during the cell cycle and during cellular migration.

The mode of GJIC regulation or junctional gating has been widely studied for gap junctions especially gap junctions composed of Cx43. Some factors exert their inhibitory effects on GJIC indirectly, for example, by altering the lipid environment and cell membrane fluidity, whereas other GJIC inhibitors include oncogenes, growth factors, and tumor promoters, which induce various modifications of the Cx43. Disruption of junctional permeability may be necessary for mediating the specific biological functions of the latter group. These agents initiate complex signaling pathways consisting of the activation of kinases, phosphatases, and interacting proteins. understanding the mechanisms of action of these GJIC modulators will not only define their respective signaling pathways responsible for junctional regulation, but will also provide experimental tools for characterising the biological functions of GJIC and connexins. Changes in the phosphorylation of specific sites of the cytoplasmic carboxy terminal domain of Cx43 appear to be pivotal to the opening and closing of the gap junctional channel. Phosphorylation of the carboxy terminal domain may also be important to the process of bringing Cx43 gap junctional hemicomplex to the cell membrane, its internalisation and degradation. Connexins have half-lives (hours) that are much shorter than most plasma membrane proteins (days), e.g. the half-life of Cx43 in rat heart is less than 1½ hour. Thus, regulation of the turnover rate would be an important factor in regulating GJIC.

The carboxy terminal domain contains putative phosphorylation sites for multiple protein kinases (PKA, PKC, PKG, MAPK, CaMkII and tyrosine kinase). Phosphorylation of these sites of the carboxy terminal domain results in closure of gap junctional channels and various inhibitors of Cx43 gap junctional channels use different signalling pathways to induce phosphorylation of the carboxy terminal domain. The cell type and the particular inhibitor determine which signalling pathways to be used and the type of the involved protein kinase points to the intracellular messenger system utilised. Thus activation of PKA requires involvement of the cAMP second messenger system while PKC requires involvement of the phosphoinositol intracellular signalling system.

Other mechanisms regulating channel gating include intracellular levels of hydrogen and calcium ions, transjunctional voltage, and free radicals. Decreased pH or pCa induce channel closure in a cell- and connexin-specific manner.

Many physiological roles besides growth control have been proposed for GJIC. Homeostasis: GJIC permits the rapid equilibration of nutrients, ions, and fluids between cells. This might be the most ancient, widespread, and important function for these channels. Electrical coupling: Gap junctions serve as electrical synapses in electrically excitable cells such as cardiac myocytes, smooth muscle cells, and neurones. In these tissues, electrical coupling permits more rapid cell-to-cell transmission of action potentials than chemical synapses. In cardiomyocytes and smooth muscle cells, this enables their synchronous contraction. Tissue response to hormones: GJIC may enhance the responsiveness of tissues to external stimuli. Second messengers such as cyclic nucleotides, calcium, and inositol phosphates are small enough to pass from hormonally activated cells to quiescent cells through junctional channels and activate the latter. Such an effect may increase the tissue response to an agonist. Regulation of embryonic development: Gap junctions may serve as intercellular pathways for chemical and/or electrical developmental signals in embryos and for defining the boundaries of developmental compartments. GJIC occurs in specific patterns in embryonic cells and the impairment of GJIC has been related to developmental anomalies and the teratogenic effects of many chemicals.

The intercellular communication ensures that the activities of the individual cells happen in a co-ordinated fashion and integrates these activities into the dynamics of a working tissue serving the organism in which it is set. It is therefore not very surprising that a wide variety of pathological conditions have been associated with decreased GJIC. The link between abnormalities in connexins and a range of disease states has been established both in vitro and in vivo. One example is regulation of gap junctional communication by a pro-inflammatory cytokine in airway epithelium, where Chanson M, Berclaz P Y, Scerri I, Dudez T, Wernke-Dollries K, Pizurki L, Pavirani A, Fiedler M A, Suter S. (Am J Pathol 2001 May; 158(5):1775-84) found that decreased intercellular communication induced by TNF-alpha progressively led to inflammation.

In summary, there is plenty of evidence linking malfunction, such as gating or closure or even absence of gap junctions to an increased risk of disease. No currently available drug for the treatment of said diseases acts as a facilitator of intercellular communication by facilitating or increasing gap junction function. However a group of peptides (the antiarrhythmic peptides) capable of increasing gap junction conductance has been described in the past. A summary is presented in PCT/DK01/00127 which is hereby incorporated by reference. A summary of the present invention is disclosed in U.S. Ser. No. 09/792,286 as filed on Feb. 22, 2001. The disclosure of the U.S. Ser. No. 09/792,286 is incorporated herein by reference.

The antiarrhythmic peptides are a group of peptides that exert their effect selectively on gap junctions and thus decrease cellular uncoupling and also reduce dispersion of action potential duration. However, the native AAP as well as the synthetic AAP10 possess several undesired features, such as, low stability, high effective concentration etc. that has hitherto prevented their utilisation as drugs. Grover and Dhein[21] have characterised two semi cyclic conformations of AAP10 using nuclear magnetic resonance spectroscopy. Therefore, one approach to obtaining a stable antiarrhythmic peptide could be the provision of cyclic derivatives of antiarrhythmic peptides. DE19707854 discloses apparently cyclic $CF_3C(OH)$-Gly-Ala-Gly-4Hyp-Pro-Tyr-CONH (SEQ ID NO: 1) and cyclic CO-Gly-Ala-Gly-4Hyp-Pro-Tyr-CONH (SEQ ID NO: 1) having the same antiarrhythmic properties as AAP and AAP10, but stated to have improved stability in aqueous solution and after repeated cycles of freezing and thawing. However, the experimental conditions described in DE19707854 are insufficient for the preparation of said cyclic compounds, and the chemical identification data given therein using HPLC is not sufficient for identification of said cyclic compounds. U.S. Pat. No. 4,775,743 discloses HP5, a peptide derivative having the sequence N-3-(4-hydroxyphenyl)propionyl-Pro-4Hyp-Gly-Ala-Gly-OH (SEQ ID NO: 2) and being active against platelet agglutination. Dhein and Tudyka[22] have reviewed the literature on peptides including peptide derivatives belonging to the group of antiarrhythmic peptides for activity and concentration, cf. table 1 therein, and found only 7 compounds to be active and further 4 compounds to be weakly active. However, none of these peptides or peptide derivatives have been shown to be sufficiently stable to be effective in a therapy regimen.

The peptides herein increase gap junction intercellular communication (GJIC) in vertebrate tissue, and specifically in mammalian tissue, and are useful in the treatment of a wide spectrum of diseases and ailments in vertebrates, such as mammals, relating to or caused by a decreased function of intercellular gap junction communication as is described below.

Thus, it is a purpose of the present invention to provide a method of preventing or treating diseases and medical conditions that are characterised in reduced or impaired cellular communication, such as caused by impaired gap junctional intercellular communication or impaired coupling through gap junctions. Examples of diseases and medical conditions are inflammation of airway epithelium, disorders of alveolar tissue, bladder incontinence, impaired hearing due to diseases of the cochlea, endothelial lesions, diabetic retinopathy and diabetic neuropathy, ischemia of the central nervous system and spinal cord, dental tissue disorders including periodontal disease, kidney diseases, and failures of bone marrow transplantation as mentioned above.

SUMMARY OF THE INVENTION

The purpose of the present invention is achieved with the present peptides including antiarrhythmic peptide compounds.

There is in the present invention provided methods for preventing or treating diseases caused by impaired cellular communication or impaired gap junction function. Illustrative diseases include those effecting the respiratory, circulatory or nervous systems, vision and hearing, dental tissues, smooth musculature, and transplantation of cells and tissues. Such methods can be used alone as the sole therapeutic regimen or in combination with one or more other established protocols for addressing a particular disease or condition. Preferred invention practice involves treatment of mammals e.g., primates, rodents (including mice, rats, hamsters, and lagomorphs, such as rabbits), dogs, pigs and goats. A preferred primate is a human patient. Compounds useful in the methods of the invention are characterised in functioning as facilitators of GJIC.

More specifically the present invention relates to a method of preventing or treating non-proliferative diseases caused by impaired gap junction function by facilitating (maintaining) the intercellular communication in the diseased cells and tissues occurring through gap junctions, preferably by administering a therapeutically effective amount of at least one compound which facilitates gap junction intercellular communication to a patient suffering from said disease.

The compounds that are useful in the present invention all share the feature of facilitating or mediating GJIC in cells and tissues. The mechanisms through which this GJIC mediation is effected may vary since there are many cellular mechanisms that affect connexin functioning and/or mediate gap junction function. These mechanisms include, e.g.
- control of the cellular quantity of gap junctions by upregulating or normalising the expression of connexins,
- inhibition of degradation of gap junctions and connexins including regulation of the turnover rate of connexins by increasing the half life,
- increasing cellular trafficking of connexins to the plasma membrane,
- mediating the assembly of connexins into functional gap junctions,
- inducing opening of existing gap junctions, e.g. when they have been closed or gated by inhibitors. This mechanism can be described as a reversal of the gap junction closure effected by inhibitors of GJIC acting through a direct or indirect mechanism, such as e.g. hyperphosphorylation of the cytoplasmic carboxy terminal domain of the connexins, e.g. Cx43.

The carboxy terminal domain contains putative phosphorylation sites for multiple protein kinases (PKA, PKC, PKG, MAPK, CaMkII and tyrosine kinase). Phosphorylation of these sites of the carboxy terminal domain results in closure of gap junctional channels and various inhibitors of Cx43 gap junctional channels use different signalling pathways to induce phosphorylation of the carboxy terminal domain. The cell type and the particular inhibitor determine which signalling pathways are used and the type of protein kinase involved points to the intracellular messenger system utilised. Thus, activation of PKA has been reported to require involvement of the cAMP second messenger system while PKC requires involvement of the phosphoinositol intracellular signalling system. Other mechanisms regulating channel gating include intracellular levels of hydrogen and calcium ions, transjunctional voltage, low oxygen and glucose availability, and free radicals. Decreased pH or pCa induce channel closure in a cell- and connexin-specific manner.

Further provided by the present invention are the use of peptides, such as antiarrhythmic peptides, and preferably the peptides described below in detail (described in PCT/DK01/00127 and the U.S. Ser. No. 09/792,286 both filed on 22 Feb. 2001. The U.S. Ser. No. 09/792,286 application is a continuation of U.S.provisional application 60/251,659 filed on Dec. 6, 2000 which application claims benefit to Danish patent application DK PA2000 00288 filed on Feb. 23, 2000 and DK PA2000 00738 filed on May 4, 2000. The disclosures of said U.S. Ser. Nos. 09/792,286, 60/251,659 and Danish applications DK PA2000 00288 and DK PA2000 00738 are each incorporated herein by reference ) that are agonists of an AAP receptor, for the treatment of specific diseases including inflammation of airway epithelium, disorders of alveolar tissue, wounds, erectile dysfunction, urinary bladder incontinence, impaired hearing due to diseases of the cochlea, endothelial lesions, diabetic retinopathy and diabetic neuropathy, neuropathic pain, ischemia of the central nervous system, spinal cord injuries, dental tissue disorders including periodontal disease, kidney diseases, subchronic and chronic inflammation, cancer and failures of bone marrow and stem cell transplantation. Such diseases or medical conditions are characterised as having impaired GJIC as a leading cause of the disease or progression of the disease.

The antiarrhythmic peptides disclosed in PCT/DK01/00127 and functional analogs thereof are useful in the present invention.

Said antiarrhythmic peptides include a group of peptides that exert their effect selectively on gap junctions and thus decrease cellular uncoupling and reduce dispersion of action potential duration similar to the effect described above for the antiarrhythmic peptide AAP10. The molecular target or receptor for the antiarrhythmic peptides is presently unknown. However, the structure of the binding site for APP10 on a putative receptor has been hypothesised by R. Grover and S. Dhein (Peptides 2001, 22 1011-1021). It is assumed that a peptide which is useful in the present invention is an agonist of a receptor for an antiarrhythmic peptide, such as APP10, and that the physiological effect of the interaction between peptide and receptor is an increased cellular coupling through gap junctions or a potentiation or mediation of GJIC. However, there are many more theoretical signaling pathways that may regulate gap junction functioning, and the present inventors do not wish to be bound by any specific theory behind the biological action of GJIC modulation.

Generally, the present invention provides methods for the treatment of diseases and tissue disturbances caused by an excess of reactive oxygen species and/or free radicals and/or nitric oxide. An example is diabetic neuropathy and wounds where free radicals cause a depletion of gluthation and consequently a reduction of gap junctions, or an uncoupling of the gap junction communication. Low oxygen supply and/or high concentration of free radicals is significant in wounds with necrotic tissue, in diabetes, in arteriosclerosis, in surgery wounds, oedema, infection, burn wounds and in venous insufficiency will lower the gap junction communication. Free radicals are of importance for nerve terminal destruction, decreased conductance, demyelination and increased inflammatory response. Noise induced hearing loss, presbycusis, is known to be associated with production of free radicals and is related to inhibition of gap junction coupling. Excess of free radicals may also reduce endothelial repair and capillary sprouting during angiogenesis.

For example, and in one embodiment, the invention provides methods for treating or preventing airway inflammation. Preferred methods include administering to a patient in need of such treatment a therapeutically effective amount of at least one compound which facilitates gap junctional intercellular communication.

Methods for treating or preventing bladder incontinence are also provided by the present invention. In one embodiment, the methods include administering to a patient in need of such treatment a therapeutically effective amount of at least one compound which facilitates gap junctional intercellular communication.

The invention also provides methods for treating or preventing impaired hearing due to diseases of the cochlea. For example, and in one embodiment, the methods include administering to a patient in need of such treatment a therapeutically effective amount of at least one compound which facilitates gap junctional intercellular communication.

Specifically, the invention relates to the use of a compound which facilitates cellular communication, such as gap junctional intercellular communication for the manufacture of a pharmaceutical composition for the prevention or treatment of diseases and preferably non-proliferative diseases including, e.g. inflammation of airway epithelium, disorders of alveolar tissue, wounds, erectile dysfunction, urinary bladder incontinence, impaired hearing due to diseases of the cochlea, endothelial lesions, diabetic retinopathy and diabetic neuropathy, neuropathic pain, ischemia of the central nervous system, spinal cord injuries, dental tissue disorders including periodontal disease, kidney diseases, subchronic and chronic inflammation, cancer and failures of bone marrow and stem cell transplantation.

DETAILED DESCRIPTION OF THE INVENTION

Figure 1:
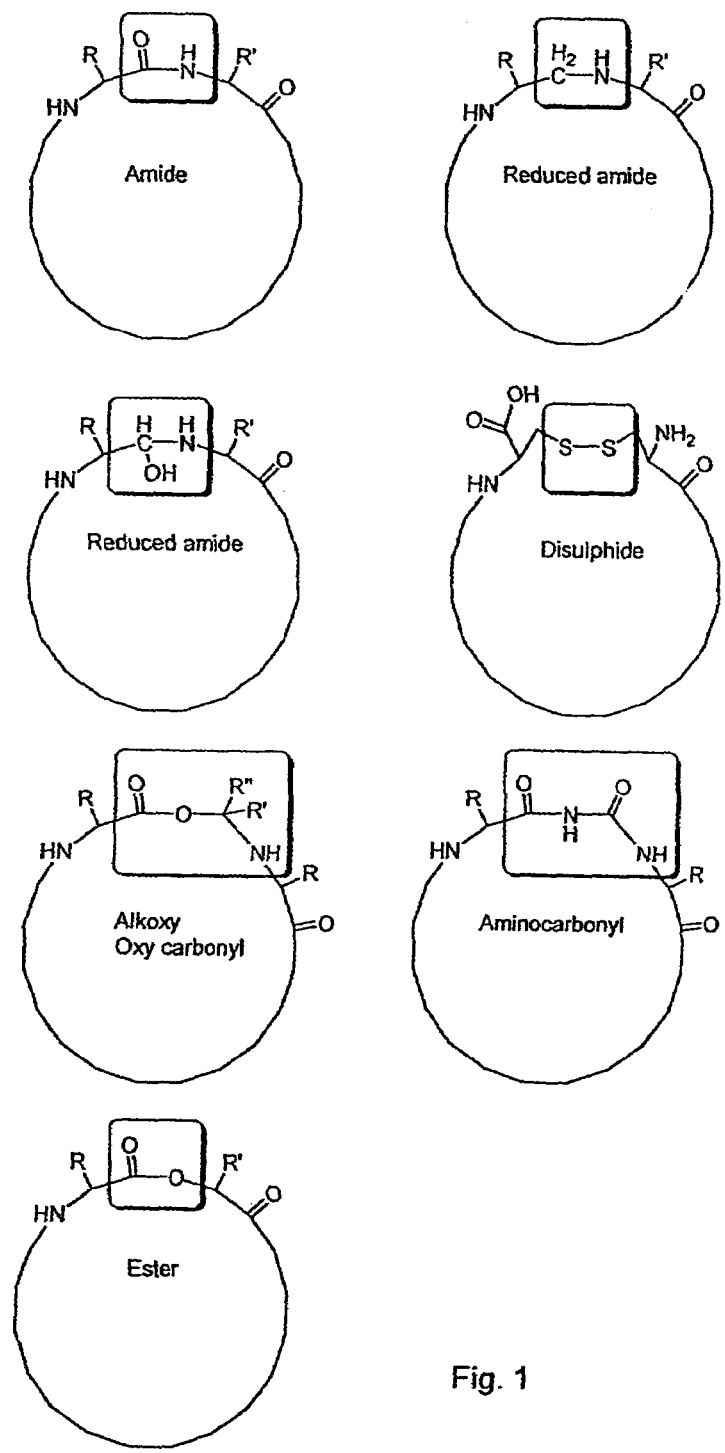
FIG. 1 is a set of schematic drawings showing a general outline of seven different cyclic structures within the scope of the present invention.

Peptides useful in the present invention include compounds of the general formula

```
  ┌---X—A—B—Y---┐
  └---------L---------┘
``` where the dashed line indicates that formula I is optionally cyclic, and the bonds shown represent covalent bonds; and wherein A represents a chemical moiety having an amino group (radical) and a carboxy group (radical) that forms part of the peptide bond connecting A to X and B; B represents a chemical moiety having an amino group (radical) and a carboxy group (radical) that forms part of the peptide bond connecting B to A and Y; X represents a peptide sequence of from 1 to 3 amino acid residues which independently may be an L or D form when Y represents a C-terminal peptide sequence of from 2 to 5 amino acid residues which may independently be L- or D-forms; or X represents an N-terminal modification of the group A-B when Y represents a C-terminal peptide sequence of from 2 to 5 amino acid residues which may independently be L- or D-forms; or X represents a peptide sequence of from 2 to 5 amino acid residues which may independently be L- or D-forms when Y represents a C-terminal peptide sequence of from 1 to 3 amino acid residues which independently may be an L or D form; and when formula I represents a linear peptide X is optionally chemically modified at its N-terminal, and L is an optional linking group comprising from 0 to 8 backbone atoms; and a mirror image or a retro analogue of formula I, or a derivative of formula I which is a pharmaceutically acceptable salt, an alkyl, aryl or aralkyl ester, an amide, a mono or disubstituted amide where the substituent is an alkyl, an aryl or an aralkyl, a hydrazide, or an alcohol; providing that the compounds

| | |
|---|---|
| H-Gly-Pro-Leu-Gly-Pro-OH, | (SEQ ID NO: 3) |
| H-Pro-4Hyp-Gly-Ala-Gly-OH, | (SEQ ID NO: 2) |
| N-3-(4-hydroxyphenyl)propionyl-Pro-4Hyp-Gly-Ala-Gly-OH, | (SEQ ID NO: 2) |
| N-3-phenylpropionyl-Pro-4Hyp-Gly-Ala-Gly-OH, | (SEQ ID NO: 2) |
| N-3-phenylpropyl-Pro-4Hyp-Gly-Ala-Gly-OH, | (SEQ ID NO: 2) |
| N-3-(4-hydroxyphenyl)propionyl-Pro-4Hyp-Gly-Ala-OH, | |
| N-3-(4-hydroxyphenyl)propionyl-Pro-4Hyp-Gly-OH, | |
| N-3-(4-hydroxyphenyl)propionyl-Pro-4Hyp-OH, | |
| N-3-(4-hydroxyphenyl)propionyl-Pro-Pro-Gly-Ala-Gly-OH, | (SEQ ID NO: 4) |
| H-Gly-Ala-Gly-4Hyp-Pro-Tyr-NH₂, | (SEQ ID NO: 1) |
| H-Gly-Ala-Gly-4Hyp-Pro-Tyr-OH, | (SEQ ID NO: 1) |
| H-Ala-Gly-4Hyp-Pro-Tyr-NH₂, | (SEQ ID NO: 5) |
| H-Gly-Sar-Pro-Gly-Ala-Gly-OH, | (SEQ ID NO: 6) |
| H-Gly-Pro-Sar-Gly-Ala-GlyOH, | (SEQ ID NO: 7) |
| H-Gly-Sar-Sar-Gly-Ala-Gly-OH, | (SEQ ID NO: 8) |
| H-Gly-Ala-Gly-Hyp-Pro-Tyr(3-I)-NH₂, | (SEQ ID NO: 9) |
| H-Gly-Ala-Gly-Hyp-Pro-Tyr(3-F)-NH₂ | (SEQ ID NO: 10) |
| H-Gly-Ala-Gly-Hyp-Pro-Tyr(3-Cl)-NH₂ | (SEQ ID NO: 11) |
| H-Gly-Ala-Gly-Hyp-Pro-Tyr(3-Br)-NH₂ | (SEQ ID NO: 12) |
| H-Arg-Ala-Gly-Hyp-Pro-Tyr-NH₂ | (SEQ ID NO: 13) |
| H-Val-Ala-Gly-Hyp-Pro-Tyr-NH₂ | (SEQ ID NO: 14) |
| H-Ala-Ala-Gly-Hyp-Pro-Tyr-NH₂ | (SEQ ID NO: 15) |
| H-Gly-Ala-Gly-Hyp-His-Tyr-NH₂ | (SEQ ID NO: 16) |
| H-Gly-Ala-Gly-Hyp-Pro-Phe-NH₂ | (SEQ ID NO: 17) |
| Cyclo(CF₃C(OH)-Gly-Ala-Gly-4Hyp-Pro-Tyr-CONH), | (SEQ ID NO: 1) |
| Cyclo(CO-Gly-Ala-Gly-4Hyp-Pro-Tyr-CONH). | (SEQ ID NO: 1) |
| CF₃C(OH)-Gly-Ala-Gly-4Hyp-Pro-Tyr-CONH, and | (SEQ ID NO: 1) |
| CO-Gly-Ala-Gly-4Hyp-Pro-Tyr-CONH | (SEQ ID NO: 1) | are not covered by said general formula. It is preferred that the covalent bonds are selected from peptide bonds, disulphide bonds, ester bonds, reduced amide bonds, alkoxy bonds, oxycarbonyl bonds, and acyloxyalkoxy bonds. Examples of A and B include the formula Z $$
\begin{array}{c}
\text{R} \\
| \\
\diagup \diagdown \\
—\text{N} \quad (\text{CH}_2)_n \\
\diagdown \diagup \\
| \\
(\text{O})\text{C} \diagdown
\end{array}
\tag{Z}
$$

wherein n is an integer having the value 3, 4, or 5, and R represents an optional substituent, preferably selected from the group consisting of halogen, phenyl, hydroxy, NH₂, and C(1-6)alkyl. In a preferred embodiment of the invention A and B each represents an amino acid or an amino acid derivative having functional amino and carboxylic acid groups. Further examples of A and B are represented by the formula Za

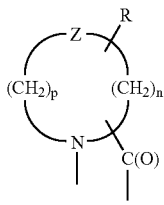

(Za)

Wherein n is an integer having the value 0, 1, 2, and 3, p is an integer having the value 0, 1, 2, and 3, Z represents O or S, and R represents an optional substituent, preferably selected from the group consisting of halogen, phenyl, hydroxy, $NH_2$, and C(1-6)alkyl. Exemplary compounds of the invention wherein A or B is represented by the formula Za are

```
Compound 11    H-Gly-Ala-Gly-NCG-Pro-Tyr-
               NH₂
Compound 12    H-Gly-Ala-Gly-T4C- Pro-Tyr-
               NH₂
Compound 13    H-Gly-Ala-Gly-A2C-Pro-Tyr-
               NH₂
Compound 14    H-Gly-Ala-Gly-PC-Pro-Tyr-
               NH₂
``` and salts thereof.

Examples of A and B include but are not limited to N— and C(O)— radicals of the following compounds:
D/L-azetidin-3-carboxylic acid,
D/L-azetidin-2-carboxylic acid,
D/L-Indolin-2-carboxylic acid,
D/L-1,3-dihydro-isoindol-1-carboxylic acid,
D/L-thiazolidin-4-carboxylic acid,
D/L-pipecolinic acid,
D/L-Nipecotinic acid,
Isonipecotinic acid,
L/D-2-carboxymorpholin,
L/D-1,2,3,4-tetrahydroquinolin-3-carboxylic acid,
L/D-1,2,3,4-tetrahydroquinolin-3-carboxylic acid, and
4-carboxy-4-phenyl-piperidin.

Preferably, the chemical moiety of A and B each represents an amino acid residue having a saturated carbocyclic structure of 4, 5 or 6 members comprising one or more heteroatoms, such as N and S. Said amino acids include L and D forms, natural and unnatural amino acids and derivatives thereof, such as a Prolin residue having one or more substituents in the 3, 4 or 5 position, said substituents being preferably selected from hydroxy, amino or phenyl; and N-substituted amino acids, such as Sarcosin, N-cyclohexylglycine, and N-phenylglycine. Preferably the sequence A-B represents a dipeptide selected from the group consisting of Sar-Sar, Sar-Hyp, Hyp-Sar, Pro-Sar, Sar-Pro, Pro-Hyp, Pro-Pro, Hyp-Pro, and Hyp-Hyp, where Pro and Hyp independently may be an L or D form, where the ring structure of Pro and Hyp is optionally substituted with halogen, nitro, methyl, amino, or phenyl, and Hyp represents 3-hydroxyproline or 4-hydroxyproline, or one or both of the amino acid residues of A-B is a Sar, or N-cyclohexylglycine residue.

The general formula above may represents a linear peptide wherein said chemical modification of the N-terminal of X is an acylation with an optionally substituted C(1-22)alkyl carboxylic acid, such as acetic acid, propionic acid, butyric acid and other fatty acids, or an optionally substituted C(2-22) alkenyl carboxylic acid, or an aryl carboxylic acid, such as benzoic acid, where the substitutent is selected from hydroxy, halogen, C(1-6)alkyl, nitro or cyano and may be situated on the carbon chain or the aromatic moiety; or an alkylation with an optionally substituted C(1-22)alkyl, C(2-22)alkenyl, or aryl C(1-22)alkyl, such as methyl, ethyl, propyl, butyl, phenylpropyl, 2-hydroxyphenylpropyl, and 4-hydroxyphenylpropyl, where the substitutent is selected from hydroxy, halogen, C(1-6)alkyl, nitro or cyano and may be situated on the carbon chain or the aromatic moiety. More preferably, X is selected from the group consisting of L-Tyr and D-Tyr optionally acylated with a C(1-4)carboxylic acid, preferably acetic acid, when Y represents a C-terminal peptide sequence of from 2 to 5 amino acid residues as defined above. It is also preferred that X represents an N-terminal modification of the group A-B, said modifications being preferably selected from phenylpropionic acid and derivatives thereof, such as 4HPP and 2HPP; phenylacetic acid and derivatives thereof, such as 4HPA, 3HPA and 2HPA; phenoxyacetic acid and derivatives thereof, such as 4HPPA, 2HPPA and 4HMPA; benzoylglycine and derivatives thereof, such as 4HBG, 3HBG and 2HBG; and phenylglycine and derivatives thereof bound via an amide bond to A.

A-B is more preferably selected from the group consisting of Pro-Hyp, Pro-Pro, Hyp-Pro, and Hyp-Hyp where Pro and Hyp independently may be an L or D form and Hyp preferably represents 4Hyp. Preferably, Y represents a peptide of from 3 to 5 amino acid residues, or preferably 3 or 4 amino acid residues, being independently L- or D-forms, and preferably having Sar or Gly at its C-terminal, and more preferably Y represents a peptide sequence selected from the group consisting of

```
Gly-L-Ala-Gly-OH,
Gly-L-Ala-Gly-NH₂,
Gly-D-Ala-Gly-OH,
Gly-D-Ala-Gly-NH₂, and
```

Sar-Aib-Sar-OH/$NH_2$, when X represents a single amino acid.

Examples of linear compounds of formula I are

| | |
|---|---|
| H-Gly-Ala-Gly-Gly-Pro-Tyr-OH/NH₂, | (SEQ ID NO: 18) |
| Ac-L-Tyr-L-Pro-L-4Hyp-Gly-L-Ala-Gly-OH/NH₂, | (SEQ ID NO: 19) |
| Ac-D-Tyr-D-Pro-D-4Hyp-Gly-D-Ala-Gly-OH, | |
| Ac-D-Tyr-D-Pro-D-4Hyp-Gly-D-Ala-Gly-NH₂ (Compound 2) | |
| Ac-Tyr-Pro-4Hyp-Gly-Ala-Gly-OH (Compound 1) | (SEQ ID NO: 19) |
| Ac-Tyr-Pro-4Hyp-Gly-Ala-Gly-NH₂ | (SEQ ID NO: 19) |
| Ac-Tyr-Pro-Pro-Gly-Ala-Gly-OH/NH₂ | (SEQ ID NO: 20) |
| Ac-D-Tyr-D-Pro-D-Pro-Gly-D-Ala-Gly-OH/NH₂ | |

-continued

Ac-Tyr-4Hyp-Pro-Gly-Ala-Gly-OH/NH$_2$ (SEQ ID NO: 21)

Ac-D-Tyr-D-4Hyp-D-Pro-Gly-D-Ala-Gly-OH/NH$_2$

Ac-Tyr-4Hyp-4Hyp-Gly-Ala-Gly-OH/NH$_2$ (SEQ ID NO: 22)

Ac-D-Tyr-D-4Hyp-D-4Hyp-Gly-D-Ala-Gly-OH/NH$_2$

Ac-Tyr-Sar-4Hyp-Gly-Ala-Gly-OH/NH$_2$ (SEQ ID NO: 23)

Ac-D-Tyr-Sar-D-4Hyp-Gly-D-Ala-Gly-OH/NH$_2$

Ac-Tyr-4Hyp-Sar-Gly-Ala-Gly-OH/NH$_2$ (SEQ ID NO: 24)

Ac-D-Tyr-D-4Hyp-Sar-Gly-D-Ala-Gly-OH/NH$_2$

Ac-Tyr-Pro-Sar-Gly-Ala-Gly-OH/NH$_2$ (SEQ ID NO: 25)

Ac-D-Tyr-D-Pro-Sar-Gly-D-Ala-Gly-OH/NH$_2$

Ac-Tyr-Sar-Pro-Gly-Ala-Gly-OH/NH$_2$ (SEQ ID NO: 26)

Ac-D-Tyr-Sar-D-Pro-Gly-D-Ala-Gly-OH/NH$_2$

Ac-Tyr-Sar-Sar-Gly-Ala-Gly-OH/NH$_2$ (SEQ ID NO: 27)

Ac-D-Tyr-Sar-Sar-Gly-D-Ala-Gly-OH/NH$_2$

Tfa-L-Tyr-L-Pro-L-4Hyp-Gly-L-Ala-Gly-OH, (SEQ ID NO: 19)

Tfa-D-Tyr-D-Pro-D-4Hyp-Gly-D-Ala-Gly-OH,

Tfa-Tyr-Pro-4Hyp-Gly-Ala-Gly-OH (SEQ ID NO: 19)

Tfa-Tyr-Pro-4Hyp-Gly-Ala-Gly-NH$_2$ (SEQ ID NO: 19)

Tfa-D-Tyr-D-Pro-D-4Hyp-Gly-D-Ala-Gly-NH$_2$

Tfa-Tyr-Pro-Pro-Gly-Ala-Gly-OH/NH$_2$ (SEQ ID NO: 20)

Tfa-D-Tyr-D-Pro-D-Pro-Gly-D-Ala-Gly-OH/NH$_2$

Tfa-Tyr-4Hyp-Pro-Gly-Ala-Gly-OH/NH$_2$ (SEQ ID NO: 21)

Tfa-D-Tyr-D-4Hyp-D-Pro-Gly-D-Ala-Gly-OH/NH$_2$

Tfa-Tyr-4Hyp-4Hyp-Gly-Ala-Gly-OH/NH$_2$ (SEQ ID NO: 22)

Tfa-D-Tyr-D-4Hyp-D-4Hyp-Gly-D-Ala-Gly-OH/NH$_2$

Tfa-Tyr-Sar-4Hyp-Gly-Ala-Gly-OH/NH$_2$ (SEQ ID NO: 23)

Tfa-D-Tyr-Sar-D-4Hyp-Gly-D-Ala-Gly-OH/NH$_2$

Tfa-Tyr-4Hyp-Sar-Gly-Ala-Gly-OH/NH$_2$ (SEQ ID NO: 24)

Tfa-D-Tyr-D-4Hyp-Sar-Gly-D-Ala-Gly-OH/NH$_2$

Tfa-Tyr-Pro-Sar-Gly-Ala-Gly-OH/NH$_2$ (SEQ ID NO: 25)

Tfa-D-Tyr-D-Pro-Sar-Gly-D-Ala-Gly-OH/NH$_2$

Tfa-Tyr-Sar-Pro-Gly-Ala-Gly-OH/NH$_2$ (SEQ ID NO: 26)

Tfa-D-Tyr-Sar-D-Pro-Gly-D-Ala-Gly-OH/NH$_2$

Tfa-Tyr-Sar-Sar-Gly-Ala-Gly-OH/NH$_2$ (SEQ ID NO: 27)

Tfa-D-Tyr-Sar-Sar-Gly-D-Ala-Gly-OH/NH$_2$

4HPP-D-Pro-D-4Hyp-Gly-D-Ala-Gly-OH/NH$_2$

4HPPA-Pro-4Hyp-Gly-Ala-Gly-OH/NH$_2$ (SEQ ID NO: 2)

4HPPA-D-Pro-D-4Hyp-Gly-D-Ala-Gly-OH/NH$_2$

4HMPA-Pro-4Hyp-Gly-Ala-Gly-OH/NH$_2$ (SEQ ID NO: 2)

4HMPA-D-Pro-D-4Hyp-Gly-D-Ala-Gly-OH/NH$_2$

4HPA-Pro-4Hyp-Gly-Ala-Gly-OH/NH$_2$ (SEQ ID NO: 2)

4HPA-D-Pro-D-4Hyp-Gly-D-Ala-Gly-OH/NH$_2$

4HBG-Pro-4Hyp-Gly-Ala-Gly-OH/NH$_2$ (SEQ ID NO: 2)

4HBG-D-Pro-D-4Hyp-Gly-D-Ala-Gly-OH/NH$_2$

4HPP-Pro-Pro-Gly-Ala-Gly-OH/NH$_2$ (SEQ ID NO: 28)

4HPP-D-Pro-D-Pro-Gly-D-Ala-Gly-OH/NH$_2$

4HPPA-Pro-Pro-Gly-Ala-Gly-OH/NH$_2$ (SEQ ID NO: 28)

4HPPA-D-Pro-D-Pro-Gly-D-Ala-Gly-OH/NH$_2$

4HMPA-Pro-Pro-Gly-Ala-Gly-OH/NH$_2$ (SEQ ID NO: 28)

4HMPA-D-Pro-D-Pro-Gly-D-Ala-Gly-OH/NH$_2$

4HPA-Pro-Pro-Gly-Ala-Gly-OH/NH$_2$ (SEQ ID NO: 28)

4HPA-D-Pro-D-Pro-Gly-D-Ala-Gly-OH/NH$_2$

4HBG-Pro-Pro-Gly-Ala-Gly-OH/NH$_2$ (SEQ ID NO: 28)

4HBG-D-Pro-D-Pro-Gly-D-Ala-Gly-OH/NH$_2$

4HPP-4Hyp-4Hyp-Gly-Ala-Gly-OH/NH$_2$

4HPP-D-4Hyp-D-4Hyp-Gly-D-Ala-Gly-OH/NH$_2$

4HPPA-4Hyp-4Hyp-Gly-Ala-Gly-OH/NH$_2$

4HPPA-D-4Hyp-D-4Hyp-Gly-D-Ala-Gly-OH/NH$_2$

4HMPA-4Hyp-4Hyp-Gly-Ala-Gly-OH/NH$_2$

4HMPA-D-4Hyp-D-4Hyp-Gly-D-Ala-Gly-OH/NH$_2$

-continued

| | |
|---|---|
| 4HPA-4Hyp-4Hyp-Gly-Ala-Gly-OH/NH₂ | |
| 4HPA-D-4Hyp-D-4Hyp-Gly-D-Ala-Gly-OH/NH₂ | |
| 4HBG-4Hyp-4Hyp-Gly-Ala-Gly-OH/NH₂4HBG-D-4Hyp-D-4Hyp-Gly-D-Ala-Gly-OH/NH₂ | |
| 4HPP-4Hyp-Pro-Gly-Ala-Gly-OH/NH₂ | (SEQ ID NO: 29) |
| 4HPP-D-4Hyp-D-Pro-Gly-D-Ala-Gly-OH/NH₂ | |
| 4HPPA-4Hyp-Pro-Gly-Ala-Gly-OH/NH₂ | (SEQ ID NO: 29) |
| 4HPPA-D-4Hyp-D-Pro-Gly-D-Ala-Gly-OH/NH₂ | |
| 4HMPA-4Hyp-Pro-Gly-Ala-Gly-OH/NH₂ | (SEQ ID NO: 29) |
| 4HMPA-D-4Hyp-D-Pro-Gly-D-Ala-Gly-OH/NH₂ | |
| 4HPA-4Hyp-Pro-Gly-Ala-Gly-OH/NH₂ | (SEQ ID NO: 29) |
| 4HPA-D-4Hyp-D-Pro-Gly-D-Ala-Gly-OH/NH₂ | |
| 4HBG-4Hyp-Pro-Gly-Ala-Gly-OH/NH₂ | (SEQ ID NO: 29) |
| 4HBG-D-4Hyp-D-Pro-Gly-D-Ala-Gly-OH/NH₂ | |
| 4HPP-Sar-Pro-Gly-Ala-Gly-OH/NH₂ | (SEQ ID NO: 30) |
| 4HPP-Sar-D-Pro-Gly-D-Ala-Gly-OH/NH₂ | |
| 4HPPA-Sar-Pro-Gly-Ala-Gly-OH/NH₂ | (SEQ ID NO: 30) |
| 4HPPA-Sar-D-Pro-Gly-D-Ala-Gly-OH/NH₂ | |
| 4HMPA-Sar-Pro-Gly-Ala-Gly-OH/NH₂ | (SEQ ID NO: 30) |
| 4HMPA-Sar-D-Pro-Gly-D-Ala-Gly-OH/NH₂ | |
| 4HPA-Sar-Pro-Gly-Ala-Gly-OH/NH₂ | (SEQ ID NO: 30) |
| 4HPA-Sar-D-Pro-Gly-D-Ala-Gly-OH/NH₂ | |
| 4HBG-Sar-Pro-Gly-Ala-Gly-OH/NH₂ | (SEQ ID NO: 30) |
| 4HBG-Sar-D-Pro-Gly-D-Ala-Gly-OH/NH₂ | |
| 4HPP-Pro-Sar-Gly-Ala-Gly-OH/NH₂ | (SEQ ID NO: 31) |
| 4HPP-D-Pro-Sar-Gly-D-Ala-Gly-OH/NH₂ | |
| 4HPPA-Pro-Sar-Gly-Ala-Gly-OH/NH₂ | (SEQ ID NO: 31) |
| 4HPPA-D-Pro-Sar-Gly-D-Ala-Gly-OH/NH₂ | |
| 4HMPA-Pro-Sar-Gly-Ala-Gly-OH/NH₂ | (SEQ ID NO: 31) |
| 4HMPA-D-Pro-Sar-Gly-D-Ala-Gly-OH/NH₂ | |
| 4HPA-Pro-Sar-Gly-Ala-Gly-OH/NH₂ | (SEQ ID NO: 31) |
| 4HPA-D-Pro-Sar-Gly-D-Ala-Gly-OH/NH₂ | |

-continued

| | |
|---|---|
| 4HBG-Pro-Sar-Gly-Ala-Gly-OH/NH₂ | (SEQ ID NO: 31) |
| 4HBG-D-Pro-Sar-Gly-D-Ala-Gly-OH/NH₂ | |
| 4HPP-Sar-4Hyp-Gly-Ala-Gly-OH/NH₂ | |
| 4HPP-Sar-D-4Hyp-Gly-D-Ala-Gly-OH/NH₂ | |
| 4HPPA-Sar-4Hyp-Gly-Ala-Gly-OH/NH₂ | |
| 4HPPA-Sar-D-4Hyp-Gly-D-Ala-Gly-OH/NH₂ | |
| 4HMPA-Sar-4Hyp-Gly-Ala-Gly-OH/NH₂ | |
| 4HMPA-Sar-D-4Hyp-Gly-D-Ala-Gly-OH/NH₂ | |
| 4HPA-Sar-4Hyp-Gly-Ala-Gly-OH/NH₂ | |
| 4HPA-Sar-D-4Hyp-Gly-D-Ala-Gly-OH/NH₂ | |
| 4HBG-Sar-4Hyp-Gly-Ala-Gly-OH/NH₂ | |
| 4HBG-Sar-D-4Hyp-Gly-D-Ala-Gly-OH/NH₂ | |
| 4HPP-4Hyp-Sar-Gly-Ala-Gly-OH/NH₂ | |
| 4HPP-D-4Hyp-Sar-Gly-D-Ala-Gly-OH/NH₂ | |
| 4HPPA-4Hyp-Sar-Gly-Ala-Gly-OH/NH₂ | |
| 4HPPA-D-4Hyp-Sar-Gly-D-Ala-Gly-OH/NH₂ | |
| 4HMPA-4Hyp-Sar-Gly-Ala-Gly-OH/NH₂ | |
| 4HMPA-D-4Hyp-Sar-Gly-D-Ala-Gly-OH/NH₂ | |
| 4HPA-4Hyp-Sar-Gly-Ala-Gly-OH/NH₂ | |
| 4HPA-D-4Hyp-Sar-Gly-D-Ala-Gly-OH/NH₂ | |
| 4HBG-4Hyp-Sar-Gly-Ala-Gly-OH/NH₂ | |
| 4HBG-D-4Hyp-Sar-Gly-D-Ala-Gly-OH/NH₂ | |
| 4HPP-Sar-Sar-Gly-Ala-Gly-OH/NH₂ | |
| 4HPP-Sar-Sar-Gly-D-Ala-Gly-OH/NH₂ | |
| 4HPPA-Sar-Sar-Gly-Ala-Gly-OH/NH₂ | |
| 4HPPA-Sar-Sar-Gly-D-Ala-Gly-OH/NH₂ | |
| 4HMPA-Sar-Sar-Gly-Ala-Gly-OH/NH₂ | |
| 4HMPA-Sar-Sar-Gly-D-Ala-Gly-OH/NH₂ | |
| 4HPA-Sar-Sar-Gly-Ala-Gly-OH/NH₂ | |
| 4HPA-Sar-Sar-Gly-D-Ala-Gly-OH/NH₂ | |
| 4HBG-Sar-Sar-Gly-Ala-Gly-OH/NH₂ | |
| 4HBG-Sar-Sar-Gly-D-Ala-Gly-OH/NH₂ | |
| Ac-Tyr-Pro-4Hyp-Sar-Ala-Sar-OH/NH₂ | |
| Ac-D-Tyr-D-Pro-D-4Hyp-Sar-D-Ala-Sar-OH/NH₂ | |

Ac-Tyr-Pro-Pro-Sar-Ala-Sar-OH/NH$_2$ (SEQ ID NO: 32)

Ac-D-Tyr-D-Pro-D-Pro-Sar-D-Ala-Sar-OH/NH$_2$

Ac-Tyr-4Hyp-Pro-Sar-Ala-Sar-OH/NH$_2$

Ac-D-Tyr-D-4Hyp-D-Pro-Sar-D-Ala-Sar-OH/NH$_2$

Ac-Tyr-4Hyp-4Hyp-Sar-Ala-Sar-OH/NH$_2$

Ac-D-Tyr-D-4Hyp-D-4Hyp-Sar-D-Ala-Sar-OH/NH$_2$

Ac-Tyr-Sar-4Hyp-Sar-Ala-Sar-OH/NH$_2$

Ac-D-Tyr-Sar-D-4Hyp-Sar-D-Ala-Sar-OH/NH$_2$

Ac-Tyr-4Hyp-Sar-Sar-Ala-Sar-OH/NH$_2$

Ac-D-Tyr-D-4Hyp-Sar-Sar-D-Ala-Sar-OH/NH$_2$

Ac-Tyr-Pro-Sar-Sar-Ala-Sar-OH/NH$_2$

Ac-D-Tyr-D-Pro-Sar-Sar-D-Ala-Sar-OH/NH$_2$

Ac-Tyr-Sar-Pro-Sar-Ala-Sar-OH/NH$_2$

Ac-D-Tyr-Sar-D-Pro-Sar-D-Ala-Sar-OH/NH$_2$

Tfa-Tyr-Pro-4Hyp-Sar-Ala-Sar-OH/NH$_2$

Tfa-D-Tyr-D-Pro-D-4Hyp-Sar-D-Ala-Sar-OH/NH$_2$

Tfa-Tyr-Pro-Pro-Sar-Ala-Sar-OH/NH$_2$ (SEQ ID NO: 32)

Tfa-D-Tyr-D-Pro-D-Pro-Sar-D-Ala-Sar-OH/NH$_2$

Tfa-Tyr-4Hyp-Pro-Sar-Ala-Sar-OH/NH$_2$

Tfa-D-Tyr-D-4Hyp-D-Pro-Sar-D-Ala-Sar-OH/NH$_2$

Tfa-Tyr-4Hyp-4Hyp-Sar-Ala-Sar-OH/NH$_2$

Tfa-D-Tyr-D-4Hyp-D-4Hyp-Sar-D-Ala-Sar-OH/NH$_2$

Tfa-Tyr-Sar-4Hyp-Sar-Ala-Sar-OH/NH$_2$

Tfa-D-Tyr-Sar-D-4Hyp-Sar-D-Ala-Sar-OH/NH$_2$

Tfa-Tyr-4Hyp-Sar-Sar-Ala-Sar-OH/NH$_2$

Tfa-D-Tyr-D-4Hyp-Sar-Sar-D-Ala-Sar-OH/NH$_2$

Tfa-Tyr-Pro-Sar-Sar-Ala-Sar-OH/NH$_2$

Tfa-D-Tyr-D-Pro-Sar-Sar-D-Ala-Sar-OH/NH$_2$

Tfa-Tyr-Sar-Pro-Sar-Ala-Sar-OH/NH$_2$

Tfa-D-Tyr-Sar-D-Pro-Sar-D-Ala-Sar-OH/NH$_2$

4HPP-Pro-4Hyp-Sar-Ala-Sar-OH/NH$_2$

4HPP-D-Pro-D-4Hyp-Sar-D-Ala-Sar-OH/NH$_2$

4HPPA-Pro-4Hyp-Sar-Ala-Sar-OH/NH$_2$

4HPPA-D-Pro-D-4Hyp-Sar-D-Ala-Sar-OH/NH$_2$

4HMPA-Pro-4Hyp-Sar-Ala-Sar-OH/NH$_2$

4HMPA-D-Pro-D-4Hyp-Sar-D-Ala-Sar-OH/NH$_2$

4HPA-Pro-4Hyp-Sar-Ala-Sar-OH/NH$_2$

4HPA-D-Pro-D-4Hyp-Sar-D-Ala-Sar-OH/NH$_2$

4HBG-Pro-4Hyp-Sar-Ala-Sar-OH/NH$_2$

4HBG-D-Pro-D-4Hyp-Sar-D-Ala-Sar-OH/NH$_2$

4HPP-Pro-Pro-Sar-Ala-Sar-OH/NH$_2$

4HPP-D-Pro-D-Pro-Sar-D-Ala-Sar-OH/NH$_2$

4HPPA-Pro-Pro-Sar-Ala-Sar-OH/NH$_2$

4HPPA-D-Pro-D-Pro-Sar-D-Ala-Sar-OH/NH$_2$

4HMPA-Pro-Pro-Sar-Ala-Sar-OH/NH$_2$

4HMPA-D-Pro-D-Pro-Sar-D-Ala-Sar-OH/NH$_2$

4HPA-Pro-Pro-Sar-Ala-Sar-OH/NH$_2$

4HPA-D-Pro-D-Pro-Sar-D-Ala-Sar-OH/NH$_2$

4HBG-Pro-Pro-Sar-Ala-Sar-OH/NH$_2$

4HBG-D-Pro-D-Pro-Sar-D-Ala-Sar-OH/NH$_2$

4HPP-4Hyp-4Hyp-Sar-Ala-Sar-OH/NH$_2$

4HPP-D-4Hyp-D-4Hyp-Sar-D-Ala-Sar-OH/NH$_2$

4HPPA-4Hyp-4Hyp-Sar-Ala-Sar-OH/NH$_2$

4HPPA-D-4Hyp-D-4Hyp-Sar-D-Ala-Sar-OH/NH$_2$

4HMPA-4Hyp-4Hyp-Sar-Ala-Sar-OH/NH$_2$

4HMPA-D-4Hyp-D-4Hyp-Sar-D-Ala-Sar-OH/NH$_2$

4HPA-4Hyp-4Hyp-Sar-Ala-Sar-OH/NH$_2$

4HPA-D-4Hyp-D-4Hyp-Sar-D-Ala-Sar-OH/NH$_2$

4HBG-4Hyp-4Hyp-Sar-Ala-Sar-OH/NH$_2$

4HBG-D-4Hyp-D-4Hyp-Sar-D-Ala-Sar-OH/NH$_2$

4HPP-4Hyp-Pro-Sar-Ala-Sar-OH/NH$_2$

4HPP-D-4Hyp-D-Pro-Sar-D-Ala-Sar-OH/NH$_2$

-continued

4HPPA-4Hyp-Pro-Sar-Ala-Sar-OH/NH$_2$

4HPPA-D-4Hyp-D-Pro-Sar-D-Ala-Sar-OH/NH$_2$

4HMPA-4Hyp-Pro-Sar-Ala-Sar-OH/NH$_2$

4HMPA-D-4Hyp-D-Pro-Sar-D-Ala-Sar-OH/NH$_2$

4HPA-4Hyp-Pro-Sar-Ala-Sar-OH/NH$_2$

4HPA-D-4Hyp-D-Pro-Sar-D-Ala-Sar-OH/NH$_2$

4HBG-4Hyp-Pro-Sar-Ala-Sar-OH/NH$_2$

4HBG-D-4Hyp-D-Pro-Sar-D-Ala-Sar-OH/NH$_2$

4HPP-Sar-Pro-Sar-Ala-Sar-OH/NH$_2$

4HPP-Sar-D-Pro-Sar-D-Ala-Sar-OH/NH$_2$

4HPPA-Sar-Pro-Sar-Ala-Sar-OH/NH$_2$

4HPPA-Sar-D-Pro-Sar-D-Ala-Sar-OH/NH$_2$

4HMPA-Sar-Pro-Sar-Ala-Sar-OH/NH$_2$

4HMPA-Sar-D-Pro-Sar-D-Ala-Sar-OH/NH$_2$

4HPA-Sar-Pro-Sar-Ala-Sar-OH/NH$_2$

4HPA-Sar-D-Pro-Sar-D-Ala-Sar-OH/NH$_2$

4HBG-Sar-Pro-Sar-Ala-Sar-OH/NH$_2$

4HBG-Sar-D-Pro-Sar-D-Ala-Sar-OH/NH$_2$

4HPP-Pro-Sar-Sar-Ala-Sar-OH/NH$_2$

4HPP-D-Pro-Sar-Sar-D-Ala-Sar-OH/NH$_2$

4HPPA-Pro-Sar-Sar-Ala-Sar-OH/NH$_2$

4HPPA-D-Pro-Sar-Sar-D-Ala-Sar-OH/NH$_2$

4HMPA-Pro-Sar-Sar-Ala-Sar-OH/NH$_2$

4HMPA-D-Pro-Sar-Sar-D-Ala-Sar-OH/NH$_2$

4HPA-Pro-Sar-Sar-Ala-Sar-OH/NH$_2$

4HPA-D-Pro-Sar-Sar-D-Ala-Sar-OH/NH$_2$

4HBG-Pro-Sar-Sar-Ala-Sar-OH/NH$_2$

4HBG-D-Pro-Sar-Sar-D-Ala-Sar-OH/NH$_2$

4HPP-Sar-4Hyp-Sar-Ala-Sar-OH/NH$_2$

4HPP-Sar-D-4Hyp-Sar-D-Ala-Sar-OH/NH$_2$

4HPPA-Sar-4Hyp-Sar-Ala-Sar-OH/NH$_2$

4HPPA-Sar-D-4Hyp-Sar-D-Ala-Sar-OH/NH$_2$

4HMPA-Sar-4Hyp-Sar-Ala-Sar-OH/NH$_2$

4HMPA-Sar-D-4Hyp-Sar-D-Ala-Sar-OH/NH$_2$

4HPA-Sar-4Hyp-Sar-Ala-Sar-OH/NH$_2$

4HPA-Sar-D-4Hyp-Sar-D-Ala-Sar-OH/NH$_2$

4HBG-Sar-4Hyp-Sar-Ala-Sar-OH/NH$_2$

4HBG-Sar-D-4Hyp-Sar-D-Ala-Sar-OH/NH$_2$

4HPP-4Hyp-Sar-Sar-Ala-Sar-OH/NH$_2$

4HPP-D-4Hyp-Sar-Sar-D-Ala-Sar-OH/NH$_2$

4HPPA-4Hyp-Sar-Sar-Ala-Sar-OH/NH$_2$

4HPPA-D-4Hyp-Sar-Sar-D-Ala-Sar-OH/NH$_2$

4HMPA-4Hyp-Sar-Sar-Ala-Sar-OH/NH$_2$

4HMPA-D-4Hyp-Sar-Sar-D-Ala-Sar-OH/NH$_2$

4HPA-4Hyp-Sar-Sar-Ala-Sar-OH/NH$_2$

4HPA-D-4Hyp-Sar-Sar-D-Ala-Sar-OH/NH$_2$

4HBG-4Hyp-Sar-Sar-Ala-Sar-OH/NH$_2$

4HBG-D-4Hyp-Sar-Sar-D-Ala-Sar-OH/NH$_2$

4HPP-Sar-Sar-Sar-Ala-Sar-OH/NH$_2$

4HPP-Sar-Sar-Sar-D-Ala-Sar-OH/NH$_2$

4HPPA-Sar-Sar-Sar-Ala-Sar-OH/NH$_2$

4HPPA-Sar-Sar-Sar-D-Ala-Sar-OH/NH$_2$

4HMPA-Sar-Sar-Sar-Ala-Sar-OH/NH$_2$

4HMPA-Sar-Sar-Sar-D-Ala-Sar-OH/NH$_2$

4HPA-Sar-Sar-Sar-Ala-Sar-OH/NH$_2$

4HPA-Sar-Sar-Sar-D-Ala-Sar-OH/NH$_2$

4HBG-Sar-Sar-Sar-Ala-Sar-OH/NH$_2$

4HBG-Sar-Sar-Sar-D-Ala-Sar-OH/NH$_2$

Ac-Tyr-Pro-4Hyp-Sar-Ala-Gly-OH/NH$_2$ (SEQ ID NO: 33)

Ac-D-Tyr-D-Pro-D-4Hyp-Sar-D-Ala-Gly-OH/NH$_2$

Ac-Tyr-Pro-Pro-Sar-Ala-Gly-OH/NH$_2$ (SEQ ID NO: 34)

Ac-D-Tyr-D-Pro-D-Pro-Sar-D-Ala-Gly-OH/NH$_2$

Ac-Tyr-4Hyp-Pro-Sar-Ala-Gly-OH/NH$_2$ (SEQ ID NO: 35)

Ac-D-Tyr-D-4Hyp-D-Pro-Sar-D-Ala-Gly-OH/NH$_2$

Ac-Tyr-4Hyp-4Hyp-Sar-Ala-Gly-OH/NH$_2$

Ac-D-Tyr-D-4Hyp-D-4Hyp-Sar-D-Ala-Gly-OH/NH₂

Ac-Tyr-Sar-4Hyp-Sar-Ala-Gly-OH/NH₂

Ac-D-Tyr-Sar-D-4Hyp-Sar-D-Ala-Gly-OH/NH₂

Ac-Tyr-4Hyp-Sar-Sar-Ala-Gly-OH/NH₂

Ac-D-Tyr-D-4Hyp-Sar-Sar-D-Ala-Gly-OH/NH₂

Ac-Tyr-Pro-Sar-Sar-Ala-Gly-OH/NH₂ (SEQ ID NO: 36)

Ac-D-Tyr-D-Pro-Sar-Sar-D-Ala-Gly-OH/NH₂

Ac-Tyr-Sar-Pro-Sar-Ala-Gly-OH/NH₂ (SEQ ID NO: 37)

Ac-D-Tyr-Sar-D-Pro-Sar-D-Ala-Gly-OH/NH₂

Tfa-Tyr-Pro-4Hyp-Sar-Ala-Gly-OH/NH₂ (SEQ ID NO: 33)

Tfa-D-Tyr-D-Pro-D-4Hyp-Sar-D-Ala-Gly-OH/NH₂

Tfa-Tyr-Pro-Pro-Sar-Ala-Gly-OH/NH₂ (SEQ ID NO: 34)

Tfa-D-Tyr-D-Pro-D-Pro-Sar-D-Ala-Gly-OH/NH₂

Tfa-Tyr-4Hyp-Pro-Sar-Ala-Gly-OH/NH₂ (SEQ ID NO: 35)

Tfa-D-Tyr-D-4Hyp-D-Pro-Sar-D-Ala-Gly-OH/NH₂

Tfa-Tyr-4Hyp-4Hyp-Sar-Ala-Gly-OH/NH₂

Tfa-D-Tyr-D-4Hyp-D-4Hyp-Sar-D-Ala-Gly-OH/NH₂

Tfa-Tyr-Sar-4Hyp-Sar-Ala-Gly-OH/NH₂

Tfa-D-Tyr-Sar-D-4Hyp-Sar-D-Ala-Gly-OH/NH₂

Tfa-Tyr-4Hyp-Sar-Sar-Ala-Gly-OH/NH₂

Tfa-D-Tyr-D-4Hyp-Sar-Sar-D-Ala-Gly-OH/NH₂

Tfa-Tyr-Pro-Sar-Sar-Ala-Gly-OH/NH₂ (SEQ ID NO: 36)

Tfa-D-Tyr-D-Pro-Sar-Sar-D-Ala-Gly-OH/NH₂

Tfa-Tyr-Sar-Pro-Sar-Ala-Gly-OH/NH₂ (SEQ ID NO: 37)

Tfa-D-Tyr-Sar-D-Pro-Sar-D-Ala-Gly-OH/NH₂

4HPP-Pro-4Hyp-Sar-Ala-Gly-OH/NH₂

4HPP-D-Pro-D-4Hyp-Sar-D-Ala-Gly-OH/NH₂

4HPPA-Pro-4Hyp-Sar-Ala-Gly-OH/NH₂

4HPPA-D-Pro-D-4Hyp-Sar-D-Ala-Gly-OH/NH₂

4HMPA-Pro-4Hyp-Sar-Ala-Gly-OH/NH₂

4HMPA-D-Pro-D-4Hyp-Sar-D-Ala-Gly-OH/NH₂

4HPA-Pro-4Hyp-Sar-Ala-Gly-OH/NH₂

4HPA-D-Pro-D-4Hyp-Sar-D-Ala-Gly-OH/NH₂

4HBG-Pro-4Hyp-Sar-Ala-Gly-OH/NH₂

4HBG-D-Pro-D-4Hyp-Sar-D-Ala-Gly-OH/NH₂

4HPP-Pro-Pro-Sar-Ala-Gly-OH/NH₂ (SEQ ID NO: 38)

4HPP-D-Pro-D-Pro-Sar-D-Ala-Gly-OH/NH₂

4HPPA-Pro-Pro-Sar-Ala-Gly-OH/NH₂ (SEQ ID NO: 38)

4HPPA-D-Pro-D-Pro-Sar-D-Ala-Gly-OH/NH₂

4HMPA-Pro-Pro-Sar-Ala-Gly-OH/NH₂ (SEQ ID NO: 38)

4HMPA-D-Pro-D-Pro-Sar-D-Ala-Gly-OH/NH₂

4HPA-Pro-Pro-Sar-Ala-Gly-OH/NH₂ (SEQ ID NO: 38)

4HPA-D-Pro-D-Pro-Sar-D-Ala-Gly-OH/NH₂

4HBG-Pro-Pro-Sar-Ala-Gly-OH/NH₂ (SEQ ID NO: 38)

4HBG-D-Pro-D-Pro-Sar-D-Ala-Gly-OH/NH₂

4HPP-4Hyp-4Hyp-Sar-Ala-Gly-OH/NH₂

4HPP-D-4Hyp-D-4Hyp-Sar-D-Ala-Gly-OH/NH₂

4HPPA-4Hyp-4Hyp-Sar-Ala-Gly-OH/NH₂

4HPPA-D-4Hyp-D-4Hyp-Sar-D-Ala-Gly-OH/NH₂

4HMPA-4Hyp-4Hyp-Sar-Ala-Gly-OH/NH₂

4HMPA-D-4Hyp-D-4Hyp-Sar-D-Ala-Gly-OH/NH₂

4HPA-4Hyp-4Hyp-Sar-Ala-Gly-OH/NH₂

4HPA-D-4Hyp-D-4Hyp-Sar-D-Ala-Gly-OH/NH₂

4HBG-4Hyp-4Hyp-Sar-Ala-Gly-OH/NH₂

4HBG-D-4Hyp-D-4Hyp-Sar-D-Ala-Gly-OH/NH₂

4HPP-4Hyp-Pro-Sar-Ala-Gly-OH/NH₂

4HPP-D-4Hyp-D-Pro-Sar-D-Ala-Gly-OH/NH₂

4HPPA-4Hyp-Pro-Sar-Ala-Gly-OH/NH₂

4HPPA-D-4Hyp-D-Pro-Sar-D-Ala-Gly-OH/NH₂

4HMPA-4Hyp-Pro-Sar-Ala-Gly-OH/NH₂

4HMPA-D-4Hyp-D-Pro-Sar-D-Ala-Gly-OH/NH₂

-continued

4HPA-4Hyp-Pro-Sar-Ala-Gly-OH/NH$_2$

4HPA-D-4Hyp-D-Pro-Sar-D-Ala-Gly-OH/NH$_2$

4HBG-4Hyp-Pro-Sar-Ala-Gly-OH/NH$_2$

4HBG-D-4Hyp-D-Pro-Sar-D-Ala-Gly-OH/NH$_2$

4HPP-Sar-Pro-Sar-Ala-Gly-OH/NH$_2$

4HPP-Sar-D-Pro-Sar-D-Ala-Gly-OH/NH$_2$

4HPPA-Sar-Pro-Sar-Ala-Gly-OH/NH$_2$

4HPPA-Sar-D-Pro-Sar-D-Ala-Gly-OH/NH$_2$

4HMPA-Sar-Pro-Sar-Ala-Gly-OH/NH$_2$

4HMPA-Sar-D-Pro-Sar-D-Ala-Gly-OH/NH$_2$

4HPA-Sar-Pro-Sar-Ala-Gly-OH/NH$_2$

4HPA-Sar-D-Pro-Sar-D-Ala-Gly-OH/NH$_2$

4HBG-Sar-Pro-Sar-Ala-Gly-OH/NH$_2$

4HBG-Sar-D-Pro-Sar-D-Ala-Gly-OH/NH$_2$

4HPP-Pro-Sar-Sar-Ala-Gly-OH/NH$_2$

4HPP-D-Pro-Sar-Sar-D-Ala-Gly-OH/NH$_2$

4HPPA-Pro-Sar-Sar-Ala-Gly-OH/NH$_2$

4HPPA-D-Pro-Sar-Sar-D-Ala-Gly-OH/NH$_2$

4HMPA-Pro-Sar-Sar-Ala-Gly-OH/NH$_2$

4HMPA-D-Pro-Sar-Sar-D-Ala-Gly-OH/NH$_2$

4HPA-Pro-Sar-Sar-Ala-Gly-OH/NH$_2$

4HPA-D-Pro-Sar-Sar-D-Ala-Gly-OH/NH$_2$

4HBG-Pro-Sar-Sar-Ala-Gly-OH/NH$_2$

4HBG-D-Pro-Sar-Sar-D-Ala-Gly-OH/NH$_2$

4HPP-Sar-4Hyp-Sar-Ala-Gly-OH/NH$_2$

4HPP-Sar-D-4Hyp-Sar-D-Ala-Gly-OH/NH$_2$

4HPPA-Sar-4Hyp-Sar-Ala-Gly-OH/NH$_2$

4HPPA-Sar-D-4Hyp-Sar-D-Ala-Gly-OH/NH$_2$

4HMPA-Sar-4Hyp-Sar-Ala-Gly-OH/NH$_2$

4HMPA-Sar-D-4Hyp-Sar-D-Ala-Gly-OH/NH$_2$

4HPA-Sar-4Hyp-Sar-Ala-Gly-OH/NH$_2$

4HPA-Sar-D-4Hyp-Sar-D-Ala-Gly-OH/NH$_2$

4HBG-Sar-4Hyp-Sar-Ala-Gly-OH/NH$_2$

4HBG-Sar-D-4Hyp-Sar-D-Ala-Gly-OH/NH$_2$

4HPP-4Hyp-Sar-Sar-Ala-Gly-OH/NH$_2$

4HPP-D-4Hyp-Sar-Sar-D-Ala-Gly-OH/NH$_2$

4HPPA-4Hyp-Sar-Sar-Ala-Gly-OH/NH$_2$

4HPPA-D-4Hyp-Sar-Sar-D-Ala-Gly-OH/NH$_2$

4HMPA-4Hyp-Sar-Sar-Ala-Gly-OH/NH$_2$

4HMPA-D-4Hyp-Sar-Sar-D-Ala-Gly-OH/NH$_2$

4HPA-4Hyp-Sar-Sar-Ala-Gly-OH/NH$_2$

4HPA-D-4Hyp-Sar-Sar-D-Ala-Gly-OH/NH$_2$

4HBG-4Hyp-Sar-Sar-Ala-Gly-OH/NH$_2$

4HBG-D-4Hyp-Sar-Sar-D-Ala-Gly-OH/NH$_2$

Ac-Tyr-Pro-4Hyp-Gly-Ala-Sar-OH/NH$_2$    (SEQ ID NO: 39)

Ac-D-Tyr-D-Pro-D-4Hyp-Gly-D-Ala-Sar-OH/NH$_2$

Ac-Tyr-Pro-Pro-Gly-Ala-Sar-OH/NH$_2$    (SEQ ID NO: 40)

Ac-D-Tyr-D-Pro-D-Pro-Gly-D-Ala-Sar-OH/NH$_2$

Ac-Tyr-4Hyp-Pro-Gly-Ala-Sar-OH/NH$_2$    (SEQ ID NO: 41)

Ac-D-Tyr-D-4Hyp-D-Pro-Gly-D-Ala-Sar-OH/NH$_2$

Ac-Tyr-4Hyp-4Hyp-Gly-Ala-Sar-OH/NH$_2$

Ac-D-Tyr-D-4Hyp-D-4Hyp-Gly-D-Ala-Sar-OH/NH$_2$

Ac-Tyr-Sar-4Hyp-Gly-Ala-Sar-OH/NH$_2$

Ac-D-Tyr-Sar-D-4Hyp-Gly-D-Ala-Sar-OH/NH$_2$

Ac-Tyr-4Hyp-Sar-Gly-Ala-Sar-OH/NH$_2$

Ac-D-Tyr-D-4Hyp-Sar-Gly-D-Ala-Sar-OH/NH$_2$

Ac-Tyr-Pro-Sar-Gly-Ala-Sar-OH/NH$_2$    (SEQ ID NO: 42)

Ac-D-Tyr-D-Pro-Sar-Gly-D-Ala-Sar-OH/NH$_2$

Ac-Tyr-Sar-Pro-Gly-Ala-Sar-OH/NH$_2$    (SEQ ID NO: 43)

Ac-D-Tyr-Sar-D-Pro-Gly-D-Ala-Sar-OH/NH$_2$

Ac-Tyr-Sar-Sar-Gly-Ala-Sar-OH/NH$_2$

Ac-D-Tyr-Sar-Sar-Gly-D-Ala-Sar-OH/NH$_2$

-continued

Tfa-Tyr-Pro-4Hyp-Gly-Ala-Sar-OH/NH$_2$ (SEQ ID NO: 39)

Tfa-D-Tyr-D-Pro-D-4Hyp-Gly-D-Ala-Sar-OH/NH$_2$

Tfa-Tyr-Pro-Pro-Gly-Ala-Sar-OH/NH$_2$ (SEQ ID NO: 40)

Tfa-D-Tyr-D-Pro-D-Pro-Gly-D-Ala-Sar-OH/NH$_2$

Tfa-Tyr-4Hyp-Pro-Gly-Ala-Sar-OH/NH$_2$ (SEQ ID NO: 41)

Tfa-D-Tyr-D-4Hyp-D-Pro-Gly-D-Ala-Sar-OH/NH$_2$

Tfa-Tyr-4Hyp-4Hyp-Gly-Ala-Sar-OH/NH$_2$

Tfa-D-Tyr-D-4Hyp-D-4Hyp-Gly-D-Ala-Sar-OH/NH$_2$

Tfa-Tyr-Sar-4Hyp-Gly-Ala-Sar-OH/NH$_2$

Tfa-D-Tyr-Sar-D-4Hyp-Gly-D-Ala-Sar-OH/NH$_2$

Tfa-Tyr-4Hyp-Sar-Gly-Ala-Sar-OH/NH$_2$

Tfa-D-Tyr-D-4Hyp-Sar-Gly-D-Ala-Sar-OH/NH$_2$

Tfa-Tyr-Pro-Sar-Gly-Ala-Sar-OH/NH$_2$ (SEQ ID NO: 42)

Tfa-D-Tyr-D-Pro-Sar-Gly-D-Ala-Sar-OH/NH$_2$

Tfa-Tyr-Sar-Pro-Gly-Ala-Sar-OH/NH$_2$ (SEQ ID NO: 43)

Tfa-D-Tyr-Sar-D-Pro-Gly-D-Ala-Sar-OH/NH$_2$

Tfa-Tyr-Sar-Sar-Gly-Ala-Sar-OH/NH$_2$

Tfa-D-Tyr-Sar-Sar-Gly-D-Ala-Sar-OH/NH$_2$

4HPP-Pro-4Hyp-Gly-Ala-Sar-OH/NH$_2$

4HPP-D-Pro-D-4Hyp-Gly-D-Ala-Sar-OH/NH$_2$

4HPPA-Pro-4Hyp-Gly-Ala-Sar-OH/NH$_2$

4HPPA-D-Pro-D-4Hyp-Gly-D-Ala-Sar-OH/NH$_2$

4HMPA-Pro-4Hyp-Gly-Ala-Sar-OH/NH$_2$

4HMPA-D-Pro-D-4Hyp-Gly-D-Ala-Sar-OH/NH$_2$

4HPA-Pro-4Hyp-Gly-Ala-Sar-OH/NH$_2$

4HPA-D-Pro-D-4Hyp-Gly-D-Ala-Sar-OH/NH$_2$

4HBG-Pro-4Hyp-Gly-Ala-Sar-OH/NH$_2$

4HBG-D-Pro-D-4Hyp-Gly-D-Ala-Sar-OH/NH$_2$

4HPP-Pro-Pro-Gly-Ala-Sar-OH/NH$_2$ (SEQ ID NO: 44)

4HPP-D-Pro-D-Pro-Gly-D-Ala-Sar-OH/NH$_2$

4HPPA-Pro-Pro-Gly-Ala-Sar-OH/NH$_2$ (SEQ ID NO: 44)

4HPPA-D-Pro-D-Pro-Gly-D-Ala-Sar-OH/NH$_2$

4HMPA-Pro-Pro-Gly-Ala-Sar-OH/NH$_2$ (SEQ ID NO: 44)

4HMPA-D-Pro-D-Pro-Gly-D-Ala-Sar-OH/NH$_2$

4HPA-Pro-Pro-Gly-Ala-Sar-OH/NH$_2$ (SEQ ID NO: 44)

4HPA-D-Pro-D-Pro-Gly-D-Ala-Sar-OH/NH$_2$

4HBG-Pro-Pro-Gly-Ala-Sar-OH/NH$_2$ (SEQ ID NO: 44)

4HBG-D-Pro-D-Pro-Gly-D-Ala-Sar-OH/NH$_2$

4HPP-4Hyp-4Hyp-Gly-Ala-Sar-OH/NH$_2$

4HPP-D-4Hyp-D-4Hyp-Gly-D-Ala-Sar-OH/NH$_2$

4HPPA-4Hyp-4Hyp-Gly-Ala-Sar-OH/NH$_2$

4HPPA-D-4Hyp-D-4Hyp-Gly-D-Ala-Sar-OH/NH$_2$

4HMPA-4Hyp-4Hyp-Gly-Ala-Sar-OH/NH$_2$

4HMPA-D-4Hyp-D-4Hyp-Gly-D-Ala-Sar-OH/NH$_2$

4HPA-4Hyp-4Hyp-Gly-Ala-Sar-OH/NH$_2$

4HPA-D-4Hyp-D-4Hyp-Gly-D-Ala-Sar-OH/NH$_2$

4HBG-4Hyp-4Hyp-Gly-Ala-Sar-OH/NH$_2$

4HBG-D-4Hyp-D-4Hyp-Gly-D-Ala-Sar-OH/NH$_2$

4HPP-4Hyp-Pro-Gly-Ala-Sar-OH/NH$_2$

4HPP-D-4Hyp-D-Pro-Gly-D-Ala-Sar-OH/NH$_2$

4HPPA-4Hyp-Pro-Gly-Ala-Sar-OH/NH$_2$

4HPPA-D-4Hyp-D-Pro-Gly-D-Ala-Sar-OH/NH$_2$

4HMPA-4Hyp-Pro-Gly-Ala-Sar-OH/NH$_2$

4HMPA-D-4Hyp-D-Pro-Gly-D-Ala-Sar-OH/NH$_2$

4HPA-4Hyp-Pro-Gly-Ala-Sar-OH/NH$_2$

4HPA-D-4Hyp-D-Pro-Gly-D-Ala-Sar-OH/NH$_2$

4HBG-4Hyp-Pro-Gly-Ala-Sar-OH/NH$_2$

4HBG-D-4Hyp-D-Pro-Gly-D-Ala-Sar-OH/NH$_2$

4HPP-Sar-Pro-Gly-Ala-Sar-OH/NH$_2$

4HPP-Sar-D-Pro-Gly-D-Ala-Sar-OH/NH$_2$

4HPPA-Sar-Pro-Gly-Ala-Sar-OH/NH$_2$

4HPPA-Sar-D-Pro-Gly-D-Ala-Sar-OH/NH$_2$

-continued

4HMPA-Sar-Pro-Gly-Ala-Sar-OH/NH₂

4HMPA-Sar-D-Pro-Gly-D-Ala-Sar-OH/NH₂

4HPA-Sar-Pro-Gly-Ala-Sar-OH/NH₂

4HPA-Sar-D-Pro-Gly-D-Ala-Sar-OH/NH₂

4HBG-Sar-Pro-Gly-Ala-Sar-OH/NH₂

4HBG-Sar-D-Pro-Gly-D-Ala-Sar-OH/NH₂

4HPP-Pro-Sar-Gly-Ala-Sar-OH/NH₂

4HPP-D-Pro-Sar-Gly-D-Ala-Sar-OH/NH₂

4HPPA-Pro-Sar-Gly-Ala-Sar-OH/NH₂

4HPPA-D-Pro-Sar-Gly-D-Ala-Sar-OH/NH₂

4HMPA-Pro-Sar-Gly-Ala-Sar-OH/NH₂

4HMPA-D-Pro-Sar-Gly-D-Ala-Sar-OH/NH₂

4HPA-Pro-Sar-Gly-Ala-Sar-OH/NH₂

4HPA-D-Pro-Sar-Gly-D-Ala-Sar-OH/NH₂

4HBG-Pro-Sar-Gly-Ala-Sar-OH/NH₂

4HBG-D-Pro-Sar-Gly-D-Ala-Sar-OH/NH₂

4HPP-Sar-4Hyp-Gly-Ala-Sar-OH/NH₂

4HPP-Sar-D-4Hyp-Gly-D-Ala-Sar-OH/NH₂

4HPPA-Sar-4Hyp-Gly-Ala-Sar-OH/NH₂

4HPPA-Sar-D-4Hyp-Gly-D-Ala-Sar-OH/NH₂

4HMPA-Sar-4Hyp-Gly-Ala-Sar-OH/NH₂

4HMPA-Sar-D-4Hyp-Gly-D-Ala-Sar-OH/NH₂

4HPA-Sar-4Hyp-Gly-Ala-Sar-OH/NH₂

4HPA-Sar-D-4Hyp-Gly-D-Ala-Sar-OH/NH₂

4HBG-Sar-4Hyp-Gly-Ala-Sar-OH/NH₂

4HBG-Sar-D-4Hyp-Gly-D-Ala-Sar-OH/NH₂

4HPP-4Hyp-Sar-Gly-Ala-Sar-OH/NH₂

4HPP-D-4Hyp-Sar-Gly-D-Ala-Sar-OH/NH₂

4HPPA-4Hyp-Sar-Gly-Ala-Sar-OH/NH₂

4HPPA-D-4Hyp-Sar-Gly-D-Ala-Sar-OH/NH₂

4HMPA-4Hyp-Sar-Gly-Ala-Sar-OH/NH₂

4HMPA-D-4Hyp-Sar-Gly-D-Ala-Sar-OH/NH₂

4HPA-4Hyp-Sar-Gly-Ala-Sar-OH/NH₂

4HPA-D-4Hyp-Sar-Gly-D-Ala-Sar-OH/NH₂

4HBG-4Hyp-Sar-Gly-Ala-Sar-OH/NH₂

4HBG-D-4Hyp-Sar-Gly-D-Ala-Sar-OH/NH₂

4HPP-Sar-Sar-Gly-Ala-Sar-OH/NH₂

4HPP-Sar-Sar-Gly-D-Ala-Sar-OH/NH₂

4HPPA-Sar-Sar-Gly-Ala-Sar-OH/NH₂

4HPPA-Sar-Sar-Gly-D-Ala-Sar-OH/NH₂

4HMPA-Sar-Sar-Gly-Ala-Sar-OH/NH₂

4HMPA-Sar-Sar-Gly-D-Ala-Sar-OH/NH₂

4HPA-Sar-Sar-Gly-Ala-Sar-OH/NH₂

4HPA-Sar-Sar-Gly-D-Ala-Sar-OH/NH₂

4HBG-Sar-Sar-Gly-Ala-Sar-OH/NH₂

4HBG-Sar-Sar-Gly-D-Ala-Sar-OH/NH₂

Ac-Tyr-Pro-4Hyp-Gly-Aib-Gly-OH/NH₂ (SEQ ID NO: 45)

Ac-D-Tyr-D-Pro-D-4Hyp-Gly-Aib-Gly-OH/NH₂

Ac-Tyr-Pro-Pro-Gly-Aib-Gly-OH/NH₂ (SEQ ID NO: 46)

Ac-D-Tyr-D-Pro-D-Pro-Gly-Aib-Gly-OH/NH₂

Ac-Tyr-4Hyp-Pro-Gly-Aib-Gly-OH/NH₂ (SEQ ID NO: 47)

Ac-D-Tyr-D-4Hyp-D-Pro-Gly-Aib-Gly-OH/NH₂

Ac-Tyr-4Hyp-4Hyp-Gly-Aib-Gly-OH/NH₂

Ac-D-Tyr-D-4Hyp-D-4Hyp-Gly-Aib-Gly-OH/NH₂

Ac-Tyr-Sar-4Hyp-Gly-Aib-Gly-OH/NH₂

Ac-D-Tyr-Sar-D-4Hyp-Gly-Aib-Gly-OH/NH₂

Ac-Tyr-4Hyp-Sar-Gly-Aib-Gly-OH/NH₂

Ac-D-Tyr-D-4Hyp-Sar-Gly-Aib-Gly-OH/NH₂

Ac-Tyr-Pro-Sar-Gly-Aib-Gly-OH/NH₂ (SEQ ID NO: 48)

Ac-D-Tyr-D-Pro-Sar-Gly-Aib-Gly-OH/NH₂

Ac-Tyr-Sar-Pro-Gly-Aib-Gly-OH/NH₂ (SEQ ID NO: 49)

Ac-D-Tyr-Sar-D-Pro-Gly-Aib-Gly-OH/NH₂

Ac-Tyr-Sar-Sar-Gly-Aib-Gly-OH/NH₂

Ac-D-Tyr-Sar-Sar-Gly-Aib-Gly-OH/NH₂

4HPP-Pro-4Hyp-Gly-Aib-Gly-OH/NH₂

-continued

Tfa-Tyr-Pro-4Hyp-Gly-Aib-Gly-OH/NH₂ (SEQ ID NO: 45)

Tfa-D-Tyr-D-Pro-D-4Hyp-Gly-Aib-Gly-OH/NH₂

Tfa-Tyr-Pro-Pro-Gly-Aib-Gly-OH/NH₂ (SEQ ID NO: 46)

Tfa-D-Tyr-D-Pro-D-Pro-Gly-Aib-Gly-OH/NH₂

Tfa-Tyr-4Hyp-Pro-Gly-Aib-Gly-OH/NH₂ (SEQ ID NO: 47)

Tfa-D-Tyr-D-4Hyp-D-Pro-Gly-Aib-Gly-OH/NH₂

Tfa-Tyr-4Hyp-4Hyp-Gly-Aib-Gly-OH/NH₂

Tfa-D-Tyr-D-4Hyp-D-4Hyp-Gly-Aib-Gly-OH/NH₂

Tfa-Tyr-Sar-4Hyp-Gly-Aib-Gly-OH/NH₂

Tfa-D-Tyr-Sar-D-4Hyp-Gly-Aib-Gly-OH/NH₂

Tfa-Tyr-4Hyp-Sar-Gly-Aib-Gly-OH/NH₂

Tfa-D-Tyr-D-4Hyp-Sar-Gly-Aib-Gly-OH/NH₂

Tfa-Tyr-Pro-Sar-Gly-Aib-Gly-OH/NH₂ (SEQ ID NO: 48)

Tfa-D-Tyr-D-Pro-Sar-Gly-Aib-Gly-OH/NH₂

Tfa-Tyr-Sar-Pro-Gly-Aib-Gly-OH/NH₂ (SEQ ID NO: 49)

Tfa-D-Tyr-Sar-D-Pro-Gly-Aib-Gly-OH/NH₂

Tfa-Tyr-Sar-Sar-Gly-Aib-Gly-OH/NH₂

Tfa-D-Tyr-Sar-Sar-Gly-Aib-Gly-OH/NH₂

4HPP-D-Pro-D-4Hyp-Gly-Aib-Gly-OH/NH₂

4HPPA-Pro-4Hyp-Gly-Aib-Gly-OH/NH₂

4HPPA-D-Pro-D-4Hyp-Gly-Aib-Gly-OH/NH₂

4HMPA-Pro-4Hyp-Gly-Aib-Gly-OH/NH₂

4HMPA-D-Pro-D-4Hyp-Gly-Aib-Gly-OH/NH₂

4HPA-Pro-4Hyp-Gly-Aib-Gly-OH/NH₂

4HPA-D-Pro-D-4Hyp-Gly-Aib-Gly-OH/NH₂

4HBG-Pro-4Hyp-Gly-Aib-Gly-OH/NH₂

4HBG-D-Pro-D-4Hyp-Gly-Aib-Gly-OH/NH₂

4HPP-Pro-Pro-Gly-Aib-Gly-OH/NH₂ (SEQ ID NO: 50)

4HPP-D-Pro-D-Pro-Gly-Aib-Gly-OH/NH₂

4HPPA-Pro-Pro-Gly-Aib-Gly-OH/NH₂ (SEQ ID NO: 50)

4HPPA-D-Pro-D-Pro-Gly-Aib-Gly-OH/NH₂

4HMPA-Pro-Pro-Gly-Aib-Gly-OH/NH₂ (SEQ ID NO: 50)

4HMPA-D-Pro-D-Pro-Gly-Aib-Gly-OH/NH₂

4HPA-Pro-Pro-Gly-Aib-Gly-OH/NH₂ (SEQ ID NO: 50)

4HPA-D-Pro-D-Pro-Gly-Aib-Gly-OH/NH₂

4HBG-Pro-Pro-Gly-Aib-Gly-OH/NH₂ (SEQ ID NO: 50)

4HBG-D-Pro-D-Pro-Gly-Aib-Gly-OH/NH₂

4HPP-4Hyp-4Hyp-Gly-Aib-Gly-OH/NH₂

4HPP-D-4Hyp-D-4Hyp-Gly-Aib-Gly-OH/NH₂

4HPPA-4Hyp-4Hyp-Gly-Aib-Gly-OH/NH₂

4HPPA-D-4Hyp-D-4Hyp-Gly-Aib-Gly-OH/NH₂

4HMPA-4Hyp-4Hyp-Gly-Aib-Gly-OH/NH₂

4HMPA-D-4Hyp-D-4Hyp-Gly-Aib-Gly-OH/NH₂

4HPA-4Hyp-4Hyp-Gly-Aib-Gly-OH/NH₂

4HPA-D-4Hyp-D-4Hyp-Gly-Aib-Gly-OH/NH₂

4HBG-4Hyp-4Hyp-Gly-Aib-Gly-OH/NH₂

4HBG-D-4Hyp-D-4Hyp-Gly-Aib-Gly-OH/NH₂

4HPP-4Hyp-Pro-Gly-Aib-Gly-OH/NH₂

4HPP-D-4Hyp-D-Pro-Gly-Aib-Gly-OH/NH₂

4HPPA-4Hyp-Pro-Gly-Aib-Gly-OH/NH₂

4HPPA-D-4Hyp-D-Pro-Gly-Aib-Gly-OH/NH₂

4HMPA-4Hyp-Pro-Gly-Aib-Gly-OH/NH₂

4HMPA-D-4Hyp-D-Pro-Gly-Aib-Gly-OH/NH₂

4HPA-4Hyp-Pro-Gly-Aib-Gly-OH/NH₂

4HPA-D-4Hyp-D-Pro-Gly-Aib-Gly-OH/NH₂

4HBG-4Hyp-Pro-Gly-Aib-Gly-OH/NH₂

4HBG-D-4Hyp-D-Pro-Gly-Aib-Gly-OH/NH₂

4HPP-Sar-Pro-Gly-Aib-Gly-OH/NH₂

4HPP-Sar-D-Pro-Gly-Aib-Gly-OH/NH₂

4HPPA-Sar-Pro-Gly-Aib-Gly-OH/NH₂

4HPPA-Sar-D-Pro-Gly-Aib-Gly-OH/NH₂

4HMPA-Sar-Pro-Gly-Aib-Gly-OH/NH₂

-continued

4HMPA-Sar-D-Pro-Gly-Aib-Gly-OH/NH₂
4HPA-Sar-Pro-Gly-Aib-Gly-OH/NH₂
4HPA-Sar-D-Pro-Gly-Aib-Gly-OH/NH₂
4HBG-Sar-Pro-Gly-Aib-Gly-OH/NH₂
4HBG-Sar-D-Pro-Gly-Aib-Gly-OH/NH₂
4HPP-Pro-Sar-Gly-Aib-Gly-OH/NH₂
4HPP-D-Pro-Sar-Gly-Aib-Gly-OH/NH₂
4HPPA-Pro-Sar-Gly-Aib-Gly-OH/NH₂
4HPPA-D-Pro-Sar-Gly-Aib-Gly-OH/NH₂
4HMPA-Pro-Sar-Gly-Aib-Gly-OH/NH₂
4HMPA-D-Pro-Sar-Gly-Aib-Gly-OH/NH₂
4HPA-Pro-Sar-Gly-Aib-Gly-OH/NH₂
4HPA-D-Pro-Sar-Gly-Aib-Gly-OH/NH₂
4HBG-Pro-Sar-Gly-Aib-Gly-OH/NH₂
4HBG-D-Pro-Sar-Gly-Aib-Gly-OH/NH₂
4HPP-Sar-4Hyp-Gly-Aib-Gly-OH/NH₂
4HPP-Sar-D-4Hyp-Gly-Aib-Gly-OH/NH₂
4HPPA-Sar-4Hyp-Gly-Aib-Gly-OH/NH₂
4HPPA-Sar-D-4Hyp-Gly-Aib-Gly-OH/NH₂
4HMPA-Sar-4Hyp-Gly-Aib-Gly-OH/NH₂
4HMPA-Sar-D-4Hyp-Gly-Aib-Gly-OH/NH₂
4HPA-Sar-4Hyp-Gly-Aib-Gly-OH/NH₂
4HPA-Sar-D-4Hyp-Gly-Aib-Gly-OH/NH₂
4HBG-Sar-4Hyp-Gly-Aib-Gly-OH/NH₂
4HBG-Sar-D-4Hyp-Gly-Aib-Gly-OH/NH₂
4HPP-4Hyp-Sar-Gly-Aib-Gly-OH/NH₂
4HPP-D-4Hyp-Sar-Gly-Aib-Gly-OH/NH₂
4HPPA-4Hyp-Sar-Gly-Aib-Gly-OH/NH₂
4HPPA-D-4Hyp-Sar-Gly-Aib-Gly-OH/NH₂
4HMPA-4Hyp-Sar-Gly-Aib-Gly-OH/NH₂
4HMPA-D-4Hyp-Sar-Gly-Aib-Gly-OH/NH₂
4HPA-4Hyp-Sar-Gly-Aib-Gly-OH/NH₂
4HPA-D-4Hyp-Sar-Gly-Aib-Gly-OH/NH₂
4HBG-4Hyp-Sar-Gly-Aib-Gly-OH/NH₂
4HBG-D-4Hyp-Sar-Gly-Aib-Gly-OH/NH₂
4HPP-Sar-Sar-Gly-Aib-Gly-OH/NH₂
4HPPA-Sar-Sar-Gly-Aib-Gly-OH/NH₂
4HMPA-Sar-Sar-Gly-Aib-Gly-OH/NH₂

-continued

4HPA-Sar-Sar-Gly-Aib-Gly-OH/NH₂
4HBG-Sar-Sar-Gly-Aib-Gly-OH/NH₂
Ac-Tyr-Pro-4Hyp-Sar-Aib-Sar-OH/NH₂
Ac-D-Tyr-D-Pro-D-4Hyp-Sar-Aib-Sar-OH/NH₂
Ac-Tyr-Pro-Pro-Sar-Aib-Sar-OH/NH₂
Ac-D-Tyr-D-Pro-D-Pro-Sar-Aib-Sar-OH/NH₂
Ac-Tyr-4Hyp-Pro-Sar-Aib-Sar-OH/NH₂
Ac-D-Tyr-D-4Hyp-D-Pro-Sar-Aib-Sar-OH/NH₂
Ac-Tyr-4Hyp-4Hyp-Sar-Aib-Sar-OH/NH₂
Ac-D-Tyr-D-4Hyp-D-4Hyp-Sar-Aib-Sar-OH/NH₂
Ac-Tyr-Sar-4Hyp-Sar-Aib-Sar-OH/NH₂
Ac-D-Tyr-Sar-D-4Hyp-Sar-Aib-Sar-OH/NH₂
Ac-Tyr-4Hyp-Sar-Sar-Aib-Sar-OH/NH₂
Ac-D-Tyr-D-4Hyp-Sar-Sar-Aib-Sar-OH/NH₂
Ac-Tyr-Pro-Sar-Sar-Aib-Sar-OH/NH₂
Ac-D-Tyr-D-Pro-Sar-Sar-Aib-Sar-OH/NH₂
Ac-Tyr-Sar-Pro-Sar-Aib-Sar-OH/NH₂
Ac-D-Tyr-Sar-D-Pro-Sar-Aib-Sar-OH/NH₂
Ac-Tyr-Sar-Sar-Sar-Aib-Sar-OH/NH₂
Ac-D-Tyr-Sar-Sar-Sar-Aib-Sar-OH/NH₂
Tfa-Tyr-Pro-4Hyp-Sar-Aib-Sar-OH/NH₂
Tfa-D-Tyr-D-Pro-D-4Hyp-Sar-Aib-Sar-OH/NH₂
Tfa-Tyr-Pro-Pro-Sar-Aib-Sar-OH/NH₂
Tfa-D-Tyr-D-Pro-D-Pro-Sar-Aib-Sar-OH/NH₂
Tfa-Tyr-4Hyp-Pro-Sar-Aib-Sar-OH/NH₂
Tfa-D-Tyr-D-4Hyp-D-Pro-Sar-Aib-Sar-OH/NH₂
Tfa-Tyr-4Hyp-4Hyp-Sar-Aib-Sar-OH/NH₂
Tfa-D-Tyr-D-4Hyp-D-4Hyp-Sar-Aib-Sar-OH/NH₂
Tfa-Tyr-Sar-4Hyp-Sar-Aib-Sar-OH/NH₂
Tfa-D-Tyr-Sar-D-4Hyp-Sar-Aib-Sar-OH/NH₂

-continued

Tfa-Tyr-4Hyp-Sar-Sar-Aib-Sar-OH/NH$_2$

Tfa-D-Tyr-D-4Hyp-Sar-Sar-Aib-Sar-OH/NH$_2$

Tfa-Tyr-Pro-Sar-Sar-Aib-Sar-OH/NH$_2$

Tfa-D-Tyr-D-Pro-Sar-Sar-Aib-Sar-OH/NH$_2$

Tfa-Tyr-Sar-Pro-Sar-Aib-Sar-OH/NH$_2$

Tfa-D-Tyr-Sar-D-Pro-Sar-Aib-Sar-OH/NH$_2$

Tfa-Tyr-Sar-Sar-Sar-Aib-Sar-OH/NH$_2$

Tfa-D-Tyr-Sar-Sar-Sar-Aib-Sar-OH/NH$_2$

4HPP-Pro-4Hyp-Sar-Aib-Sar-OH/NH$_2$

4HPP-D-Pro-D-4Hyp-Sar-Aib-Sar-OH/NH$_2$

4HPPA-Pro-4Hyp-Sar-Aib-Sar-OH/NH$_2$

4HPPA-D-Pro-D-4Hyp-Sar-Aib-Sar-OH/NH$_2$

4HMPA-Pro-4Hyp-Sar-Aib-Sar-OH/NH$_2$

4HMPA-D-Pro-D-4Hyp-Sar-Aib-Sar-OH/NH$_2$

4HPA-Pro-4Hyp-Sar-Aib-Sar-OH/NH$_2$

4HPA-D-Pro-D-4Hyp-Sar-Aib-Sar-OH/NH$_2$

4HBG-Pro-4Hyp-Sar-Aib-Sar-OH/NH$_2$

4HBG-D-Pro-D-4Hyp-Sar-Aib-Sar-OH/NH$_2$

4HPP-Pro-Pro-Sar-Aib-Sar-OH/NH$_2$

4HPP-D-Pro-D-Pro-Sar-Aib-Sar-OH/NH$_2$

4HPPA-Pro-Pro-Sar-Aib-Sar-OH/NH$_2$

4HPPA-D-Pro-D-Pro-Sar-Aib-Sar-OH/NH$_2$

4HMPA-Pro-Pro-Sar-Aib-Sar-OH/NH$_2$

4HMPA-D-Pro-D-Pro-Sar-Aib-Sar-OH/NH$_2$

4HPA-Pro-Pro-Sar-Aib-Sar-OH/NH$_2$

4HPA-D-Pro-D-Pro-Sar-Aib-Sar-OH/NH$_2$

4HBG-Pro-Pro-Sar-Aib-Sar-OH/NH$_2$

4HBG-D-Pro-D-Pro-Sar-Aib-Sar-OH/NH$_2$

4HPP-4Hyp-4Hyp-Sar-Aib-Sar-OH/NH$_2$

4HPP-D-4Hyp-D-4Hyp-Sar-Aib-Sar-OH/NH$_2$

4HPPA-4Hyp-4Hyp-Sar-Aib-Sar-OH/NH$_2$

4HPPA-D-4Hyp-D-4Hyp-Sar-Aib-Sar-OH/NH$_2$

4HMPA-4Hyp-4Hyp-Sar-Aib-Sar-OH/NH$_2$

4HMPA-D-4Hyp-D-4Hyp-Sar-Aib-Sar-OH/NH$_2$

4HPA-4Hyp-4Hyp-Sar-Aib-Sar-OH/NH$_2$

4HPA-D-4Hyp-D-4Hyp-Sar-Aib-Sar-OH/NH$_2$

4HBG-4Hyp-4Hyp-Sar-Aib-Sar-OH/NH$_2$

4HBG-D-4Hyp-D-4Hyp-Sar-Aib-Sar-OH/NH$_2$

4HPP-4Hyp-Pro-Sar-Aib-Sar-OH/NH$_2$

4HPP-D-4Hyp-D-Pro-Sar-Aib-Sar-OH/NH$_2$

4HPPA-4Hyp-Pro-Sar-Aib-Sar-OH/NH$_2$

4HPPA-D-4Hyp-D-Pro-Sar-Aib-Sar-OH/NH$_2$

4HMPA-4Hyp-Pro-Sar-Aib-Sar-OH/NH$_2$

4HMPA-D-4Hyp-D-Pro-Sar-Aib-Sar-OH/NH$_2$

4HPA-4Hyp-Pro-Sar-Aib-Sar-OH/NH$_2$

4HPA-D-4Hyp-D-Pro-Sar-Aib-Sar-OH/NH$_2$

4HBG-4Hyp-Pro-Sar-Aib-Sar-OH/NH$_2$

4HBG-D-4Hyp-D-Pro-Sar-Aib-Sar-OH/NH$_2$

4HPP-Sar-Pro-Sar-Aib-Sar-OH/NH$_2$

4HPP-Sar-D-Pro-Sar-Aib-Sar-OH/NH$_2$

4HPPA-Sar-Pro-Sar-Aib-Sar-OH/NH$_2$

4HPPA-Sar-D-Pro-Sar-Aib-Sar-OH/NH$_2$

4HMPA-Sar-Pro-Sar-Aib-Sar-OH/NH$_2$

4HMPA-Sar-D-Pro-Sar-Aib-Sar-OH/NH$_2$

4HPA-Sar-Pro-Sar-Aib-Sar-OH/NH$_2$

4HPA-Sar-D-Pro-Sar-Aib-Sar-OH/NH$_2$

4HBG-Sar-Pro-Sar-Aib-Sar-OH/NH$_2$

4HBG-Sar-D-Pro-Sar-Aib-Sar-OH/NH$_2$

4HPP-Pro-Sar-Sar-Aib-Sar-OH/NH$_2$

4HPP-D-Pro-Sar-Sar-Aib-Sar-OH/NH$_2$

4HPPA-Pro-Sar-Sar-Aib-Sar-OH/NH$_2$

4HPPA-D-Pro-Sar-Sar-Aib-Sar-OH/NH$_2$

4HMPA-Pro-Sar-Sar-Aib-Sar-OH/NH$_2$

4HMPA-D-Pro-Sar-Sar-Aib-Sar-OH/NH$_2$

4HPA-Pro-Sar-Sar-Aib-Sar-OH/NH$_2$

-continued

4HPA-D-Pro-Sar-Sar-Aib-Sar-OH/NH$_2$

4HBG-Pro-Sar-Sar-Aib-Sar-OH/NH$_2$

4HBG-D-Pro-Sar-Sar-Aib-Sar-OH/NH$_2$

4HPP-Sar-4Hyp-Sar-Aib-Sar-OH/NH$_2$

4HPP-Sar-D-4Hyp-Sar-Aib-Sar-OH/NH$_2$

4HPPA-Sar-4Hyp-Sar-Aib-Sar-OH/NH$_2$

4HPPA-Sar-D-4Hyp-Sar-Aib-Sar-OH/NH$_2$

4HMPA-Sar-4Hyp-Sar-Aib-Sar-OH/NH$_2$

4HMPA-Sar-D-4Hyp-Sar-Aib-Sar-OH/NH$_2$

4HPA-Sar-4Hyp-Sar-Aib-Sar-OH/NH$_2$

4HPA-Sar-D-4Hyp-Sar-Aib-Sar-OH/NH$_2$

4HBG-Sar-4Hyp-Sar-Aib-Sar-OH/NH$_2$

4HBG-Sar-D-4Hyp-Sar-Aib-Sar-OH/NH$_2$

4HPP-4Hyp-Sar-Sar-Aib-Sar-OH/NH$_2$

4HPP-D-4Hyp-Sar-Sar-Aib-Sar-OH/NH$_2$

4HPPA-4Hyp-Sar-Sar-Aib-Sar-OH/NH$_2$

4HPPA-D-4Hyp-Sar-Sar-Aib-Sar-OH/NH$_2$

4HMPA-4Hyp-Sar-Sar-Aib-Sar-OH/NH$_2$

4HMPA-D-4Hyp-Sar-Sar-Aib-Sar-OH/NH$_2$

4HPA-4Hyp-Sar-Sar-Aib-Sar-OH/NH$_2$

4HPA-D-4Hyp-Sar-Sar-Aib-Sar-OH/NH$_2$

4HBG-4Hyp-Sar-Sar-Aib-Sar-OH/NH$_2$

4HBG-D-4Hyp-Sar-Sar-Aib-Sar-OH/NH$_2$

4HPP-Sar-Sar-Sar-Aib-Sar-OH/NH$_2$

4HPPA-Sar-Sar-Sar-Aib-Sar-OH/NH$_2$

4HMPA-Sar-Sar-Sar-Aib-Sar-OH/NH$_2$

4HPA-Sar-Sar-Sar-Aib-Sar-OH/NH$_2$

4HBG-Sar-Sar-Sar-Aib-Sar-OH/NH$_2$

Ac-Tyr-Pro-4Hyp-Sar-Aib-Gly-OH/NH$_2$

Ac-D-Tyr-D-Pro-D-4Hyp-Sar-Aib-Gly-OH/NH$_2$

Ac-Tyr-Pro-Pro-Sar-Aib-Gly-OH/NH$_2$ (SEQ ID NO: 51)

Ac-D-Tyr-D-Pro-D-Pro-Sar-Aib-Gly-OH/NH$_2$

Ac-Tyr-4Hyp-Pro-Sar-Aib-Gly-OH/NH$_2$

Ac-D-Tyr-D-4Hyp-D-Pro-Sar-Aib-Gly-OH/NH$_2$

Ac-Tyr-4Hyp-4Hyp-Sar-Aib-Gly-OH/NH$_2$

Ac-D-Tyr-D-4Hyp-D-4Hyp-Sar-Aib-Gly-OH/NH$_2$

Ac-Tyr-Sar-4Hyp-Sar-Aib-Gly-OH/NH$_2$

Ac-D-Tyr-Sar-D-4Hyp-Sar-Aib-Gly-OH/NH$_2$

Ac-Tyr-4Hyp-Sar-Sar-Aib-Gly-OH/NH$_2$

Ac-D-Tyr-D-4Hyp-Sar-Sar-Aib-Gly-OH/NH$_2$

Ac-Tyr-Pro-Sar-Sar-Aib-Gly-OH/NH$_2$

Ac-D-Tyr-D-Pro-Sar-Sar-Aib-Gly-OH/NH$_2$

Ac-Tyr-Sar-Pro-Sar-Aib-Gly-OH/NH$_2$

Ac-D-Tyr-Sar-D-Pro-Sar-Aib-Gly-OH/NH$_2$

Ac-Tyr-Sar-Sar-Sar-Aib-Gly-OH/NH$_2$

Ac-D-Tyr-Sar-Sar-Sar-Aib-Gly-OH/NH$_2$

4HPP-Pro-4Hyp-Sar-Aib-Gly-OH/NH$_2$

Tfa-Tyr-Pro-4Hyp-Sar-Aib-Gly-OH/NH$_2$

Tfa-D-Tyr-D-Pro-D-4Hyp-Sar-Aib-Gly-OH/NH$_2$

Tfa-Tyr-Pro-Pro-Sar-Aib-Gly-OH/NH$_2$ (SEQ ID NO: 51)

Tfa-D-Tyr-D-Pro-D-Pro-Sar-Aib-Gly-OH/NH$_2$

Tfa-Tyr-4Hyp-Pro-Sar-Aib-Gly-OH/NH$_2$

Tfa-D-Tyr-D-4Hyp-D-Pro-Sar-Aib-Gly-OH/NH$_2$

Tfa-Tyr-4Hyp-4Hyp-Sar-Aib-Gly-OH/NH$_2$

Tfa-D-Tyr-D-4Hyp-D-4Hyp-Sar-Aib-Gly-OH/NH$_2$

Tfa-Tyr-Sar-4Hyp-Sar-Aib-Gly-OH/NH$_2$

Tfa-D-Tyr-Sar-D-4Hyp-Sar-Aib-Gly-OH/NH$_2$

Tfa-Tyr-4Hyp-Sar-Sar-Aib-Gly-OH/NH$_2$

Tfa-D-Tyr-D-4Hyp-Sar-Sar-Aib-Gly-OH/NH$_2$

Tfa-Tyr-Pro-Sar-Sar-Aib-Gly-OH/NH$_2$

Tfa-D-Tyr-D-Pro-Sar-Sar-Aib-Gly-OH/NH$_2$

Tfa-Tyr-Sar-Pro-Sar-Aib-Gly-OH/NH$_2$

Tfa-D-Tyr-Sar-D-Pro-Sar-Aib-Gly-OH/NH$_2$

Tfa-Tyr-Sar-Sar-Sar-Aib-Gly-OH/NH$_2$

Tfa-D-Tyr-Sar-Sar-Sar-Aib-Gly-OH/NH$_2$

4HPP-D-Pro-D-4Hyp-Sar-Aib-Gly-OH/NH$_2$

-continued

4HPPA-Pro-4Hyp-Sar-Aib-Gly-OH/NH$_2$

4HPPA-D-Pro-D-4Hyp-Sar-Aib-Gly-OH/NH$_2$

4HMPA-Pro-4Hyp-Sar-Aib-Gly-OH/NH$_2$

4HMPA-D-Pro-D-4Hyp-Sar-Aib-Gly-OH/NH$_2$

4HPA-Pro-4Hyp-Sar-Aib-Gly-OH/NH$_2$

4HPA-D-Pro-D-4Hyp-Sar-Aib-Gly-OH/NH$_2$

4HBG-Pro-4Hyp-Sar-Aib-Gly-OH/NH$_2$

4HBG-D-Pro-D-4Hyp-Sar-Aib-Gly-OH/NH$_2$

4HPP-Pro-Pro-Sar-Aib-Gly-OH/NH$_2$

4HPP-D-Pro-D-Pro-Sar-Aib-Gly-OH/NH$_2$

4HPPA-Pro-Pro-Sar-Aib-Gly-OH/NH$_2$

4HPPA-D-Pro-D-Pro-Sar-Aib-Gly-OH/NH$_2$

4HMPA-Pro-Pro-Sar-Aib-Gly-OH/NH$_2$

4HMPA-D-Pro-D-Pro-Sar-Aib-Gly-OH/NH$_2$

4HPA-Pro-Pro-Sar-Aib-Gly-OH/NH$_2$

4HPA-D-Pro-D-Pro-Sar-Aib-Gly-OH/NH$_2$

4HBG-Pro-Pro-Sar-Aib-Gly-OH/NH$_2$

4HBG-D-Pro-D-Pro-Sar-Aib-Gly-OH/NH$_2$

4HPP-4Hyp-4Hyp-Sar-Aib-Gly-OH/NH$_2$

4HPP-D-4Hyp-D-4Hyp-Sar-Aib-Gly-OH/NH$_2$

4HPPA-4Hyp-4Hyp-Sar-Aib-Gly-OH/NH$_2$

4HPPA-D-4Hyp-D-4Hyp-Sar-Aib-Gly-OH/NH$_2$

4HMPA-4Hyp-4Hyp-Sar-Aib-Gly-OH/NH$_2$

4HMPA-D-4Hyp-D-4Hyp-Sar-Aib-Gly-OH/NH$_2$

4HPA-4Hyp-4Hyp-Sar-Aib-Gly-OH/NH$_2$

4HPA-D-4Hyp-D-4Hyp-Sar-Aib-Gly-OH/NH$_2$

4HBG-4Hyp-4Hyp-Sar-Aib-Gly-OH/NH$_2$

4HBG-D-4Hyp-D-4Hyp-Sar-Aib-Gly-OH/NH$_2$

4HPP-4Hyp-Pro-Sar-Aib-Gly-OH/NH$_2$

4HPP-D-4Hyp-D-Pro-Sar-Aib-Gly-OH/NH$_2$

4HPPA-4Hyp-Pro-Sar-Aib-Gly-OH/NH$_2$

4HPPA-D-4Hyp-D-Pro-Sar-Aib-Gly-OH/NH$_2$

-continued

4HMPA-4Hyp-Pro-Sar-Aib-Gly-OH/NH$_2$

4HMPA-D-4Hyp-D-Pro-Sar-Aib-Gly-OH/NH$_2$

4HPA-4Hyp-Pro-Sar-Aib-Gly-OH/NH$_2$

4HPA-D-4Hyp-D-Pro-Sar-Aib-Gly-OH/NH$_2$

4HBG-4Hyp-Pro-Sar-Aib-Gly-OH/NH$_2$

4HBG-D-4Hyp-D-Pro-Sar-Aib-Gly-OH/NH$_2$

4HPP-Sar-Pro-Sar-Aib-Gly-OH/NH$_2$

4HPP-Sar-D-Pro-Sar-Aib-Gly-OH/NH$_2$

4HPPA-Sar-Pro-Sar-Aib-Gly-OH/NH$_2$

4HPPA-Sar-D-Pro-Sar-Aib-Gly-OH/NH$_2$

4HMPA-Sar-Pro-Sar-Aib-Gly-OH/NH$_2$

4HMPA-Sar-D-Pro-Sar-Aib-Gly-OH/NH$_2$

4HPA-Sar-Pro-Sar-Aib-Gly-OH/NH$_2$

4HPA-Sar-D-Pro-Sar-Aib-Gly-OH/NH$_2$

4HBG-Sar-Pro-Sar-Aib-Gly-OH/NH$_2$

4HBG-Sar-D-Pro-Sar-Aib-Gly-OH/NH$_2$

4HPP-Pro-Sar-Sar-Aib-Gly-OH/NH$_2$

4HPP-D-Pro-Sar-Sar-Aib-Gly-OH/NH$_2$

4HPPA-Pro-Sar-Sar-Aib-Gly-OH/NH$_2$

4HPPA-D-Pro-Sar-Sar-Aib-Gly-OH/NH$_2$

4HMPA-Pro-Sar-Sar-Aib-Gly-OH/NH$_2$

4HMPA-D-Pro-Sar-Sar-Aib-Gly-OH/NH$_2$

4HPA-Pro-Sar-Sar-Aib-Gly-OH/NH$_2$

4HPA-D-Pro-Sar-Sar-Aib-Gly-OH/NH$_2$

4HBG-Pro-Sar-Sar-Aib-Gly-OH/NH$_2$

4HBG-D-Pro-Sar-Sar-Aib-Gly-OH/NH$_2$

4HPP-Sar-4Hyp-Sar-Aib-Gly-OH/NH$_2$

4HPP-Sar-D-4Hyp-Sar-Aib-Gly-OH/NH$_2$

4HPPA-Sa r-4Hyp-Sar-Aib-Gly-OH/NH$_2$

4HPPA-Sar-D-4Hyp-Sar-Aib-Gly-OH/NH$_2$

4HMPA-Sar-4Hyp-Sar-Aib-Gly-OH/NH$_2$

4HMPA-Sar-D-4Hyp-Sar-Aib-Gly-OH/NH$_2$

4HPA-Sar-4Hyp-Sar-Aib-Gly-OH/NH$_2$

4HPA-Sar-D-4Hyp-Sar-Aib-Gly-OH/NH$_2$

4HBG-Sar-4Hyp-Sar-Aib-Gly-OH/NH$_2$

4HBG-Sar-D-4Hyp-Sar-Aib-Gly-OH/NH$_2$

4HPP-4Hyp-Sar-Sar-Aib-Gly-OH/NH$_2$

-continued

4HPP-D-4Hyp-Sar-Sar-Aib-Gly-OH/NH₂

4HPPA-4Hyp-Sar-Sar-Aib-Gly-OH/NH₂

4HPPA-D-4Hyp-Sar-Sar-Aib-Gly-OH/NH₂

4HMPA-4Hyp-Sar-Sar-Aib-Gly-OH/NH₂

4HMPA-D-4Hyp-Sar-Sar-Aib-Gly-OH/NH₂

4HPA-4Hyp-Sar-Sar-Aib-Gly-OH/NH₂

4HPA-D-4Hyp-Sar-Sar-Aib-Gly-OH/NH₂

4HBG-4Hyp-Sar-Sar-Aib-Gly-OH/NH₂

4HBG-D-4Hyp- Sar-Sar-Aib-Gly-OH/NH₂

4HPP-Sar-Sar-Sar-Aib-Gly-OH/NH₂

4HPPA-Sar-Sar-Sar-Aib-Gly-OH/NH₂

4HMPA-Sar-Sar-Sar-Aib-Gly-OH/NH₂

4HPA-Sar-Sar-Sar-Aib-Gly-OH/NH₂

4HBG-Sar-Sar-Sar-Aib-Gly-OH/NH₂

Ac-Tyr-Pro-4Hyp-Gly-Aib-Sar-OH/NH₂

Ac-D-Tyr-D-Pro-D-4Hyp-Gly-Aib-Sar-OH/NH₂

Ac-Tyr-Pro-Pro-Gly-Aib-Sar-OH/NH₂    (SEQ ID NO: 52)

Ac-D-Tyr-D-Pro-D-Pro-Gly-Aib-Sar-OH/NH₂

Ac-Tyr-4Hyp-Pro-Gly-Aib-Sar-OH/NH₂

Ac-D-Tyr-D-4Hyp-D-Pro-Gly-Aib-Sar-OH/NH₂

Ac-Tyr-4Hyp-4Hyp-Gly-Aib-Sar-OH/NH₂

Ac-D-Tyr-D-4Hyp-D-4Hyp-Gly-Aib-Sar-OH/NH₂

Ac-Tyr-Sar-4Hyp-Gly-Aib-Sar-OH/NH₂

Ac-D-Tyr-Sar-D-4Hyp-Gly-Aib-Sar-OH/NH₂

Ac-Tyr-4Hyp-Sar-Gly-Aib-Sar-OH/NH₂

Ac-D-Tyr-D-4Hyp-Sar-Gly-Aib-Sar-OH/NH₂

Ac-Tyr-Pro-Sar-Gly-Aib-Sar-OH/NH₂

Ac-D-Tyr-D-Pro-Sar-Gly-Aib-Sar-OH/NH₂

Ac-Tyr-Sar-Pro-Gly-Aib-Sar-OH/NH₂

Ac-D-Tyr-Sar-D-Pro-Gly-Aib-Sar-OH/NH₂

Ac-Tyr-Sar-Sar-Gly-Aib-Sar-OH/NH₂

Ac-D-Tyr-Sar-Sar-Gly-Aib-Sar-OH/NH₂

-continued

4HPP-Pro-4Hyp-Gly-Aib-Sar-OH/NH₂

Tfa-Tyr-Pro-4Hyp-Gly-Aib-Sar-OH/NH₂

Tfa-D-Tyr-D-Pro-D-4Hyp-Gly-Aib-Sar-OH/NH₂

Tfa-Tyr-Pro-Pro-Gly-Aib-Sar-OH/NH₂    (SEQ ID NO: 52)

Tfa-D-Tyr-D-Pro-D-Pro-Gly-Aib-Sar-OH/NH₂

Tfa-Tyr-4Hyp-Pro-Gly-Aib-Sar-OH/NH₂

Tfa-D-Tyr-D-4Hyp-D-Pro-Gly-Aib-Sar-OH/NH₂

Tfa-Tyr-4Hyp-4Hyp-Gly-Aib-Sar-OH/NH₂

Tfa-D-Tyr-D-4Hyp-D-4Hyp-Gly-Aib-Sar-OH/NH₂

Tfa-Tyr-Sar-4Hyp-Gly-Aib-Sar-OH/NH₂

Tfa-D-Tyr-Sar-D-4Hyp-Gly-Aib-Sar-OH/NH₂

Tfa-Tyr-4Hyp-Sar-Gly-Aib-Sar-OH/NH₂

Tfa-D-Tyr-D-4Hyp-Sar-Gly-Aib-Sar-OH/NH₂

Tfa-Tyr-Pro-Sar-Gly-Aib-Sar-OH/NH₂

Tfa-D-Tyr-D-Pro-Sar-Gly-Aib-Sar-OH/NH₂

Tfa-Tyr-Sar-Pro-Gly-Aib-Sar-OH/NH₂

Tfa-D-Tyr-Sar-D-Pro-Gly-Aib-Sar-OH/NH₂

Tfa-Tyr-Sar-Sar-Gly-Aib-Sar-OH/NH₂

Tfa-D-Tyr-Sar-Sar-Gly-Aib-Sar-OH/NH₂

4HPP-D-Pro-D-4Hyp-Gly-Aib-Sar-OH/NH₂

4HPPA-Pro-4Hyp-Gly-Aib-Sar-OH/NH₂

4HPPA-D-Pro-D-4Hyp-Gly-Aib-Sar-OH/NH₂

4HMPA-Pro-4Hyp-Gly-Aib-Sar-OH/NH₂

4HMPA-D-Pro-D-4Hyp-Gly-Aib-Sar-OH/NH₂

4HPA-Pro-4Hyp-Gly-Aib-Sar-OH/NH₂

4HPA-D-Pro-D-4Hyp-Gly-Aib-Sar-OH/NH₂

4HBG-Pro-4Hyp-Gly-Aib-Sar-OH/NH₂

4HBG-D-Pro-D-4Hyp-Gly-Aib-Sar-OH/NH₂

4HPP-Pro-Pro-Gly-Aib-Sar-OH/NH$_2$

4HPP-D-Pro-D-Pro-Gly-Aib-Sar-OH/NH$_2$

4HPPA-Pro-Pro-Gly-Aib-Sar-OH/NH$_2$

4HPPA-D-Pro-D-Pro-Gly-Aib-Sar-OH/NH$_2$

4HMPA-Pro-Pro-Gly-Aib-Sar-OH/NH$_2$

4HMPA-D-Pro-D-Pro-Gly-Aib-Sar-OH/NH$_2$

4HPA-Pro-Pro-Gly-Aib-Sar-OH/NH$_2$

4HPA-D-Pro-D-Pro-Gly-Aib-Sar-OH/NH$_2$

4HBG-Pro-Pro-Gly-Aib-Sar-OH/NH$_2$

4HBG-D-Pro-D-Pro-Gly-Aib-Sar-OH/NH$_2$

4HPP-4Hyp-4Hyp-Gly-Aib-Sar-OH/NH$_2$

4HPP-D-4Hyp-D-4Hyp-Gly-Aib-Sar-OH/NH$_2$

4HPPA-4Hyp-4Hyp-Gly-Aib-Sar-OH/NH$_2$

4HPPA-D-4Hyp-D-4Hyp-Gly-Aib-Sar-OH/NH$_2$

4HMPA-4Hyp-4Hyp-Gly-Aib-Sar-OH/NH$_2$

4HMPA-D-4Hyp-D-4Hyp-Gly-Aib-Sar-OH/NH$_2$

4HPA-4Hyp-4Hyp-Gly-Aib-Sar-OH/NH$_2$

4HPA-D-4Hyp-D-4Hyp-Gly-Aib-Sar-OH/NH$_2$

4HBG-4Hyp-4Hyp-Gly-Aib-Sar-OH/NH$_2$

4HBG-D-4Hyp-D-4Hyp-Gly-Aib-Sar-OH/NH$_2$

4HPP-4Hyp-Pro-Gly-Aib-Sar-OH/NH$_2$

4HPP-D-4Hyp-D-Pro-Gly-Aib-Sar-OH/NH$_2$

4HPPA-4Hyp-Pro-Gly-Aib-Sar-OH/NH$_2$

4HPPA-D-4Hyp-D-Pro-Gly-Aib-Sar-OH/NH$_2$

4HMPA-4Hyp-Pro-Gly-Aib-Sar-OH/NH$_2$

4HMPA-D-4Hyp-D-Pro-Gly-Aib-Sar-OH/NH$_2$

4HPA-4Hyp-Pro-Gly-Aib-Sar-OH/NH$_2$

4HPA-D-4Hyp-D-Pro-Gly-Aib-Sar-OH/NH$_2$

4HBG-4Hyp-Pro-Gly-Aib-Sar-OH/NH$_2$

4HBG-D-4Hyp-D-Pro-Gly-Aib-Sar-OH/NH$_2$

4HPP-Sar-Pro-Gly-Aib-Sar-OH/NH$_2$

4HPP-Sar-D-Pro-Gly-Aib-Sar-OH/NH$_2$

4HPPA-Sar-Pro-Gly-Aib-Sar-OH/NH$_2$

4HPPA-Sar-D-Pro-Gly-Aib-Sar-OH/NH$_2$

4HMPA-Sar-Pro-Gly-Aib-Sar-OH/NH$_2$

4HMPA-Sar-D-Pro-Gly-Aib-Sar-OH/NH$_2$

4HPA-Sar-Pro-Gly-Aib-Sar-OH/NH$_2$

4HPA-Sar-D-Pro-Gly-Aib-Sar-OH/NH$_2$

4HBG-Sar-Pro-Gly-Aib-Sar-OH/NH$_2$

4HBG-Sar-D-Pro-Gly-Aib-Sar-OH/NH$_2$

4HPP-Pro-Sar-Gly-Aib-Sar-OH/NH$_2$

4HPP-D-Pro-Sar-Gly-Aib-Sar-OH/NH$_2$

4HPPA-Pro-Sar-Gly-Aib-Sar-OH/NH$_2$

4HPPA-D-Pro-Sar-Gly-Aib-Sar-OH/NH$_2$

4HMPA-Pro-Sar-Gly-Aib-Sar-OH/NH$_2$

4HMPA-D-Pro-Sar-Gly-Aib-Sar-OH/NH$_2$

4HPA-Pro-Sar-Gly-Aib-Sar-OH/NH$_2$

4HPA-D-Pro-Sar-Gly-Aib-Sar-OH/NH$_2$

4HBG-Pro-Sar-Gly-Aib-Sar-OH/NH$_2$

4HBG-D-Pro-Sar-Gly-Aib-Sar-OH/NH$_2$

4HPP-Sar-4Hyp-Gly-Aib-Sar-OH/NH$_2$

4HPP-Sar-D-4Hyp-Gly-Aib-Sar-OH/NH$_2$

4HPPA-Sar-4Hyp-Gly-Aib-Sar-OH/NH$_2$

4HPPA-Sar-D-4Hyp-Gly-Aib-Sar-OH/NH$_2$

4HMPA-Sar-4Hyp-Gly-Aib-Sar-OH/NH$_2$

4HMPA-Sar-D-4Hyp-Gly-Aib-Sar-OH/NH$_2$

4HPA-Sar-4Hyp-Gly-Aib-Sar-OH/NH$_2$

4HPA-Sar-D-4Hyp-Gly-Aib-Sar-OH/NH$_2$

4HBG-Sar-4Hyp-Gly-Aib-Sar-OH/NH$_2$

4HBG-Sar-D-4Hyp-Gly-Aib-Sar-OH/NH$_2$

4HPP-4Hyp-Sar-Gly-Aib-Sar-OH/NH$_2$

4HPP-D-4Hyp-Sar-Gly-Aib-Sar-OH/NH$_2$

4HPPA-4Hyp-Sar-Gly-Aib-Sar-OH/NH$_2$

4HPPA-D-4Hyp-Sar-Gly-Aib-Sar-OH/NH$_2$

4HMPA-4Hyp-Sar-Gly-Aib-Sar-OH/NH$_2$

4HMPA-D-4Hyp-Sar-Gly-Aib-Sar-OH/NH$_2$

4HPA-4Hyp-Sar-Gly-Aib-Sar-OH/NH$_2$

4HPA-D-4Hyp-Sar-Gly-Aib-Sar-OH/NH$_2$

4HBG-4Hyp-Sar-Gly-Aib-Sar-OH/NH$_2$

4HBG-D-4Hyp-Sar-Gly-Aib-Sar-OH/NH$_2$

```
-continued
4HPP-Sar-Sar-Gly-Aib-Sar-OH/NH₂

4HPPA-Sar-Sar-Gly-Aib-Sar-OH/NH₂

4HMPA-Sar-Sar-Gly-Aib-Sar-OH/NH₂

4HPA-Sar-Sar-Gly-Aib-Sar-OH/NH₂

4HBG-Sar-Sar-Gly-Aib-Sar-OH/NH₂
``` and the mirror images thereof, the retro analogues thereof, and derivatives thereof which are selected from the group consisting of pharmaceutically acceptable salts; alkyl, aryl and aralkyl esters; mono and disubstituted amides where the substituent is selected from the group consisting of alkyl, aryl, and aralkyl; hydrazides; and alcohols.

In another preferred embodiment of the invention, formula I represents a cyclic peptide wherein A-B is selected from the group consisting of Sar-Sar, Sar-Hyp, Hyp-Sar, Pro-Sar, Sar-Pro, Pro-Hyp, Pro-Pro, Hyp-Pro, and Hyp-Hyp where Pro and Hyp independently may be an L or D form and Hyp preferably represents 4-hydroxyproline. More preferably, A-B represents unsubstituted L-Pro-L-4Hyp, L-4Hyp-L-Pro, D-Pro-D-4Hyp, or D-4Hyp-D-Pro.

X represents a single amino acid residue, preferably L-Tyr or D-Tyr optionally further substituted with halogen, phenyl, hydroxy, NH₂, and C(1-6)alkyl optionally substituted with halogen, at its aromatic ring when Y represents a peptide of 3 or 4 amino acid residues being independently L- or D-forms, preferably having Asp or Glu at its C-terminal, and more preferably when Y represents a peptide sequence selected from the group consisting of

```
Gly-L-Ala-L-Asn,

Gly-D-Ala-L-Asn,

Gly-L-Ala-Gly-L-Asn,     (SEQ ID NO: 53)

Gly-L-Ala-Gly-D-Asn,

Gly-L-Ala-L-Gln,

Gly-L-Ala-Gly-L-Gln,     (SEQ ID NO: 54)

Gly-L-Ala-Gly-D-Gln,

Gly-D-Ala- D-Asn,

Gly-D-Ala-Gly-D-Asn,

Gly-D-Ala-Gly-L-Asn,

Gly-D-Ala-D-Gln,

Gly-D-Ala-Gly-D-Gln,

Gly-D-Ala-L-Gln,

Gly-D-Ala-Gly-D-Gln,

Gly-L-Ala-L-Asp,

Gly-D-Ala-L-Asp,

Gly-L-Ala-Gly-L-Asp,     (SEQ ID NO: 55)

Gly-L-Ala-Gly-D-Asp,

Gly-L-Ala-L-Glu,
```

```
-continued
Gly-L-Ala-Gly-L-Glu,     (SEQ ID NO: 56)

Gly-L-Ala-Gly-D-Glu,

Gly-D-Ala-D-Asp,

Gly-D-Ala-Gly-D-Asp,

Gly-D-Ala-Gly-L-Asp,

Gly-D-Ala-D-Glu,

Gly-D-Ala-Gly-D-Glu,

Gly-D-Ala-L-Glu,

Gly-D-Ala-Gly-D-Glu,
```

Or X represents a peptide sequence preferably selected from the group consisting of Gly-L-Ala-L-Asp,

```
Gly-L-Ala-Gly-L-Asp,     (SEQ ID NO: 55)

Gly-L-Ala-L-Glu,

Gly-L-Ala-Gly-L-Glu,     (SEQ ID NO: 56)

Gly-D-Ala-D-Asp,

Gly-D-Ala-Gly-D-Asp,

Gly-D-Ala-D-Glu,

Gly-D-Ala-Gly-D-Glu,
``` when Y represents a single amino acid residue, preferably L-Tyr or D-Tyr optionally further substituted with halogen, such as Cl, at its aromatic ring.

Formula I may represent a cyclic peptide sequence comprising all L-forms, all D-forms, or a sequence of mixed L- and D-forms of the amino acid residues. FIG. 1 shows a general outline of seven different cyclic structures within the scope of the present invention.

Examples of cyclic compounds of formula I are

```
Cyclo(L-Tyr-L-Pro-L-4Hyp-Gly-L-   (SEQ ID NO: 57)
Ala-L-Asn)                        (Compound 4), Cyclo(L-Tyr-L-Pro-L-4Hyp-Gly-D-
Ala-L-Asn), Cyclo(L-Tyr-L-Pro-L-4Hyp-Gly-L-   (SEQ ID NO: 58)
Ala-L-Asp), Cyclo(L-Tyr-L-Pro-L-4Hyp-Gly-L-   (SEQ ID NO: 59)
Ala-Gly-L-Asn)                    (Compound 3), Cyclo(L-Tyr-L-Pro-L-4Hyp-Gly-L-   (SEQ ID NO: 60)
Ala-Gly-L-Asp), Cyclo(D-Tyr-L-Pro-L-4Hyp-Gly-L-
Ala-Gly-L-Asp), Cyclo(D-Tyr-D-Pro-D-4Hyp-Gly-D-
Ala-D-Asn), Cyclo(D-Tyr-D-Pro-D-4Hyp-Gly-D-
Ala-D-Asp), Cyclo(D-Tyr-L-Pro-L-4Hyp-Gly-D-
Ala-D-Asp),
```

```
Cyclo(D-Tyr-D-Pro-D-4Hyp-Gly-D-
Ala-Gly-D-Asn),

Cyclo(D-Tyr-L-Pro-L-4Hyp-Gly-D-
Ala-Gly-L-Asn),

Cyclo(D-Tyr-D-Pro-D-4Hyp-Gly-D-
Ala-Gly-D-Asp),

Cyclo(L-Tyr-L-Pro-L-4Hyp-Gly-L-    (SEQ ID NO: 61)
Ala-L-Gln),

Cyclo(L-Tyr-L-Pro-L-4Hyp-Gly-D-
Ala-L-Gln),

Cyclo(L-Tyr-L-Pro-L-4Hyp-Gly-L-    (SEQ ID NO: 62)
Ala-L-Glu),

Cyclo(L-Tyr-L-Pro-L-4Hyp-Gly-L-    (SEQ ID NO: 63)
Ala-Gly-L-Gln),

Cyclo(L-Tyr-L-Pro-L-4Hyp-Gly-L-    (SEQ ID NO: 64)
Ala-Gly-L-Glu),

Cyclo(D-Tyr-L-Pro-L-4Hyp-Gly-L-
Ala-Gly-L-Glu),

Cyclo(D-Tyr-D-Pro-D-4Hyp-Gly-D-
Ala-D-Gln),

Cyclo(D-Tyr-D-Pro-D-4Hyp-Gly-D-
Ala-D-Glu),

Cyclo(D-Tyr-L-Pro-L-4Hyp-Gly-D-
Ala-D-Glu),

Cyclo(D-Tyr-D-Pro-D-4Hyp-Gly-D-
Ala-Gly-D-Gln),

Cyclo(D-Tyr-L-Pro-L-4Hyp-Gly-D-
Ala-Gly-L-Gln),

Cyclo(D-Tyr-D-Pro-D-4Hyp-Gly-D-
Ala-Gly-D-Glu),

Cyclo(-Tyr-Ala-Ser-Ala-Gly-Asn-)   (SEQ ID NO: 65)
                                   Compound 44

Cyclo(-Tyr-Gly-Asn-Tyr-Gly-Asn-)   (SEQ ID NO: 66)
                                   Compound 45

Cyclo(-Tyr-Gly-Asn-Tyr-Ala-Gly-    (SEQ ID NO: 67)
Asn-)                              Compound 46

Cyclo(-Tyr-Val-Ser-Gly-Ala-Gly-    (SEQ ID NO: 68)
Asn-)                              Compound 47
``` and the mirror images thereof, the retro analogues thereof, and derivatives thereof, such as pharmaceutically acceptable salts and amides.

In another preferred embodiment of the invention formula I represents a cyclic compound where the groups X and Y are connected via an amino carbonyl bond, an alkoxy bond, an ester bond, a reduced amide bond, or a disulphide bond. Examples of compounds where X and Y are connected via an alkoxy bond having the linker L of the formula

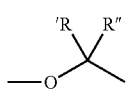

wherein R' and R" each represents hydrogen or lower alkyl and/or lower aryl, preferably methyl and phenyl are listed below

```
Cyclo(O-C(R',R")-Tyr-Pro-4Hyp-Gly-   (SEQ ID NO: 19)
Ala-Gly)

Cyclo(O-C(R',R")-Tyr-4-Hyp-Pro-      (SEQ ID NO: 21)
Gly-Ala-Gly)

Cyclo(O-C(R',R")-Tyr-4-Hyp-4-Hyp-    (SEQ ID NO: 22)
Gly-Ala-Gly)

Cyclo(O-C(R',R")-Tyr-Pro-Pro-Gly-    (SEQ ID NO: 20)
Ala-Gly)

Cyclo(O-C(R',R")-Tyr-Sar-Sar-Gly-    (SEQ ID NO: 27)
Ala-Gly)

Cyclo(O-C(R',R")-Tyr-Sar-Pro-Gly-    (SEQ ID NO: 26)
Ala-Gly)

Cyclo(O-C(R',R")-Tyr-4-Hyp-Sar-      (SEQ ID NO: 24)
Gly-Ala-Gly)

Cyclo(O-CH₂-Tyr-Pro-Sar-Gly-Ala-     (SEQ ID NO: 25)
Gly)

Cyclo(O-C(methyl,phenyl)-Tyr-Sar-    (SEQ ID NO: 23)
4-Hyp-Gly-Ala-Gly)
``` and the mirror images thereof, the retro analogues thereof, and derivatives thereof, such as pharmaceutically acceptable salts and amides.

Examples of compounds where X and Y are connected via an amino carbonyl bond having the linker L of the formula

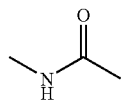

are listed below:

```
Cyclo(HNC(O)-Tyr-Pro-4Hyp-Gly-Ala-   (SEQ ID NO: 19)
Gly)

Cyclo(HNC(O)-Tyr-4-Hyp-Pro-Gly-      (SEQ ID NO: 21)
Ala-Gly)

Cyclo(HNC(O)-Tyr-4-Hyp-4-Hyp-Gly-    (SEQ ID NO: 22)
Ala-Gly)

Cyclo(HNC(O)-Tyr-Pro-Pro-Gly-Ala-    (SEQ ID NO: 20)
Gly)

Cyclo(HNC(O)-Tyr-Sar-Sar-Gly-Ala-    (SEQ ID NO: 27)
Gly)

Cyclo(HNC(O)-Tyr-Sar-Pro-Gly-Ala-    (SEQ ID NO: 26)
Gly)

Cyclo(HNC(O)-Tyr-4-Hyp-Sar-Gly-      (SEQ ID NO: 24)
Ala-Gly)

Cyclo(HNC(O)-Tyr-Pro-Sar-Gly-Ala-    (SEQ ID NO: 25)
Gly)

Cyclo(HNC(O)-Tyr-Sar-4-Hyp-Gly-      (SEQ ID NO: 23)
Ala-Gly)
``` and the mirror images thereof, the retro analogues thereof, and derivatives thereof, such as pharmaceutically acceptable salts and amides.

Examples of compounds where X and Y are connected via an ester bond having the linker L of the formula

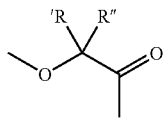

wherein R' and R" each represents hydrogen or lower alkyl and/or lower aryl, preferably methyl and phenyl, preferably R'≠R", are listed below:

```
Cyclo(O-C(R',R")C(O)-Tyr-Pro-4Hyp-      (SEQ ID NO: 19)
Gly-Ala-Gly)

Cyclo(O-C(R',R")C(O)-Tyr-4-Hyp-         (SEQ ID NO: 21)
Pro-Gly-Ala-Gly)

Cyclo(O-C(R',R")C(O)-Tyr-4-Hyp-4-       (SEQ ID NO: 22)
Hyp-Gly-Ala-Gly)

Cyclo(O-C(R',R")C(O)-Tyr-Pro-Pro-       (SEQ ID NO: 20)
Gly-Ala-Gly)

Cyclo(O-C(R',R")C(O)-Tyr-Sar-Sar-       (SEQ ID NO: 27)
Gly-Ala-Gly)

Cyclo(O-C(R',R")C(O)-Tyr-Sar-Pro-       (SEQ ID NO: 26)
Gly-Ala-Gly)

Cyclo(O-C(R',R")C(O)-Tyr-4-Hyp-         (SEQ ID NO: 24)
Sar-Gly-Ala-Gly)

Cyclo(O-C(R',R")C(O)-Tyr-Pro-Sar-       (SEQ ID NO: 25)
Gly-Ala-Gly)

Cyclo(O-C(phenyl,methyl)C(O)-Tyr-       (SEQ ID NO: 23)
Sar-4-Hyp-Gly-Ala-Gly)
``` and the mirror images thereof, the retro analogues thereof, and derivatives thereof, such as pharmaceutically acceptable salts and amides.

When an ester bond is part of the backbone in the cyclic compounds of the invention, L may be derived from a hydroxy-carboxylic acid, such as a hydroxy C(3-6)alkyl carbocylic acid. In one embodiment L is derived from an α-hydroxy-carboxylic acid preferably of the general formula HO—C(R1)(R2)-COOH wherein R1 and R2 independently is H, C(1-6)-alkyl, C(2-6)-alkenyl, aryl, aryl-C(1-4)-alkyl, heteroaryl or heteroaryl-C(1-4)-alkyl; or R1 and R2 together with the carbon atom to which they are bound form a cyclopentyl, cyclohexyl, or cycloheptyl ring; where an alkyl or alkenyl group may be substituted with from one to three substituents selected from amino, cyano, halogen, isocyano, isothiocyano, thiocyano, sulfamyl, C(1-4)-alkylthio, mono- or di-C(1-4)-alkyl-amino, hydroxy, C(1-4)-alkoxy, aryl, heteroaryl, aryloxy, carboxy, C(1-4)-alkoxycarbonyl, C(1-4)-alkylcarbonyloxy, aminocarbonyl, mono- or di-C(1-4)-alkyl-aminocarbonyl, mono- or di-C(1-4)-alkyl-amino, mono- or di-C(1-4)-alkyl-amino-C(1-4)-alkyl, C(1-4)-alkylcarbonyl-amino, sulfono, and sulfino; and where a aryl or a heteroaryl group may be substituted with from one to three substituents selected from C(1-4)-alkyl, C(2-4)-alkenyl, nitro, amino, cyano, halogen, isocyano, isothiocyano, thiocyano, sulfamyl, C(1-4)-alkylthio, mono- or di-C(1-4)-alkyl-amino, hydroxy, C(1-4)-alkoxy, aryloxy, carboxy, C(1-4)-alkoxycarbonyl, C(1-4)-alkylcarbonyloxy, aminocarbonyl, mono- or di-C(1-4)-alkyl-aminocarbonyl, mono- or di-C(1-4)-alkyl-amino, mono- or di-C(1-4)-alkyl-amino-C(1-4)-alkyl, C(1-4)-alkyl-carbonylamino, sulfono, and sulfino. In another embodiment L is derived from a hydroxy aryl-C(3-6)-alkyl-carboxylic acid, or L is derived from a hydroxy C(2-6)alkenyl-carboxylic acid, or L is derived from a hydroxy C(3-6)alkyl carboxylic acid. It is preferred that R1 and R2 represent different groups.

In cyclic compounds of the invention where the cyclisation is formed as an ester bond and the number of amino acid residues is 5, the group A-B is selected from the group consisting of Sar-Hyp, Hyp-Sar, Pro-Hyp, Pro-Pro, Hyp-Pro, and Hyp-Hyp where Pro and Hyp independently may be an L or D form and Hyp preferably represents 4-hydroxyproline. More preferably, A-B represents unsubstituted L-Pro-L-4Hyp, L-4Hyp-L-Pro, D-Pro-D-4Hyp, or D-4Hyp-D-Pro.

Examples of compounds of the invention are

Cyclo(O—(CH$_2$)$_5$C(O)-Tyr-Pro-4-Hyp-Gly-Ala-Gly) (SEQ ID NO: 19) and

Cyclo(O—(CH$_2$)$_5$C(O)-Tyr-4-Hyp-Pro-Gly-Ala-Gly) (SEQ ID NO: 21) when L is a hydroxy C(3-6)alkyl carbocylic acid, and Cyclo(O-(4-hydroxymethylbenzoyl)C(O)-Tyr-Pro-4-Hyp-Gly-Ala-Gly) (SEQ ID NO: 19) and Cyclo(O-(4-hydroxymethylbenzoyl)C(O)-Tyr-4-Hyp-Pro-Gly-Ala-Gly) (SEQ ID NO: 21) when L is a hydroxy aryl-C(1-4)alkyl carboxylic acid, and the mirror images thereof, the retro analogues thereof, and derivatives thereof, such as pharmaceutically acceptable salts and amides.

Cyclic compounds of the invention where the cyclisation is formed with Serine:

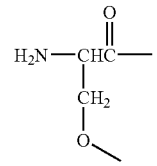

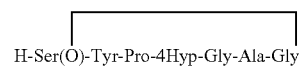
(SEQ ID NO: 69)
H-Ser(O)-Tyr-Pro-4Hyp-Gly-Ala-Gly

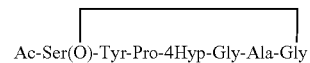
(SEQ ID NO: 69)
Ac-Ser(O)-Tyr-Pro-4Hyp-Gly-Ala-Gly and with Threonine:

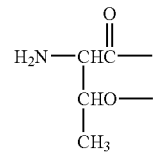

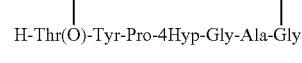
(SEQ ID NO: 70)
H-Thr(O)-Tyr-Pro-4Hyp-Gly-Ala-Gly

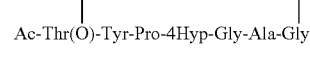
(SEQ ID NO: 70)
Ac-Thr(O)-Tyr-Pro-4Hyp-Gly-Ala-Gly

Examples of cyclic compounds of the invention having a disulphide bond are

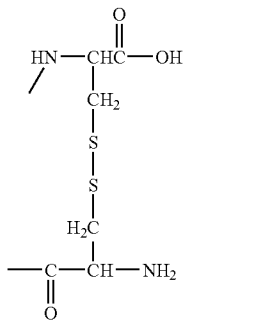

(SEQ ID NO: 71)

H-Cys-Gly-Hyp-Pro-Tyr-Cys-NH₂/OH, cf. Compound 21 or Ex. 21

(SEQ ID NO: 72)

H-Cys-Tyr-Pro-4Hyp-Gly-Ala-Gly-Cys-OH/NH₂

(SEQ ID NO 73)

H-Cys-Tyr-Pro-4Hyp-Gly-Ala-Cys-OH/NH₂

(SEQ ID NO: 74)

H-Cys-Tyr-Pro-4Hyp-Gly-Cys-OH/NH₂, cf. Compound 20 of Ex. 20

(SEQ ID NO: 75)

H-Cys-Tyr-Pro-4Hyp-Cys-OH/NHs

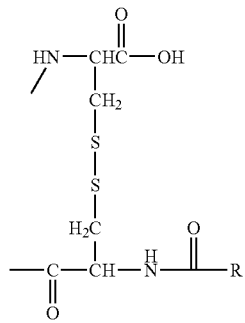

(SEQ ID NO:72)

R-C(O)-Cys-Tyr-Pro-4Hyp-Gly-Ala-Gly-Cys-OH/NH₂

(SEQ ID NO: 73)

R-C(O)-Cys-Tyr-Pro-4Hyp-Gly-Ala-Cys-OH/NH₂

(SEQ ID NO: 74)

R-C(O)-Cys-Tyr-Pro-4Hyp-Gly-Cys-OH/NH₂

(SEQ ID NO: 75)

R-C(O)-Cys-Tyr-Pro-4Hyp-Cys-OH/NH₂ including compounds having combinations of L and D amino acids, amino acid substituted with Sar and other N-substituted natural amino acids, and the mirror image of each of them, their retro analogues as well as derivatives, such as pharmaceutically acceptable salts and amides.

Examples of compounds where X and Y are connected via a reduced amide bond having the linker L of the formula

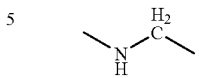

are listed below:

| | |
|---|---|
| Cyclo(ψCH₂NH)-Tyr-Pro-4Hyp-Gly-Ala-Gly) | (SEQ ID NO: 19) |
| Cyclo(ψCH₂NH)-Tyr-4-Hyp-Pro-Gly-Ala-Gly) | (SEQ ID NO: 21) |
| Cyclo(ψCH₂NH)-Tyr-4-Hyp-4-Hyp-Gly-Ala-Gly) | (SEQ ID NO: 22) |
| Cyclo(ψCH₂NH)-Tyr-Pro-Pro-Gly-Ala-Gly) | (SEQ ID NO: 20) |
| Cyclo(ψCH₂NH)-Tyr-Sar-Sar-Gly-Ala-Gly) | (SEQ ID NO: 27) |
| Cyclo(ψCH₂NH)-Tyr-Sar-Pro-Gly-Ala-Gly) | (SEQ ID NO: 26) |
| Cyclo(ψCH₂NH)-Tyr-4-Hyp-Sar-Gly-Ala-Gly) | (SEQ ID NO: 24) |
| Cyclo(ψCH₂NH)-Tyr-Pro-Sar-Gly-Ala-Gly) | (SEQ ID NO: 25) |
| Cyclo(ψCH₂NH)-Tyr-Sar-4-Hyp-Gly-Ala-Gly) | (SEQ ID NO: 23) | and the mirror images thereof, the retro analogues thereof, and derivatives thereof, such as pharmaceutically acceptable salts and amides.

Examples of compounds where X and Y are connected via a reduced amide bond having the linker L of the formula

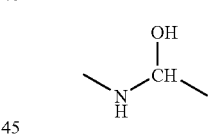

are listed below

| | |
|---|---|
| Cyclo(ψCH(OH)NH)-Tyr-Pro-4Hyp-Gly-Ala-Gly) | (SEQ ID NO: 19) |
| Cyclo(ψCH(OH)NH)-Tyr-4-Hyp-Pro-Gly-Ala-Gly) | (SEQ ID NO: 21) |
| Cyclo(ψCH(OH)NH)-Tyr-4-Hyp-4-Hyp-Gly-Ala-Gly) | (SEQ ID NO: 22) |
| Cyclo(ψCH(OH)NH)-Tyr-Pro-Pro-Gly-Ala-Gly) | (SEQ ID NO: 20) |
| Cyclo(ψCH(OH)NH)-Tyr-Sar-Sar-Gly-Ala-Gly) | (SEQ ID NO: 27) |
| Cyclo(ψCH(OH)NH)-Tyr-Sar-Pro-Gly-Ala-Gly) | (SEQ ID NO: 26) |
| Cyclo(ψCH(OH)NH)-Tyr-4-Hyp-Sar-Gly-Ala-Gly) | (SEQ ID NO: 24) |

```
                           -continued
Cyclo(ψCH(OH)NH)-Tyr-Pro-Sar-Gly-      (SEQ ID NO: 25)
Ala-Gly)

Cyclo(ψCH(OH)NH)-Tyr-Sar-4-Hyp-        (SEQ ID NO: 23)
Gly-Ala-Gly)
``` and the mirror images thereof, the retro analogues thereof, and derivatives thereof, such as pharmaceutically acceptable salts and amides.

More preferably, the invention relates to peptides and peptide derivatives of formula I and the retro form, all D form, or retro all-D form of the peptide sequence of formula I, and
salts and amides thereof.

In preferred embodiments of formula I X is preferably selected from the group consisting of photoprobes such as ASAL optionally iodinated in position 5, such as 2-hydroxy-4-azido-5-iodo benzoyl, and AB, and an acyl group such as Ac. $R_7$ is preferably $NH_2$. $R_a$ is preferably the amino acid side chain of Pro. $R_b$ is preferably the amino acid side chain of Hyp. $R_c$ is preferably the amino acid side chain of Gly or Tyr. $R_d$ is preferably the amino acid side chain of Gly, Asp, Glu, Dapa, or Dab. $R_e$ is preferably Ala. $R_f$ is preferably the amino

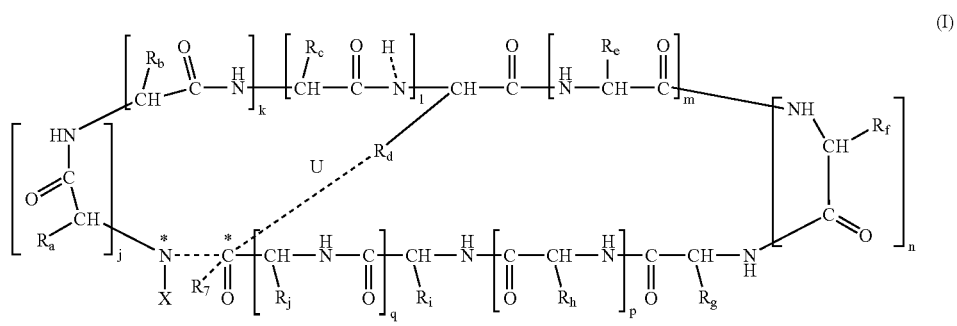

(I)

repesenting a peptide sequence wherein the amino acid residues may be D- and/or L-forms, having the N-terminal at N* and the C-terminal at C* and being optionally cyclic via a covalent bond between N* and C* as shown by a broken line or between $R_d$ and C* as shown by the broken line U; and wherein X represents an N-terminal moiety such as a photoprobe capable of being bond to the amino terminal N*, or an acyl group derived from a C(2-22)alkyl carboxylic acid, such as acetic acid, propionic acid, butyric acid and other fatty acids, such as behenic acid, optionally substituted with one or more substituents selected from the group consisting of hydroxy, halogen, C(1-6)alkyl, nitro and cyano; or X represents hydrogen;

$R_7$ represents OH, $NH_2$, $NHNH_2$ or $OR_8$ when the bond between N* and C* is missing, or $R_7$ is absent when there is a bond between N* and C*; $R_8$ represents H or a straight or branched C(1-6)alkyl group, an aryl or an aralkyl group.

$R_a$ represents the amino acid side chain of Hyp or Pro;
$R_b$ represents the amino acid side chain of Hyp or Pro;
$R_c$ represents the amino acid side chain of Gly, Sar, an aromatic amino acid side chain optionally substituted with one or more hydroxy, halogen or lower alkoxy group in the aromatic ring or $R_c$;
$R_d$ represents the amino acid side chain of Ala, Gly, Glu, Asp, Dab, Da pa, Lys, Asn, Gln, Orn, or Cys;
$R_e$ represents the amino acid side chain of Ala;
$R_f$ represents the amino acid side chain of Ala, Sar or Gly;
$R_g$ represents any amino acid side chain except the side chain of L-4Hyp or a moiety of formula Z or Za;
$R_h$ represents the amino acid side chain of Ala, or $R_h$ represents a moiety of formula Z or Za, preferably Pro;
$R_i$ represents the amino acid side chain of Gly or $R_i$ represents an aromatic amino acid optionally substituted with one or more halogen groups in the aromatic ring, preferably Tyr, Phe, Trp or Nal;
$R_j$ represents Asn, Gln, Asp, Glu, Cys, or Tyr;
and each of j, k, l, m, n, p and q is independently 0 or 1;

acid side chain of Gly or Ala. $R_g$ is preferably the amino acid side chain of Asn, Gly, D-4Hyp or L-/D-Pro when formula I represents a linear peptide, or when formula I represents a peptide cyclised between N* and C* then $R_g$ represents the amino acid side chain of L-/D-4Hyp or L-/D-Pro. $R_h$ is preferably the amino acid side chain of Ala when U is missing, or $R_h$ is Pro or Hyp when U is present. R1 is preferably Tyr, Phe, Trp, Nal optionally substituted with one or more hydroxy or halogen group, preferably F or Cl, in the aromatic ring. $R_j$ is preferably the amino acid side chain of Asp or Glu. $R_8$ represents H, benzyl, tert-butyl or $CH_3$.

j and k are preferably 0 when U is present, and j and k are preferably 1 when U is missing and formula I represents a cyclic peptide, m is preferably 0 when U is missing, p is preferably 1 when U is present, and q is preferably 0 when U is present. Non-cyclic or linear peptides of formula I are preferably of the retro all-D form. When formula I represents a cyclic peptide, then the peptide preferably consists of between 3 and 9 amino acid residues, more preferably between 3 and 7 amino acid residues. It will be apparent to a person skilled in the art that peptide-like compounds having a formula comparable to formula I, but wherein one or more of the peptide bonds have been changed into a covalent bond selected from, i.a., a disulphide bond, an ester bond, a reduced amide bond, an alkoxy bond, an oxycarbonyl bond, and an acyloxyalkoxy bond would be useful for the treatment of the same conditions and ailments as the compounds of the present invention.

In a preferred embodiment the invention relates to compounds of the general formula II

specifying a peptide sequence wherein the amino acid residues may be L and/or D forms, and wherein X represents H or Ac; when all amino acid residues are L-forms then X represents Ac;

G' represents a glycine residue or a glycine analogue such as Sar, G' is preferably glycine;
A represents alanine;
Px represents an amino acid residue of formula Z or Za such as Hyp or Pro, preferably proline;
Y' represents tyrosine or phenylalanine optionally substituted in the phenyl ring with halogen or hydroxy; Y' is preferably tyrosine;
a and b are independently 0 or 1,
$R_7$ represents OH, $NH_2$, $NHNH_2$, Asn-$NH_2$, or Gln-$NH_2$;
and retro forms thereof having the formula IIa: X—$(Y')_b$-$(Px)_2$-G'-A-$(G')_a$-$R_7$ wherein all amino acid residues preferably are D-forms and wherein all symbols have the same meaning as defined above for formula II;
and peptide compounds of formula II wherein at least one Px residue is a D-amino acid and the rest are L-amino acids;
and cyclic sequences of formula II wherein X represents H, $R_7$ represents Asn or Gln having a covalent bond to Y', b is 1, and a is 1;
and salts thereof.

Preferred cyclic peptide compounds of formula I are characterised in having one of the general formulae III or IV:

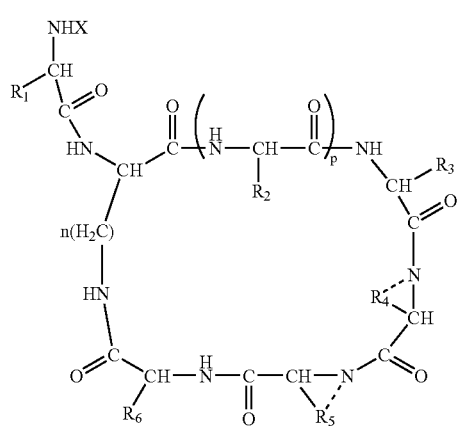

III wherein
X represents H or an N-terminal moiety such as a photoprobe capable of to the N terminal or an acylation with a C(2-22) alkyl carboxylic acid, such as acetic acid, propionic acid, butyric acid and other fatty acids such as behenic acid, being optionally substituted with one or more substituents selected from the group consisting of hydroxy, halogen, C(1-6)alkyl, nitro and cyano;
$R_1$ represents H or $CH_3$, preferably H;
$R_2$ and $R_3$ are different or the same and represent any possible amino acid side chain, preferably H or $CH_3$;

represents an optional bond;
$R_5$ and $R_4$ represent any possible amino acid side chain or when the optional bond is present $R_5$ and $R_4$ represent together with the attached C and N atoms a proline ring which is optionally substituted with OH, preferably in the 4-position, or $R_5$ and $R_4$ represent together with the attached C and N atoms a moiety of formula Z or Za above, preferably Pro or Hyp;

$R_6$ represents an aromatic amino acid side chain, preferably benzyl optionally substituted in the phenyl ring with one or more substituents selected from halogen, nitro and hydroxy, preferably $R_6$ represents Tyr;
p is 0 or 1;
n is 1, 2, 3 or 4; preferably n is 1;
and salts thereof.

Exemplary compounds of formula III are

 (SEQ ID NO: 76)

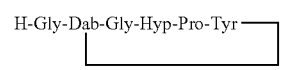 (SEQ ID NO: 77)

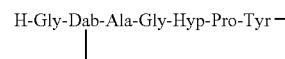 (SEQ ID NO: 78)

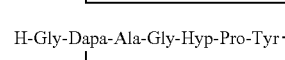 (SEQ ID NO: 79)

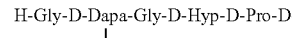

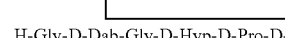

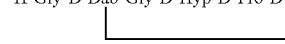

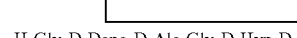

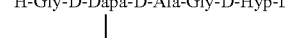

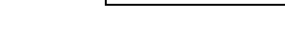

and their salts.

IV

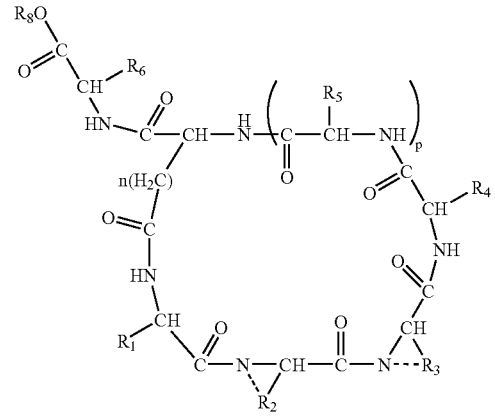

Wherein $R_8$ is the same as defined above, preferably H;
$R_6$ represents H or $CH_3$, preferably H;
$R_4$ and $R_5$ are different or the same and represent any possible amino acid side chain, preferably Gly or Ala;

represents an optional bond;
$R_2$ and $R_3$ represent any possible amino acid side chain, or when the optional bond is present $R_2$ and $R_3$ represent together with the attached C and N atoms a proline ring which is optionally substituted with OH preferably in the 4-position or $R_2$ and $R_3$ represent a moiety of formula Z or Za;

$R_1$ represents an aromatic amino acid side chain, preferably a Tyr side chain;

p is 0 or 1;

n is 1, 2, 3 or 4; preferably n is 1;

and salts thereof.

Exemplary compounds of formula IV are

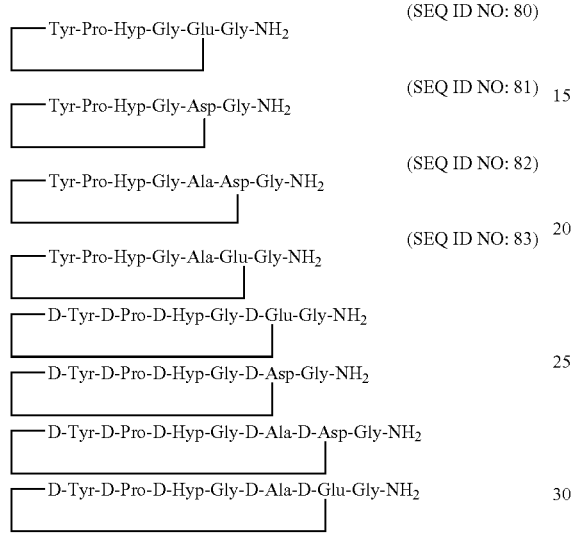

Furthermore, it has surprisingly been found that substituting an asparagine or a glutamine residue for the Hyp-Pro sequence in AAP10 results in a novel antiarrhythmic peptide, Compound 21 of Example 21 below. Thus, a preferred embodiment of the invention relates to peptide compounds wherein the amino acid residues may be D- and/or L-forms, and having the general formula V

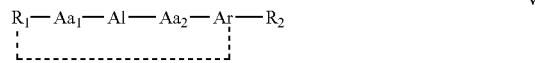

Wherein $R_1$ represents an optional amide bond between the N and the C terminal of the peptide, H or Ac;

Aa$_1$ represents a peptide sequence, preferably of between 0 and 4 amino acid residues, when Aa$_1$ represents a peptide sequence of from 1 to 4 amino acid residues Aa$_1$ is preferably selected from the group consisting of Ala, Gly-Ala, Gly-Asn-Tyr, and Gly-Asn-Tyr-Ala (SEQ ID NO: 103);

Al represents an amino acid residue selected from the group consisting of Gly, beta Alanine and Sar;

Aa$_2$ represents an amino acid residue selected from the group consisting of Asn, Gln, Gly, Tyr, or a chemical unit, such as a hydroxy acid, an amino sulphonic acid, a phosphate group or a hydrocarbon chain connecting G and Ar via 4 covalent bonds;

Ar represents an aromatic amino acid residue, such as a Tyr, Trp, Phe, His, or Nal, optionally substituted with one or more halogen, such as F, Cl, Br, I, OH, $NO_2$, $NH_2$, COOH, CONH;

$R_2$ represents OH, $NH_2$ or is missing;

and retro analogues, retro all-D analogues-(retro-inverse analogues) and salts thereof.

Exemplary compounds of formula V are

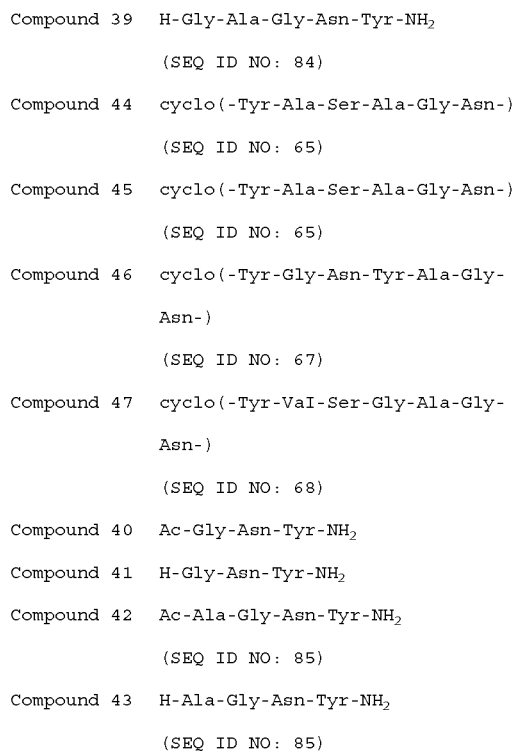

and their salts as defined herein.

Photo/Thermo Labile Peptide Derivatives

Affinity labeling is a frequently used technique for studying the interactions of biologically active molecules. A photo or a thermo labile analogue of the compound is used for the investigation.

A photolabile analogue of the compound under investigation, which is stable in the dark, is converted by illumination into a reactive intermediate that can participate in insertion reactions. This, by forming a covalent bond, stabilizes the interaction based on biological affinity. As photo probes aromatic azides and stabilized diazo compounds produce on photolysis very reactive and nonspecific intermediates, nitrenes and carbenes, respectively capable of participating in insertion reactions. Thus, photo affinity labeling using aryl azides and stabilized diazo compounds as photo probes can be done on any binding site which contains carbon-hydrogen bonds and do not require the presence of a particular reactive functional group at the binding site. Specificity of labeling therefore depends solely on the specific binding of the ligand to the receptor, which is then followed by a nonspecific covalent bond forming reaction that guarantees labeling of the binding site. Photoaffinity probes is particularly useful for labeling hormone receptor sites where reactive functional groups may not be present, but which surely contains carbon-hydrogen bonds. As photo active functionality the azido, diazirino, α-diazo ketones, thia- and selenodiazoles, benzophenone, nitrophenyl are especially useful. The labeling process using aryl azides includes photolysis at $\lambda_{ex}$=300-320 nm for approx. 0.5-2 h at room temperature of an aqueous solution containing the photo labile peptide analogue and the receptor.

A thermo labile compound contains a reactive group which can form a covalent bond in a thermal controlled reaction with specificity towards amino or mercapto groups. As thermo probes aliphatic halides especially iodine and bromine, active esters such as N-hydroxysuccinimid, acid chlorides, pyridyldisulphides, isocyanates, isothiocyanates, carbodiimides, and maleimido can be used.

Labels for in vitro applications are most often chosen as radioactive isotopes such as Iodine-125 and 131, C-14 and tritium or fluorescence probes or biotin or haptens. The influence of the label on the binding activity of the ligand needs to be investigated, in order to secure that the receptor affinity is maintained. As radioactive label Iodine-125 is often used for in-vitro applications, due to its 60 days half-life and low energy photon emissions. The long half-life permits the preparation and storage of labeled photoactive analogues and the resulting labeled protein products for extended periods prior to usage or analysis. The incorporation of Iodine (I-125) into peptide ligands can easily be done if e.g. tyrosine og histidine are present in the peptide sequence. The influence of the labeling of the peptide on the biological activity of the ligand needs to be investigated, in order to secure that the biological activity is maintained. Dhein et al. (WO96/21674) have shown that a derivative of AAP10 where the phenyl ring of the Tyr residues carries an Iodine-125 substituent has biological activity. However, the use of said AAP10 variant as an affinity probe is not possible due to the reversible binding to a possible ligand or receptor. Photoaffinity labeling using aryl azides results generally in 50-60% peptide ligand non-reversibly attached to the target protein (receptor). Thus, it is a purpose of the present invention to further provide an antiarrhythmic peptide suitably modified with a photo or a thermo probe and optionally a radioactive label to be used in assays for the identification of possible ligands or receptors for the antiarrhythmic peptide. Said purpose is achieved with a compound of formulae I, II or 9 herein, derivatised with one of the above mentioned photo probes, preferably 4-azidosalicyloyl (ASAL) and AB (4-azidobenzoyl). Preferably, said derivatised compound is further substituted with a radioactive label, such as Iodine-125.

Exemplary photo probe modified and radioactively labeled compounds of Formula I, or 9 are

```
Compound 31    ASAL-Pro-Hyp-Gly-Ala-Gly-NH2
               (SEQ ID NO: 2)

Compound 32    ASAL(3-I)-Pro-Hyp-Gly-Ala-Gly-NH2
               (SEQ ID NO: 2)

Compound 32a   ASAL(6-I)-Pro-Hyp-Gly-Ala-Gly-NH2
               (SEQ ID NO: 2)

Compound 33    AB-Tyr-Pro-Hyp-Gly-Ala-Gly-NH2
               (SEQ ID NO: 19)

Compound 34    AB-Tyr(3,5-di-I)-Pro-Hyp-Gly-Ala-Gly-
               NH2
               (SEQ ID NO: 86)
``` and salts thereof, cf. Synthesis Examples 31-34 below.

Furthermore, the invention relates to peptide compounds selected from the group consisting of the general formulae 2: H-GAG-(Pa)$_2$—NH$_2$ wherein Pa is any amino acid residue or a moiety of formula Z or Za; at least one of Pa is a D amino acid; preferably Pa is Hyp, P, G or A;

3: H-GAG-(Px)$_2$-Y—NH$_2$ wherein Px is a moiety of formula Z or Za, where one Px is a moiety of formula II, IIa and the other Px is P or Hyp;

4: Ac—Y'-(Px)$_2$-GAG-OH wherein Y' is Y or F, and Px is P or Hyp;

5: Cys(Acm)-AAP10*-Cys(Acm) (SEQ ID NO: 90) or Cys(Acm)-retroAAP10*-Cys(Acm) (SEQ ID NO: 90) wherein Acm is acetamidomethyl radical and AAP10* is the AAP10 sequence or a truncated form thereof;

6: X-D-Y-(D-Px)$_2$-G-D-A-G-NH$_2$ or the retro form thereof X-G-D-A-G-(D-PX)$_2$-D-Y-NH$_2$ or X-G-D-A-G-(D-Px)$_2$-D-Y-D-(Asn)-NH$_2$ wherein X is H or Ac; Px is a moiety of formula Z or Za, preferably Hyp or P; and (Asn) is optional, where both formulae optionally has one or more C or N isotopes;

7: H-(Px)$_n$-Y(N/Q)G-AG-(Px)-NH$_2$ wherein Px is P or Hyp, n is 1 or 2, and m is 0 or 1, preferably m=0 when n=2, and m=1 when n=1;

8: H-G'-A-G'-(Px)$_2$-Y—NH$_2$ wherein G' is Sar or Gly and at least one G' is Sar, and Px is P or Hyp;

9: X—(Y)$_p$-(Px)$_2$-GAG-NH$_2$ wherein X is ASAL or AB, p is 0 or 1, and the phenyl ring of Y has optionally one or more halogen substitutent, preferably I, and Px is P or Hyp;

10: Cyclo(-GAG-(Px)$_2$-Y—N/Q-) wherein Px is P or Hyp;

11: Cyclo(-Y-(Px)$_2$-GA-(G)$_q$-N/Q-) wherein q is 0 or 1, the phenyl ring of Y has optionally one or more halogen substitutents, preferably I, and Px is P or Hyp;

12: X-Zd-G(N/Q)Y—NH$_2$ wherein Zd is a sequence of 0, 1, or 2 amino acid residues selected from G or A, and X is H or Ac;

and the salts thereof.

Further compounds in accord with the invention have the following general formula VI:

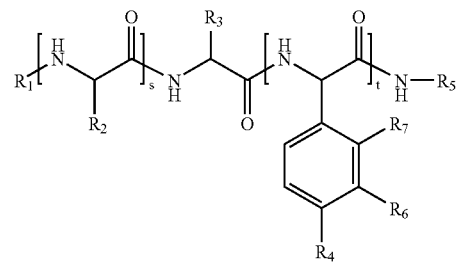

R1: H, Ac, HAA, THAA(thiohydroxyacetic acid), Tfa, aroyl, acetyl

R2: H

R3: the side chain of G, A, N, K, C

R4: OH, NO$_2$, Halogen (F, Cl,Br, I) NH$_2$ or H

R5: (4-hydroxyphenyl or 4-nitrophenyl or 4-Fluorophenyl or 4-Chlorophenyl or 4-Bromophenyl or 4-Iodophenyl or 4-aminophenyl or 4-alkoxyphenyl or H R6: OH, NO$_2$, Halogen (F, Cl,Br, I) NH$_2$ or H R7: OH, NO$_2$, Halogen (F, Cl,Br, I) NH$_2$ or H s: 0 or 1 t: 0 or 1 and salts thereof

Further preferred compounds which are useful in the method of the present invention are represented by the general formula VII (VII) wherein

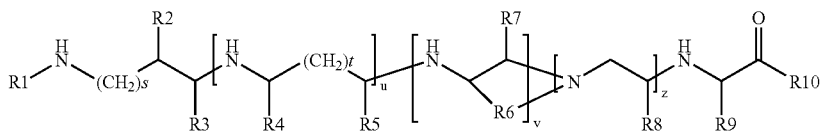

R1 represents H or acetyl (Ac)
R2 represents a sidechain of one of the amino acids G, Y, D-Y, F and D-F,
R3 represents O or H
R4 represents any amino acid sidechain
R5 represents O OR H
R6 represents a C(1-4)alkyl group, such as $CH_2$, $(CH_2)_2$, $(CH_2)_3$, and $(CH_2)_4$
R7 represents O OR H
R8 represents O OR H
R9 represents a sidechain of one of the amino acids G, Y, D-Y, F and D-F,
R10 represents OH or NH2,
and S, T, U, V and Z are integers defined as follows
S: 0, 1 or 2
T: 0, 1 or 2
U: 0 or 1
V: 0 or 1
Z: 0 or 1
and salts thereof.

More specifically, compounds useful in the present invention have the following Formula VIII:

R1-X1-X2-X3-R2    (VIII)

wherein,
X1 is 0, Ala, Gly, B-Ala, Tyr, D-Tyr, Asp, HM
X2 is 0; Ala-Gly-T4c-Pro; Ala-Sar-Hyp-Pro; Ala-6ring-; Ala-Asn; D-Asn-D-Ala; D-Asn;
γAbu; Gly, Ala; D-Ala; β-Ala; Pamh; Asn; or HAA;
X3 is Tyr; D-Tyr; Gly, Pamb, or Phe; and
R1 is H or Ac, with the proviso that X1 and X2 are not both 0;
and salts thereof.

In a particular embodiment, the following specific compounds of Table 1 are represented by Formula VII or VIII above.

Table 1. Compounds of Formulae VII and VIII

Gly-Ala-6ring-Tyr,    (SEQ ID NO: 87)

Gly-Ala-Asn-Tyr,

D-Tyr-D-Asn-D-Ala-Gly,

D-Tyr-D-Asn-Gly,

Gly-γAbu-Tyr,

Gly-γAbu-D-Tyr,

Gly-Gly-Tyr,

Gly-Ala-Tyr,

D-Tyr-D-Ala-Gly,

Gly-D-Asn-Tyr,

Gly-βAla-Tyr,

βAla-βAla-Tyr,

Gly-γAbu-Tyr,

βAla-γAbu-Tyr,

βAla-γAbu-D-Tyr,

Gly-βAla-Phe,

Gly-Pamh-Tyr,

Gly-Pamh-D-Tyr,

D-Tyr-Pamh-Gly,

βAla-Pamh-Tyr,

βAla-Pamh-D-Tyr,

Gly-Asn-Phe,

Gly-Ala-Gly-Pamb,

Asn-Tyr,

Ac-Gly-Tyr,

Ac-Ala-Tyr,

AC-HAA-Y,

HAA-NY,

HAA-GY,

AC-HAA-GY, (reducedGly)-Gly-Tyr(H$_2$N-CH$_2$-CH$_2$-NH-CH$_2$-C(O)-Tyr),

The compound Gly-Ala-6ring-Tyr has the formula shown below

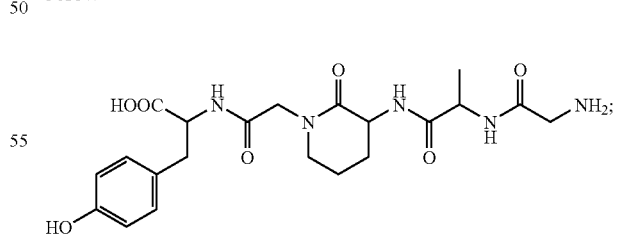

and salts thereof.

Salts

It is preferred that compounds of the invention are used in the form of a pharmaceutically acceptable salt, an alkyl ester, an amide, an alkylamide, a dialkylamide or a hydrazide formed with the C-terminal carboxylic acid function of a linear compound or a free carboxylic acid function, if present, of a cyclic compound. Amides and lower alkyl amides of linear compounds are among the preferred compounds of the invention. Salts include pharmaceutically acceptable salts, such as acid addition salts and basic salts. Examples of acid addition salts are hydrochloride salts, sodium salts, calcium salts, potassium salts, etc. Examples of basic salts are salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_1$-$C_6$-alkyl, optionally substituted $C_{2-6}$-alkenyl, optionally substituted aryl, or optionally substituted heteroaryl. Other examples of pharmaceutically acceptable salts are; e.g., those described in "Remington's Pharmaceutical Sciences" 17. Ed. Alfonso R. Gennaro (Ed.), Mark Publishing Company, Easton, Pa., U.S.A., 1985 and more recent editions, and in Encyclopedia of Pharmaceutical Technology.

Definitions

Throughout the description and claims the three letter code for natural amino acids is used as well as generally accepted three letter codes for other α-amino acids, such as Sarcosin (Sar), α-Amino-iso-butanoic acid (Aib), Naphthylalanine (Nal) including 1-naphthylalanine (1Nal) and 2-naphthylalanine (2Nal), Phenylglycine Phg, 2,4-Diaminobutanoic acid (Dab), 2,3-Diaminopropanoic acid (Dapa), and Hydroxyproline (Hyp). Where nothing is specified Hyp represents 4-hydroxyproline. The natural or essential amino acids are the amino acid constituents of proteins. The aromatic amino acids are Phe, Tyr, Trp, 1Nal, 2Nal and His. Where the L or D form has not been specified it is to be understood that the amino acid in question has the natural L form, cf. Pure & Appl. Chem. Vol. 56(5) pp595-624 (1984). Where nothing is specified it is to be understood that the C-terminal amino acid of a compound of the invention exists as the free carboxylic acid, this may also be specified as "—OH". The C-terminal amino acid of a compound of the invention may be shown to have the terminal function "—OH/NH$_2$" which means that there are two preferred forms of the compound: the free carboxylic acid and the amidated derivative. Hexapeptide compounds of the invention comprising the sequence Ala-Gly-Hyp and having an —NH$_2$ group at the C-terminal do not contain a C-terminal Phe or Tyr or derivatives thereof having a halogen substitution in the phenyl ring.

By "functional analogues" of antiarrhythmic peptides is meant any chemical entity or compound which has a structural conformation and/or binding properties that are sufficiently similar to the endogeneous AAP to provide one or more of the beneficial antiarrhythmic or antithrombotic properties of the endogeneous AAP.

The term "heteroaryl" includes 5- or 6-membered aromatic monocyclic heterocyclic groups containing 1-4 heteroatoms selected from nitrogen, oxygen and sulfur, such as pyrrolyl, furyl, pyrazolyl, imidazolyl, oxazolyl, isoxazolyl, thiazolyl, isothiazolyl, oxadiazolyl, thiadiazolyl, triazolyl, pyridyl, and aromatic bicyclic heterocyclic groups containing 1-6 heteroatoms selected from nitrogen, oxygen and sulfur, such as quinolinyl.

The term "retro analogue" is intended to mean a peptide whose sequence is the reverse of the named peptide.

The term "halogen" refers to F, Cl, Br, and I, where F and I are preferred.

The term "alkyl" refers to univalent groups derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary and tertiary alkyl groups respectively. C(1-22)alkyl refers to any alkyl group having from 1 to 22 carbon atoms and includes C(1-6)alkyl, such as methyl, ethyl, propyl, iso-propyl, butyl, pentyl and hexyl and all possible isomers thereof. By "lower alkyl" is meant C(1-6)alkyl, preferably C(1-4)alkyl, more preferably, methyl and ethyl.

The term "alkenyl" refers to a straight or branched or cyclic hydrocarbon group containing one or more carbon-carbon double bonds. C(2-22)alkenyl refers to any alkenyl group having from 1 to 22 carbon atoms and includes C(2-6)alkenyl, vinyl, allyl, 1-butenyl, etc.

The term "aralkyl" refers to aryl C(1-22)alkyl, and the term "aryl" throughout this specification means phenyl or naphthyl.

HPP refers to hydroxyphenylpropionyl
4HPP refers to 3-(4-hydroxyphenyl)propionyl
2HPP refers to 3-(2-hydroxyphenyl)propionyl
HAA refers to hydroxy acetic acid
4HPPA refers to 4-hydroxyphenoxyacetic acid
2HPPA refers to 2-hydroxyphenoxyacetic acid
4HMPA refers to 4-(hydroxymethyl)phenoxyacetic acid
4HPA refers to 4-hydroxyphenylacetic acid
3HPA refers to 3-hydroxyphenylacetic acid
2HPA refers to 2-hydroxyphenylacetic acid
4HBG refers to N-(4-hydroxybenzoyl)glycine
3HBG refers to N-(3-hydroxybenzoyl)glycine
2HBG refers to N-(2-hydroxybenzoyl)glycine
4HPG refers to N-(4-hydroxyphenyl)glycine
Ac refers to the acetyl radical
Pc or PC refers to L-pipecolic acid radical
Tfa refers to trifluoroacetyl radical
T4c refers to L-thiazolidin-4-carboxylic acid radical
ASAL refers to 4-azidosalicyloyl radical
AB refers to 4-azidobenzoyl radical
HOBt refers to 1-hydroxybenzotriazole
HOAt refers to 1-Hydroxy-7-azabenzotriazole
Acm refers to Acetamidomethyl radical
Pd(PPh$_3$)$_4$ is tetrakis(triphenylphosphine)palladium(0)
DNP refers to dinitrophenyl.
Pamh refers to 4-amino-6-methylheptanoic acid
Pamb refers to 4-aminomethyl benzoic acid
DBF is defined as 2-aminoethyl-6-dibenzofuranpropionic acid
"6-ring" is used for 3-amino-1-carboxymethylvalerolactam
yAbu refers to gamma aminobutyric acid By the phrase "amino acid residue" is meant a natural as well as an unnatural amino acid unit, which herein is represented by the generally accepted three letter codes for amino acids, such as Sarcosin (Sar), alpha-Amino-iso-butanoic acid (Aib), Naphthylalanine (Nal) including 1-naphthylalanine (1Nal) and 2-naphthylalanine (2Nal), Phenylglycine Phg, 2,4-Diaminobutanoic acid (Dab), 2,3-Diaminopropanoic acid (Dapa), and Hydroxyproline (Hyp) and beta-Ala for beta-alanine. Where nothing is specified Hyp or 4Hyp represents 4-hydroxyproline. The natural or essential amino acids are the amino acid constituents of proteins and may be represented by the generally accepted one-letter code. The aromatic amino acids are Phe, Tyr, Trp, 1Nal, 2Nal and His. Where the L or D form has not been specified it is to be understood that the amino acid in question has the natural L form, cf. Pure & Appl. Chem. Vol. 56(5) pp595-624 (1984). Where nothing is specified it is to be understood that the C-terminal amino acid of a compound of the invention exists as the free carboxylic acid, this may also be specified as "—OH". The C-terminal amino acid of a compound of the invention may be shown to have the terminal function "—OH/NH2" which means that there are two preferred forms of the compound: the free carboxylic acid and the amidated derivative. It is to be understood that this definition of amino acid residue includes compounds, such as DBF, T4c, Pc, DNP, and 3-amino-1-carboxymethylvalerolactam that are amino acid like. DNP functions as a hapten for antibody recognition, and compounds of the invention that contain a DNP moiety may preferably be used as research tools.

The term "peptide mimetic" refers to compounds of both peptide and non-peptide nature. The objective behind the creation of peptidomimetics is to create scaffolds which can replace the peptide backbone. It is assumed that the secondary amide bonds in peptides are responsible for instability and possibly poor peptide transport properties across cell membranes. Proper placement of amino acid side chains with appropriate trajectories is viewed as the key design tactic in peptide peptidomimetics to achieve biological activity. The backbone modifikations include reduced amide bonds and alkylated amide bonds and the use of isosteric bonds such as thioamide bonds, $CH_2$—$CH_2$, $CH$=$CH$, etc.

The term "peptoid" refers to compounds that may be characterised by topological similarity between the structural formula of the peptoid and the parent peptide. Thus, a peptoid may be a compound consisting of peptide-like chains of amino acids bearing side chains on the backbone nitrogen atom rather than on the alpha-carbon as in true peptides Petidomimetics and peptoids may comprise amino acid units having modified side chains, such as Nal, Dab, and Dapa, or they may comprise D-amino acids. The various modifications of peptide and peptidomimetic structure described by EI Tayar, N et al. (Amino Acids (1995) 8: 125-139) are included in the definitions herein.

The terms "intercellular communication facilitating compound", "gap junction facilitator", "compound that facilitates gap junction communication" and "gap junction opener" etc. all refer to a compound that facilitates or mediates GJIC irrespective of the particular mechanism behind the resulting improved or normalised GJIC. More specifically, the term "gap junction opener" may refer to a substance that upon stimulation of a cell which expresses connexins produces increased conductance of the gap junctional channel, which in turn results in an increased exchange of molecules that are able to pass through gap junctions between extracellular and intracellular space and/or increased GJIC.

The term "agonist" refers to an endogenous substance or a drug that can interact with a receptor and initiate a physiological or a pharmacological response characteristic of that receptor (contraction, relaxation, secretion, enzyme activation, etc.). An "antiarrhythmic peptide receptor agonist" or "AAP—R agonist" as used herein may or may not be equivalent with a "gap junction opener" depending on the specific biological mechanism behind the effect of the compound.

General Background on Gap Junctions

In a multicellular organism, co-ordination between cells is of paramount importance. Among the various means of cellular cross talk, gap junctions provide the most direct pathway. Gap junctions are one type of junctional complex formed between adjacent cells and consist of aggregated channels that directly link the interiors (cytoplasm) of neighbouring cells. In the adult mammal, gap junctions are found in most cell types with one known exception being circulating blood elements.

The structural unit of the gap junction channel is the connexon or hemi-channel. Each connexon is comprised of six connexin polypeptides (Cx) which oligomerise to form an aqueous pore that spans a single plasma membrane. To form a complete gap junction channel, two connexons from adjacent cells align and dock with each other to form a continuous channel, linking the cytoplasm of the two cells.

The gap junction channel-forming connexins comprise a multi-gene family with at least fourteen mammalian connexins discovered thus far. Connexin expression is tissue and cell specific, with some cells expressing multiple connexin isoforms. Experimental evidence suggests two different hybrid configurations are possible: heterotypic cell-to-cell channels in which each connexon or hemichannel consists of a specific connexin isoform; or heteromeric channels where each connexon is a mixture of the different connexin isoforms expressed in a particular cell type. Connexins are expressed in a cell-, tissue-, and development-specific manner.

Relatively little is known about the connexin gene structure. Results reported for mouse Cx43 revealed that Cx43 contains two exons and an intron located in the 5' untranslated region. Further analysis showed that the Cx43 transcription start point in both embryos and adult tissues. Several putative transcription factor binding sites have been identified in the 5' proximal promotor. In vitro studies have shown that permeable channels could be produced by hemichannels composed of different pairs of Cx. For example, Cx43 can produce functional channels with Cx32, Cx 37 and endogenous Cx of oocytes (Cx38) but not with Cx26 oocytes. However, very little is known about their properties as well as about the regulation of permeability of these heterochannels. Cx are expressed in the vast majority of tissues and single cell are able to express several different Cx. Permeable gap junctions can be formed between cells, which express different types of Cx. Thus the gap junction intracellular communication (GJIC) in tissues appears to be very important for maintenance of tissue integrity. It appears that several genes are making the equivalent products in order to prevent the loss of GJIC due to a mutation in one of the genes.

The pore diameter of the gap junction channel formed has been reported to be in the range of 0.8-1.4 nm. Gap junctions are relatively non-selective and allow the passage of molecules up to about 1000 Daltons. Such substances are, i.a., ions, water, sugars, nucleotides, amino acids, fatty acids, small peptides, drugs, and carcinogens. Channel passage does not require ATP and appears to result from passive diffusion. This flux of materials between cells via gap junction channels is known as gap junctional intercellular communication (GJIC), which plays an important role in the regulation of cell metabolism, proliferation, and cell-to-cell signalling. One of the most significant physiological implications for GJIC is that gap junction coupled cells within a tissue are not individual, discrete entities, but are highly integrated with their neighbors. This property facilitates homeostasis and also permits the rapid, direct transfer of second messengers between cells to co-ordinate cellular responses within the tissue.

The process of GJIC is regulated by a variety of mechanisms that can be broadly divided into two major categories. The first type of regulation controls the cellular quantity of gap junctions by influencing the expression, degradation, cellular trafficking of connexins to the plasma membrane, or assembly of connexins into functional gap junctions. Impaired GJIC caused by the down-regulation of connexin expression in tumour cells is an example of this mode of regulation. The second type of regulation does not generally involve any gross alteration of the cellular levels of gap junctions or connexins, but induces opening or closure or gating of existing gap junctions. Extracellular soluble factors, such as mitogens (e.g. DDT), hormones (e.g. catecholamines), anaesthetics (e.g. halothane), intracellular biomolecules (e.g. CAMP), and cell stress (e.g. mechanical or metabolic stress) can result in this type of regulation. Additionally, GJIC is regulated during the cell cycle and during cellular migration.

The mode of GJIC regulation or junctional gating has been widely studied for gap junctions especially gap junctions composed of connexin43 (Cx43) and thus used as a representative of all connexins. Some factors exert their inhibitory effects on GJIC indirectly, for example, by altering the lipid environment and cell membrane fluidity, whereas other GJIC inhibitors include oncogenes, growth factors, and tumour promoters, which induce various modifications of the Cx43. Disruption of junctional permeability may be necessary for mediating the specific biological functions of the latter group. These agents initiate complex signalling pathways consisting of the activation of kinases, phosphatases, and interacting proteins. Understanding the mechanisms of action of these GJIC modulators will not only define their respective signalling pathways responsible for junctional regulation, but will also provide experimental tools for characterising the biological functions of GJIC and connexins.

Changes in the phosphorylation of specific sites of the cytoplasmic carboxy terminal domain of Cx43 appear to be pivotal to the opening and closing of the gap junctional channel. Phosphorylation of the carboxy terminal domain may also be important to the process of bringing Cx43 gap junctional hemicomplex to the surface membrane, its internalisation and degradation. Connexins have half-lives (hours) that are much shorter than most plasma membrane proteins (days), e.g. the half-life of Cx43 in rat heart is less than 1½ hour. Thus, regulation of the turnover rate would be an important factor in regulating GJIC.

The carboxy terminal domain contains putative phosphorylation sites for multiple protein kinases (PKA, PKC, PKG, MAPK, CaMkII and tyrosine kinase). Phosphorylation of these sites of the carboxy terminal domain results in closure of gap junctional channels and various inhibitors of Cx43 gap junctional channels use different signalling pathways to induce phosphorylation of the carboxy terminal domain. The cell type and the particular inhibitor determine which signalling pathways to be used and the type of the involved protein kinase points to the intracellular messenger system utilised. Thus activation of PKA has been reported by to require involvement of the cAMP second messenger system while PKC requires involvement of the phosphoinositol intracellular signalling system.

Other mechanisms regulating channel gating include intracellular levels of hydrogen and calcium ions, transjunctional voltage, and free radicals. Decreased pH or pCa induce channel closure in a cell- and connexin-specific manner.

Many physiological roles besides growth control have been proposed for GJIC:

Homeostasis. GJIC permits the rapid equilibration of nutrients, ions, and fluids between cells. This might be the most ancient, widespread, and important function for these channels.

Electrical coupling. Gap junctions serve as electrical synapses in electrically excitable cells such as cardiac myocytes, smooth muscle cells, and neurones. In these tissues, electrical coupling permits more rapid cell-to-cell transmission of action potentials than chemical synapses. In cardiomyocytes and smooth muscle cells, this enables their synchronous contraction.

Tissue response to hormones. GJIC may enhance the responsiveness of tissues to external stimuli. Second messengers such as cyclic nucleotides, calcium, and inositol phosphates are small enough to pass from hormonally activated cells to quiescent cells through junctional channels and activate the latter. Such an effect may increase the tissue response to an agonist.

Regulation of embryonic development. Gap junctions may serve as intercellular pathways for chemical and/or electrical developmental signals in embryos and for defining the boundaries of developmental compartments. GJIC occurs in specific patterns in embryonic cells and the impairment of GJIC has been related to developmental anomalies and the teratogenic effects of many chemicals.

The intercellular communication ensures that the activities of the individual cells happen in co-ordinated fashion and integrate these activities into the dynamics of a working tissue serving the organism in which it is set. It is therefore not very surprising that a wide variety of pathological conditions have been associated with decreased GJIC.

Pharmacology

Cardiac Indications

As outlined in the desciption of background of the invention, there is ample evidence supporting an important role of GJIC in cardiomyocytes under normal and pathological conditions. Specific cardiac conditions associated with impaired GJIC are discussed below and in vitro and in vivo evidence are presented to demonstrate that compounds that increase GJIC in the heart are useful for the prevention and/or treatment of a series of pathological conditions in the heart.

Reentry Arrhythmias

Cardiac arrhythmiac are caused by either abnormal impulse initiation or abnormal impulse conduction. Among arrhythmias with abnormal impulse conduction, arrhythmias caused by a reentrant mechanism are the most serious.

Ventricular Reentry:

Reentry is the major cause of sustained ventricular fibrillation and sudden cardiac death. Reentry occurs when the propagating impulse does not die out after complete activation of the heart, but persists to reexcite the heart after the end of the refractory period. The induction of reentry is facilitated by slow conduction, increased dispersion of repolarization, non-uniform anisotropy and unidirectional conduction block. The underlying disease responsible for the majority of cases of ventricular reentry is ischemic heart disease (e.g., acute myocardial infarction, chronic myocardial infarction, stable angina pectoris, and unstable angina pectoris). During acute ischemia the gap junction channels close leading to an uncoupling of neighboring cells. Heterogeneous changes in ion channel and gap junction function lead to increased dispersion of action potential duration and effective refractory period especially in the border zone separating the ischemic area from the normal myocardium. Increased dispersion of action potential duration has long been known to facilitate the induction of ventricular fibrillation[23]. Normally, in well-coupled cells, the difference in action potential duration is smoothened due to the electrical coupling. However, uncoupling will prevent this smoothening and contribute to an unmasking of dispersion of action potential duration and refractory period[24]. If ischemia is prolonged a reduced degree of Cx43 expression and a changed pattern of distribution can be observed. The closure of gap junction channels during acute ischemia as well as the changes in expression and distribution pattern in chronic ischemia may lead to slow conduction, increased dispersion, non-uniform anisotropy, and unidirectional conduction block, and thereby facilitate the induction of reentry arrhythmias. Thus, experimental studies have shown a correlation between the site of abnormal connexin expression and distribution and the location of reentrant ventricular tachycardia circuits[25].

The conditions that favor the development of reentry, i.e., slow conduction, increased dispersion of repolarization, non-uniform anisotropy and unidirectional conduction block are present to a various extent in a lot of other heart diseases. Thus, in infectious or autonomic cardiomyopathy the inflammation that takes place may lead to deposition of fibrous tissue in the myocardium thereby creating foci of slow conduction increased dispersion and possibly unidirectional conduction block. Hypertrophic cardiomyopathy (e.g. due to hypertension, aortic stenosis, congenital) may result in reentry arrhythmias due to the mismatch between the large amount of myocardial tissue and the relative small amount of conductive tissue which may lead to slow conduction, increased dispersion and unidirectional conduction block. Congenital diseases (e.g., the long-QT syndrome) and drugs that prolong the QT interval (e.g., antiarrhythmic drugs, antipsycotic drugs, antihistamines, antibacterial drugs etc.) also increase the dispersion of action potential duration possibly due to the heterogeneity of distribution of ion channels throughout the different layers of the myocardium and is a major cause of reentry-induced sudden death in younger subjects[26].

Atrial Reentry

Atrial fibrillation—the most common cardiac arrhythmia—is also caused by a reentrant mechanism. In this case multiple wavelets travel across the atria and re-excite the tissue that is no longer refractory. Atrial fibrillation can persist for years and will eventually lead to a remodelling of the atrias. An important part of the remodelling process is the changes in distribution of gap junctions. Thus, the Cx40 distribution pattern becomes increasingly heterogeneous. The time course of changes in the distribution and content of Cx40 gap junctions correlates with an increase in stability and complexity of AF and suggests that Cx40 gap junctional remodeling might be involved in the pathogenesis of sustained atrial fibrillation[27]. Moreover, several lines of evidence support the notion that during conditions with slowing of atrial conduction the susceptibility to atrial fibrillation is elevated.

Repolarization Alternans

The appearance of electrocardiographic T-wave alternans with elevated heart rate or metabolic insult has been observed for nearly a century. Macroscopic T-wave alternans is often noted as a harbinger of sudden arrhythmic death. Recent work suggest a common mechanism that may link the presence of discordant repolarization alternans to the initiation of diverse reentrant arrhythmias, depending on the anatomic nature of the substrate[28]. Under chronotropic or metabolic stress, the repolarization phase of the myocardial action potential develops an alternation in morphology and duration. With additional stress or in the presence of structural barriers, repolarization alternans becomes spatially discordant. Discordant alternans leads to sufficiently large repolarization gradients to produce unidirectional block and reentry. Without a structural barrier, the reentry is functional and manifests as ventricular fibrillation or polymorphic ventricular tachycardia. In the setting of a structural barrier, reentry can become anatomically fixed, resulting in monomorphic ventricular tachycardia[29].

In summary, it appears that a substance such as the compounds of the present invention, which increases gap junction conductance and make the anisotropy more uniform will prevent unidirectional block and reentry arrhythmias. Such a substance will be useful is patients with reentry circuits of both atrial and ventricular origin. Patients with T-wave alternans are prone to reentry arrhythmias, and a substance that increases gap junctional coupling and decreases anisotropy may be useful in the prevention of lethal ventricular arrhythmias in these patients.

Bradyarrhythmias

Bradyarrhythmias can be caused by slowed conduction or conduction block of the sinoatrial node, atrioventricular node, bundle of His or right or left bundle branch. The major connexin responsible for the conductance throughout the conductive system is Cx40. Mice homozygous for a knock-out of the Cx40 gene have significantly slower atrial, atrioventricular, and His-Purkinje conduction and are at increased risk of arrhythmias and bundle branch block[4-6]. Thus, normal functioning Cx40 gap junctions are essential for the maintenance of normal rhythm.

A substance, such as the compounds of the present invention which increases gap junction conductance is useful in the prevention and/or treatment of slowed conduction in the heart.

Reduced Contractility

Reduced contractility is a common feature of many chronic heart diseases. During the worst case scenario, (i.e., end-stage heart failure), the contractility is reduced to a point where the ejection fraction is so low that the basal needs for organ perfusion can no longer be maintained. Experimental as well as clinical evidence has shown that the expression and distribution of connexins in hearts from patients with endstage heart failure is changed. Thus, Cx43 is significantly down-regulated with a highly irregular distribution in the abnormal tissue. Cx45 expression, which under normal conditions is very limited, is significantly increased in failing hearts; however, the conductive properties of Cx45 are inferior to the properties of Cx43 and therefore can not compensate for the reduction in Cx43. Recent evidence indicates that some regulatory ion channels and receptors are concentrated at sites of inter-cellular junction and it is therefore highly likely that the changes in expression and distribution of Cx43 can affect the excitation-contraction coupling and thus the contractility[30]. A strong evidence for a link between gap junction function and contractility is the fact that chimeric mice formed from Cx43-null embryonic stem cells and wild-type blastocysts, thus expressing a heterogeneous loss of Cx43, develop severe contractile defects[31].

We suggest that a substance, which increases gap junction conductance will improve the intercellular communication of the mediators involved in excitation-contraction coupling and thereby improve contractility.

EXPERIMENTAL EXAMPLE 1

Effect of Compound 2 on GJIC in Cardiomyocytes

Cell preparation: Cells were isolated from guinea pig hearts by perfusion with collagenase according to the Langendorf method. In brief, guinea pigs were heparinised with an intraperitoneal injection of heparin (1000 IU/kg). After 30 minutes the animal was sacrificed by a blow to the neck followed by cutting the spine at the neck. The chest was opened and the aorta cannulated. Then the cannula was fixed to the aorta by a ligature, exised and perfused with Tyrodes solution for a couple of minutes. The Tyrodes solution had the following composition in mM: $Na^+$ 135.33, $K^+$ 4, $Cl^-$ 145, $PO_4^-$ 0.33, $Mg^{2+}$ 1, $Ca^{2+}$ 2, Hepes 10, Glucose 10, pH 7.4. All perfusion media were bubled by 100% oxygen. After this the heart was perfused for two minutes with Tyrodes solution without $Ca^{2+}$, followed by perusion for two minutes with a high $K^+$ solution containing in mM: $Na^+$ 20, $K^+$ 120, $Cl^-$ 22, glutamate 120, $Mg^{2+}$ 1, $Ca^{2+}$ 25 µM, Hepes 10, Glucose 10, pH 7.4.

Then the heart was perfused with high $K^+$ solution with 0.6 mg/ml collagenase, this was done for 10-15 minutes judged from the apperance of the heart. The atria were cut off, the ventricles minced, whereafter the pieces were stirred in the collagenase solution by gently bubbling with 100% oxygen. The cells were then passed throug a sieve to isolate the liberated cells, and the collagenase was removed by centrifugation. The cells were resuspended in $Ca^{2+}$ free Tyrodes solution and $Ca^{2+}$ was slowly increased to 0.65 mM. The cells were kept in this solution at room temperature until transferred to the experimental chamber.

Electrophysiology: Cover slips are mounted in an open chamber on the stage of an inverted microscope, where the cells are superfused with Dulbeccos phosphate buffered saline (PBS) at 1 ml/min, 37° C. The solution contain (in mM): $Na^+$ 152, $K^+$ 4.2, $Cl^-$ 141.5, $PO_4^{3-}$ 9.5, $Ca^{2+}$ 0.9, $Mg^{2+}$ 0.5, pH 7.2. Patch clamp pipettes are pulled from 1.5 mm glass capillaries (GC150F-15, Harvard Apparatus) on a Sutter Flaming-Brown P-87 microelectrode puller and fire polished to a resistance of 4-6 MΩ. Pipettes are filled with an intracellular like solution containing in mM: $K^+$ 145, $Na^+$ 15, $Cl^-$ 5, $Gluconate^-$ 153, Pyruvate 5, EGTA 1, HEPES 5, $Ca^{2+}$ 0.42 mM, $Mg^{2+}$ 1.6, pH 7.2. To this solution amphotericin B (240 µg/mi) is added from a 60 mg/ml stock solution (Solvent: DMSO).

The patch clamp set-up consists of two synchronised discontinuous amplifiers (SEC-05LX, NPI electronics) and data is digitised using an INT-10 interface (NPI electronics) and a PC1200 data acquisition board (National Instruments). Both current and voltage signals are low pass filtered at 1 kHz using the internal filters of the amplifiers and digitised at 10 kHz.

One cell of a pair is approached with an electrode using a PatchMan 5173 micromanipulator (Eppendorf). When contact with the cell is obtained (seen as a sudden increase in input resistance), suction is applied until the Giga seal configuration is established. This procedure is then repeated on the other cell. Then the membrane under the pipettes are broken by a brief application of suction and the potential of the cell interior is clamped to −70 mV, which is close to the spontaneous membrane potential of the cells. For every 10 second each of the cells are consecutively hyperpolarised by 10 mV for 1 second and resulting current change in the other cell can the be used to calculate the intercellular conductance ($G_j$) using the formula:

$$G_j = \frac{\Delta I_p}{\Delta U_j} = \frac{I_{p,pulse} - I_{p,rest}}{U_p - U_a} \quad \text{(Equation 1)}$$

Where $I_{p,pulse}$ and $I_{p,rest}$ represent the current in the passive cell during the pulse and before the pulse respectively, and $U_p$ and $U_a$ represent the voltage of the passive and active cell. This kind of experiments does not allow comparison on absolute $G_j$ values due to differences in cell-to-cell contact and therefore the amount of functional gap junction channels. However, the change in $G_j$ value to a standardized intervention like a drug can be analysed by comparing the relative changes in $G_j$.

Figure 2:
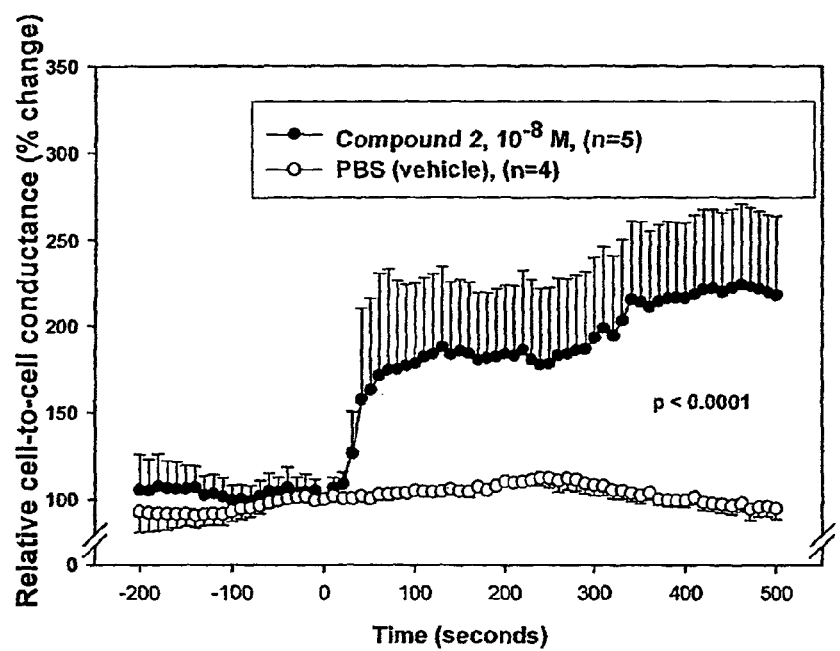
FIG. 2 is a graph showing the relative $G_j$ as a function of time before and during stimulation with Compound 2 ($10^{-8}$ M).

Results: The results from nine successful experiments are summarized in FIG. 2. This figure shows the relative $G_j$ as a function of time before and during stimulation with Compound 2 ($10^{-8}$ M). In all five experiments where the cells were treated with Compound 2, the compound produced a significant increase in $G_j$, which reached a steady-state level after about 400 seconds of stimulation ($\Delta G_j$=+120±46%). The conductance was unchanged throughout in all four vehicle treated preparations ($\Delta G_j$=−3±5%).

These findings are in good agreement with experiments reported in the literature using the synthetic AAP analogue AAP10, showing an increased electrical coupling between cardiomyocytes after stimulation[32]. However, in the study by Müller et al.[32], gap junction conductance was not stable during control conditions. Thus, in three out of six experiments application of AAP10 did not increase the conductance, but prevented run-down of gap junction conductance and in two out of six experiments gap junction conductance actually increased during the control period. In the experiments presented herein, Compound 2 increased gap junction conductance in preprations with stable control conditions.

EXPERIMENTAL EXAMPLE 2

Binding of Compound 2 to Tissue Preparations of Murine Heart

Preparation

Hearts are excised from mice (Balb/cJ, 20 g), rinsed twice in ice-cold (0° C.) 0.32 M sucrose and homogenized on ice in 10 volumes of sucrose with an Ultra Turrax homogeniser (1000 rpm) for 2 minutes. The homogenate is centrifuged at 1000 $g_{mean}$ for 10 minutes at 4° C. and the supernatant collected and filtrated through 4 layers of gauze. The filtrate is then centrifuged at 50,000 $g_{mean}$ for 45 min at 4° C. and the pellet resuspended in 10 $vol_{org.\ wet\ weight}$ ice-cold distilled water and incubated for 60 min at 0° C. and re-centrifuged at 50,000 $g_{mean}$ at 45 min at 4° C. The resulting pellet is resuspended in 2 $vol_{org.\ wet\ weight}$ of PBS (Phosphate Buffered Saline) and stored at −80° C. until use.

Displacement Experiments with Compound 2

40-250 µg filtrate or membrane material are incubated in a total volume of 100 µl D-PBS (Dulbecco's Phosphate Buffered Saline containing 1 g/l $MgCl_2 \cdot 6H_2O$ & $CaCl_2$) containing 0.8 nM [$^{125}$I]AAP10 and increasing concentration of the test compounds AAP and Compound 2. Non-specific binding is determined at 10 µM AAP10 (CE2).

Calculations

Data from the displacement experiments are fitted to the equation:

$$f=(\text{Total}-ns)/(1+s/IC_{50})+ns$$

where Total is the total bound radioactivity at concentration s of labelled ligand, ns is non-specific binding and $IC_{50}$ is the concentration of test compound reducing specific binding (Total−ns) to 50% of maximum specific binding.

Results

TABLE 2

Displacement of 0.8 nM [$^{125}$I]AAP10 from murine heart tissue preparations (n.t.: not tested).

| Test Compounds | Filtrate $IC_{50}$ (nM) | Membranes $IC_{50}$ (nM) |
|---|---|---|
| AAP | 1.2 | n.t. |
| AAP10 (CE 2) | 1.2 | n.t. |
| Compound 2 | 3.6 | 1.2 |

The values given in Table 2 above are in the same order of magnitude (0.2 nM) as that given for AAP10 by Dhein et al.[33] using membranes from rabbit heart.

Method of in situ Binding on Intact Cells

CHO cell Cultures

CHO cells are seeded in 24-multi well dishes in a density of 7,900 cells/cm$^2$ (~15,000 cells/well) and grown for 3 Days In Vitro (DIV) in 1 ml/well of F-12K Nutrient Mixture supplemented with 10% Foetal Calf Serum (FCS) and 1000 units penicillin/1000 µg streptomycin (pen/strep) in an atmosphere of 5% $CO_2$ and 100% humidity at 37° C. The cell density has at that time increased to 295,000 cells/cm$^2$ (152 $pg_{prot}$/cell~85 $µg_{prot}$/well).

Pre-treatment

On the day of analysis cells are removed from the incubator and each well is washed twice with, depending on the experiment, either 2 ml pre-warmed (37° C.) or ice-cold (0° C.) D-PBS to remove serum. It is important to keep the period to a minimum during which cells are left without physiological solutions to avoid that they dry out during washing procedures. The cold washed cells are used directly for binding assays while the warm washed cells are used for experiments with glucose and oxygen deprivation.

Glucose and Oxygen Deprivation

Cells are incubated for 10 min in an $N_2$-atmosphere in glucose free D-PBS (pH 7.2) pre-equilibrated with $N_2$ for at least 10 min at 37° C. Control cells are incubated likewise for 10 min at 37° C., only, at normal atmospheric conditions and in D-PBS containing glucose (6 mM).

Binding Assay

The in situ binding is performed by a modified protocol based on the description by Koenig[34]. D-PBS is removed from the cell culture and 0.50 ml [$^{125}$I]AAP10 solution with or without unlabeled ligand or test compound is added. Cells incubate overnight at 4° C. to reach equilibrium. Each well, one at the time, is then rinsed rapidly with 2×1 ml D-PBS and left to dry.

0.25 ml of 0.5% Triton-X-100 (v/v) is added to each well and cells left for at least 1 h to solubilize. The extract is transferred to counting vials, the wells rinsed with 0.25 ml water and the rinse extract added to the corresponding vials. The vials are counted in a γ-counter.

TABLE 3

In situ binding, $IC_{50}$ (nM).

| Test compounds | $IC_{50}$ (nM) |
| --- | --- |
| AAP (CE1) | 0.8 |
| AAP10 (CE2) | 130 |
| Compound 2 | 0.5 |
| Compound 32 | 0.5 |
| Compound 24 | 65 |

These results demonstrate high affinity binding to CHO cells by several different substances of the present invention comparable to peptides of the prior art.

EXPERIMENTAL EXAMPLE 3

Effect of Compound 2 on cAMP Formation in CHO Cells

CHO cell Cultures

CHO cells are seeded in 96-well microtiter plates in a density of 6,000 cells/cm$^2$ (~2,000 cells/well) and grown for 4 days in vitro in 200 µl/well of growth media as described in the previous section.

Pre-treatment

On the day of analysis cells are removed from the incubator and washed twice with 200 µl pre-warmed (37° C.) D-PBS (pH 7.2) to remove serum. Cells are incubated for 10 min in glucose free D-PBS and an $N_2$-atmosphere as described in the previous section.

cAMP Efficacy Assay

CHO cells are incubated at 37° C. in D-PBS (pH 7.2) containing 6 mM glucose, 2.0 mM IBMX (phosphodiesterase blocker), 10 µM forskoline (stimulates cAMP formation) and increasing concentrations of test peptide. The reaction is stopped after 20 min by addition of 20 µl 0.5 M HCl and left for at least 20 min at room temperature.

The content of cAMP is analysed by mixing 20 µl of the acid cell extract into FlashPlate™ wells (NEN assay kit SMP001) containing 180 µl [$^{125}$I]cAMP tracer solution. FlashPlates™ are incubated overnight at 4° C. and plate bound radioactivity counted in TopCount (Packard Instrument). Data are calculated as described in the previous section.

Results

The inhibition of forskoline-stimulated cAMP formation of APP-like compounds in CHO cells indicates that AAP receptors are negatively coupled to the cAMP second messenger system. Moreover, it demonstrates the presence of functional AAP receptors in CHO cells.

TABLE 4

Inhibition of forskoline stimulated cAMP formation in CHO cells

| Test compounds | $EC_{50}$ (nM) |
| --- | --- |
| AAP | 53 |
| AAP10 (CE 2) | 11 |
| Compound 2 | 6.2 |

EXPERIMENTAL EXAMPLE 4

Phosphoinositol-analysis in Rat Primary Cardiomyocytes

Primary Cardiomyocyte Culture

Neonatal Wistar rats (1-2 days old) are used. Hank's calcium- and magnesium-free balanced salt solution, buffered with 10 mM HEPES is used for washing during cell separation procedures. The hearts are excised, the ventricles isolated and the tissue cut into small pieces. The myocardial cells are isolated by stepwise enzymatic degradation with collagenase 0.05%, as described by [35]. After repeated rounds of centrifugation and washing, the precipitated cells are resuspended in culture medium M199 with Earle's salt, 10% NCS, penicillin (75 U/mL), and streptomycin (75 U/mL) and pre-plated in a Petri dish for 90 minutes. The non-adherent cells are collected in the culture medium and plated in multidishes at 2.5*10$^5$ cells/well. The cultures are kept in a water-saturated $CO_2$-incubator at 37° C. The cardiomyocyte cultures are used for analyses after 6-7 days.

Analysis of Phosphoinositol-turnover

Cardiomyocyte cultures are incubated for 48 hours in culture medium containing 4 µCi/mL myo-[2-$^3$H]inositol to label the inositol phospholipids. On the day of analysis the medium is replaced by a buffer solution containing lithium and incubated at 37° C., as described by Meier et al.[36]. After at least five minutes this buffer is replaced by the same volume of buffer containing test compound and incubated for exactly 20 minutes. The reaction is stopped by rapid replacement of the buffer by ice cold 4% v/v perchloric acid (PCA) and incubation for at least 20 minutes at 0° C. The PCA-extract is neutralised and the [$^3$H]inositol phosphates are separated by anion-exchange chromatography using Amprep™ columns containing 100 mg SAX Quaternary amine. The [$^3$H]inositol mono-phosphates are eluted and radioactivity in the fraction measured by liquid scintillation counting.

Glucose and Oxygen Deprivation

Before adding test substances to the cultures, the cells are depleted of glucose and oxygen by incubating them in a $N_2$-atmosphere in glucose-free lithium-buffer for 10 minutes at 37° C. Control cells are incubated likewise only at normal atmospheric conditions and in a buffer containing glucose.

Figure 3:
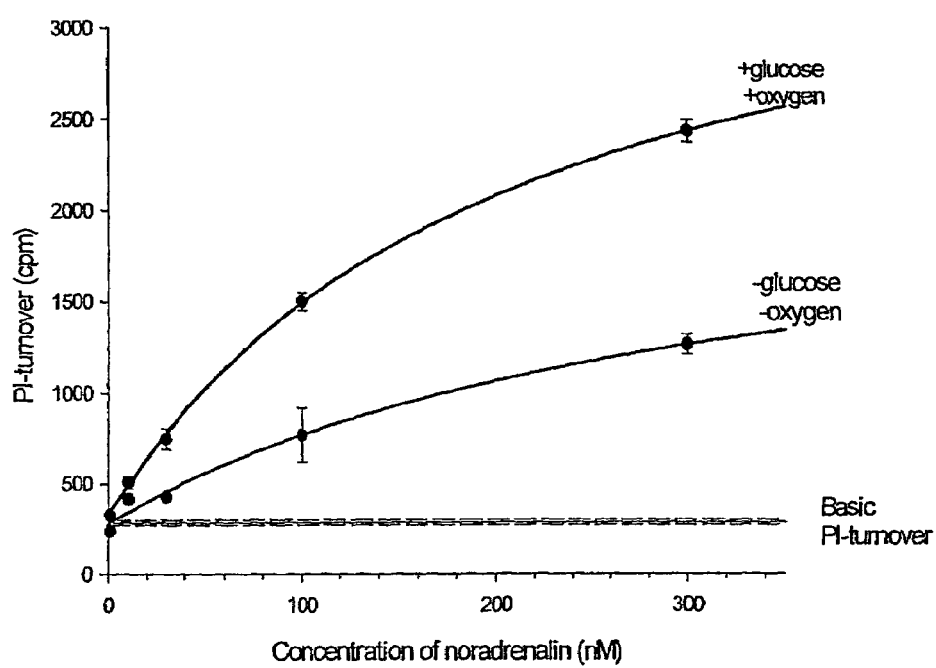
FIG. 3 is a graph showing that the ability of noradrenaline (300 nM NA) to stimulate phosphoinositol turnover is considerably reduced in cultures following 10 minutes of glucose and oxygen deprivation.

Noradrenaline (NA) stimulates phosphoinositol turnover in the cardiomyocyte cultures in a concentration-dependent manner. However, the ability of noradrenaline (300 nM NA) to stimulate phosphoinositol turnover is considerably reduced in cultures following 10 minutes of glucose and oxygen deprivation as shown in FIG. 3.

Under normal atmospheric and nutritional conditions we obtained an $E_{max}$ value of 3852±266 cpm and an $EC_{50}$ value of 203 nM ($SD_R$=1.2), whereas in cells subjected to an atmosphere of $N_2$ and depleted of glucose, an $E_{max}$ value of 2248±702 cpm and an $EC_{50}$ value of 303 nM ($SD_R$=1.7) were demonstrated.

To examine the effect of substances of this invention on the attenuated noradrenaline-induced increase in phospho-inositol turnover during cell stress induced by ischemia and glucose starvation, Compound 2 or APP10 (CE 2) were added to the cardiomyocyte cultures. Both substances very potently enhanced phospho-inositol turnover, with Compound 2 being the most potent. As illustrated in Table 5 below, the $EC_{50}$ value for AAP10 (CE 2) was 200 fold higher during normoxia and 10-fold higher during metabolic stress induced by anoxia and glucose deprivation than the $EC_{50}$ value for Compound 2.

TABLE 5

Enhancement of phospho-inositol turnover during metabolic stress induced by anoxia and glucose starvation by Compound 2 and AAP10

|  | $EC_{50}$ (nM) AAP10 (CE2) | $EC_{50}$ (nM) Compound 2 |
| --- | --- | --- |
| Normal conditions | 2000 | 10 |
| Glucose and oxygen deprivation | 100 | 10 |

Figure 4:
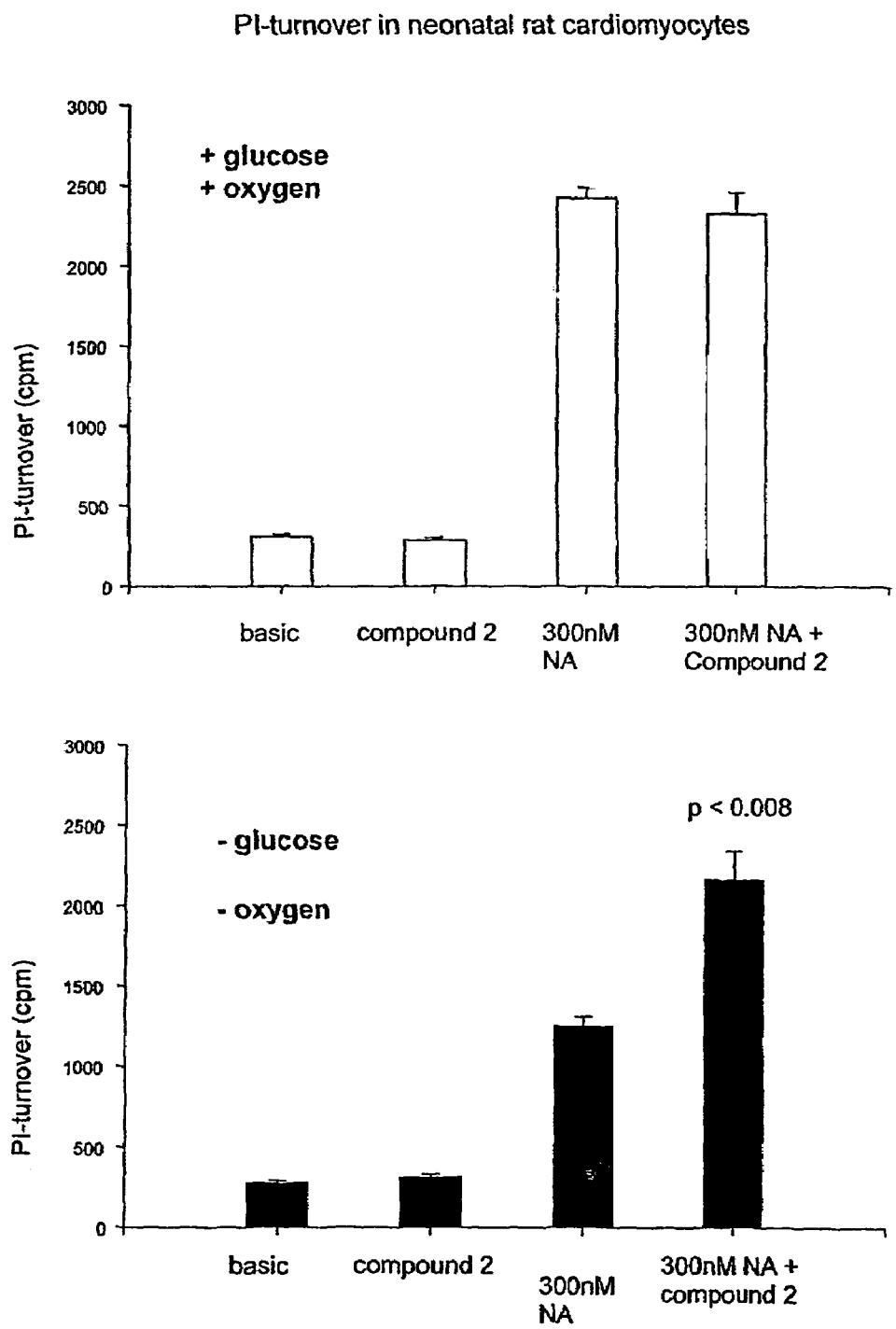
FIG. 4 is a set of graphs showing that addition of Compound 2 (100 nM) had no further effect on noradrenaline (300 nM) induced increase in phosphoinositol turnover in neonatal rat cardiomyocytes during control conditions, but in cells subjected to anoxia and glucose deprivation (metabolic stress), addition of Compound 2 (100 nM)+noradrenaline (300 nM) normalized the impaired phosphoinositol turnover, an increase that was about 70% higher than the increase effected by noradrenaline alone.

Addition of Compound 2 (100 nM) had no further effect on noradrenaline (300 nM) induced increase in phospho-inositol turnover in neonatal rat cardiomyocytes during control conditions, but in cells subjected to anoxia and glucose deprivation (metabolic stress), addition of Compound 2 (100 nM)+noradrenaline (300 nM) normalized the impaired phospho-inositol turnover as shown in FIG. 4, an increase that was about 70% higher than the increase effected by noradrenaline alone.

EXPERIMENTAL EXAMPLE 5

Calcium-induced Arhythmia Model in Mice

The antiarrhythmic effects of compounds of this invention were tested in an in vivo model of calcium-induced arrythmias according to the model of Lynch et al.[37]. Mice (25-30 g) were anaesthetised with a neurolept anaesthetic combination (Hypnorm® (fentanyl citrate 0.315 mg/ml and fuanisone 10 mg/ml)+midazolam (5 mg/ml)). Commercial solutions of hypnorm and midazolam were diluted 1:1 in distilled water and one part diluted Hypnorm® is mixed with one part diluted midazolam.

The anaesthesia was induced by s.c. administration in a dose of 0.05-0.075 µl/10 gram mouse. An i.v. cannula was inserted into the tail vein. The lead II ECG signal was recorded continuously by positioning of a stainless steel ECG electrodes on the right forelimb and on the left hind limb. The ground electrode was placed on the right hind limb. The signal was amplified (x5.000-10.000) and filtered (0.1-150 Hz) via a Hugo Sachs Electronic model 689 ECG module. The analogue signal was digitised via a 12 bit data acquisition board (Data Translation model DT321) and sampled at 1000 Hz using the Notocord HEM 3.1 software for Windows NT. After a 10-min equilibration period, the test sample of drug was injected into the tail vein. Mice pre-treated with vehicle were tested as a measure of the control level in untreated animals. The injection volume was 100 µl in all experiments. Infusion of $CaCl_2$ (30 mg/ml, 0.1 ml/min≈100 mg/kg/min (calciumchlorid-2-hydrat, Riedel-de Haën, Germany)) was started 3 min after i.v. administration of drug or vehicle.

The time lag to onset of 2nd degree AV-block was determined as the time from the start of $CaCl_2$ infusion until the first arrhythmic event occured. An event of 2nd degree AV-block was defined as intermittent failure of the AV conduction characterised by a P-wave without the concomitant QRS complex.

Responses were expressed relative to the time until 2nd degree AV-block occurred in vehicle treated mice. The maximal effect of each of the tested substances is summarized in Table 6 below.

Table 6, In vivo antiarrhythmic activity of compounds of the invention. +++ refers to >60% increase in time until arrhythmia; ++ refers to 30-50% increase in time until arrhythmia; + refers to 15-29% increase in time until arrhythmia; (+) refers to <15% in time until arrhythmia, and nd to "not determined".

| Cpd No. | Compound name | In vivo activity |
| --- | --- | --- |
| Group 1 | Comparative examples | |
| CE-1 | H-Gly-Pro-Hyp-Gly-Ala-Gly-OH (AAP) (SEQ ID NO: 88) | ++ |
| CE-2 | H-Gly-Ala-Gly-Hyp-Pro-Tyr-NH$_2$ (AAP10) (SEQ ID NO: 1) | +++ |
| | 3-(4-hydroxyphenyl)propionyl-Pro-Hyp-Gly-Ala-Gly-OH | |
| CE-3 | (HP5) (SEQ ID NO: 2) | ++ |

| Cpd No. | Compound name | In vivo activity |
|---|---|---|
| Group 2 Formula 2 | H-GAG-(Pa)₂-NH₂: Pa is any amino acid residue or a moiety of formula Z or Za; at least one of Pa is a D amino acid; preferably Pa is Hyp, P, G or A; | |
| 5 | H-Gly-Ala-Gly-D-Hyp-Pro-Tyr-NH₂ | ++ |
| 6 | H-Gly-Ala-Gly-D-Pro-Pro-Tyr-NH₂ | Nd |
| 7 | H-Gly-Ala-Gly-D-Pro-Ala-Tyr-NH₂ | Nd |
| 8 | H-Gly-Ala-Gly-Gly-D-Pro-Tyr-NH₂ | Nd |
| 9 | H-Gly-Ala-Gly-D-Hyp-Ala-Tyr-NH₂ | + |
| 10 | H-Gly-Ala-Gly-D-Hyp-D-Pro-Tyr-NH₂ | +++ |
| Group 3 Formula 3 | H-GAG-(Px)₂-Y-NH₂: Px is a moiety of formula Z or Za, where one Px is a moiety of formula II, IIa and the other Px is P or Hyp | |
| 11 | H-Gly-Ala-Gly-NCG-Pro-Tyr-NH₂ | Nd |
| 12 | H-Gly-Ala-Gly-T4C-Pro-Tyr-NH₂ | ++ |
| 13 | H-Gly-Ala-Gly-A2C-Pro-Tyr-NH₂ | Nd |
| 14 | H-Gly-Ala-Gly-Pc-Pro-Tyr-NH₂ | + |
| Group 4 Formula 4 | Ac-Y'-(Px)₂-GAG-OH: Y' is Y or F; Px is P or Hyp | |
| 1 | Ac-Tyr-Pro-Hyp-Gly-Ala-Gly-OH (SEQ ID NO: 19) | + |
| 15 | Ac-Tyr-Pro-Hyp-Gly-Ala-Gly-NH₂ (SEQ ID NO: 19) | Nd |
| Group 5 Formula 5 | Cys(Acm)-AAP10*cys(Acm) or Cys(Acm)retroAAP10*-Cys(Acm) | |
| 16 | H-Cys(Acm)-Gly-Ala-Gly-Hyp-Pro-Tyr-Cys(Acm)-NH₂ (SEQ ID NO: 90) | + |
| 17 | H-Cys(Acm)-Gly-Hyp-Pro-Tyr-Cys(Acm)-NH₂ (SEQ ID NO: 91) | Nd |
| 18 | H-Cys(Acm)-Tyr-Pro-Hyp-Gly-Ala-Gly-Cys(Acm)-NH₂ (SEQ ID NO: 92) | Nd |
| 19 | H-Cys(Acm)-Tyr-Pro-Hyp-Gly-Cys(Acm)-NH₂ (SEQ ID NO: 93) | Nd |
| Group 6 Formula 6 | X-D-Y-(D-Px)₂-G-D-A-G-NH₂ or the retro form thereof X-G-D-A-G-(D-Px)₂-D-Y-NH₂ or X-G-D-A-G-(D-Px)₂-D-Y-D-(Asn)-NH2: X is H or Ac; Px is a moiety of formula Z or Za, preferably Hyp or P; and (Asn) is optional, where both formulae optionally has one or more C or N isotopes | |
| 22 | H-Gly-D-Ala-Gly-D-Hyp-D-Pro-D-Tyr-NH₂ | Nd |
| 23 | H-Gly-D-Ala-Gly-D-Hyp-D-Pro-D-Tyr-D-Asp-OH | Nd |
| 2 | Ac-D-Tyr-D-Pro-D-Hyp-Gly-D-Ala-Gly-NH₂ | +++ |
| 24 | Ac-D-Tyr(3,5-di-I)-D-Pro-D-Hyp-Gly-D-Ala-Gly-NH₂ | Nd |
| 25 | Ac-D-Tyr(phenyl ring mono-iodo substituted)-D-Pro-D-Hyp-Gly-D-Ala-Gly-NH₂ | Nd |
| 26 | Ac-D-Tyr-D-Pro-D-Hyp-(1,2¹³C,¹⁵N-Gly)-D-Ala-(1,2¹³C,¹⁵N-Gly)-NH₂ | nd |
| Group 7 Formula 7 | H-(PX)ₙ-Y(N/Q)G-AG(PX)ₘ-NH₂: Px is P or Hyp, n is 1 or 2; m is 0 or 1; preferably m = 0 when n = 2 and m = 1 when n = 1 | |
| 27 | H-Pro-Tyr-Asn-Gly-Ala-Gly-Hyp-NH₂ (SEQ ID NO: 94) | nd |
| 28 | H-Hyp-Pro-Tyr-Asn-Gly-Ala-Gly-NH₂ (SEQ ID NO: 95) | (+) |
| Group 8 Formula 8 | H-G'-A-G'-(Px)₂-Y-NH₂: G' is Sar or Gly and at least one G' is Sar; Px is P or Hyp | |
| 29 | H-Sar-Ala-Sar-Hyp-Pro-Tyr-NH₂ | + |
| 30 | H-Gly-Ala-Sar-Hyp-Pro-Tyr-NH₂ (SEQ ID NO: 96) | ++ |
| Group 9 Formula 9 | X-(Y)ₚ-(Px)₂-GAG-NH₂: X is ASAL or AB; p is 0 or 1; phenyl ring of Y has optionally one or more halogen substitutent, preferably I; Px is P or Hyp | |
| 31 | ASAL-Pro-Hyp-Gly-Ala-Gly-NH₂ (SEQ ID NO: 2) | nd |
| 32 | ASAL(mono-iodo substituted)-Pro-Hyp-Gly-Ala-Gly-NH₂ (SEQ ID NO: 2) | +++ |
| 33 | AB-Tyr-Pro-Hyp-Gly-Ala-Gly-NH₂ (SEQ ID NO: 19) | nd |
| 34 | AB-Tyr(3,5-di-I)-Pro-Hyp-Gly-Ala-Gly-NH₂ (SEQ ID NO: 86) | nd |
| Group 10 Formula 10 | Cyclo(-GAG-(Px)₂-Y-N/Q-): Px is P or Hyp | |
| 35 | cyclo(-Gly-Ala-Gly-Hyp-Pro-Tyr-Gln-) (SEQ ID NO: 97) | ++ |
| 36 | cyclo(-Gly-Ala-Gly-Hyp-Pro-Tyr-Asn-) (SEQ ID NO: 98) | +++ |
| 37 | cyclo(-Gly-Ala-Gly-Pro-Pro-Tyr-Asn-) (SEQ ID NO: 99) | nd |
| Group 11 Formula 11 | Cyclo(-Y-(Px)₂-GA-(G)q-N/Q-) q is 0 or 1, phenyl ring of Y has optionally one or more halogen substituents, preferably I; Px is P or Hyp | |
| 3 | cyclo(-Tyr-Pro-Hyp-Gly-Ala-Gly-Asn-) (SEQ ID NO: 59) | +++ |
| 4 | cyclo(-Tyr-Pro-Hyp-Gly-Ala-Asn-) (SEQ ID NO: 57) | nd |

-continued

| Cpd No. | Compound name | In vivo activity |
|---|---|---|
| 38 | cyclo(-Tyr(3-I, 5-I)-Pro-4Hyp-Gly-Ala-Gly-Asn) (SEQ ID NO: 100) | nd |
| Group 12 Formula 12 | X-Zd-G(N/Q)Y-NH$_2$: Zd is a sequence of 0, 1, or 2 amino acid residues selected from G or A; X is H, Ac | |
| 39 | H-Gly-Ala-Gly-Asn-Tyr-NH$_2$ (SEQ ID NO: 84) | +++ |
| 40 | Ac-Gly-Asn-Tyr-NH$_2$ | ++ |
| 41 | H-Gly-Asn-Tyr-NH$_2$ | ++ |
| 42 | Ac-Ala-Gly-Asn-Tyr-NH$_2$ (SEQ ID NO: 85) | nd |
| 43 | H-Ala-Gly-Asn-Tyr-NH$_2$ (SEQ ID NO: 85) | nd |

As can be seen from the results shown in Table 6 a wide range of novel compounds of the present invention exhibit antiarrhythmic activity comparable to the compounds AAP, AAP10 and HP5 of the prior art.

EXPERIMENTAL EXAMPLE 6

Effects of Compound 2 on Isolated Perfused Rabbit Hearts

The Principle of the Langendorff Technique

The Langendorff technique provides a method of maintaining adequate metabolic requirements to an isolated heart, thereby enabling in vitro experiments on the entire heart for several hours. In the Langendorff set-up the heart is perfused retrogradely through a cannula inserted into aorta. When the perfusion solution enters aorta the resulting pressure in aorta closes the aortic valves, thereby preventing fluid from entering the heart chambers. Instead the perfusion solution enters the coronary circulation supplying the heart. In the Langendorff technique total flow in aorta thus equals coronary flow. The Langendorff experiments are performed using the ISOLATED HEART SIZE 5, Type 833 apparatus manufactured by Hugo Sachs Elektronik, Germany. The central component of this apparatus is the aortic block to which the heart is attached by a cannula. The aortic block is directly connected to an artificial flow resistor operated by a rotary knob thereby enabling adjustments of the afterload and hence the perfusion pressure. Perfusion fluid is delivered from a thermostated reservoir to the aortic block by tubes connected to a roller pump. The volume delivered by the pump can be adjusted to accommodate different needs. Excessive fluid flows back from the aortic block into the reservoir. Beneath the aortic block is a thermostated heart chamber that can be elevated to cover the heart. This set-up allows for continuous recordings of coronary flow, left ventricular pressure (LVP), perfusion pressure, a 12-lead ECG, and 8 monophasic action potentials (MAP's). The output of these multiple recordings is analyzed using the NOTOCORD HEM 3.3 software. This software enables calculations of a wide range of cardiac electrophysiological and hemodynamic parameters.

Perfusion Technique and Perfusion Media

The experiments are conducted in the constant pressure perfusion mode. The flow pump is set to give 70 ml/min and the afterload is set at 50 mmHg, ensuring a perfusion pressure of approximately 60 mmHg. The hearts are, unless otherwise specified, perfused with a pre-warmed (38° C.) modified Krebs-Henseleit solution with the following composition (mmol/l): NaCl: 118, KCl: 4.7, CaCl$_2$, 2H$_2$O: 2.52, KH$_2$PO$_4$: 1.18, Mg$_2$SO$_4$,7H$_2$O: 1.64, sodium pyruvate: 2.0, NaHCO$_3$: 24.88, glucose: 5.55. The solution is filtered through a 45 µm bottletop filter prior to use.

A pH of approximately 7.4 and adequate oxygen content of the solution is obtained by continuously bubbling with carbogen (95% O$_2$/5% CO$_2$). Volumes of 2 or more liters are allowed to equilibrate with carbogen for at least 20 min whereas volumes less than 1 liter are allowed to equilibrate for 10 min.

Anaesthesia, Surgery, and Experimental Procedures

Male Ssc:CPH rabbits (2.5-4.0 kg) obtained from Hvidesten, Allerød, Denmark are used. They are sedated with 1.2 ml Hypnorm® (fentanyl citrate 0.315 mg/ml and fluanisone 10 mg/ml) i.m. Ten min later anaesthesia is induced by slow i.v. administration of 0.55 ml Dormicum® (midazolam 5 mg/ml). In addition, they are given 500 IU of heparin i.v. to prevent coagulation.

The rabbits are placed on the back with the forelegs fixed to the sides and an incision is made to expose trachea. Tracheotomy is performed and the rabbits are ventilated with oxygen using a Ugo Basile rodent ventilator (tidal volume: 18 ml, frequency: 60 pr. min). The abdominal cavity is opened just caudally to the xiphoid proces and the abdominal muscles are cut laterally in both sides. To gain access to the thoracic cavity the diaphragm is opened substernally and the cut is extended bilaterally along the costal curvature. Mediastinum is cut as close to sternum as possible and the ribs are cut in both sides on a line parallel to sternum to allow the thoracic wall to be lifted in the cranial direction. The lifted thorax wall is fixed over the rabbit's head to provide a full overview of the thoracic cavity. The pericardial sac is opened and aorta is exposed. A loose ligature is placed around aorta. The caudal vena cava is clamped just cranially to the liver to reduce back flow to the heart and the cranial vena cava and pulmonary artery are opened to reduce volume overload of the heart. Aorta is opened and the cannula, connected to the aortic block by an extension tube filled with perfusion fluid, is immediately inserted into aorta to allow for artificial perfusion. The ligature is tightened and the heart is excised and transferred to the perfusion apparatus. The time from clamping of the caudal vena cava to insertion of the cannula is approximately 30 sec.

When the heart has been transferred to the apparatus an incision is made in the left auricle to allow for the insertion of a fluid filled balloon (size 12) in the left ventricle for measurements of left ventricular pressure. The volume of the balloon is adjusted to give an end-diastolic pressure of approximately 10 mmHg. The electrode ring for measurements of a 12-lead ECG is placed around the heart at the level of the coronary sulcus, with the tip of the left auricle between the 5$^{th}$ and 6$^{th}$ precordial lead. The 8 MAP electrodes are placed on the heart in direct contact with the epicardium. MAP5 and MAP6 are placed on the right ventricle whereas the other MAP electrodes are evenly distributed over the left ventricle. This method is similar to the one used by Zabel et al.[38] When all electrodes are in place the heart chamber is elevated to insure that the heart is immersed in 38° C. Krebs-Henseleit solution at all times.

Before the experiment is started, a ligature is placed around a major branch of the circumflex artery supplying a large part of the left ventricle. Both ends of the ligature are passed through a small plastic tube enabling induction of ischemia by pressing the plastic tube against the heart and clamping the ends of the ligature. All hearts are allowed to equilibrate for 15 min before the beginning of the experiment.

The time schedule for the experiment is as follows:

1. 15 min of perfusion with normal Krebs-Henseleit buffer (the equilibration period)
2. 15 min of perfusion with compound added to normal Krebs-Henseleit buffer (the normokalemic control period; t=0-15 min).
3. 15 min of perfusion with compound added to Krebs-Henseleit solution containing a reduced $K^+$ concentration (2.5 mM) (the hypokalemic control period: t=15-30 min).
4. Induction of regional ischemia followed by 30 min of perfusion with compound added to Krebs-Henseleit solution containing a reduced $K^+$ concentration (2.5 mM) (the hypokalemic ischemia period; t=30-60 min).

At the end of the experiment the hearts are perfused with Evans Blue dye to evaluate the area at risk of infarction. The atria's and the right ventricle are cut off and the remaining left ventricle is separated into the area stained by Evans Blue and the area that does not stain, i.e., the area at risk. The two areas are blotted dry using paper towel and weighed to determine the percentage area at risk of infarction.

Recordings

The following parameters are continuously recorded: coronary flow, left ventricular pressure, perfusion pressure, a 12-lead ECG, and 8 MAP recordings. The ECG and the MAP's are sampled at 2000 Hz, and the pressure and flow parameters at 500 Hz. Average action potential duration is calculated from the 8 MAP recordings as the average duration from the time of maximal depolarizatrion (time of dV/dt Max) to the time of 90% of repolarization. This duration is referred to as $APD_{90}$ and the $APD_{90}$ dispersion is measured as the standard deviation of the 8 measurements of $APD_{90}$.

Results

Figure 5:
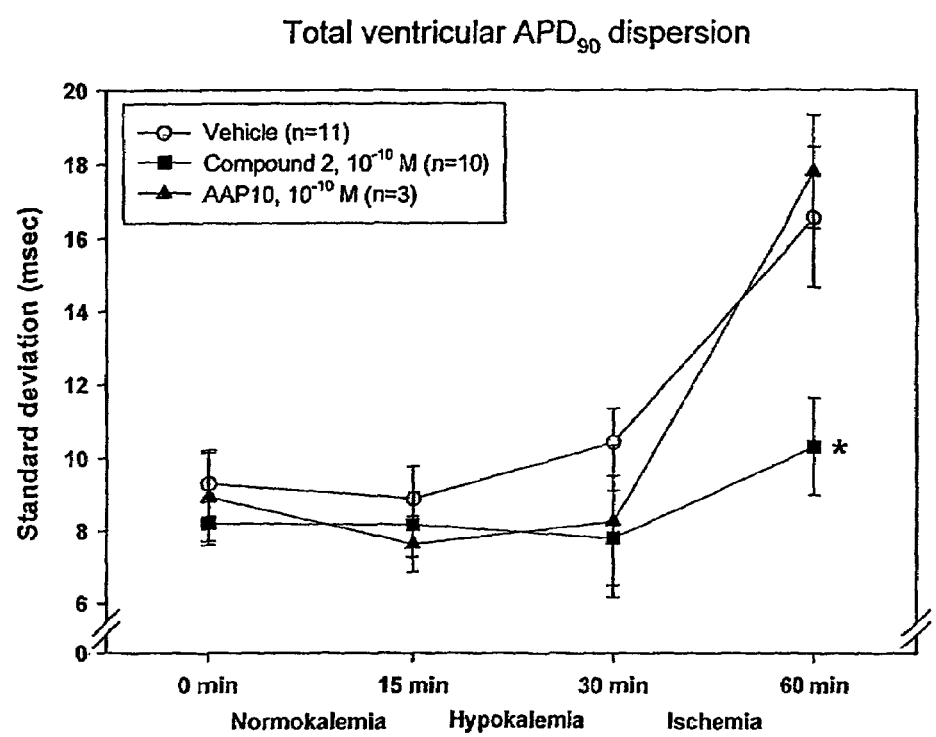
FIG. 5 is a graph showing rabbit hearts perfused with either Krebs-Henseleit buffer alone (vehicle; n=11 experiments), $10^{-10}$ mol/l Compound 2, (n=10 experiments), or $10^{-10}$ mol/l of AAP10 (CE2; n=3 experiments). The increase in $APD_{90}$ dispersion observed during hypokalemic, acute myocardial ischemia in vehicle-treated rabbit hearts was prevented by $10^{-10}$ mol/l of Compound 2, but not by $10^{-10}$ mol/l of AAP10 (CE2).

As illustrated in FIG. 5, three groups were studied. The rabbit hearts were either perfused with Krebs-Henseleit buffer alone (vehicle; n=11 experiments), $10_{-10}$ mol/l Compound 2, (n=10 experiments), or $10_{-10}$ mol/l of AAP10 (CE2; n=3 experiments). The increase in $APD_{90}$ dispersion observed during hypokalemic, acute myocardial ischemia in vehicle-treated rabbit hearts was prevented by $10^{-10}$ mol/l of Compound 2, but not by $10^{-10}$ mol/l of AAP10 (CE2). These findings demonstrate that Compound 2 prevents the increase in electrical dispersion during ischemia and it suggests that the antiarrhythmic properties of Compound 2 are related to this mechanism. It has previously been reported that AAP10 (CE2) is able to reduce the dispersion of the epicardial activation-recovery interval and diminish alterations of epicardial activation patterns induced by regional ischemia in the rabbit with maximal effect at a concentration of $10^{-8}$ mol/l [39]. In our experiments, Compound 2 effectively prevented the increase in electrical dispersion induced during ischemia at a concentration of $10^{-10}$ mol/l while AAP10 (CE2) was ineffective at this concentration. These differences were not due to differences in the size of the myocardial infarction because the decrease in coronary flow during ischemia and the area of risk were similar in all groups. These results indicate that Compound 2 is more potent that AAP10 (CE2).

EXPERIMENTAL EXAMPLE 7

Effect of Compound 2 on Ventricular Reentry Arrhytmias in Dogs

The influence of gap junctions in arrhythmias has been clarified in studies on the influence of connexin 43 (Cx43) in conduction properties of the ventricle[33]. In a heterozygote knockout mouse deficient in Cx43, there is two times the frequency of spontaneous VT with coronary artery occlusion (CAO)[3]. Ischemia down regulates the effect of Cx43 after 6 hours in the dog showing 60% decrease in end-to-end CX43 and 49% decrease in side-to-side Cx43 [40], probably secondary to dephosphorylation. In subacute ischemia in the dog, epicardial reentry is facilitated in areas where Cx43 is decreased[25]. Thus reentrant mechanisms may be critically dependent on ischemia mediated down regulation of CX43 and presumably resistance of gap junctions making heterogeneity of recovery and conduction properties predisposing to VT and VF.

In the studies described below, we examined the effect of Compound 2 on reentry arrhythmias during myocardial ischemia elicited by CAO of the anterior descending artery.

Animal Preparation

Three dogs were studied in the anesthetized, open chest state to facilitate electrode placement for mapping. α-chloralose was given as a bolus (200 mg/kg) and then a constant infusion at 8 mg/kg/hr (dissolved in polyethylene glycol, MW=200). The femoral vein and artery was cannulated for administration of fluid and drugs and for measurement of ascending aortic pressure, respectively.

Electrophysiological Methods

The sinus node was clamped and the atrial appendage was paced with a programmable stimulator with constant current outputs at two times diastolic threshold. Pacing rate was $\geq$200 b/min to control heart rates. Ventricular pacing one pole of a multipolar needle in the normal zone employed an anode (7 $cm^2$ stainless steel) in the abdominal muscle. Endocardial Effective Refractory Period (ERP) was measured by the standard extrastimulus technique. Late ventricular diastolic threshold was measured during each intervention; the pacing current was four times threshold.

Recording of Electrogram

Test sites were chosen along the shaft of 16 pole needles (J. Kassell, Fayetteville, N.C.); each pole completely surrounds the needle shaft to prevent directionality of needle orientation from recording of adjacent Purkinje strands. Six bipolar electrograms (1 mm spacing) were recorded sequentially down the shaft of the needle by amplifying up to 1000 times, filtering from 3-1300 Hz and recording via oscilloscope during atrial pacing. Four intramural electrograms are recorded on each multipolar needle. Epicardial electrograms are activated latest on each needle. An array of 23 multipolar electrodes was used with 17 in the infarcted risk zone of the anterior descending coronary artery and 6 in the surrounding normal zone as decribed in detail by Xing and Martins[41]. Interneedle distance measured on epicardium varies over 6-10 mm in dogs weighing 12-16 kg.

Arrhythmia Induction

The endocardium was paced at the base, apical septum and lateral free wall just outside the risk zone. After ERP was determined, the S1-S2 interval was prolonged by 4 msec>ERP and a S3 was added to the protocol initially with an S2-S3 interval equal to 50 msec >S1-S2. The intervals were shortened until failure to capture. If ventricular tachycardia was not induced at any pacing site, a third (S4) and fourth (S5) extrastimulus was added. We performed a full ventricular tachycardia induction protocol prior to CAO to exclude artifact ventricular tachycardia due to needle mass or ischemia due to needles compromising blood flow. After confirming physiological blood gases and adequate anesthesia the anterior descending CAO was ligated. After 60 minutes the infarct size is nearly 75% of the risk zone and further enlargement of the infarct zone is negligible. Then ventricular tachycardia was induced at least twice before interventions. Repeat testing was done every 20 minutes and continued up to 3 hours after CAO. Normal cardiac muscle ERP was recorded with each intervention.

Arrhythmia Mapping

Epicardial mapping was perfomed using a computer based system from BARD Electrophysiology Inc. The software takes 64 channels of data at 12-bit resolution with a sampling frequency of 1 kHz/channel. Filtering was from 30-300 Hz. Eight-second windows are triggered externally including up to 8 sec of data prior to the trigger signal. This system is used to record from the outer, epicardial 2-3 bipoles on each recording electrode.

Customized computer software system was used to resolve the Purkinje signals from the inner 3 bipoles on each endocardial multipolar electrode by sampling at 3 kHz per channel. The filters incorporate Purkinje frequency (3-1300 Hz). The sampling rate was 235 kHz. The PC was interfaced with an amplifier consisting of an analog signal multiplexor and 64 instrument amplifier circuits. Each had selectable gain (up to 1000), and bandwidth cutoffs. Acquisition, processing and visualization of the electrophysiological data was performed by software. High-speed acquisition, allowed us 14 sec of data including up to 8 sec before a trigger signal.

Mapping Analysis

Mapping analysis was done off line. The computer selects activation times using the first maximum dv/dt. Electrograms were considered uninterpretable and excluded from maps only if not reproducible with stimuli; there was no exclusion based on voltage of electrograms. Electrotonic or far field potentials are considered present when substantial voltage and dv/dt loss occurs in a complex with coupling intervals shorter than refractoriness. Isochrones are drawn by hand. Ventricular tachycardia mechanisms are defined as follows: Reentrant ventricular tachycardia occurs where the electrode recording the earliest activity, occurring after unidirectional block is located immediately adjacent to the site of the latest activation from the previous complex and diastolic activity is recorded between complexes. Epicardial reentry is most always recorded in acute ischemia, so retrograde activation (epicardial to endocardial) of the wall is observed.

Experimental Protocol

After instrumentation of the heart and one hour of CAO had taken place, pacing protocols to induce ventricular tachycardia were performed to confirm either reproducible inducibility (induction twice of ventricular tachycardias with similar surface morphologies) or failure of inducibility (pacing all three sites twice without ventricular tachycardia over one hour). In three dogs with reinducable ventricular tachycardia a reentry mechanism was identified. In these three dogs, Compound 2 was given as an i.v. bolus injection followed by 30 min constant infusion at three dose levels in two dogs, while the third dog was treated with saline. Extrastimulus testing was then repeated through the entire protocol at all sites to determine if the ventricular tachycardia was present, or not. Compound 2 was administered i.v. at three dose levels in order to produce plasma concentrations of $10^{-10}$ M (bolus: 0.1 µg/kg; infusion: 2 ng/kg/min), $10^{-9}$ M (bolus: 1.1 µg/kg; infusion: 21 ng/kg/min), and $10^{-8}$ M (bolus: 11 µg/kg; infusion: 210 ng/kg/min), respectively.

Results

Figure 6:
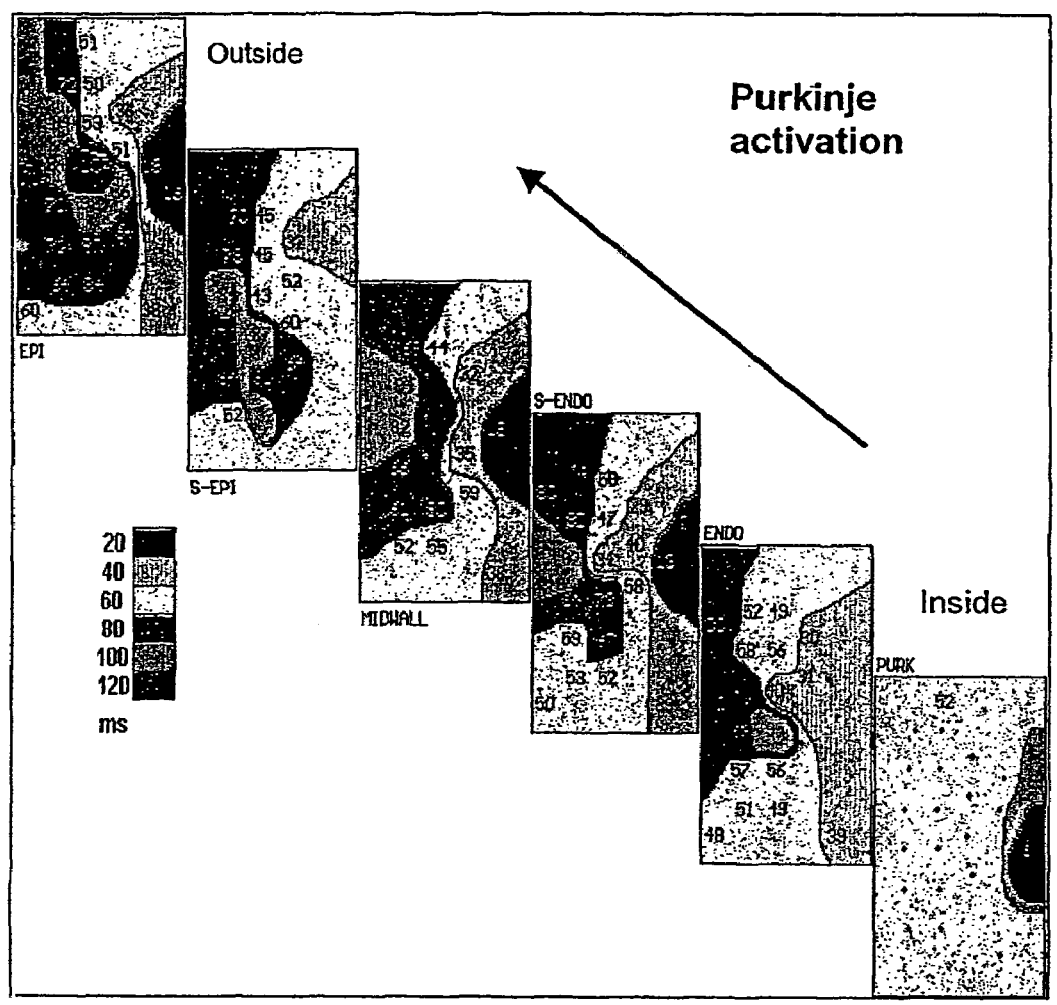
FIG. 6 is an activation map after septal stimulation is presented which failed to elicit ventricular tachycardia.

The first animal, from which FIGS. 6-9 are enclosed, was studied after induction of sustained monomorphic VT was induced only from the lateral ventricular pacing site twice in succession occurring at 2 hours and 10 minutes and repeated at 2 hours and 20 minutes following CAO. In FIG. 6, an activation map after septal stimulation is presented which failed to elicit VT. This shows the normal orthograde activation pattern with early activation of the PURK pacing site activated at 6 msec after the stimulus and the late activation of the epicardial site activated latest at 107 msec. Note that the adjacent activation time at 86 msec immediately east and south of the latest activation on the epicardium is E-S on FIG. 7. Epicardial activation of the first complex of the VT, which starts at −44 msec prior to the onset of the surface QRS and which corresponds to the electrogram recorded at E-C in FIG. 7.

Figure 7:
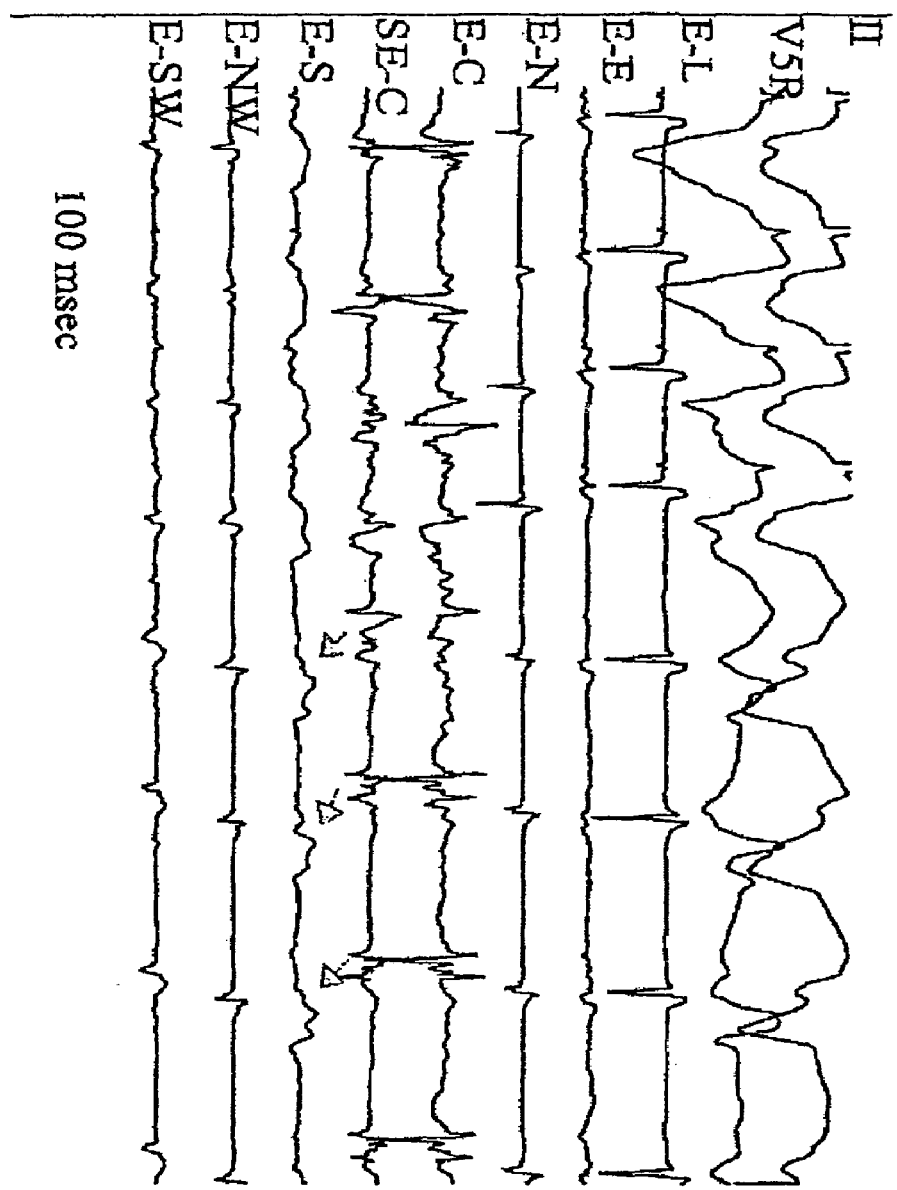
FIG. 7 is a graph showing the sustained monomorphic ventricular tachycardia (VT) induced by stimulation at the lateral epicardial ventricular pacing site caused a reentry circuit.

In FIG. 7, the sustained monomorphic ventricular tachycardia (VT) induced by stimulation at the lateral epicardial ventricular pacing site causing a reentry circuit is shown. Activation proceeds in a double loop reentry activating first at −17 msec and then proceeding to 57 msec on the northwest loop. The southeast loop activating first to 2 msec, 31 msec and then to 57 msec. The protocol which induced VT was S1-S2=150, S1-S3=280, S1-S4=390, S1-S5=490 msec. The figure illustrates epicardial (E-) electrograms recorded with surface lead ECG II and V5R during the second through fifth premature extra-stimuli (seen best on E-L) with ensuring 4 complexes of VT. The electrograms are recorded from the lateral, border zone (L) pacing site and east (E), north (N), centrally (C), subepicardially (SE), below E-C, as well as south (S), and northwest (NW), and southwest (SW) of E-C. E-C show gradually dissociated electrograms with the last premature showing a block of the second component (perpendicular lines). Adjacent conduction delay on ES allowed for conduction to proceed around and back to the central site (EC) with the reentrant excitation continuing between EC and ES (straight line and line with arrow).

Figure 8:
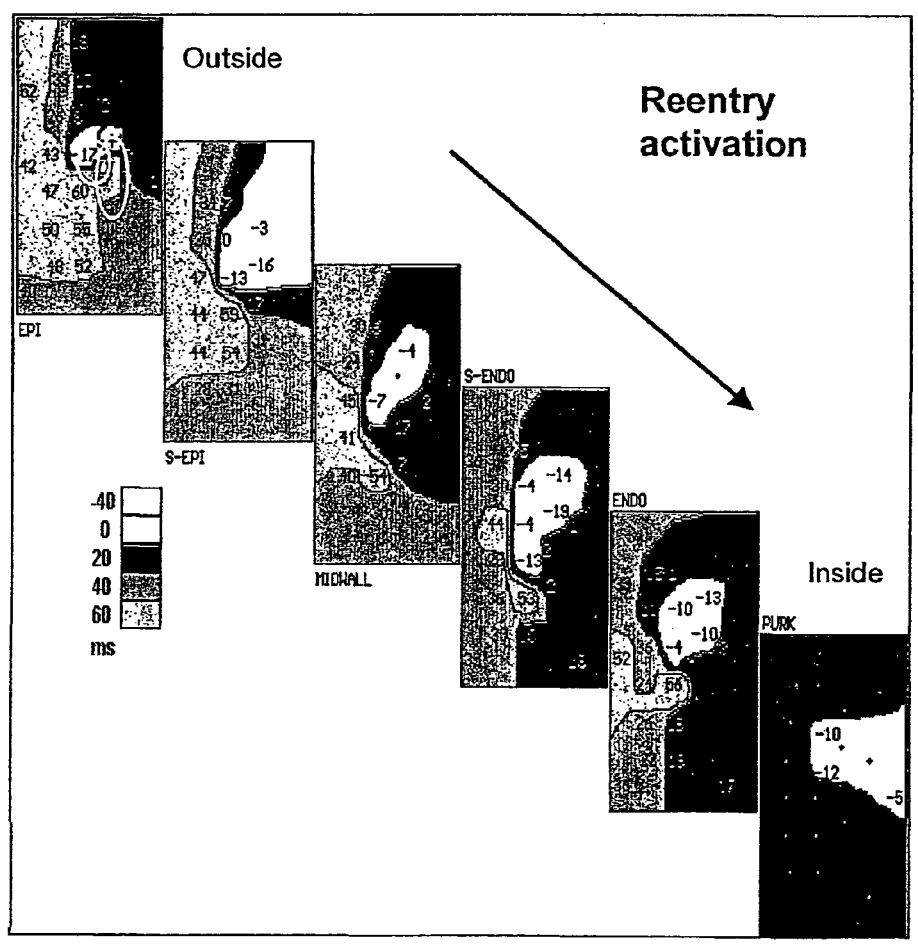
FIG. 8 is an activation map during epicardial activation of the first complex of the VT, which starts at −44 msec prior to the onset of the surface QRS and which corresponds to the electrogram recorded at E-C in FIG. 7.

FIG. 8 illustrates the activation map during epicardial activation of the first complex of the ventricular tachycardia, which starts at −44 msec prior to the onset of the surface QRS and which corresponds to the electrogram recorded at E-C in FIG. 7. Activation proceeds in a double loop reentry activating first at −17 msec and then proceeding to 57 msec on the northwest loop. The southeast loop activating first to 2 msec, 31 msec and then to 57 msec. This activation map also illustrates the retrograde activation of the ventricular wall during the reentry arrhythmia.

Figure 9:
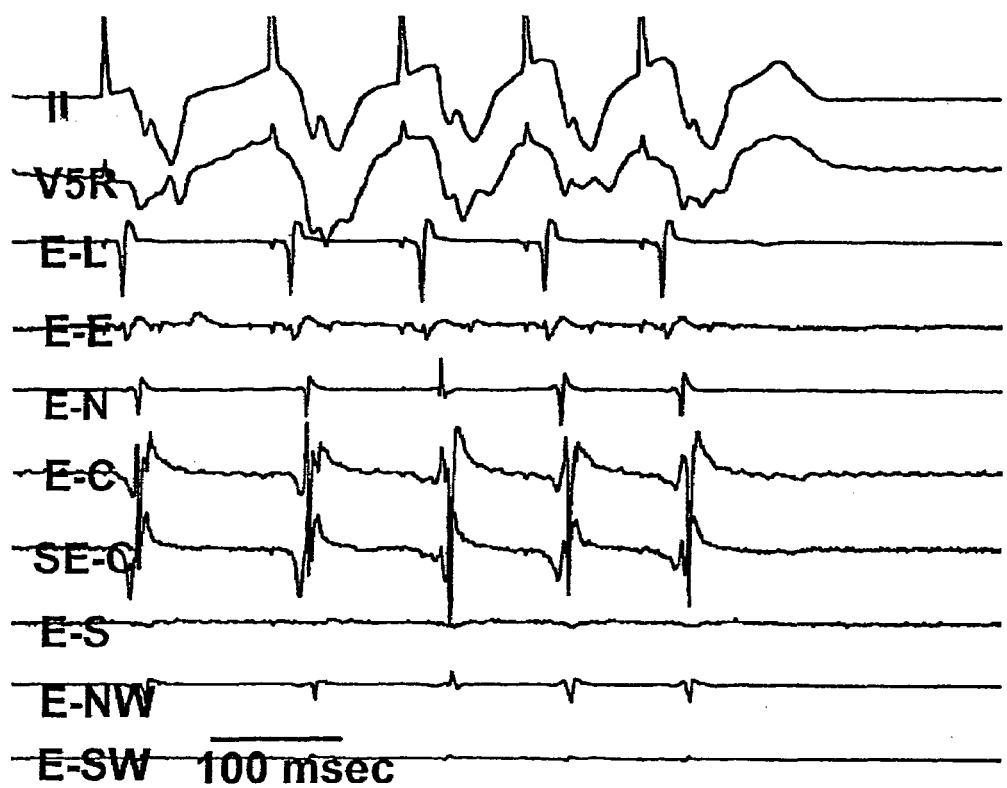
FIG. 9 is a graph showing electrocardiographic recordings after i.v. administration of the lowest dose of Compound 2. These results demonstrate that Compound 2 effectively blocked reentry VT in this dog.

Compound 2 was administered in three incremental IV doses, which did not alter mean arterial pressure (MAP=80 mmHg). Effective refractory period in control was 150 msec, 154 msec after the lowest dose and was 148 msec at the highest and last dose. The VT that was inducible was typical epicardial reentry shown in FIGS. 7 and 8. After the first dose of Compound 2 (bolus: 0.1 µg/kg; infusion: 2 ng/kg/min), VT was no longer inducible despite the fact that the induction protocols induced VT prior to administration of Compound 2 were reproducibally achieved; the protocol which induced VT prior to drug administration was S1-S2=150, S1-S3=280, S1-S4=390, S1-S5=490 msec and during infusion of Compound 2 the intervals were 150, 270, 370 and 470 msec, respectively. No VT was inducible up to an hour and a half after infusion of the lowest dose of Compound 2 was started. Electrocardiographic recordings after i.v. administration of the lowest dose of Compound 2 are shown in FIG. 9. These results demonstrate that Compound 2 effectively blocked reentry VT in this dog.

A second dog was studied with inducible VT, this time from two border-zone, pacing sites located laterally and septally. Again Compound 2 produced no change in MAP, which started out 90 mmHg and ended at 90 mmHg. Effective refractory period in the two sites of induction remained at 163 and 144 msec respectively throughout the testing period of Compound 2, which started 85 minutes after CAO and continued for 2 further hours. After the lowest dose of Compound 2, the VT induced from the lateral wall was no longer inducible; mechanism of this VT was epicardial reentry, very similar to that shown in FIGS. 7-9. The VT induced from the septal site was also epicardial reentry prior to administration of Compound 2, but following i.v. administration of Compound 2 the epicardial reentry was completely blocked. Thus in these two experiments epicardial reentrant VT was inducible prior to induction of the lowest dose of Compound 2 and following administration of the substance no reentry was reinducible at any dose. Finally one additional animal underwent electrophysiologic testing during the time frame used in the two experiments described above without introduction of Compound 2 but with saline. Epicardial reentry was induced one hour after CAO and the same VT morphology and reentrant mechanism was induced 1½-2½ hours of CAO. Thus the reproduceability of reentrant VT in this time controlled experiment is consistent with Compound 2 being an effective antiarrhythmic compound during conditions with reentry arrhythmias.

These experiments demonstrate that Compound 2 is efficacious in the prevention and/or treatment of lethal reentry arrhythmias. Thus, it is a purpose of the present invention to provide compounds for the preparation of medicaments useful in prevention and/or treatment of cardiac reentry arrhythmias of either supraventricular or ventricular origin. This purpose is achieved with the present peptide compounds, such as the compounds of formulae I to VIII, formulae 2 to 12, and the compounds of tables 1 and 8 herein, more specifically the compounds of Synthesis Examples 1-55 herein.

EXPERIMENTAL EXAMPLE 8

Effect of Gap Junction Openers on Bone Cells

Background

Osteoblasts, which are the bone-forming cells, and osteocytes are well connected. Osteoblast-osteoblast, osteoblast-osteocyte, and osteocyte-osteocyte connections have been found in bone slices, examined by electron microscopy[42]. The most interesting connexin in relation to bone is Cx43, like in the heart. In bone cells, the expression of these proteins is linked to the expression of some osteoblast specific proteins. Calciotropic hormones can also regulate the expression of the gap junction proteins.

Human osteoblasts (HOB) and bone marrow derived stromal cells (BMSC) are both shown to express Cx43 and Cx45. They are functionally coupled as demonstrated with the Lucifer Yellow (LY) dye transfer technique[43]. The rat osteoblastic cell lines differ from the human primary cultures; the ROS 17/2.8 cells express only Cx43 and are well coupled, whereas UMR 106-01 predominantly express Cx45 and are poorly dye coupled[44]. Both rat osteoblastic cell lines are electrically coupled. Transfection of Cx43 into the UMR cells resulted in cells highly dye coupled. Thus, Cx43 permits transfer of LY and other larger molecules, whereas Cx45 does not permit this passage. In contrast, introduction of Cx45 to Cx43 expressing cells decreases the dye coupling. In osteoblast differentiation, Cx43 expression changes; thus, the more mature the osteoblasts is, the higher is Cx43 expression[45].

The effect of different stimuli on bone cells and the relation to changes in gap junction communication has been investigated. It is well known that moderate mechanical stress on bone, increases the bone density. To imitate this situation, ROS 17/2.8 cells were exposed to cyclic stress, which resulted in an increase in dye coupling of the cells. Cyclic stress applied to the poorly coupled UMR 106-01 cells resulted in an increase in dye coupling as well, but less dramatically compared to the ROS cells. No increase in mRNA for Cx43 was found, but more phosphorylated forms of Cx43 were found, indicating that cyclic stress on osteoblastic cells increases gap junctional communication between the cells by modulating intracellular localization of the gap junction protein Cx43. The same group has shown that transfection of Cx43 into the poorly coupled UMR 106-01 cells not only increases the dye coupling[46], but also increases the expression of the products of mature osteoblasts, osteocalcin and bone sialoprotein (BSP). Decreasing the coupling between osteoblastic cells (ROS) by transfecting Cx45 into the cells decreases the expression of osteocalcin and BSP, genes pivotal to bone matrix formation and calcification. A recent study showed that Cx43 knock-out mice have deficient bone formation and development compared to wild type mice[47]. Thus, a communicating intercellular network is required for the full elaboration of a differentiated osteoblastic phenotype as well as normal bone formation and turnover. Deficient gap junctional communication may therefore result in increased bone loss.

Gap junctions have also been shown to be partly responsible for the propagation of intercellular calcium signals in bone cells. Mechanical stimulation of one human osteoblast in a cell monolayer in vitro induces a calcium pulse, which is propagated to a number of surrounding cells. The propagation of this signal involves the passage of a messenger molecule through gap junctions, with subsequent activation of neighbouring cells[48;49]. These signals are probably propagated throughout the cellular network in bone in vivo in response to mechanical stimuli, and might be responsible for the increased bone formation in response to mechanical loading on bone.

Gap junctional communication and the effect of calciotropic hormones are linked. $1,25(OH)_2$ vit.$D_3$ stimulation of human skin fibroblasts has been shown to enhance communication via gap junctions as well as increase the levels of Cx43 protein and mRNA[50], but only in the presence of functional vitamin D receptors (VDR). Loss of Cx43 expression is shown to decrease the responsiveness of cells to PTH, without any change in the PTH receptor number or cAMP response[51]. The other way round, PTH and PGE2 enhance gap junctional communication in osteoblastic cell cultures via two mechanisms; an initial rapid redistribution of Cx43 to the cell membrane, and a later stimulation of Cx43 gene expression[52]. Thus, modulation of intercellular communication represents a mechanism by which osteotropic factors regulate the activity of bone forming cells.

Gap junctional intercellular communication may very well prove to be one of the most important mechanisms by which bone cells coordinate their activities and responses to mechanical and hormonal stimuli. Thus, if gap junctional communication between bone cells could be increased pharmacologically, osteoblast activity could be increased, enhancing bone formation in vivo.

Cardiac myocytes are also connected by gap junctions, and like in osteoblasts, the predominant connexin is Cx43. Certain compounds have been found to increase gap junctional communication between cardiac myocytes of which the artificially synthesized AAP10 (CE2) is the best investigated. Cardiac myocytes respond to ischaemia with a decrease in cellular coupling. In in vitro experiments, adding AAP10 (CE2) to cardiac myocytes exposed to ischaemia, some of the lost cellular coupling was restored. If cardiac myocytes can respond to this group of compounds with an increased gap junctional coupling, osteoblasts might do the same. In this case, it is evident that the increase in cellular coupling very well could be accompanied by an increase in osteoblast maturation and activity, and subsequent increase in bone formation. To investigate this hypothesis, we have examined the effect of Compound 2 on GJIC in human osteoblasts and rat osteosarcoma cells. Moreover, we have studied the effect of Compound 2 on a marker (i.e., alkaline phosphatase) for human osteoblast activity and bone formation.

Methods

Cell Culture

Human osteblast cells (hOB): Cells were isolated from human bone marrow obtained by puncture of the posterior iliac spine of healthy volunteers (aged 20-36): 10-15 ml marrow material was collected in 15 ml PBS+Ca,Mg (Life Technologies, Cat.No. 14040) with 100 U/ml Heparin (Sigma, Cat.No. H-3149). The mononuclear fraction of the marrow was isolated on a Lymphoprep gradient (Nycomed Pharma, Cat.No. 1001967), by centrifugation at 2200 rpm for 30 min. After harvesting, the mononuclear fraction was washed once with culture medium and centrifuged at 1800 rpm for 10 min. Subsequently cells were counted and plated in culture medium at $8 \times 10^6$ cells/100 mm dish. hOB medium (all reagents obtained from Life Technologies): MEM w/o Phenol Red w/Glutamax (Cat.No. 041-93013) supplemented with 10% heat inactivated fetal calf serum (Cat.No. 10106) and 0.1% Penicillin/Streptomycin (Cat.No. 15140). Medium was changed the following day and the cells were cultured at 37° C. in 5% $CO_2$ with medium change every 7 days. After 3-4 weeks of culture the cells had reached 70% confluence. The medium was then supplemented with 100 nM Dexamethasone (Sigma, Cat.No. D-4902) for 7 days. Cells were then plated for video imaging experiments: a 25 mm #1 glass coverslip was placed in a 35 mm dish (or each well of a 6-well multidish), cells were plated at $2.5 \times 10^5$ cells/coverslip and cultured for 2-3 days before use.

ROS 17/2.8 cells: Cells were cultured in 100 mm dishes at 37° C. with 5% $CO_2$ and medium change every 2-3 days. ROS medium (all reagents obtained from Life Technologies): MEM (Cat.No. 31095) supplemented with 10% heat-inactivated calf serum (Cat.No. 16170), 1% NEAA (Cat.No. 11140), 1% Sodium Pyruvate (Cat.No. 11360), 1% L-Glutamine (Cat.No. 25030) and 0.1% Penicillin/Streptomycin (Cat,No. 15140). For video imaging experiments, cells were plated on coverslips at $2-3 \times 10^5$ cells/coverslip and cultured for 2-3 days before use.

Measurement of Calcium Waves

The cells cultured on coverslips were loaded with 5 μM fura-2-AM (Molecular Probes, Cat.No. F-1221), for 30 minutes at 37° C., and incubated in fresh medium for 20 minutes. Coverslips were then affixed to a PDMI-2 culture chamber (Medical Systems Corp.), maintained at 37° C. with superfused $CO_2$, on a Zeiss Axiovert microscope. Intercellular calcium waves were induced by mechanical stimulation of a single cell using a borosilicate glass micro pipette affixed to an Eppendorf 5171 micromanipulator. Imaging was performed using a MetaMorph imaging system (Universal Imaging). The excitation light (340 and 380 nm) was provided by a monochromator (T.I.L.L. Photonics GmbH). Images were acquired with an intensified CCD camera (Dage MTI) and digitized with a Matrox MVP image processing board.

Microinjection

The cells cultured on coverslips were placed in the microscope as described above. Microinjections were performed using the Eppendorf 5171 micromanipulator and the Eppendorf Transjector 5346 system. A micropipette was loaded with a 10 mM Lucifer Yellow (LY) solution (Sigma, Cat.No. L-0259). A cell in the monolayer was carefully injected with LY for 30 seconds, the micropipette was removed from the cell and after 30 seconds the number of cells that showed dye transfer were counted. The excitation light for LY was 430 nm, and images were acquired as described above.

Alkaline phosphatase Assay

Day 1: Cells were plated in 96-well plates at a conc. of 8000 cells/well (hOB) or 3000 cells/well (ROS) in 200 μl normal culture medium.

Day 2: Medium was changed on the cells.

Day 4: (Day 3 for ROS): Cells were washed with 200 μl MEM, 0.1% BSA (Sigma, Cat.No. A-9418). 200 μl MEM, 0.1% BSA containing various concentrations of Compound 2 was added to the cells, and culture was continued for 4 days (2 days for ROS cells).

Day 8: (Day 5 for ROS): Alkaline Phosphatase (ALP) assay is a colorimetric endpoint method for measuring enzyme activity, and was done using Alkaline Phosphatase Kit (Sigma, Cat.No. 104-LL): Cells were washed once with 200 μl PBS+Ca,Mg. 100μl Alkaline Buffer Solution was added to each well and plate was placed at 37° C. for 10 min. 100 μl Substrate Solution was added to each well and plate was incubated at 37° C. for 30 min. 100 μl 2.0 N NaOH was added to each well to stop the reaction. Absorbance was measured using a plate reader at 405 nm.

Effects of Compound 2 on GJIC

Figure 10:
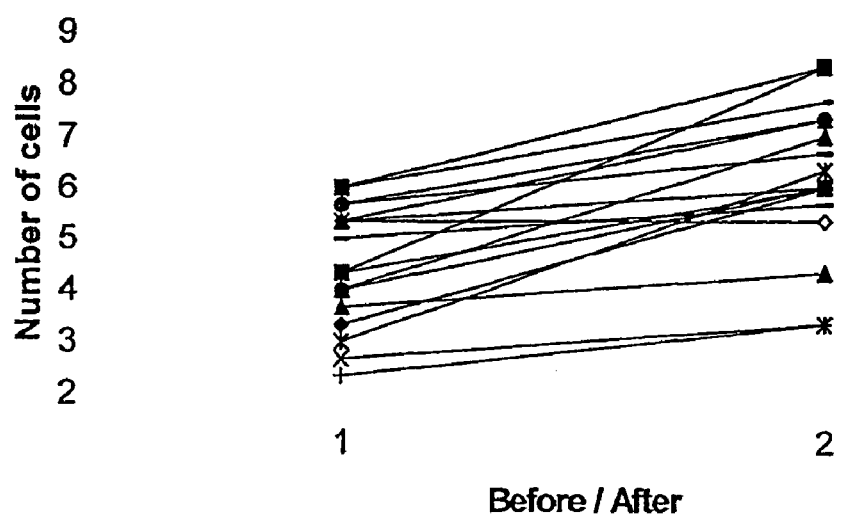
FIG. 10 is a graph showing that, after 10 minutes of incubation with $10^{-8}$ mol/l Compound 2, one single cell stimulated mechanically exhibited increased in intracellular calcium concentration, with a subsequent propagation of the wave, which extended to an average of 6.2 cells, a significant increase compared to before adding Compound 2 (4.5 cells).

In order to assess the ability of gap junction modifiers to increase communication via gap junction mediated intercellular calcium signals, monolayers of human osteoblastic cells on glass coverslips were loaded with fura-2. During real-time imaging, a mechanical stimulation with a glass micropipette was performed. An increase in the intracellular calcium appeared, with a subsequent spread of the signal to surrounding cells. The average number of cells in the wave was 6.5 cells. Next, 100 μM adenosine tri-phosphate (ATP) was added in order to desensitize purinergic receptors. After desensitization, the calcium wave propagation depends exclusively on GJIC. Upon ATP stimulation an increase in intracellular calcium was seen in most cells in the field of view. Again, one single cell was stimulated mechanically. Now, the wave propagation was limited to an average of only 4.5 cells in the wave. Compound 2 was added in a concentration of $10^{-8}$ mol/l to the bathing solution. An increase in intracellular calcium concentrations was seen in most cells in the field of view. After 10 minutes of incubation with Compound 2, one single cell was stimulated mechanically. Again, the stimulated cell increased in intracellular calcium concentration, with a subsequent propagation of the wave. Now the wave extended to an average of 6.2 cells (FIG. 10), which is a significant increase compared to before adding Compound 2.

Figure 11:
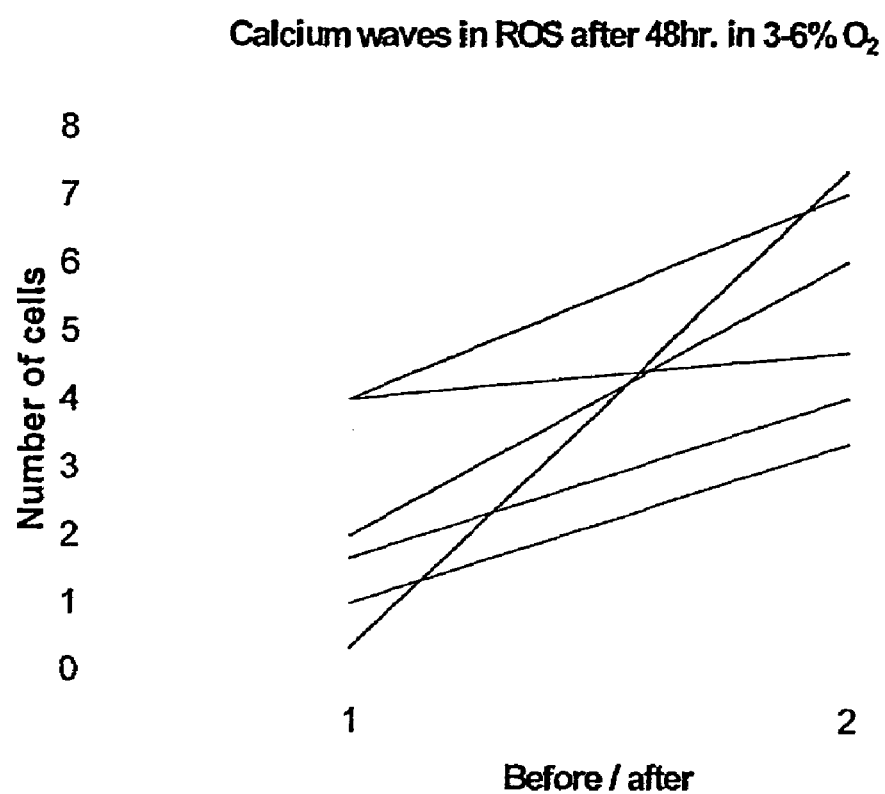
FIG. 11 is graph showing that Compound 2 can efficiently increases gap junctional mediated intercellular calcium waves in the osteoblastic cell line ROS 17/2.8 (ROS), after incubation of the cells for 48 hours under hypoxic conditions (3-6% $O_2$).

In order to test the compound's ability to restore suppressed gap junctional coupling, similar experiments were performed on the osteoblastic cell line ROS 17/2.8 (ROS), but after incubation of the cells for 48 hours under hypoxic conditions, with only 3-6% $O_2$, conditions known to decrease cellular coupling. ROS cells in monolayers were loaded with fura-2, and under the same conditions as above, a mechanical stimulation was performed. As ROS cells do not express purinergic receptors, pre-treatment with ATP was not done. Upon stimulation, the intracellular calcium concentration increased in the stimulated cell, and a wave was initiated, spreading to a total average of 2.2 cells (n=18). Then Compound 2 was added to the bathing solution in a final concentration of $10^{-8}$ M. After 10 minutes, the mechanical stimulation was repeated. Now, the wave propagated to an average of 5.4 cells (n=18) (FIG. 11), which is a significant increase compared to before the compound was added. Thus, Compound 2 efficiently increases gap junctional mediated intercellular calcium waves.

To assess the effect of the compound on direct cellular coupling, microinjection experiments were performed according to the method described above. The dye Lucifer Yellow (LY) was injected into one single human osteoblast in a monolayer. After 30 seconds, the number of cells containing dye was assessed. Under physiological conditions, the dye spread to an average of 14 cells (n=19). To suppress cellular coupling, cells were now incubated during hypoxia (3-6% $O_2$) for 48 hours. Then cellular coupling was re-assessed by microinjecting LY, and at this point the dye was only passed to an average of 7 cells (n=10). Compound 2 was added to the medium, and after 10 minutes, dye coupling was assessed again. Already after 10 minutes of incubation with Compound 2, the cellular coupling was increased with dye transfer to 9 cells (n=11).

Figure 12:
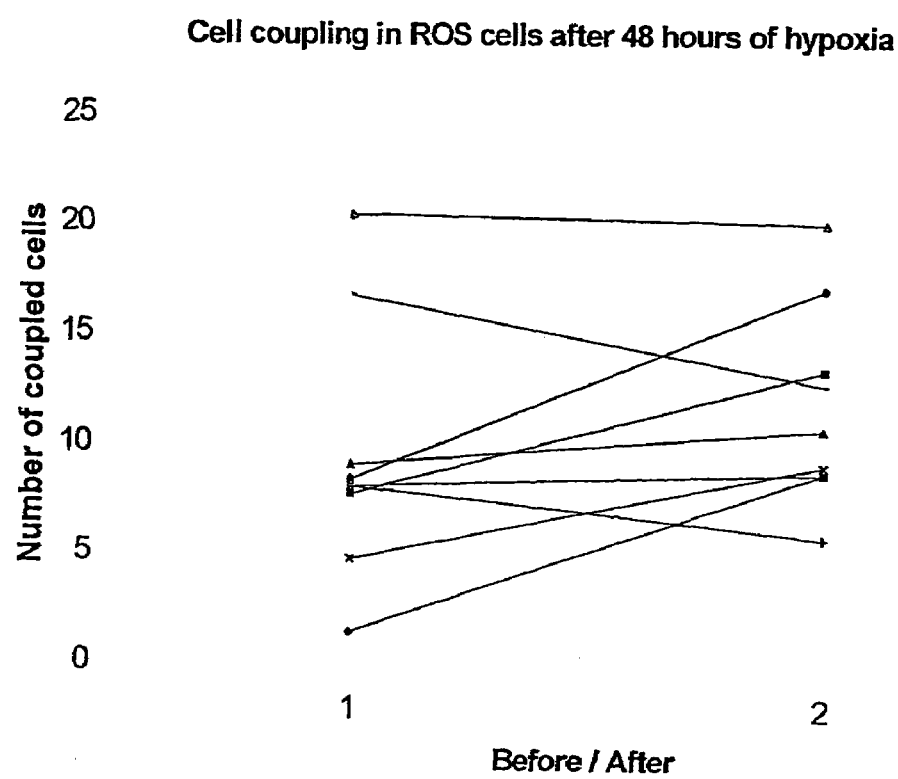
FIG. 12 is a graph showing that Compound 2 is able to increase gap junctional communication and restore hypoxia-induced reductions in cellular coupling. Basic coupling under physiological conditions in ROS cells was 12 cells (n=19). After 48 hours incubation in 3-6% $O_2$, a reduction in dye transfer was seen to 9 cells (n=27). Compound 2 was added to the bathing solution, and the cellular coupling was restored to pre-hypoxic levels, with an average dye transfer to 12 cells (n=27).

Similar experiments were performed with ROS cells. Basic coupling under physiological conditions in ROS cells was 12 cells (n=19). After 48 hours incubation in 3-6% $O_2$, a reduction in dye transfer was seen to 9 cells (n=27). Again, Compound 2 was added to the bathing solution, and the cellular coupling was actually restored to pre-hypoxic levels, with an average dye transfer to 12 cells (n=27), (FIG. 12). Thus, Compound 2 is able to increase gap junctional communication and restore hypoxia-induced reductions in cellular coupling.

Figure 13:
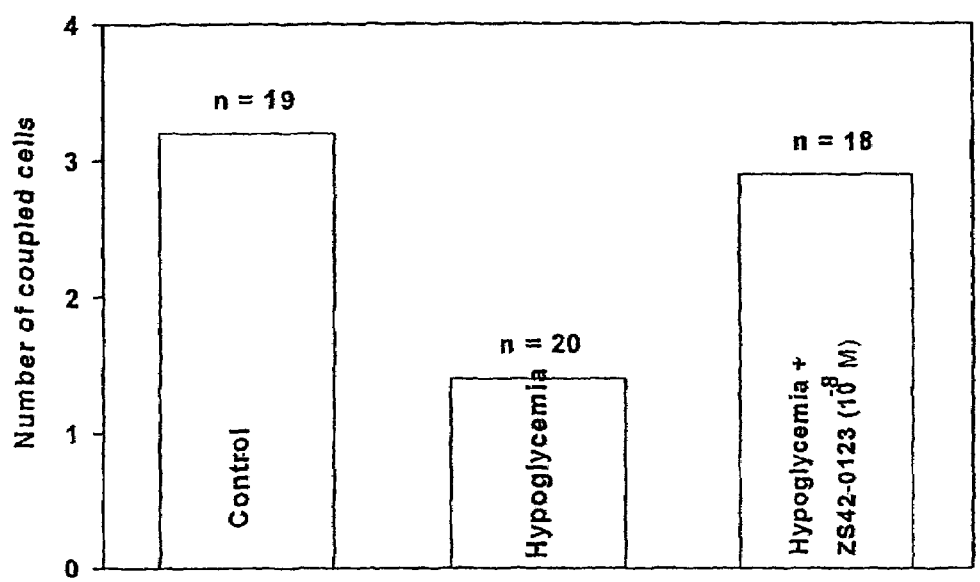
FIG. 13 is a graph showing that Compound 2 is able to restore hypoglycemia-induced uncoupling of cells. Human osteoblastic cells were cultured in monolayers on glass coverslips and loaded with fura-2. After ATP desensitization, one single cell was stimulated mechanically, and the number of cells in the wave was recorded. Here, the wave extended to an average of 3.2 cells (n=19). Medium was changed to medium without glucose, and after 8 minutes another mechanical stimulation was performed. Now, the wave was almost blocked, with a wave propagation of only 1.4 cells (n=20). Compound 2 was added to the medium in a final concentration of $10^{-8}$ M. A final stimulation was performed, and now the wave was almost restored, with an average extension to 2.9 cells (n=18).

Metabolic stress induced by hypoglycemia is also known to decrease gap junctional communication. Therefore, we wanted to assess whether Compound 2 could reverse the hypoglycemia-induced reduction in cellular coupling. Human osteoblastic cells were cultured in monolayers on glass coverslips and loaded with fura-2. After ATP desensitization as described above, one single cell was stimulated mechanically, and the number of cells in the wave was recorded. In this set of experiments, the wave extended to an average of 3.2 cells (n=19). Medium was changed to medium without glucose, and after 8 minutes another mechanical stimulation was performed. Now, the wave was almost blocked, with a wave propagation of only 1.4 cells (n=20). Compound 2 was added to the medium in a final concentration of $10^{-8}$ M. A final stimulation was performed, and now the wave was almost restored, with an average extension to 2.9 cells (n=18), (FIG. 13). Thus, Compound 2 is able to restore hypoglycemia-induced uncoupling of cells.

Figure 14:
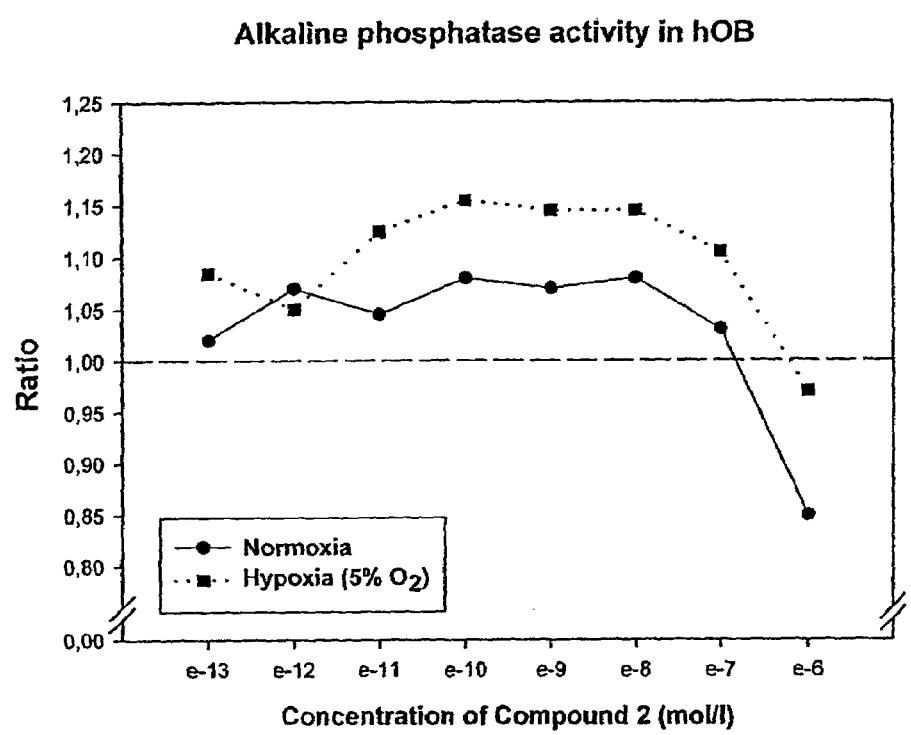
FIG. 14 is a graph showing that compound 2 increased alkaline phosphatase (ALP) activity at most of the concentrations tested, except for the highest concentration ($10^{-6}$ mol/l), which may be toxic. To assess the effect of Compound 2 on bone formation and osteoblast activity, we measured the effect of the compound on the ALP activity of the cells. Human osteoblasts were stimulated with different concentrations of Compound 2 from $1\times10^{-13}$ to $1\times10^{-6}$, and compared to untreated controls.
Figure 15:
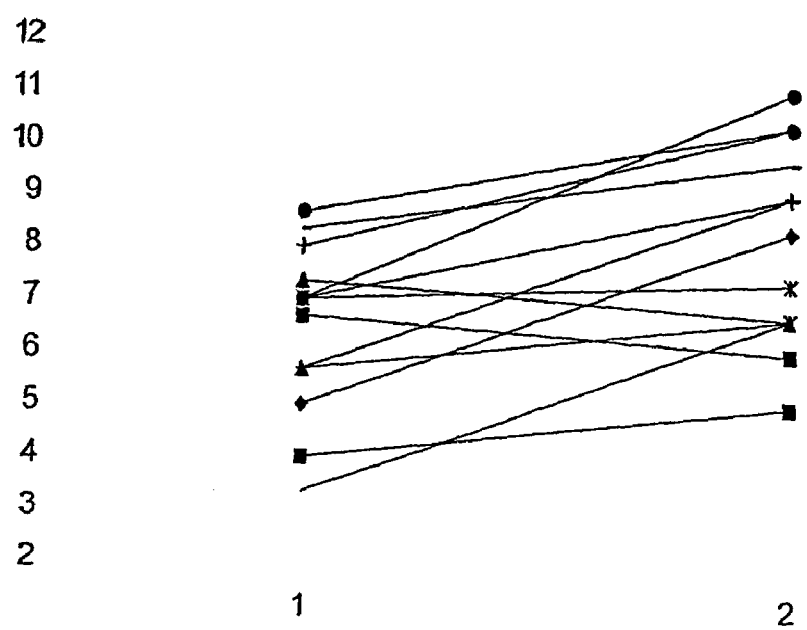
FIG. 15 is a graph showing the effect of compound 2 on ALP activity during hypoxic conditions. Human osteoblasts were cultured for four days in 5% $O_2$. The medium was enriched with Compound 2 in different concentrations, and compared to the responses during normoxic conditions. During hypoxia, the Compound 2-induced stimulation of ALP activity was about 15% greater than during normoxia at all concentrations in the range $10^{-11}$ to $10^{-8}$ mol/l.

Finally, to assess the effect of Compound 2 on bone formation and osteoblast activity, we measured the effect of the compound on the alkaline phosphatase (ALP) activity of the cells. Human osteoblasts were stimulated with different concentrations of Compound 2 from $1\times10^{-13}$ to $1\times10^{-6}$, and compared to untreated controls. Under normal culture conditions, Compound 2 increased ALP activity at most of the concentrations tested, except for the highest concentration ($10^{-6}$ mol/l), which may be toxic (FIG. 14). Moreover, the effect of the compound on ALP activity was also tested during hypoxic conditions. Human osteoblasts were cultured for four days in 5% $O_2$. The medium was enriched with Compound 2 in different concentrations, and compared to the responses during normoxic conditions. During hypoxia, the Compound 2-induced stimulation of ALP activity was about 15% greater than during normoxia at all concentrations in the range $10^{-11}$ to $10^{-8}$ mol/l, (FIG. 15).

In summary, these results demonstrate that Compound 2 is able to normalize the attenuated GJIC between human osteoblast during hypoxia. Moreover, Compound 2 stimulates the production of alkaline phosphatase suggesting that Compound 2 is able to stimulate the activity of osteoblats, and therefore bone formation. Thus, Compound 2 may be useful in the treatment of bone diseases with impaired bone formation relative to bone resorption. The effect of Compound 2 on cell-to-cell coupling during hypoxia suggests that substances of the present invention may be useful in the treatment and/or prevention of bone diseases associated with poor vascularization, hypoxia and ischemia in bone tissue.

From these experiments it can be concluded that substances of this invention that increase GJIC may be useful for the preparation of medicaments for prevention and/or treatment of osteoporosis. In some instances, osteoporosis is a manifestation of another disease, such as Cushing's syndrome or osteogenesis imperfecta. In most cases of osteoporosis, however, no other disease is apparent. One form occurs in children or young adults of both sexes and with normal gonadal function and is frequently termed idiopathic osteoporosis, although most of the other forms are also of unknown pathogenesis. Type I osteoporosis occurs in a subset of postmenopausal women who are between 51 and 75 years of age and is characterized by an accelerated and disproportionate loss of trabecular bone. Fractures of vertebral bodies, and the distal forearm are common complications. Decreased parathyroid gland function may be compensatory to increased bone resorption. Type II osteoporosis occurs in women and men over the age of 70 and is associated with fractures of the femoral neck, proximal humerus, proximal tibia, and pelvis, sites that contain both cortical and trabecular bone. In addition to osteoporosis, substances that increase GJIC may also increase bone formation in metabolic bone diseases such as rickets and osteomalacia and in osteoporosis due to chronic glucocorticoid administration or chronic renal failure. Thus, it is a purpose of the present invention to provide compounds for the preparation of medicaments useful in prevention and /or treatment of osteoporosis. This purpose is achieved with the present peptide compounds, such as the compounds of formulae I to VIII, formulae 2 to 12, and the compounds of tables 1 and 8 herein, more specifically the compounds of Synthesis Examples 1-55 herein.

Effects of Gap Junction Openers on Cartilage

Articular cartilage is a tissue designed to withstand compression during joint movement and, in vivo, is subjected to a wide range of mechanical loading forces. Mechanosensitivity has been demonstrated to influence chondrocyte metabolism and cartilage homeostasis. In many cell types mechanical stimulation induces increases of the cytosolic $Ca^{2+}$ concentration that propagates from cell to cell as an intercellular $Ca^{2+}$ wave. Cell-to-cell communication through gap junctions underlies tissue co-ordination of metabolism and sensitivity to extracellular stimuli: gap junctional permeability to intracellular second messengers allows signal transduction pathways to be shared among several cells, ultimately resulting in co-ordinated tissue responses. Mechanically-induced $Ca^{2+}$ signalling has been investigated in chondrocytes and it has been demonstrated that gap junctional communication is essential for mechanically-induced $Ca^{2+}$ signaling in chondrocytes[53]. Moreover, mechanical stimulation activates phospholipase C, thus leading to an increase of intracellular inositol 1,4,5-trisphosphate. The second messenger, by permeating gap junctions, stimulates intracellular $Ca^{2+}$ release in neighbouring cells and this system is considered very important for the coordinated signaling in chondrocytes during mechanical strain and it may provide a mechanism for co-ordinating metabolic activity during metabolic stress in chondrocytes[53;54]. The predominant connexin in cartilage is Cx43 and it in addition to its role in the cell-to-cell regulation of metabolism and signalling, Cx43 is essential for normal chondrogenesis[47;55].

In addition, the cytoarchitecture of meniscal cells partly depends on gap junction communication. The fibrocartilage part of the meniscal as well as the fibrocartilage structure of tendons depend on intercellular communication. During injuries gap junction openers will improve the speed of repair.

Thus, it appears that substances of this invention that increase GJIC may be used for the prevention and/or treatment of joint diseases that involves impaired cell-to-cell coupling. Like we have demonstrated in human osteoblastic cells, we suggest that substances that increase GJIC may be used for the prevention and/or treatment of joint diseases that involves metabolic stress. These would include any form of arthritis associated with decreased vascularization or healing of fractured cartilage tissue. The effect of Compound 2 and Compound 40 on decrease in gap junctional communication induced by DDT in human chondrocytes will be tested in the same way as described for osteoblastic cells below. The test compounds will be used in a concentration range of from 10-10-10-6 mol/kg and it is expected that the test compounds will reverse the decrease in gap junctional communication, induced by the tumor promoting agent, DDT. Thus, it is a purpose of the present invention to provide compounds for the preparation of medicaments useful in prevention and/or treatment of joint diseases including arthritis. This purpose is achieved with the present peptide compounds, such as the compounds of formulae I to VIII, formulae 2 to 12, and the compounds of tables 1 and 8 herein, more specifically the compounds of Synthesis Examples 1-55 herein. Administration will be orally, parenterally or intraarticular administration.

Effects of Gap Junction Openers on Cancer

The gap junction permeability and the regulation of GJIC happen on different levels in the cell. Decrease or absence of GJIC may be the result of changes in the Cx expression during transcription and translation, alteration of post translational processing and alteration of connexon assembly and insertion into the plasma membrane. An unusual feature of Cx is their short half-life in comparison with other membrane proteins. The rapid turn over of connexins has been found to be between 1.5 and 2 h. The degradation of Cx has been shown to dependent on phosphorylation, which leads to destabilization of some connexin subtypes. The fast turnover rate provides an additional mechanism by which GJIC can be rapidly regulated by substances affecting Cx mRNA half-life, translation, intracellular transport and assembly of Cx into gap junctions.

Another way to regulate gap junctional permeability is complete or partial closure of gap junction channels under certain circumstances by mechanically twisting of the six subunits of connexon. The gating of gap junctions is known to be effected by tumour promoters which decrease GJIC. Tumor promoters are agents, which enhance or accelerate carcinogenesis when given repeatedly after tumor initiation. The mechanisms by which tumor promoters modulate GJIC are not fully understood, but there is evidence to support that tumor promoters may affect GJIC by alteration of phosphorylation of Cx and/or inhibition of Cx expression and assembly. Recent results have shown that retrovirus-mediated in vivo gene transfer of connexin 43 in malignancies with low GJIC capacity significantly reduced the tumorigenecity[56]. In further support of an essential role of normal GJIC in the prevention of cancer, it has been shown that Cx32 deficient mice have a very high incidence of spontaneous liver tumors and an increase susceptibility to develop chemically-induced liver tumors[57]. Furthermore, the tumor promoting action of Phenobarbital requires functional Cx32 for tumor progression[58]. This suggest that uncoupling of GJIC is important for the oncogenic actions of phenobarbital[58].

Carcinogenesis is characterized by the progressive impairment of growth control mechanisms in which growth factors, oncogenes and tumor suppressor genes are involved. Since the alteration of GJIC might result in the alteration of growth control, the effect of growth factors and oncogenes on GJIC might be crucial for tumorigenesis. Several oncogens have been shown to mediate a down regulation of GJIC[59]. It is shown that pp60$^{v-src}$ mediate Cx43 gap junction closure via a ball and chain mechanism which involves a C-terminal serine residue phoshorylation by the MAP kinase[59]. Interestingly, in some cases oncogene transfected cells could communicate with each other, but lack the heterologous communication with the adjacent normal cells.

Permeability of gap junctions in tumor cells using the dye-transfer assay was lower than GJIC in surrounding liver tissue. Interestingly, many tumors are encapsulated in an extracellular matrix-like structure and physically separated from the normal tissue.

Neoplastic transformation in the normal human tissues occurs as a result of an accumulation of genetic alterations. However, a general theme in carcinogenesis and tumorigenesis is the down regulation of the GJIC. The various connexins are expressed in a tissue specific manner. Cx43, Cx26, Cx32 has been detected in normal breast tissue. A panel of human breast cancers was analysed for the expression level of Cx43. Cx43 gap junctions were not observed in ductal carcinomas in situ, infiltrating ductal carcinomas, and infiltrating lobular carcinomas, and they seem to be independent of estrogen, progesterone, and erbB2 receptor status. In contrast, human breast cancer cell lines and rodent mammary carcinoma tissues showed a down regulation of Cx43 and It turned out to be at the mRNA level, suggesting a transcriptional mechanism for the decrease of Cx43 protein in breast cancer [60]. Another example on the connection between cancer and GJIC is hepatocellular carcinoma were the connexin 32 knock out have shown to be prone for this specific cancer type[57]. Studies with oval cells have indicated that they can differentiate into hepatocytes and that neoplastic derivatives of oval cells can produce both hepatocellular and biliary neoplasms. The specific connexin expressed by the differentiating oval cell determines whether it communicates with hepatocytes or biliary epithelial cells. This communication may be necessary for the further differentiation and regulated growth of the differentiating oval cells and impairment of GJIC may contribute to the formation of hepatocellular and cholangiocellular neoplasms. Thus, GJIC may be the key factor in the differentiation of oval cells and blocked GJIC may promote their neoplastic transformation. Furthermore, in vitro analysis of tumor invation in rat lung endothelial cells treated with malotilate showed that malotilate promoted the development of cell-to cell adhesion by gap junctions which resulted in inhibition of invation of tumor cells[61]. Taken together, these findings strongly support the hypothesis that alteration of GJIC is a critical event in carcinogenesis and that substances of this invention which increase GJIC might be beneficial in cancer therapy. Therefore, it is a further purpose of the invention to provide novel compounds that increase GJIC. We suggest that the peptide compounds of formulae I to VIII, formulae 2 to 12, and the compounds of tables 1 and 8 herein may be particularly advantageous as medicaments for the treatment of cancer due to their low effective concentration and consequently low toxicity.

Specific uses of the peptides herein include treatment of the following cancer related medical conditions:

Tumor progression: During tumorigenesis, the interruption of the physiological interaction of normal cells with their neighboring cells, and loss of features of differentiation are a common denominator in tumor progression. Alteration in gap junction communication is believed to be among the earliest changes during cell tumorgenesis (Wolburg H, Rohlmann A. Int Rev Cytol. 1995; 157: 315-73), Klaunig J E, Ruch R J. 1990; 135-46)). Kyung-Sun Kang, Jun-Won Yun, ByoungSu Yoon, Yoon-Kyu Lim and Yong-Soon Lee (Cancer Letters 166 (2001) 147-153) have shown that pre- and co-incubation with $GeO_2$ in TPA treated rat liver epithelial cells abolished down-regulation of GJIC by TPA suggesting that a substance that recovers the inhibition of GJIC may be used in the prevention or inhibition of tumor promotion. Suzuki J, Na H-K, Upham B L, Chang C_C and Trosko J E (Nutrition and Cancer, vol 36 No. 1 p. 122-8) have shown that the food additive lambda-carrageenan inhibits GJIC in rat liver epithelial cells similar to that of the well-documented tumor promotor phorbol ester (TPA), and therefore could play a role in carcinogenesis as a tumor promoting agent. Thus, the compounds of the present invention may be used in the prevention or treatment of cancer caused by tumor promoting agents, such as TPA and lambda-carrageenan.

Drug sensitivity resistance: Increased gap junction communication improves the microenvironment in tumors and Carystinos G D, Alaoui_jamali M A, Phipps J, Yen L, Batist G.

Metastasis: Loss of intercellular gap junction communication is associated with high metastatic potential in all cancers with metastatic potentials. (Saunders M M, Seraj M J, Li Z, Zhou Z, Winter C R, Welch D R Donahue H J. (Cancer Res. 2001; 61: 1765-1767), Nicolson G I, Dulski K M, Trosko J E, Porc Natl Acad Sci USA. 1988; 85: 473-6)). Prevention of matastasis is established by treatment with a gap junction opener which will preserve the gap junction communication in tumors.

Treatment is an add on to conventional chemotherapy.

EXPERIMENTAL EXAMPLE 9

The Effect of Compound 2 on Decrease in Gap Junctional Communication Induced by DDT in Human Osteoblastic Cells Protocol and Results The compound 1,1-bis(p-chlorophenyl)-2,2,2-trichlorethane, also known as the insecticide DDT, is an inhibitor of gap junctional communication, and has tumor promoting abilities. It inhibits cell-to-cell communication by reducing the gap junction number and size, as well as decreased cellular levels of phosphorylated (active) forms of the gap junction protein Cx43 and these actions are considered pivotal for the compounds oncogenic properties[62-64]. Thus, compounds with the capability of preventing tumor promoter-induced decrease of GJIC may be potential candidates for use in protection against tumor promotion and cancer treatment[65]. To examine if the substances ogf this invention prevents the tumor promoter-induced decrease in GJIC, we examined the effects of Compound 2 on DDT-induced uncoupling in human osteoblast cells.

Methods

Cell Culture

Human osteoblast cells: Cells were isolated from human bone marrow obtained by puncture of the posterior iliac spine of healthy volunteers (aged 20-36): 10-15 ml marrow material was collected in 15 ml PBS+Ca, Mg (Life Technologies, Cat.No. 14040) with 100 U/ml Heparin (Sigma, Cat.No. H-3149). The mononuclear fraction of the marrow was isolated on a Lymphoprep gradient (Nycomed Pharma, Cat.No. 1001967), by centrifugation at 2200 rpm for 30 min. After harvesting, the mononuclear fraction was washed once with culture medium and centrifuged at 1800 rpm for 10 min. Subsequently cells were counted and plated in culture medium at $8 \times 10^6$ cells/100 mm dish. hOB medium (all reagents obtained from Life Technologies): MEM w/o Phenol Red w/Glutamax (Cat.No. 041-93013) supplemented with 10% heat inactivated fetal calf serum (Cat.No. 10106) and 0.1% Penicillin/Streptomycin (Cat.No. 15140). Medium was changed the following day and the cells were cultured at 37° C. in 5%$CO_2$ with medium change every 7 days. After 3-4 weeks of culture the cells had reached 70% confluence. The medium was then supplemented with 100 nM Dexamethasone (Sigma, Cat.No. D-4902) for 7 days. Cells were then plated for video imaging experiments: a 25 mm #1 glass coverslip was placed in a 35 mm dish (or each well of a 6-well multidish), cells were plated at $2.5 \times 10^5$ cells/coverslip and cultured for 2-3 days before use.

Microinjection

Cells were cultured on coverslips, and were affixed to a PDMI-2 culture chamber (Medical Systems Corp.), maintained at 37° C. with superfused $CO_2$, on a Zeiss Axiovert microscope. Microinjections were performed using the Eppendorf 5171 micromanipulator and the Eppendorf Transjector 5346 system. A micropipette was loaded with a 10 mM Lucifer Yellow solution (Sigma, Cat.No. L-0259). A cell in the monolayer was carefully injected with LY for 30 seconds, the micropipette was removed from the cell and after 30 seconds the number of cells that showed dye transfer were counted. The excitation light (430 nm) was provided by a monochromator (T.I.L.L. Photonics GmbH). Images were acquired with an intensified CCD camera (Dage MTI) and digitized with a Matrox MVP image processing board, using the MetaMorph imaging software (Universal Imaging)

Results

In order to assess the ability of gap junction modifiers to prevent tumor promotion, we wanted to test whether gap junction modifiers could reverse the decrease in gap junctional communication, induced by a well known tumor promoting agent, DDT. Therefore, monolayers of human osteoblastic cells on glass coverslips were incubated at 37° C. in a humidified atmosphere containing 5% $CO_2$. DDT was added to the medium in a final concentration of 13 μM, and was left on for 60 minutes.

To assess the effect of Compound 2 on direct cellular coupling after DDT treatment, microinjection experiments were performed according to the method described above. The dye Lucifer Yellow (LY) was injected into one single human osteoblast in a monolayer. After 30 seconds, the number of cells containing dye was assessed. Under control conditions (no DDT treatment), the dye spread to a median of 14.5 cells (n=12). The same experiment was performed with the DDT-exposed cells. These cells showed a decreased cellular coupling with a median of 7 (n=13). Compound 2 was added to the bathing solution in a final concentration of $10^{-8}$ mol/l, and after 10 minutes, another microinjection was performed. Compound 2 produce an increase in cell-to-cell dye transfer in all preparations with a median of 8.3 cells (FIG. 15). This increase is highly significant with $p<0.01$, using the Wilcoxon non-parametric statistical test. Thus, gap junction openers are capable of reversing the decreased intercellular coupling related to tumor promotion, which suggest that the substances of this invention may be useful in the chemoprevention and/or treatment of cancer. The compounds of the present invention are useful for the preparation of medicaments for chemoprevention and/or treatment of cancer. The compounds of the present invention may also be used in a combination therapy with other anti-cancer agents. Thus, it is a purpose of the present invention to provide compounds for the preparation of medicaments useful in prevention and /or treatment of cancer. This purpose is achieved with the present peptide compounds, such as the compounds of formulae I to VIII, formulae 2 to 12, and the compounds of tables 1 and 8 herein, more specifically the compounds of Synthesis Examples 1-55 herein.

Further Pharmacological Methods

The usefulness of the peptides described herein in methods of therapeutic treatment will appear from the additional examples below.

Effects of Gap Junction Openers in Wound Healing

A wound is a discontinuation of the normal anatomy involving the skin and can be a surgical or traumatic wound, or it can be secondary to several diseases such as diabetes, arteriosclerosis, malnutrition etc. Normal wound healing is a systemic process, which occur stepwise and include hemostasis and inflammation. Remodelling follows these processes, which might last for years and is responsible for formation of scar tissue. The hemostasis with fibrin provides a surface beneath which migrations and movements of the wound edge occur. Epithelialization, fibroplasia and capillary proliferation into the healing wound begins immediately. The angiogenic capillary sprouts invade the fibrin wound clot and within few days organise into a microvascular net throughout the granulation tissue also consistent of leukocytes and phagocytic mononuclear cells. A very dynamic interaction takes place between the various tissue components involved in the wound healing process. The angiogenetic process is essential for a successful wound healing. Intercellular communication, gap junctions are essential for creation the synsythium of fibroblasts and proliferation of the capillary network. Normal distribution of connexin 43 is necessary for this growth of the different tissue component.

Several local factors often seen during pathological conditions as oedema, ischemia, low oxygen tension and infection may delay the wound healing process. Wound healing involves the interactions of many cell types, and intercellular communication mediated by gap junctions is considered to play an important role in the coordination of cellular metabolism during the growth and development of tissues and organs.[66-68].

We suggest that substances of this invention that increase GJIC may be used for the treatment of wounds, and in particular, to accelerate wound healing. Considering that experiments on cardiac and bone tissue suggest that these substances have an enhanced efficacy during metabolic stress (e.g., hypoglycemia, hypoxia, ischemia), it may be inferred that these substances may be particularly useful is the treatment of ischemic ulcers. Thus, it is a purpose of the present invention to provide compounds for the preparation of medicaments useful in treatment of wounds and in particular ischemic ulcers. This purpose is achieved with the present peptide compounds, such as the compounds of formulae I to VIII, formulae 2 to 12, and the compounds of tables 1 and 8 herein, more specifically the compounds of Synthesis Examples 1-55 herein.

Wound Healing Processes

Healing progresses are a series of overlapping phases beginning with haemostasis (coagulation). The second phase of the healing process is a cascade of inflammatory responses where microphages accumulates at the wound side and formulation of granulation tissue starts involving fibroblast and lymphocytes among other component. Epithelial cells will then start to migrate from the border of the wound to cover the area. Cappilary spouting from the normal tissue into the wound is also involved in order to ensure supply of nutrients, oxygen and the different cells. All the cells and the capillary endothelium cells have an lively intercellular communication via gap junctions (Abdullah K M, Luthra G, Bilski J J, Abdullah S A, Ryenolds L P, Grazul-Bilska A T. (Endocrine. 1999; 10: 35-41). Areas with low oxygen supply and/or high concentration of free radicals often seen in wounds with necrotic tissue, in diabetes, in arteriosclerosis, in surgery wounds, oedema, infection, burn wounds and in venous insufficiency will lower the gap junction communication (Nagy J I, Hossain M Z, Lynn B D, Cupern G E, Yang S, Turley E A. Cell Growth Diff. 1996; 7: 745-51)).

The effect of gap junction opener is tested in an in vitro fibroblast culture. Fibroblast are harvest from human gingival as described by Arora K K, Lee W, McCullock C. Am J Physiol Cell Physiol. 2000; 279: C147-57). Cell culture is exposed to 10-10-10-8 nM of the gap junction opener and a significant faster cellular growth will be seen. The growth is tested by the conventional methods measuring nuclear uptake of thymidin over time.

Gap junction openers' stimulation of endothelial cell growth and formation of endothelial tube is studied before and after exposure to the compound as described by Ashton A W, Yokota R, John G, Zhao S, Suadicani S O, Spray D C, Ware J A. (J Biol Chem. 1999; 274: 35562-70).

Gap junction openers stimulate wound healing processes in oral mucosa. Hara A, et al.(J Gastroenterol February 1999 34:1-6) identified connexins 26 and 32 in human oral mucosa an indication of the presence of gap junctions in this tissue. However, immunofluorescence study found no significant differences in the expression of the connexins between patients with aphthons stomatitis and controls. Irsogladine maleate, which reinforces gap junctional intercellular communication in vitro, was effective for the treatment of transient and relapsing aphthous stomatitis, as well as symptomatic and drug-induced aphthous stomatitis. It was also useful for prevention of episodes of relapsing aphthous stomatitis, with daily administration preverting recurrence of stomatitis. The peptides of the present invention may in the same way be used to accelerate the wound healing process in oral mucosa by reinforcing gap junctional intercellular communication among oral mucosal cells; and the peptides of the present invention are also useful for the treatment and prevention of aphthous stomatitis.

To examine wound healing in vivo, Compound 2 and Compound 40 is administered topically (concentration range 10-9- 10-6 mol/l in aqueous gel) and parenterally (10-10-10-6 mol/kg) two to four times daily to mice. Two round excisional wounds are created down the panniculus carnosus with a 6-mm punch biopsy on the back skin of each mouse. After 5 days treatment with compound 2 and compound 40 the effect of skin is evaluated histologically by microscopy of biopsies and wound healing is measured by daily measurements of the diameter of the wound. We predict that Compound 2 and Compound 40 will not affect skin structure alone but that both compounds will accelerate wound healing after biopsies.

Treatment with a gap junction opener will ensure maximal gap junction communication between the different cells considered to play an important role in the complicated repair process and thereby improve wound repair. The compound will be administered parenterally, topically, systemically or orally.

Effects of Gap Junction Openers in Healing of Gastric and Duodenal Ulcers

Gap junctions also play an important role in intercellular communication, prolifereation and differentiation in gastric mucosal cell. Gap junction opener will stimulated regenerative processes after I induced injury (Endo K, Watanabe S, Nagahara A, Hirose M, Sato N.(J Gastroenterol Hepatol. 1995;10: 589-94)).

Mine et al. have demonstrated that normal human gastric mucosa contains both connexin 32 and connexin 43[69;70]. In contrast, gastric mucosa surrounding a chronic gastric ulcer lesion contains a smaller amount of connexin 32 and connexin 43. In the studies by Mine et al. the relationship between the appearance of connexins and ulcer healing was investigated. When ulcer healing was observed, connexins 32 and 43, which decreased at the active ulcer stage, had returned almost to levels observed in normal gastric mucosa. These data indicate that disappearance of both connexin 32 and connexin 43 is closely related to the stage of chronic gastric ulcer lesions. Moreover, using a rat model of acetic acid-induced chronic gastric ulcer, the same group of investigators demonstrated that the clinical effect of the antiulcer drug cimetidine was closely related to the reappearance of connexin 32[69].

Gap junctions are important in gastric mucosal defense system and restitution from acid-induced injury. Takahashi N, Joh T, Yokoyama Y, Seno K, Nomura T, Ohara H, Ueda F, Itoh M. (J Lab Clin Med 2000 August;136(2):93-9) Evidence is accumulating that gap junctional intercellular communication (GJIC) determined whether GJIC mediates a restitution process in gastric mucosa. Male Sprague-Dawley rats were fasted and anesthetized. Gastric injury was induced by luminal perfusion with 0.2N HCl for 10 minutes. Mucosal integrity was continuously monitored by measuring the clearance of chromium 51-labeled ethylenediaminetetraacetic acid, which was used for analysis of recovery from the injury. Perfusion with 0.25% octanol (OCT; inhibitor of GJIC) was started after acid injury to assess its effect on restitution. The effect of irsogladine (IG; activator of GJIC) was also tested. Gastric mucosal GJIC was immunohistochemically evaluated with monoclonal antibody gap junction protein (connexin 32). Recovery from acid-induced mucosal injury occurred rapidly when acid perfusion was discontinued (within about 60 minutes). OCT, which didn't cause any injury to normal gastric mucosa, significantly inhibited the restitution. IG reversed this inhibition in a dose-dependent manner. In an immunohistochemical study, OCT-induced damage of gap junction was demonstrated, but not after IG pre-treatment. These findings suggest that GJIC may play a critical role in restitution in rat gastric mucosa and the peptides of the present invention are useful in the treatment of ulcers, such as gastric and duodenal ulcers. To substantiate this statement experiments in rats can be performed using the general experimental design of Takahashi N et al. 2000, above, with administration of COMPOUND 2 and COMPOUND 40 which are stable in acidic solution at concentrations in the range of $10^{-11}$-$10^{-7}$ M to the rats. These experiments are expected to show the facilitating effect of COMPOUND 2 and COMPOUND 40 on gap junctional coupling and counteract the effect of cerulein resulting in a healing of the gastric ulcer.

Administration of the peptides will be orally or parenterally, e.g. intravenously.

Therefore, the substances of this invention that increase GJIC may promote the healing of gastric and duodenal ulcers. Thus, it is a purpose of the present invention to provide compounds for the preparation of medicaments useful in treatment of gastric and duodenal ulcers. This purpose is achieved with the present peptide compounds, such as the compounds of formulae I to VIII, formulae 2 to 12, and the compounds of tables 1 and 8 herein, more specifically the compounds of Synthesis Examples 1-55 herein.

Role of Gap Junctions in Vascular Biology

Coordination of cellular responses at the endothelial interface between the blood and underlying tissues is mediated by multiple signaling mechanisms, including direct intercellular communication via gap junctions. Among the functions in which endothelial gap-junctional intercellular communication has been implicated are the migratory behavior of endothelial cells after injury, angiogenesis, endothelial growth and senescence, and the coordination of vasomotor responses[71].

The regulation of blood flow in a wide dynamic range requires coordinated responses of resistance and feeding arteries. Such a coordination between vessels can be achieved by the vascular effects of shear stress exerted by the streaming blood or by conduction of vasomotor signals along cells of the vascular wall. Indeed, local application of certain vasoactive compounds, such as acetylcholine (ACh) or norepinephrine (NE) induced not only local dilation or constriction but also vasomotor responses several millimeters upstream and downstream.[71]. Vasomotor responses can also be conducted from capillaries to arterioles and may contribute to the matching of tissue demands and blood supply. This has been demonstrated in the following way: When single muscle fibers were stimulated to contract, arterioles upstream of capillaries supplying these fibers were observed to dilate[72].

The high conduction velocity is consistent with electrotonic transmission of a signal along the vascular wall. In fact, locally induced hyperpolarizations and depolarizations have been demonstrated to be conducted several millimeters upstream in endothelial and vascular smooth muscle cells. The conduction of the electrical signal requires coupling of vascular cells by gap junctions that provide conduits of low electrical resistance between the cells. In vascular tissue, at least three different connexin (Cx) proteins (Cx37, Cx40, and Cx43) are expressed that for m gap junctions. Cx40 seems to be the predominant connexin isoform in aortic endothelial cells, whereas in smooth muscle, Cx43 expression is abundant.

Studies in Cx40 deficient mice (Cx40−/−) have demonstrated spreading of the vasodilation induced by local application of acetylcholine or bradykinin is severely attenuated in Cx40$^{-/-}$ animals compared to normal wildtype (Cx+/+) animals[73]. Moreover, arterial blood pressure is significantly elevated in Cx40$^{-/-}$ animals compared to normal wildtype (Cx+/+) mice. These results support a significant role for Cx40 in vascular intercellular communication and they indicate that impaired gap junctional communication in the vascular wall is associated with decreased transmission of endothelium-dependent vasodilator responses, which is turn increases vascular resistance and causes hypertension. Recent in vivo studies suggest that normal pressure oscillations in the kidney are extremely imporant for the regulation of blood pressure[74]. Thus, impaired vasomotor responses due to poor cell-to-cell coupling may contribute to the development of hypertension in Cx40 deficient animals.

The down-regulation of cx43 mRNA and protein levels in senescent endothelial cells suggests that impaired gap junctional intercellular communication might play a role in the vascular aging process[75].

Based on available information on the role of gap junctions in vascular responses it is likely that a pharmacological compound that increases gap junctional coupling in the vascular wall could facilitate conducted vascular responses and improve blood supply during conditions with increased metabolic demand (e.g., physical exercise, tachycardia), and during ischemia. In addition, such a substance is likely to prevent and/or treat hypertension. It is therefore a further purpose of the invention to provide compounds that increase gap junctional coupling and/or GJIC in the vascular wall and, thus, are useful for the prevention or treatment of hypertension. This purpose is achieved with the present peptide compounds, such as the compounds of formulae I to VIII, formulae 2 to 12, and the compounds of tables 1 and 8 herein, more specifically the compounds of Synthesis Examples 1-55 herein.

Experimental Procedure

For all experiments on isolated resistance arteries (internal diameter about 200 mm) from the rat mesenterium are used. The arteries are 3rd order branches of the mesenteric artery and are dissected out from the mesenterium of 14-18 weeks old male Wistar rats. The arteries are mounted in a myograph for measurements of isometric force and stretched passively to obtain maximal force. The tissue bath is divided into two and an artery is mounted in each of the two halves. The arteries are bathed in a physiological, bicarbonate buffered salt solution and unless otherwise stated gassed with 5% $CO_2$ in 21% $O_2$.

For evaluation of vasomotion the arteries are activated with noradrenaline in a submaximal concentration. This is made after removal of the endothelium and with increasing concentrations of cGMP, which we is known to increase the degree of vasomotion and intercellular communication.

For evaluation of endothelial function arteries are activated with a near maximal noradrenaline concentration and relaxed in the presence of noradrenaline with increasing concentrations of acetylcholine, which we know relaxes the arteries endothelium-dependently in these arteries, through a partly NO-dependent and partly EDHF-dependent pathway.

The effect of 10-8 M and 10-6 M of Compound 2 and Compound 40 are assessed on the vasomotion and on the responses to acetylcholine. When the drug is present at least 5 min preincubation is used.

For assessment of vasomotion one artery in the tissue bath serves as control and the other artery that is being treated with one of compound 2 and compound 40.

In experiments with hypoxia the tissues are exposed to 5% $CO_2$ in $N_2$ for at least 5 min before the experiments was performed. This procedure brings bath $PO_2$ down to about 5 mmHg.

We expect that compounds of this invention will increase acetylcholine-induced vasodilation and vasomotion. Consequently these substances will be useful in the teatment of hypertension and vasular diseases associated with vasoconstriction. Mode of administration will be oral or parenteral.

Effects of Gap Junction Openers in Nervous Tissue

Eight different connexins are expressed in the CNS (Cx 26, 30, 32, 37, 40, 43, 45, 46),. Furthermore, Cx36 seems to be preferentially expressed in neurones. The different connexins allow communication between diverse cell populations or segregate cells into isolated compartments according to their pattern of connexin expression. Compartmental interfaces where heterotypic coupling might have functional relevance are between oligodendrocytes (Cx32, Cx45) and astrocytes (Cx43, Cx45, Cx40, Cx30) or neurons (Cx26,Cx32,Cx43) [76].

It is feasible that a specific sets of connexins provide functional advantage in particular brain compartments; i.e. a higher of lower unitary conductance might be functionally facilitating or limiting in synchronising neural inputs or rapidity of conduction.

In immature neuroblasts and postnatal neurons extensive gap junction mediated intercellular coupling has been documented[76;77]. The postnatal increase of neuronal gap junctions and their cortical organization is suggestive for an essential role of these junctions in morphogenetic events underlying the critical phase of corticogenesis. The involvement of gap junction in neuronal trafficking is strengthened by the fact that neurotransmitters are able to modify gap junctional coupling.

Therefore, we suggest that the substances of this invention, which are known to increase GJIC may accelerate repair after nerve injury or during grafting of immature cells (progenitor cells) into brain tissue. Among the technologies that are currently undergoing experimental evaluation for the cellular repair in the central nervous system are grafting with progenitor cells, fetal tissue, and viral vectors to be used for treatment of diseases such as parkinsons disease, huntington's disease, and other neurodegenerative brain diseases.

Axon injury rapidly activates microglial and astroglial cells close to the axotomized neurons. Following motor axon injury, astrocytes upregulate within hour(s) the gap junction protein connexin-43, and within one day glial fibrillary acidic protein (GFAP). Concomitantly, microglial cells proliferate and migrate towards the axotomized neuron perikarya. A hypothetical scheme for glial cell activation following axon injury implies that injured neurons initially interact with adjacent astrocytes through GJIC. Subsequently, neighbouring resting microglia cells are activated. These glial reactions are amplified by paracrine and autocrine mechanisms, in which cytokines appear to be important mediators. The specific functional properties of the activated glial cells will determine their influence on neuronal survival, axon regeneration, and synaptic plasticity. The control of the induction and progression of these responses are therefore likely to be critical for the outcome of, for example, neurotrauma, brain ischemia and chronic neurodegenerative diseases[78].

Gap junctions are believed to provide the molecular link for co-ordinated long-range signalling among individual members of the glial compartment. Likewise, astrocytes are ideally suited for metabolic support of neurones since they are functionally polarized with one extremity touching the vascular bed and the other pole approximates neuronal parenchyma[76]. Thus, malfunctioning of such supportive mechanisms may be instrumental for the malfunctioning of integrated neuronal pathways and thereby the offspring of diseases in the central nervous system. Therefore, we suggest that the substances of this invention, which have been shown to increase GJIC may prevent ischemic damage in the brain by increasing the metabolic support between glia cells and neurons. Furthermore, the substances of the invention may be of great significance in patients with organic psychoses which may present with signs such as depression, anxiety, learning and memory deficit, fobias, and hallucinations. Thus, it is a purpose of the present invention to provide compounds for the preparation of medicaments useful in preventing ischemic damage in the brain and for the treatment of organic psychoses including depression, anxiety, learning and memory deficit, fobias, and hallucinations. This purpose is achieved with the peptide compounds of the invention when these are selected or formulated so as to be available to the central nervous system.

Nervous Tissue

It is well known that microglia are the main immune effector of the central nervous system (CNS), and that they are activated in response to a wide range of injuries that trigger brain inflammatory responses, including head injury and ischemia, neurodegenerative diseases, autoimmune diseases, infectious diseases, prion diseases, and brain tumors. Activated microglia migrate to injured CNS areas, where they proliferate and gradually remove cell debris. Eugenin et al showed that microglia can communicate with each other through gap junctions that are induced by inflammatory cytokines (Eugenin, E A, Eckardt, D, Theis, M, Willecke, K, Bennett, M V L and Sáez, J C: Microglia at brain stab wounds express connexin 43 and in vitro form functional gap junctions after treatment with interferon-gamma and tumor necrosis factor-alpha. Proc. Natl. Acad. Sci. USA, Vol. 98, 4190-4195, 2001). This was demonstrated in the following experiments. At brain stab wounds, microglia progressively accumulated over several days and formed aggregates that frequently showed Cx43 immunoreactivity at interfaces between cells. In primary culture, microglia showed low levels of Cx43 determined by Western blotting, diffuse intracellular Cx43 immunoreactivity, and a low incidence of dye coupling. Treatment with the immunostimulant bacterial lipopolysaccharide (LPS) or the cytokines interferon-gamma (INF-gamma ) or tumor necrosis factor-alpha (TNF-alpha ) one at a time did not increase the incidence of dye coupling. However, microglia treated with INF-gamma plus LPS showed a dramatic increase in dye coupling that was prevented by coapplication of an anti-TNF-alpha antibody, suggesting the release and autocrine action of TNF-alpha. Treatment with INF-gamma plus TNF-alpha also greatly increased the incidence of dye coupling and the Cx43 levels with translocation of Cx43 to cell-cell contacts. The cytokine-induced dye coupling was reversibly inhibited by 18-glycyrrhetinic acid, a gap junction blocker. Cultured mouse microglia also expressed Cx43 and developed dye coupling upon treatment with cytokines, but microglia from homozygous Cx43-deficient mice did not develop significant dye coupling after treatment with either INF-gamma plus LPS or INF-gamma plus TNF-alpha.

Due to the activation of gap junctional communication by COMPOUND 2 and COMPOUND 40 it is expected that these compounds will facilitate the intercellular communication of microglia and thereby augment or speed up the "healing" processes in the aforementioned diseases (brain inflammatory responses, including head injury and ischemia, neurodegenerative diseases, autoimmune diseases, infectious diseases, prion diseases, and brain tumors).

To substantiate this statement experiments in cultures of microglia can be performed using the general experimental design of Eugenin et al. 2001, above, with administration of COMPOUND 2 and COMPOUND 40 at concentrations in the range of 10-11-10-8 M to the affected microglia. These experiments are expected to show the facilitating effect of COMPOUND 2 and COMPOUND 40 on gap junctional coupling and counteract the effect of 18alpha-glycyrrhetinic acid. The compounds of the invention may also be used in the in vitro model descibed by Nagy J I and Li W E (Eur J Neurosci Dec. 12, 2000(12):4567-72) for the study of, i.a. actions of ischemia on astrocytic gap junction regulation.

Lung Tissue—Alveolar Cells

Alveolar intercellular communication via gap junctions between alveolar cells is important for the propagation of ion transport, mechanochemical signal transduction, regulation of cell growth and secretion of surfactant factor (Ashino Y, Ying X, Dobbs L G, Bhattacharya J. (Am J Physiol Lung Mol Physiol 2000; 279: L5-L13)). In vivo repair after acute and chronic inflammatory damage of the alveolar region of the lung involves formation of fibronectin as part of the extracellular matrix (Charash W E, Vincent P A, Saba T M, Minnear F L, Mc-Keown-Longo P J, Migliozzi J A, Lewis M A, Lewis E, Giunta C. ( Am Rev Respir Dis 1993; 148: 467-476) and Torikata C, Villiger B, Charles Kuhn I, McDonald J A. (Lab Invest 1985; 52: 399-408)). Alveolar epithelial cell culture studies have demonstrated an increased number of gap junctions in parallel to an increase of extracellular fibronectin concentration (Alford A I, Rannels D E. (Am J Physiol Lung Cell Mol Physiol 2001;280:L680-L688)). In vivo animal studies have found a decreased number of gap junctions after nitrogen dioxide induced severe pulmonary inflammation both in the alveolar tissue, the walls of the terminal bronchioles, alveolar ducts and peribronchiolar alveoli. These findings were dose dependent. However, if pretreated with taurin this loss of gap junctions was prevented in parallel with less pronounced inflammatory reactions. Similar findings were seen after irradiation of rat lung and after treatmen with the chemotherapeutiv compound, Bleomycin.

Thus, maintaining the gap junctional communication in lung tissue appears to be of importance for preventing lung fibrosis and decreased amount of connexin is seen as a reaction to inflammatory processes, to various toxic stimuli, such as gas inhalation, air born destructive substance and irradiation. Pretreatment with a compound that facilitates gap junction opening or gap junctional communication will be indicated prior to therapeutic irradiation where the lungs are exposed, e.g. in lung cancer, treatment of breast cancer, thyroid and esophageal cancers.

Treatment methods in accord with the invention can employ one or more of the compounds disclosed herein as the sole active agent. Preferably, one of the compounds will be employed. If desired, such compounds can be used prophylactically ie., to prevent or reduce the severity of a particular indication or condition. Alternatively, the compounds can be used in conjunction with a recognized therapeutic approach. As an illustration in embodiments in which irradiation is treated, it is generally preferred that the treatment method be "add on" ie., in conjunction with a recognized therapy for treating the condition. Such "add on" treatment methods of the invention can be conducted at the same time or at a different time then the recognized therapy as needed. Established therapuetic approaches for a variety of diseases and medical conditions have been described. See generally, *Harrison's Principles of Internal Medicine* (1991) 12 ed., McGraw-Hill, Inc. and *The Pharmacological Basis of Therapeutics* (1996) Goodman, Louis S. 9$^{th}$ ed Pergammon Press, for example; the disclosures of which are incorporated herein by reference.

Treatment with a compound that facilitates or mediates gap junction opening will prevent further deterioration of lung function in emphysema, asbestosis, silicosis, lung fibrosis, pneumonitis, drug induced lung fibrosis and in patients exposed to pulmonary toxic gasses such as nitrogen dioxide. Treatment will preferably be add on to conventional treatment of these conditions.

Compounds can be tested in vitro in alveolar epithelia cell culture with cells isolated from rat lung (Rannels S R, Rannels D E. (In: Cell Biology. A Laboratory Handbook, ed by Celis J E. San Diego, Calif.: Academic 1994, p 116-123), Abraham V, Chou M L, DeBolt K M, Koval M (Am J Physiol Lung Cell Mol Physiol 1999; 276: L825-L834)) or commercial available human cell line. Cells can be cultured in standard tissue culture collagen coated plastic dishes in Earle's minimal essential medium containing antibiotics and fetal bovine serum. Cells grow until a confluent layer. Gap junction communication is measured directly with 4% Lucifer yellow solution in 150 mM LiCl administered into a cell via microinjection. The fluorescent tracer is allowed to fill cells by simple diffusion for 3 minutes. After the injection period, the pipette is removed and the number of fluorescent cells is counted. The number of fluorescent cells is counted during various gap junction inhibitors with or without different doses of the described gap junction facilitators in the range of $10^{-10}$-$10^{-7}$ M (peptides).

A herein preferred gap junction opener, such as Compound 2 will also be tested in vivo in experimental animals during drug induced pulmonary fibrosis and irradiation induced pulmonary fibrosis. Animals are exposed to the inducers and the outcome is evaluated and compared to the outcome in animals pretreated with Compound 2. The dosages will be in the range of $10^{-10}$ to $10^{-7}$ mol/kg depending upon the compound's biological kinetics, e.g. as determined in the calciumchloride induced arrrythmia model described above. The compound may be administered orally, parenterally, nasally, or via pulmonary inhalation.

Smooth Muscles

Vascular system. Intercellular communication through gap junction channels plays a fundamental role in regulating and modulating vascular myocyte tone throughout the vascular tree (Christ G J, Spray D C, Moore L K, El-Sabban M E, Brink P R. (Circ Res. 1996; 79: 631-646)). Another important role of gap junction communication is the spread of hyperpolarization among smooth muscle cells involved in vascular relaxation response (Benny J L, Paicca C. Am J Physiol Heart Circ Physiol 1994; 266: H1465-72)).

The specialized functions of the endothelium require gap junction intercellular communication between endothelial cells within the monolayer and between endothelium and other cells present in the vessel wall. The communication between these different cell types via gap junctions in coronary capillaries as well as in all other vessels has been documented in several studies. Evidence of involvement in adaptive arteriogenesis has also been demonstrated (Cai W-J, Koltai S, Kocsis E, Scholz D, Shaper W, Schaper J (J Mol Cell Cardiol 2001; 33: 957-67), Wang H-Z, Day N, Valcic M, Hsieh K, Serels S, Brink P R, Christ G J. (Am J Physiol Cell Physiol. 2001; 281: C75-88), Schuster A, Oishi H, Benny J-L, Stergiopulos N, Meisater J-J. (Am J Physiol Heart Circ Physiol. 2001; 280: H1088-96)).

In different vascular patophysiological situations where the endothelial monolayer is disrupted as in diet induced hypercholestrolemic lesions the gap junction communication is decreased in the vascular smooth muscles (Polacek D, Bech F, McKinsey J F, Davies P F. (J Vasc Res 1997; 34: 19-30). Injury at the endothelial cellular layer is seen during venous stasis and when thrombophlebitis is developed. Kwak B R, Pepper M S, Gros D B, Meda P (Molec Biol Cell 2001; 12: 831-845) has clearly demonstrated that gap junction communication serves to coordinate cell migration during endothelial repair and also are important for capillary sprouting during angiogenesis.

Treatment with compounds that facilitate gap junction communication will improve the impaired inter cellular communication in the affected vascular areas, and will be particularly useful during organ ischemia, e.g. claudicatio intermittens and myocardial infarction.

However after baloon catheter injury in rat carotid the vascular healing process is characterised by increased gap junction communication. (Yeh H I, Lupu F, Dupont E, Severs N J, (Arterioscle Thromb Vasc Biol 1997;17:3174-84). The compound will be administered before the balloon intervention and is preferably an add-on therapy to conventional medical treatment of this condition. Administration of the compound will be parenterally.

The effect will be tested in tissue sampled before and at different time after the balloon catheter injury. Faster healing of the endothelial surface will be seen using conventional microscopy. Also improvement of gap junction communication will be found.

(Arterioscle Thromb Vasc Biol 1997;17:3174-84). Treatment with gap junction openers will increase the healing process.

Prophylactic effect of treatment with a gap junction opener, such as Compound 2 and Compound 40, will be tested in an experimental set up as described by Yeh H I, Lupu F, Dupont E, Severs N J, (Arterioscle Thromb Vasc Biol 1997;17:3174-84). Compound 2 or Compound 40 will be administered before the balloon intervention using dosages in the range of $10^{-11}$ to $10^{-8}$ depending upon the compound's biological kinetics, e.g. as determined in the calciumchloride induced arrrythmia model described above. Tissue will be sampled before and at different time after the balloon catheter injury. Faster healing of the endothelial surface will be seen using conventional microscopy. Also improvement of gap junction communication will be found.

Administration of the compound will be, e.g. parenterally.

In other diseases gap junctional communication between smooth muscle cells is disturbed. In Corpus cavernosum a syncytial cellular network is established via gap junctions and is critical to erectile function and ensures that the corporal and arterial smooth muscle cells of the penis respond in a uniform and coordinated manner. (Christ G J. (Int J Impot Res. 2000; 12 suppl. 4: S15-25), Melman A, Christ J C. (Urolog Clin North America. 2001; 28: 217-31)). Disturbed erectile function is seen in diabetes, arteriosclerosis, different neurological diseases and many chronic diseases. From studies in diabetes an inverse correlation between neural innervation and intercellular coupling point towards the potential functional plasticity of the corporal environment although not establishing the functional intercellular communication via gap junction.

Treatment with a compound that facilitates gap junction opening will improve the communication via the gap junction and thereby normalize the complex coordination between the smooth muscle cells in corpus cavernosum and the vessels.

Corporal smooth cells are isolated from rats are established as described by Christ G J, Moreno A P, Melman A, Spray D C. (Am J Physiol 1992; 263: C373-83). Gap junction communication is measured with Lucifer yellow or another fluorescent dye using the microinjection technique as described above or using a FACS method, such as described by Juul M H et al. Cell Adhes Commun 2000;7(6):501-12. The number of fluorescent cells is counted during various gap junction inhibitors with or without different doses of the described gap junction openers, e.g. Compound 2 or Compound 40, in the range of 10-10-10-8 nM. More than 25-50% improvement of gap junction communication after exposure with the gap junction openers will be identified with compound concentration within the given range.

In vivo pharmacological testing of erectile function of the compounds will be tested 10 weeks after streptozotocin (35 mg/kg i.p.) induced diabetes in rats (8 weeks old) as described by Rehman J, Cheven E, Brink P, Peterseon B, Walcott B, Wen Y P, Melman A, Christ G. (Am J Physiol 1997; 272: H1960-71). Penile reflexes and the intracavernous pressure are measured during local and systemic administration of different doses of the different gap junction openers with measures and techniques described by the same research group. An increase in penile reflexes and in the intracavernous pressure of 25% or above will be seen.

Treatment of erectile dysfunction can be administered either locally in the penil corpus, as subcutanous injection or orally. Treatment will be either monotherapy or add-on to conventional treatment of this condition.

Diabetic retinopathy can be diagnosed very early after onset of the disease by identifying alterations in the rate of blood flow (Bursell S-V, Clermont A C, Shiba T, King G L. (Curr Eye Res. 1992; 11: 287-95), breakdown in the blood-retinal barrier ( Cunha-Vaz J G, Faria de Abrue J R, Campos A J, Figo G M. (Br J Ophthalmol. 1975; 59: 649-56), Do Carmo A, Ramos P, Reis A, Proenca R, Cunha-Vaz J G. (Exp Eye Res. 1998; 67: 569-75)) and/or loss of autoregulation (Kohner E M, Patel V, Rassam S M B. (Diabetes 1995; 44: 603-607)). By using both tracer transport and double cell patch clamp techniques Oku H, Koda T, Sakagami K, Puro D G. (Invest Ophthalmol Vis Sci. 2001;42: 1915-1920) have demonstrated an extensive cell-to-cell coupling. A closure of gap junction pathways disrupts the multicellular organization of retinal microvessels and contribute to diabetic retinal vascular dysfunction. Zhou Z Y, Sugawara K, Hashi R, Muramoto K, Mawatari K, Matsukawa T, Liu Z W, Devadas M, Kato S. (Neuroscience. 2001; 102: 959-67) further demonstrated that reactive oxygen are involved in retinal gap junctional uncoupling and a recoupling when gluthation is supplied.

Gap junction openers' effect on diabetic retinopathy will be studied in vitro using the streptozotocin induced diabetic rat model as described above. Freshly isolated retinal microvessels (Sakagami K, Wu D M, Puro D G. J Physiol (Lond). 1999; 521: 637-50) will be transferred to coverslip as described by Oku H, Koda T, Sakagami K, Puro D G. (Invest Ophthalmol Vis Sci. 2001;42: 1915-1920). In this preparation the intercellular communication between the cells in the vascular wall will be measured either with dye or with tracer. Different concentrations in the range of 10-10-10-7 M of the gap junction openers Compound 2 or Compound 40 will be tested and an significant increase in intercellular communication compared to baseline will be seen in the diabetic retina. Similar improvement will be seen when compared to controls (healthy animals).

Treatment with a gap junction opener will stop or slow down the progression of the condition.

Treatment will be systemic, locally or orally.

Therapy is preferably an add-on to conventional antidiabetic treatment.

Not only diabetic retinopathy but also other vascular abnormalities in the retina as for instance arteriosclerosis will benefit from an improved gap junction communication by treatment with a gap junction opener. Gap junctions have been demonstrated to connect horizontal cells to one another and be responsible for electrical coupling between neurons (Raviola E, Gilula N B. (Proc Natl Acad Sci USA. 1975; 65: 192-222), Raviola E, Dacheux R F. (J Neurocytol. 1990; 19: 731-36), Schneeweis D M, Schnapf J L. (Science 1995;268: 1053-56)). Also transmission of scotopic signals between rods and cones via gap junctions are indicated (Bloofield S A, Dacheux R F. (Retinal Eye Res. 2001; 20: 351-384)). A gap junction opener will therefore increase the communication between not only the neurons but also be able to bypass less vital rods or cones and still bring the scotopic signal forward to the ophthalmic nerve.

Gap junction openers' effect on diet induced arteriosclerotic retinopathy will be studied in vitro using the a rat model (non-diabetic) as described above. The intercellular communication between the cells in the vascular wall will be measured either with Lucifer Yellow dye transfer method after microinjection or with the FACS method. Different concentrations in the range of 10-10-10-7 M of the gap junction openers Compound 2 or Compound 40 will be tested and a significant increase in intercellular communication compared to baseline will be seen. Similar improvement will be seen when compared to controls (healthy animals).

Compound will be administered parenterally.

Smooth muscles in the urine bladder are characterized by phasic contractions and show spontaneous phasic contractions. However the bladder is in the healthy condition able to contain several hundred milliliters of urine without showing an increased intravesical pressure. In contrast to the normal bladder unstable bladders develop spontaneous increases in intravesical pressure related to urge incontinence (Turner W H, Brading A F. (Pharmacol Therap. 1997; 75: 77-110). Compared to gastrointestinal smooth muscle, bladder smooth muscles does not spontaneously generate co-ordinated contractions (Stevens R J, Weinert J S, Publcover N G. (Am J Physiol. 199; 2777: C448-60), Hashitani H, Fukuta H, Takano H, Klemm M F, Suzuki H. (J Physiol. 2001; 530: 273-86)). Both electrical and morphological communications via gap junctions between smooth muscle cells in the bladder has recently been demonstrated (Hashitani H, Fukuta H, Takano H, Klemm M F, Suzuki H. (J Physiol. 2001; 530: 273-86), Wang H-Z, Lee S W, Day N S, Christ G J. (Urology. 2001; Suppl 6A: 111)). The importance of these gap junctions was demonstrated by specific inhibition of the communication. Waves of spontaneous excitation in bladder smooth muscle propagate through gap junctions.

The uncontrolled urged incontinence will therefore be regulated via treatment with a gap junction opener.

The improvement of gap junction communication after treatment with a gap junction opener is studied in cell culture of smooth muscle cell harvested from the urinary bladder using the FACS analysis. The compound will be dosed in concentrations ranging from 10-10 to 10-7 M and a significant increase in communication will be found in cell culture exposed to low oxygen or oxygen stress.

Intravesical pressure will be measured after pretreatment and acute treament with a gap junctional opener, preferably Compound 2 or Compound 40, in normal guinea pigs and in animals with experimentally disturbed bladder function. The animals are anesthesised with phenobarbital and the bladder is catheterized with both a urine catheter allowing water in- and outflow and a catheter with a tip-transducer. A gap junction opener will not change a normal volume—pressure relationship while this relationship will be normalized in the disturbed bladder.

Administration will be parenterally, orally or into the urinary bladder. Administration will preferably be as an add-on to treatment with drugs intended to normalize muscle contraction in the urine bladder.

Myoepithelial cells as presented in submandibular glandular ducts, in urether, in gall ducts, pancreatic ducts, tear duct are connected with gap junctions and intercellular communication is essential for the synchronization of contractile function of the myoepithelial cells (Taugner R, Schiller A. (Cell Tissue Res. 1980; 206: 65-72). Disturbed contractility in these ducts can be normalized by treatment with a gap junction opener administered either parenterally or orally.

Intercellular communication in the cardiac av node is maintained via gap junctions. Decreased function lead to decreased conduction and may lead to total a-v blockade. AV blockade is seen in acute myocardial infarction, in ischaemic heart disease, digitalis intoxication, calcium channel blocker intoxication and a Gap junction opener will improve the av conduction.

Intravenous infusion of CaCl2 (100 mg/kg/min) in neurolept anaesthetized mice induced 2nd degree av block. When pretreated with gap junction opener in doses of 10-11 to 10-6 mol/kg i.v., the dose of CaCl2 was significantly higher before av block was observed. Another measure of the effect was an increase in lack time of 30-65% until Cal induced 2 degree av block was observed. The CaCl2 induction of av block is described by Ronsberg M, Saunders T K, Chan P S, Cervoni P. Med Sci. 1986;14: 350-51).

Varying degree of av block increased gap junction communication will normalise the av conductance and normal sinus rhythm will be re-established.

Administration of gap junction opener shall be either parenterally or orally.

Effects of Gap Junction Openers on Cataract

The vertebrate eye lens is a solid cyst of cells, which grows throughout life by addition of new cells at the surface. The older cells, buried by the newer generations, differentiate into long, prismatic fibers, losing their cellular organelles and filling their cytoplasms with high concentrations of soluble proteins, the crystallins. The long-lived lens fibers are interconnected by gap junctions, both with themselves and with an anterior layer of simple cuboidal epithelial cells at the lens surface. This network of gap junctions joins the lens cells into a syncytium with respect to small molecules, permitting metabolic co-operation: intercellular diffusion of ions, metabolites, and water. In contact with nutrients at the lens surface, the epithelial cells retain their cellular organelles, and are able to provide the metabolic energy to maintain correct ion and metabolite concentrations within the lens fiber cytoplasms, such that the crystallins remain in solution and do not aggregate (cataract). Three kinds of connexins are present in the lens: Cx43, Cx46 and Cx50 and mutations in each of these gap junction proteins have been linked to cataract[79-81]. These findings demonstrate that GJIC is essential for normal metabolism and function of the lens. Therefore, we suggest that substances of this invention, which are known to increase GJIC may be used in the prevention and/or treatment of cataract.

Gap junction channels formed by Cx46 and Cx50 connexins provide pathways for communication between the fiber cells in the normal transparent lens. Knockout mice that are devoid of these connexins develop nuclear cataracts that are associated with the proteolysis of crystallins. These studies has established the importance of gap junctions in maintaining normal lens transparency by providing a cell-cell signaling pathway or structural component for the proper organization of lens membrane and cytoplasmic proteins (Gong et al., Cell Dec. 12, 1997; 91(6):833-43). Increased intracelular calcium concentration is a major stimulus for the activation of the calcium-dependent cysteine protease Lp82 which is a key initiator of the process of cataractogenesis (Baruch et al., J Biol Chem 2001;276(31):28999-9006). To examine the ability of compounds 2 and 40 of the present invention to prevent cataract, the effect of said compounds (10-10-10-6 mol/l) is tested in model of cultured ovine lens cells described by Churchill et al. (J Cell Sci 1996;109 ( Pt 2):355-65)). Briefly, cell-to-cell Ca2+ signaling is investigated in primary cultures of ovine epithelial cells using the Ca(2+)-reporter dye fura-2 and fluorescence microscopy. Mechanical stimulation of a single cell with a micropipette initiates a propagated increase in cytosolic free Ca2+ that spread from the stimulated cell through 2-8 tiers of surrounding cells. We expect that compounds 2 and 40 of this invention will increase cell-to-cell coupling between lens fiber cells and prevent cataract.

Mode of administration will be topical.

Thus, it is a purpose of the present invention to provide compounds for the preparation of medicaments useful in prevention and/or treatment of cataract. This purpose is achieved with the present peptide compounds, such as the compounds of formulae I to VIII, formulae 2 to 12, and the compounds of tables 1 and 8 herein, more specifically the compounds of Synthesis Examples 1-55 herein.

Effects of Gap Junction Openers in Ear Diseases

Many different mutations of Cx32 have been found in the hereditary peripheral neuropathy-deafness X-linked Charcot-Marie-Tooth syndrome and several mutations of Cx26 and Cx31 have been detected in deafness[80]. Thus, we suggest that substances of this invention, which are known to increase GJIC may be used in the prevention and/or treatment of certain kinds of deafness that are associated with impaired GJIC in the ear. Thus, it is a purpose of the present invention to provide compounds for the preparation of medicaments useful in prevention and/or treatment of deafness associated with impaired GJIC. This purpose is achieved with the present peptide compounds, such as the compounds of formulae I to VIII, formulae 2 to 12, and the compounds of tables 1 and 8 herein, more specifically the compounds of Synthesis Examples 1-55 herein and the compounds of Table 8, Table 1, and formulae I to VIII herein.

Role of Gap Junction Openers in the Intestines

Both Cx43 and Cx45 are expressed in the wall of the small intestine[82]. It is believed that Cx45-expressing cells along the deep muscular plexus of the small intestine are likely to act as a constituent of a pacemaker system, which may include a conductive system, by forming a cellular network operating via specific types of gap junctions. In the intestine and in the colon, the interstitial cells of Cajal (ICC) are pacemaker cells located between intestinal smooth muscles; they generate spontaneous slow waves of the smooth muscle layers and mediate neurotransmission. The three-dimensional cellular network of ICC is connected by Cx43 gap junctions both between ICC and between ICC and smooth muscle cells[83]. In patients with Hirschsprung's disease, the lack of expression of Cx43 in the aganglionic bowel suggests that the impaired intercellular communication between ICCs and smooth muscle cells may partly be responsible for the motility dysfunction in this disorder[83]. Patients with Chagas's disease (due to an infection with the protozoa *trypanosoma Cruzii*) exert marked reduction of Cx expression which is considered responsible for both the cardiomyopathy as well as the severely dilated megacolon seen in these patients[7]. Thus, normal gap junction communication between ICC and between ICC and smooth muscle cells is considered essential for normal motility in the small intestine and in the colon. It is therefore a further purpose of the invention to provide a substance that increases gap junction conductance in the intestine and therefore may be useful in the treatment of gastrointestinal motility disorders.

Reproductive Organs and Gap Junctions

Ovaries

Gap junctions between granulosa cells, and between the oocyte and the surrounding granulosa cells play an important role during ovarian follicle development. At birth, the ovary contains primordial follicles consisting of meiotically arrested oocytes surrounded by a single layer of supporting (granulosa) cells. Periodically, subsets of primordial follicles undergo further development during which the oocyte increases in size and the granulosa cells proliferate, stratify and develop a fluid-filled antrum. After ovulation, oocytes resume meiosis and granulosa cells retained in the follicle differentiate into steroidogenic cells, forming the corpus luteum.

Gap junctions directly connect adjacent cells allowing the diffusional movement of ions, metabolites, and other potential signalling molecules of importance for the regulation of the ovarian cycle and female fertility. In support for an essential role of gap junctions for normal ovary function, it has been demonstrated that Cx37-deficient mice lack mature (Graafian) follicles, fail to ovulate and develop numerous inappropriate corpora lutea. In addition, oocyte development arrests before meiotic competence is achieved. Thus, cell-cell signalling through intercellular channels critically regulates the highly coordinated set of cellular interactions required for successful oogenesis and ovulation[84].

Follicle-stimulating hormone (FSH) is the major regulator of growth and development of the ovarian follicle. Along its many actions on follicular maturation, FSH improves cell-to-cell coupling between the granulosa cells and it enhances Cx43 gene expression, and possibly, formation of new gap junctions.[85]. Conversely, luteinizing hormone (LH) interrupts cell-to-cell communication within the ovarian follicle, leading to a decrease in intra-oocyte concentrations of cAMP followed by resumption of meiosis[86].

These data illustrate that the presence of normal gap junction communication through Cx37 and Cx43 are essential for normal follicular growth and ovulation. Thus, it is likely that certain forms of female infertility is due to poor cell-to-cell coupling in the ovaries. Therefore, a substance that increases cell-to-cell coupling may be used for the treatment of female infertility in women with impaired expression and/or regulation of ovarian gap junction function. The compounds of the present invention having the ability to increase GJIC are useful for the treatment of female infertility that is due to poor cell-to-cell coupling in the ovaries.

Uterus

The powerful synchronous contractions of the uterus in labour depend on electrical coupling of myometrial smooth muscle cells by gap junctions. In humans and other mammals, gap junctions are scarce in the myometrium of the non-pregnant uterus, but become abundant at term and/or with the onset of labor. The predominant gap-junctional protein expressed by human myometrial smooth muscle cells is Cx43, but also Cx26, Cx40 and Cx45 have been identified in the human myometrium[87;88].

Due to the great significance of coordinated muscle contractions during labour, it is a further purpose of the invention to provide a substance that increases cell-to-cell coupling in the myometrium which is expected to have a positive influence on the synchronization of muscle contractions and said substance may be used along with oxytocin for the induction and facilitation of labour. Said purpose is achieved with the present peptide compounds, such as the compounds of formulae I to VIII, formulae 2 to 12, and the compounds of tables 1 and 8 herein, more specifically the compounds of Synthesis Examples 1-55 herein and the compounds of Table 8, Table 1, and formulae I to VIII herein, and the invention further relates to the use of the peptide compounds of the invention for the preparation of a medicament for the induction and facilitation of labour.

Huidobro-Toro J P, Gonzalez R, Varas J A, Rahmer A, Gonzalez R. (Rev Med Chil 2001 October; 129(10):1105-12) assessed the existence of pacemaker mechanisms related to rhythmic motor activity of human placental blood vessels, and found that the blockade of gap junctions ablated the frequency and amplitude of spontaneous contractions. They concluded that rhythmic contractions in the circular layer of chorionic and umbilical vessels are triggered by pacemaker cells located in the circular layer of the smooth muscle of blood vessels and spread via gap junctions; they likely contribute to the control of blood flow. Thus, it is a further purpose of the invention to provide a substance that increases cell-to-cell coupling in placental blood vessels which is expected to have a positive influence on placental blood circulation and the development of the fetus. Said purpose is achieved with the present peptide compounds, such as the compounds of formulae I to VIII, formulae 2 to 12, and the compounds of tables 1 and 8 herein, more specifically the compounds of Synthesis Examples 1-55 and the compounds of Table 8, Table 1, and formulae I to VII herein, and the invention further relates to the use of the peptide compounds of the invention for the preparation of a medicament useful in the treatment of reduced placental blood circulation.

Male Reproductive Organs

Cx43 is the most abundant connexin in the testis, and interestingly, rat strains with decreased Cx43 expression have impaired spermatogenesis (ebo/ebo, jun-d−/−, Cx43 ± mice), [89]. Moreover, early work suggested that hypo- or aspermic patients have decreased gap junctions in the testes[90]. These data support the suggestion that decreased cell-to-cell coupling in the testes may lead to male infertility, and it is therefore a further purpose of the invention to provide a substance that increases cell-to-cell coupling and, thus, may be a useful therapeutic in the treatment of male infertility associated with impaired cell-to-cell coupling.

Role of Gap Junctions in the Pancreas

Gap junction channels made of Cx43 functionally couples the glucose-sensitive cells of pancreatic islets and of a rat insulinoma cell line[91]. In contrast, cells of several cell lines secreting insulin abnormally do not express Cx43, have few gap junctions, and are poorly coupled. After correction of these defects by stable transfection of Cx43 cDNA, cells expressing modest levels of Cx43 and coupling, as observed in native beta-cells, show an expression of the insulin gene and an insulin content that is markedly elevated, compared with those observed in both wild-type (uncoupled) cells and in transfected cells overexpressing Cx43. These findings indicate that adequate coupling of Cx43 are required for proper insulin production and storage[91]. Moreover, in vivo stimulation of insulin release by glibenclamide is associated with increased expression of Cx43 and increased cell-to-cell coupling between neighbouring β-cells within the pancreatic islet[92].

To examine the effect of Compound 2 and Compound 40 on non-insulin dependent diabetes mellitus, 6-16 weeks old db/db are used. The animals are housed (3 mice/cage) under controlled ambient conditions (20° C., 55-75% humidity) following a 12/12-hrs light/dark cycle with light on at 6 am. They are with standard Altromin No. 1324 diet with free access to tap water. All animals are acclimatised for at least one week and handled daily for two days prior to the first oral glucose tolerance test. Furthermore, to reduce stress-induced glucose excursions the animals are subjected to at least one oral glucose tolerance test without compound as described below prior to the experiment.

Peptides are dissolved in 0.1 M phosphate-buffered saline (PBS) with 0.1% bovine albumin where pH was adjusted to 7.4 by adding 5 M NaOH. All solutions are prepared fresh on the morning immediately before the experiment. Componds are given parenterally in doses 10-10-10-6 mol/kg. Vehicle-treated animals are given PBS with 0.1% albumin alone.

The animals are fasted for 17 hours before the gluocose toleranmce test. Beginning at 9.00 am blood is taken from the tail tip (t=−15 min) and blood glucose is measured. The whole blood glucose (mM) concentration is analysed by the immobilised glucose oxidase method using a drop of blood (<5 ml, Elite Autoanalyser, Bayer, Denmark). Animals with severely elevated blood glucose on the morning of the experiment (>10.5 mM) are excluded. Immediately after the initial blood sample the animals receive an i.p. injection of vehicle or different doses of compound. Fifteen minutes after i.p. administration of the substance, a dose of 1 g/kg glucose dissolved in water (200 ml/50 g body weight) is given p.o. or i.p., and the animals are returned to their home cages (t=0). Blood glucose levels are measured at t=30 min, t=60 min, t=120 min and t=240 min. The animals were kept fasted during the observation period.

In order to analyse the effects of the compounds on glucose tolerance, the absolute and the relative difference in blood glucose from baseline (t=0) are calculated for each time point after glucose loading. The area under the curve (AUC) for the whole experiment (AUC0-240 min) is determined using the trapezoid method. Thus, two sets of AUC0-240 min values are generated, one based on absolute blood glucose values (unit: mM×min) and one based on relative changes in blood glucose (unit: %×min).

We predict that Compounds 2 and 40 of this invention will reduce the increase in blood glucose levels in response to a glucose load in db/db mice.

Administration will be orally or parenterally.

These observations indicate an important role of gap junction coupling between pancreatic islet β-cells for the production and release of insulin. Thus, a still further purpose of the present invention is to provide a substance that increases gap junctonal intercellular communication and/or the electrical conductance of gap junctions and, thus, improves glucose tolerance in subjects with non-insulin dependent diabetes mellitus. Said purpose is achieved with the peptide compounds of the invention, such as the compounds of formulae I to VIII, formulae 2 to 12, and the compounds of tables 1 and 8 herein, more specifically the compounds of Synthesis Examples 1-55 herein.

In addition, Ito T, Ogoshi K, Nakano I, Ueda F, Sakai H, Kinjo M, Nawata H (Pancreas Oct. 15, 1997 :297-303) found effect of Irsogladine on gap junctions in cerulein-induced acute pancreatitis in rats. The capacity for intercellular communication (IC) via gap junctions is found in normal pancreatic acinar cells, and the role of IC in cerulein (Cn)-induced acute pancreatitis in rats using irsogladine, an enhancer of IC via gap junction, was investigated. Acute edematous pancreatitis was induced in rats by two intraperitoneal injections of 40 micrograms/kg Cn. Rats received various doses (25, 50, or 100 mg/kg body weight) of irsogladine orally, 15 and 2 h before the first Cn injection. The normal control group received only vehicle. The severity of pancreatitis was evaluated enzymatically and histologically 5 h after the first Cn injection. In Cn-induced acute pancreatitis, irsogladine significantly lowered the serum amylase level, the pancreatic wet weight, and the pancreatic amylase and DNA contents, in a dose-dependent manner. Particularly, the amylase content improved to the level of the normal controls. Histologically, the severity of pancreatitis was reduced significantly by treatment with irsogladine and no discernible vacuolization was seen in the group with 100 mg/kg irsogladine treatment. By immunofluorostaining pancreata with anti-connexin 32 (Cx32; a gap junction protein) antibody, it was found that pancreatic acini were diffusely positive for Cx32 in the control group, but the number of Cx32-positive grains decreased markedly, to 19%, in the pancreatitis group. With 100 mg/kg irsogladine treatment, the number of Cx32 grains recovered to 70% of the normal control value. These findings indicate that IC via gap junction is disturbed in Cn-induced pancreatitis, which may result in the breakdown of tissue homeostasis and the progression of acute pancreatitis.

Thus, the peptides described herein are useful in the treatment of pancreatitis. To substantiate this statement experiments in rats can be performed using the general experimental design of Ito T et al. 2001, above, with administration of COMPOUND 2 and COMPOUND 40 at concentrations in the range of $10^{-11}$-$10^{-8}$ M to the rats. These experiments are expected to show the facilitating effect of COMPOUND 2 and COMPOUND 40 on gap junctional coupling and counteract the effect of cerulein.

Administration of the peptides will be intravenously.

Effects of Gap Junction Openers (Antiarrhythmic Peptides) in Thrombosis

An antithrombotic activity of two peptides closely related to substances of the present invention have previously been shown to have antithrombotic activity. Thus, Dikshit et al.[15] found that the peptides Gly-Pro-Prp-Gly-Ala-Gly (SEQ ID NO: 101) and Gly-Pro-Gly-Gly-Ala-Gly (SEQ ID NO: 102) prevented the development of a pulmonary embolism in mice given an i.v. dose of collagen and adrenaline. U.S. Pat. No. 4,775,743 discloses HP5, a peptide derivative of AAP having the sequence N-3-(4-hydroxyphenyl)propionyl-Pro-4Hyp-Gly-Ala-Gly-OH (SEQ ID NO: 2) and being active against platelet agglutination. The compounds of the present invention have a striking similarity and it is likely that they may show similar effects on thrombosis. Thus, the substances of this invention may be used in the prevention of thrombosis.

Immunology

Cell-to-cell interactions are crucial for lymphocyte maturation and activation. A wide rage of membrane molecules ensure intercellular adhesion and enabling cell-cell signaling during cell migration and activation in the immune system. Circulating human T, B and NK lymphocytes express Cx43 and active gap junctions between the cells have been demonstrated using dye methods as described previously. It has also been demonstrated that decrease in intercellular gap junctional coupling markedly decrease the secretion of IgM, IgG and IgA indicating that intercellular signaling across gap junctions is an important component of the mechanisms underlying metabolic cooperation in the immune system (Oviedo-Orta E, Hoy T, Evans W H. (Immunology. 2000; 99: 578-90), Oviedo-Orta E, Gasque P, Evans W H. (FASEB. 2001; 15:768-774)).

In subchronic or chronic inflammation a local increase in synthesis of immunglobulins is desirable independent of aethiology. During inflammation the tissue is often different from the normal healthy tissue and low oxygen tension produces uncoupling of the intercellular gap junctional communication (The importance of low oxygen for GJIC uncoupling has been demonstrated in several differrent cell systems suggesting that oxygen tension is a universal regulator of GJIC.

In primary cultures of neonatal rat ventricular cardiomyocytes, deprivation of oxygen and glucose leads to a decrease in the noradrenalin-induced stimulation of phosphoinositol (PI) turnover to app. 50% of the level at normal atmospheric and nutritional conditions. The gap junction modifier COMPOUND 2 has been shown to normalise this impaired noradrenalin-induced stimulation of PI turnover during oxygen and glucose deprivation by raising PI turnover to app. 90% of the normal level. Moreover is has been shown that COMPOUND 2 do not alter the noradrenalin-induced level of PI turnover during normal athmospheric and nutritional conditions (Meier, E and Beck, M M: ZS42-0123 enhances norepinephrine (NE)—induced phosphoinositol (PI) turnover in cultured cardiomyocytes during metabolic stress. 2001 International Gap Junction Conference, Aug. 4-9, 2001, Hawaii, USA, abstract no. 132). Likewise, in cultured human osteoblast cultures and in osteoblastic rat osteosarcoma cell lines hypoxia decreased intracellular calcium wave propagation as measured as dye transfer after Lucifer Yellow injections. This decrease could be completely reversed by treatment with COMPOUND 2 (Teilmann, S C, Henriksen, Z, Meier, E, Petersen, J S, Sørensen, O H and Jørgensen, N R: The gap junction opener ZS42-0123 enhances intercellular communication in osteoblastic cells. 2001 International Gap Junction Conference, Aug. 4-9, 2001, Hawaii, USA, abstract no. 176).

Due to cellular uncoupling during inflammation a gap junction opener will improve synthesis of immunglobulins during inflammation.

In vitro test of gap junction openers' effect upon synthesis of immunglobulins will be tested in stimulated and non stimulated T and B lymphocytes isolated from human tonsils and purified as described by Oviedo-Orta E, Gasque P, Evans W H. (FASEB. 2001; 15:768-74)). Immunglobulins will be measured by ELISAs and the gap junctions by FACS analysis. Gap junction openers will be tested in concentrations from 10-10 to 10-7 M. In vivo pharmacological testing will be performed in experimental inflammatory models both in non-infectious and in infectious models. In vivo pharmacological testing can be performed experimentally in a series of animal models: 1) inhibition of carrageenan-induced rat hind paw oedema (paw volume), 2) attenuation of carrageenan-induced cellular recruitment into an air pouch in rats (leukocyte recruitment and exudates volume), 3) attenuation of streptococcal cell wall (SCW)-induced arthritis in rat tibia-tarsal joint (ankle swelling), and 4) attenuation of progression of collagen-induced arthritis in rats (clinical signs and joint swelling).

Ye P, Chapple C C, Kumar R K, and Hunter N (J Pathol 192:58; September 2000) have shown that there was a striking reduction in connexins 26 and 43 in the lining epithelia of inflamed gingiva supporting the concept that the ability of the epithelia to function as an effective barrier against microbial products into the tissues is severely compromised in periodontitis. Thus, treatment of inflamed gingiva with a gap junction opener, e.g. in combination with an antibiotic, may be advantageous in restoring GJIC and the healing of the epithelia.

Peripheral Neuropathy and Neuropathic Pain

Peripheral neuropathy and pain as seen in diabetes, during dialysis, liver cirrhosis and many other conditions are reported to involve both somatic and autonomic nerves. The exact mechanisms of the peripheral nerve injury in the various conditions are still speculative but nerve terminal destruction, decreased conductance, demyelination and increased inflammatory response have been described. Common for the various conditions in experimental set up are that increased free radicals, increased nitric oxide, oxygen stress and lack of free radical scavengers are seen and reduction of gap junction communication is recorded (Pitre D A, Seifert J L, Bauer J A (Neurosci Lett. 2001; 303: 67-71), Bolanos J P, Medina J M. (J Neurochem. 1996; 66: 2019-9), Low P A, Nickander, K K. (Diabetes. 1991; 40: 873-7), Levy D, Hoke A,Zochone D W. (Neurosci Lett. 1999; 260: 207-9),Bruzzone R, Ressot C. J Eur Neurosci. 1997; 9: 1-6)).

In vitro studies will be performed in cultures of rat astrocytes or Schwanns cells and gap junction openers, such as Compound 2 and Compound 40, will be tested in nitric oxide stressed cells as described by Bolanos J P, Medina J M. (J Neurochem. 1996; 66: 2019-9) using sodium nitroprusside as nitric oxide donor (Blasits S, Maune S, Santos-Sacchi J. (Phlugers Arch. 2000; 440: 710-12)) Concentrations of compounds will be in the range of 10-10 and 10-7 M and the dose dependent gap junction opening will be measured using the FACS analysis.

Administration will be parenterally.

Hearing Deficit

Noise induced hearing loss, presbycusis known to be associated with production of free radicals are related to inhibition of gap junction coupling between both Hensen cells and Deiters cells from Corti's organ in the cochlea (Todt I, Ngezahayo A, Ernst A, Kolb H-A. (J Membrane Biol. 2001;181: 107-114), Blasits S, Maune S, Santos-Sacchi J. (Phlugers Arch. 2000; 440: 710-12) Lagostena L, Ashmore J F, Kachar B. (J Physiol. 2001; 531: 693-707)). The gap junction communication between these supporting cochlear cells provides the important homeostasis for the sensory cells and thereby a normal neuronal activity of outer hair cells (Johnstone B M, Pantuzzi R, Syka J, Sykova E. (J Physiol 1989; 408: 77-92)). This communication is disrupted during oxidative stress (Todt I, Ngezahayo A, Ernst A, Kolb H-A. (J Membrane Biol. 2001; 181: 107-114). Acquired or age dependent hearing loss will be prevented when treated with a compound which can maintain gap junction communication in the supportive cells.

In vitro testing of gap junction openers will be performed in Hensen cells from guinea pigs as described by Todt I, Ngezahayo A, Ernst A, Kolb H-A. (J Membrane Biol. 2001; 181: 107-114). The compound Compound 2 or Compound 40 in the concentration range of 10-10-10-8 M will be investigated and their effects on oxygen stressed and mechanically stressed conditions will be studied. The compound will significantly antagonize the induced gap junction uncoupling.

Rats given i.v. infusion of Compound 2 were subjected to distortion product otoacoustic emissions (DPOAE) tests. Two sine-wave tones close in frequency (f1 and f2) were presented to the ear at the same time. The sound emitted from the inner ear consists of distortion products produced by the outer hair cells. The strongest of these distortion products is typically at the frequency 2f1-f2. For example, if the tones used are at 1000 Hz (f1) and 1200 Hz (f2), the strongest distortion product will be at 2×1000-1200, or 800 Hz. The relative intensity of the distortion product, compared to the two sine waves, can be used to assess the integrity of the outer hair cells. kHz.

Compound will be administered parenterally.

Melanocytes in the vestibular organ dark cell area are communicating heavily via gap junction and may play a role in transporting material between the endolymph and perilymph and also be of importance in maintaining the homeostasis of the microenvironment in the inner ear (Masuda M, Usami S-I, Yamazaki K, Takumi Y, Shinkawa H, Kurashima K. (Anat Rec. 2001; 262; 137-146)). Endolymphatic hydrops is related to various clinical conditions characterized by dizziness and reduced hearing. A decreased capacity of gap junction communication may be of importance in regulating transmembrane transport of several substances originally secreted or excreted via specific types of transporters.

Age Dependent Anemia and Bone Marrow Transplantation

Existence of functional gap junctions between haematopoietic progenitor cells and stromal cells of the haematopoietic microenvironment was many years controversial but studies have now proofed the existence of human gap junction communication (Rosendaal M, Gregan A, Green C. Tissue Cell. 1991; 23: 457-470),Dürig J, Rosenthal C, Halfmeyer K, Wiemann M, Novotny J, Bingmann D, Dührsen U, Schirrmacher K. (Brit J Haematol. 2000; 111: 416-25)). It has also been demonstrated that the communication is bi-directional favoring the hypothesis that stromal cells control the proliferative behavour of the haematopoietic progenitor cells, but also their functional status can be regulated by immature haematopoietic cells (Gupta P, Blazar B, Gupta K, Verfaillie C. (Blood. 1998; 91: 3724-3733)).

With age the functionality of the haematopoietic tissue is decreased and anemia is often seen in elderly people.

Reduced capacity of haematopoietic tissue is also seen in haematological malignancies and after treatment with chemotherapeutics. Bone marrow transplantation from donor is used to prevent pancytopenia.

The effect of a compound that facilitates gap junction communication will be studied in pretreated rats exposed to high dose cyclophosphamide. In these animals the bone marrow has stopped producing mature haematopoietic cells. Number of reticulocytes at different time intervals after cyclophosphamide will be significantly higher in the animals pretreated with the gap junction opener Compound 2 using doses of about 100 microL of 10-10 M to about 10-8 M Compound 2 compared to non-pretreated animals.

The drug administration will be parenterally.

Pituitary and Hypothalamic Hypofunction

Hormones from the anterior pituitary gland show circadian variation in secretion within minutes, hours, days and seasons. The part of the nervous system responsible for most circadian rhythm is localized to a pair of structures in the hypothalamus known as the suprachiasmatic nucleus. In this center this biological clock is intrinsic in the individual cells. However coordinated electrical activity is mediated to neighboring cells via gap junction communication. (Colwell C S. (J Neurobiol. 2000; 43: 379-88)). Because also the anterior pituitary lacks direct innervations, gap junction-mediated cell-to-cell communication within the gland must be indispensable for the adequate cell-to-cell coordination and synchronization required to ensure appropriate and timed hormone secretion.(Vitale M L, Cardin J, Gilula N B, Carbajal M E, Pelletier R-M. (Biol Reporo. 2001; 64: 625-633)). Guerineau N C, Bonnefont X, Stoeckel L, Mollard P. (J Biol Chem. 1998; 273: 10389-95) concluded that spontaneously active endocrine cells are either single units or arranged in synchronized gap junction-coupled assemblies scattered throughout the anterior pituitary gland. Synchrony between spontaneously excitable cells may help shape the patterns of basal secretion. From the anterior pituitary gland, growth hormone, prolactin, adrenocortical hormone, thyreoid hormone, and gonadotropin hormones are synthesized under control from hypothalamus stimulating hormones. One of the mechanism in dysrhythm of the complicated hypothalamic-pituitary-endocrine glands within one of the axis is therefore also related to reduced communication via gap junctions. The diseases are diabetes insipidus, hypogonadotrope hypogonadism, myxoedema, adrenocorticoid hypofunction, and dwarfism. Treatment with a gap junction opener will improve the symptoms.

Also the neurons in the suprachiasmatic nucleus of the hypothalamus are dependent on optimal gap junction communication. In the axis mentioned above gap junction opener with mode of action in this region will also benefit patients with disturbed circadian rhythm (Shinohara K, Funabashi T, Mitsishiba D, Kimura F. (Neusosci Lett. 2000; 286: 107-10).

Renovascular Hypertension and Nephrotoxicity

Kidney and endothelial specific gap junctions are widely distributed in the kidney found in glomeruli, tubulus and vasculature including intraglomerular capillaries and juxaglomerular arterioles (Haefliger J-A, Demotz S, Braissant O, Suter E. (Kidney Int. 2001; 60: 190-201)). In that study the authors demonstrated the presence of gap junctions connecting renin-secreting cells of the afferent arteriole. The role of gap junction might contribute to the detection and propagation of blood borne signals, such as those elicited by increased blood pressure. Within the kidney, such signals need to be converted into autocrine, paracrine and endocrine stimuli by the endothelial cells of the afferent arteriole and the transmitted to the renin-secreting cells. Gap junction communication plays thus an important role in forming the interconnected juxtaglomerular apparatus. The rapid open to close transitions of gap junctions channels further imply a readily response to local vascular changes ensuring the continous feedback required to match glomerular and tubular function as well as renin secretion to physiological demands. Diseases characterized by impaired renal gap junction communication will benefit from treatment with a specific gap junction opener either administered orally or parenterally. Heavy metals are nephrotoxic and causes renal injury. It has been demonstrated that the toxic metals cadmium (Fukumoto M, Kujiraoka T, Hara M, Shibasaki T, Hosoya T, Yoshida M. (Life Sciences. 2001;69:247-54)) as well as mercury (Yoshida M, Kujiraoka T, Hara M, Nakazawas H, Sumi Y. (Arch Toxicol. 1998; 72: 192-96)) in primary cell cultures from rat proximal tubulus uncouple gap junctions and both groups suggest that renal dysfunction is related to the reduced intercellular communication.

Treatment of heavy metal poisoning with a gap junction opener will reduce the tissue damage and prevent the progressive tissue devastation.

In vitro test will be performed in cell cultures from tubulus cells and the compounds' (Compound 2 or Compound 40 in a concentration of about 10-10-10-7 M) prevention of gap junction uncoupling when exposed to heavy metals will be investigated. Gap junction communication will be tested with Lucifer dye method as described previously.

After systemic administration of heavy metal to experimental animals (rats) renal function will be measured using 3H-insulin as a clearance marker for glomerular filtration rate, 14C-labelled tetraethylammonium as a clearance marker for renal plasma flow and lithium as a marker for proximal tubular function (Petersen J S, Schalmi M, Lam H R, Christensen S, J. Pharmacol. Esp. Ther. 1991, 258:1-7) before and after different time of chronic treatment with heavy metals. Chronic treatment with a specific gap junction opener, such as Compound 2, will be initiated when renal function is compromised and an significant improvement of renal function parameters (glomerular filtration rate and blood pressure) will be seen following the treatment.

Administration of compound will be parenterally.

Non-infectious inflammation as well as infections with different microbes induces significant non specific chronic changes in renal function also characterized by reduced glomerular filtration rate, decreased excretion of electrolytes and water and changes in blood pressure. Some of these symptoms will as well be treated with a specific gap junction opener and the symptoms will decline.

Developing and Remodeling of Teeth

Murakami S and Muramatsu T (Anat Embryol. 2001;203: 367-374) confirmed previous studies that gap junction communication exists between odontoblasts and that cellular activity is coordinated via these intercellular bridges (Iguchi Y, Yamamura T, Ichikawa T, Hashomot O S, Houriuchi T, Shimono M. (Arch Oral Biol. 1984; 29: 489-497)) but in their recent study they also demonstrated that these gap junction communications are present during the early development of teeth (pre-odontoblast) as well as in the odontoblasts in young and old odontoblast. Also the pulp cells subjacent to odotoblasts have gap junctions. These findings indicate that intercellular gap junction communication is important both during development of the teeth and during lifetime when teeth are remodeled or wormed.

Treatment with a gap junction opener will normalize disturbed development of teeth. Treatment will also facilitate remodeling of teeth and make the teeth more resistant to caries.

The gap junction facilitating compounds of the present invention, such as Compound 2, can be testet in vitro for effect on odontoblast intercellular communication in an assay which is essentially comparable to the osteoblast assays described herein.

Stem Cells

Lumelsky et al (2001) have generated cells expressing insulin and other pancreatic endocrine hormones from mouse embryonic stem cells (Nadya Lumelsky, Olivier Blondel, Pascal Laeng, Ivan Velasco, Rea Ravin, Ron McKay: Differentiation of Embryonic Stem Cells to Insulin-Secreting Structures Similar to Pancreatic Islets. Science, 292, 1389-1394, 2001). The cells self-assemble to form three-dimensional clusters similar in topology to normal pancreatic islets where pancreatic cell types are in close association with neurons. Glucose triggers insulin release from these cell clusters by mechanisms similar to those employed in vivo. When injected into diabetic mice, the insulin-producing cells undergo rapid vascularization and maintain a clustered, islet-like organization.

In the clinical context, this embryonic stem cell-based system may allow simultaneous generation and assembly of insulin-secreting and other islet cell types known to play important role in regulation of insulin secretion into functional structural units. These units might provide material to optimize insulin production and analyze the fine control of glucose homeostasis. embryonic stem cells are ideal for these studies because genetic tools can be used to define the molecular basis of islet development and function. Potential for cell-based therapies is clearly an attractive goal for applications involving human and nonhuman embryonic stem and embryonic germ cells. Adult tissue may also be a useful source of functional pancreatic cells. The differentiation system described here may provide a source of functional pancreatic islets for treatment of diabetes. To our knowledge, this is the first report showing that the several cell types of endocrine pancreas can be generated from embryonic stem cells in vitro. Although pancreatic islets obtained from cadavers can function in the liver after grafting, issues of tissue rejection and availability remain to be resolved. It is clear that engineering of embryonic stem cells to produce an abundant source of immunocompatible tissue for transplantation holds a growing promise for surmounting this and other problems associated with diabetes.

Myocardial infarction leads to loss of tissue and impairment of cardiac performance. The remaining myocytes are unable to reconstitute the necrotic tissue, and the post-infarcted heart deteriorates with time. Injury to a target organ is sensed by distant stem cells, which migrate to the site of damage and undergo alternate stem cell differentiation; these events promote structural and functional repair. This high degree of stem cell plasticity prompted Orlic et al (Orlic, D, kajstura, J, Chimenti, S, Jakoniuk, I, Anderson, S M, Li, B, Pickel, J, McKay, R, Nadal-Ginard, B, Bodine, D M, Leri, A and Anversa, P: Bone marrow cells regenerate infarcted myocardium. Nature 410, 701-705 (2001)) to test whether dead myocardium could be restored by transplanting bone marrow cells in infarcted mice. They sorted lineage-negative (Lin-) bone marrow cells from transgenic mice expressing enhanced green fluorescent protein by fluorescence-activated cell sorting on the basis of c-kit expression. Shortly after coronary ligation, Lin- c-kitPOS cells were injected in the contracting wall bordering the infarct. They found that newly formed myocardium occupied 68% of the infarcted portion of the ventricle 9 days after transplanting the bone marrow cells. The developing tissue comprised proliferating myocytes and vascular structures. Their studies indicate that locally delivered bone marrow cells can generate de novo myocardium, ameliorating the outcome of coronary artery disease.

To characterize further the properties of these myocytes, they determined the expression of connexin 43. This protein is responsible for intercellular connections and electrical coupling through the generation of plasma-membrane channels between myocytes; connexin 43 was apparent in the cell cytoplasm and at the surface of closely aligned differentiating cells. These results were consistent with the expected functional competence of the heart muscle phenotype.

Since functional cells are generated from embryonic stem cells, and since connexins are indeed expressed in these cells in infarcted heart tissue, we postulate that this will be the case for other cells differentiated from embryonic stem cells. Since connexins play a dominating role in the function of these tissues (including pancreatic beta cells and heart muscle cells) we further postulate that compounds like COMPOUND 2 and COMPOUND 40 by increasing the gap junctional coupling will enhance the proliferation of embryonic stem cells into functional cells in organs wherein stem cells have been implanted.

Thus we claim that gap junction openers like COMPOUND 2 and COMPOUND 40 will stimulate the transition of stem cells to functional cells in transplanted organs like pancreas for treatment of diabetes mellitus, heart for treatment of heart infarction, and basal ganglia of the brain for treatment of Parkinsons disease.

To substantiate this statement, experiments can be performed using the general experimental design with myocardial infarction as described above by Orlic et al (Nature 410, 701-705 (2001)), with administration of COMPOUND 2 and COMPOUND 40 repeatedly during the proliferation process. These experiments are expected to show an increase in connexin 43 expression by COMPOUND 2 and COMPOUND 40 or a faster regenerative process.

Tobacco Related Disease

McKarns S C, Doolittle D J (Toxicol Appl Pharmacol October 1991 111:58-68) studied the effect of cigarette smoke condensates on intercellular communication. The objective of their study was to quantify and compare the activity of mainstream cigarette smoke condensate (CSC) from tobacco-heating and tobacco-burning cigarettes on both the rate and total amount of intercellular communication in vitro. Lucifer yellow uptake and lactate dehydrogenase release assays were used to evaluate plasma membrane toxicity. Gap junction intercellular communication (GJIC) was determined by quantifying fluorescence redistribution after photobleaching (FRAP) following a 1-hr exposure to concentrations of CSCs which were not toxic to the plasma membrane. GJIC was quantified in rat hepatic epithelial cells (WB cells) and human skin fibroblasts (MSU-2 cells) synchronized in the G1 phase of the cell cycle. In each of the cell types tested, CSC from tobacco-heating cigarettes did not inhibit GJIC at concentrations, where CSC from tobacco-burning cigarettes significantly inhibited both the total amount and the rate of GJIC. Thus we claim that gap junction openers like COMPOUND 2 and COMPOUND 40 or the peptides of formulae I to VIII and tables 1 and 8 herein will prevent or alleviate the inhibition of GJIC caused by cigarette smoke condensate. Tobacco related disease associated with uncoupling og gap junctions include impaired wound healing, especially after surgery and skin aging.

It is an object of the present invention to provide methods to treat or prevent one or more of the medical indications or conditions described herein. Typically, but not exclusively, such methods will include administration of at least one of the foregoing compounds, preferably one of same, in an amount sufficient to treat, prevent, or reduce the severity of the indication or condition. Particular administration strategies will be apparent of those of skill in this field and will vary depending eg., on the sex, weight, general health and specific indication or condition to be treated or prevented. As discussed, the compounds disclosed herein can be employed as the sole active agent in invention methods. Alternatively, they can be used in "add-on" therapies such as those in which use of the compounds I conjunction with a recognized treatment method is indicated. Preferred indications or conditions to be treated or prevented in accord with the invention are generally associated with impaired cellular communication or impaired gap junction function. More specific indications and conditions relating to the invention have been discussed above.

It would be an advantage to treat diseases associated with impaired cellular communication or reduced GJIC with a substance that more specifically affects gap junction function, such as an AAP receptor agonist which is expected to promote GJIC through signal transduction from the AAP receptor, or a substance or compound which otherwise facilitates normal function of connexins and gap junctions.

In preferred embodiments of the invention the compound that facilitates intercellular communication is selected from the group of compounds having the formula I

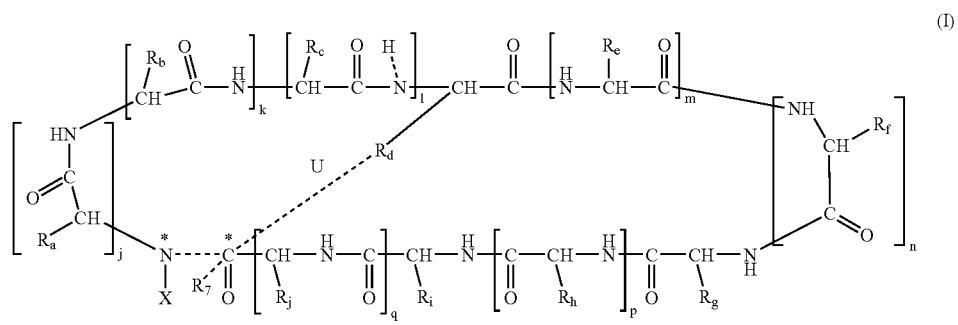

representing a peptide sequence wherein the amino acid residues may be D- and/or L-forms, and having the N-terminal at N* and the C-terminal at C* and being optionally cyclic via a covalent bond between N* and C* as shown by a broken line or between $R_d$ and C* as shown by the broken line U; the broken line between N* and C*, which when present excludes the bond U, represents an optional covalent bond and when said bond is not present then N* is bound to a hydrogen atom; when the optional covalent bond U between Rd and C* is present then R7 is void and the presence of R7 excludes the bond U;

and wherein

X represents an N-terminal moiety such as a photoprobe capable of being bond to the amino terminal N*, or an acyl group derived from a C(2-22)alkyl carboxylic acid, such as acetic acid, propionic acid, butyric acid and other fatty acids, such as behenic acid, optionally substituted with one or more substituents selected from the group consisting of hydroxy, halogen, C(1-6)alkyl, nitro and cyano; or X represents hydrogen;

$R_7$ represents OH, $NH_2$, $NHNH_2$, $NHR_8$ or $OR_8$ when the bond between N* and C* is missing, or R7 is absent when there is a bond between N* and C*;

$R_8$ represents H or a straight or branched C(1-6)alkyl group, an aryl or an aralkyl group.

$R_a$ represents the amino acid side chain of Hyp or Pro;

$R_b$ represents the amino acid side chain of Hyp or Pro;

$R_c$ represents the amino acid side chain of Gly, Sar, an aromatic amino acid side chain optionally substituted with one or more hydroxy, halogen, nitro, cyano, azido, amino, benzoyl or lower alkoxy or thioalkoxy group in the aromatic ring;

$R_d$ represents the amino acid side chain of Ala, Gly, Glu, Asp, Dab, Dapa, Lys, Asn, Gln, Orn, Thr, Ser or Cys;

$R_e$ represents the amino acid side chain of Ala;

$R_f$ represents the amino acid side chain of Ala, Sar or Gly;

$R_g$ represents any amino acid side chain except the side chain of L-4Hyp or a moiety of formula Z or Za;

$R_h$ represents the amino acid side chain of Ala, or $R_g$ represents a moiety of formula Z or Za;

$R_i$ represents the amino acid side chain of Gly or $R_i$ represents an aromatic amino acid optionally substituted with one or more hydroxy, halogen, nitro, cyano, azido, amino, benzoyl or lower alkoxy or thioalkoxy group in the aromatic ring;

$R_j$ represents the amino acid side chain of Asn, Gln, Asp, Glu, Cys or Tyr; and each of j, k, l, m, n, p and q is independently 0 or 1;

and the retro form, all D form, or retro all-D form of the peptide sequence of formula I, and salts and amides thereof.

In compounds of formula I it is preferred that $R_7$ is $NH_2$, $R_a$ is the amino acid side chain of Pro, $R_b$ is the amino acid side chain of Hyp, $R_c$ is the amino acid side chain of Gly or Tyr, $R_d$ is selected from the group consisting of the amino acid side chain of Gly, Asp or Glu, Dapa and Dab, $R_f$ is the amino acid side chain of Ala or Gly, $R_g$ is the amino acid side chain of Pro, Asn or Gly, $R_g$ is the amino acid side chain of Asn, Gly, D-4Hyp or L-/D-Pro when formula I represents a linear peptide, or when formula I represents a peptide cyclised between N* and C* then $R_g$ represents the amino acid side chain of L-/D-4Hyp or L-/D-Pro, $R_h$ is the amino acid side chain of Ala when U is missing, or $R_h$ is the amino acid side chain of Pro or Hyp when U is present, $R_i$ is preferably the amino acid side chain of Tyr, Phe, Trp, Nal optionally substituted with one or more hydroxy, F or Cl, in the aromatic ring, $R_j$ is selected from the group consisting of the amino acid side chain of Asp, Glu, and Tyr, and a linear peptide of formula I which is a retro all-D form.

It is also preferred that a peptide compound of formula I consists of between 3 and 9 amino acid residues, more preferably between 3 and 7 amino acid residues and wherein j and k are preferably 0 when U is present, j and k are preferably 1 when U is missing and formula I represents a cyclic peptide, m is preferably 0 when U is missing, p is preferably 1 when U is present, and q is preferably 0 when U is present.

More preferred are compounds of the general formula II

$$X\text{-}(G')_a\text{-}A\text{-}G'\text{-}(PX)_2\text{-}(Y')_b\text{-}R_7 \quad (II)$$

specifying a peptide sequence wherein the amino acid residues may be L and/or D forms, and wherein X represents H or Ac;

G' represents a glycine residue or a glycine analogue such as Sar;

A represents alanine;

Px represents an amino acid residue of formula Z or Za such as Hyp or Pro;

Y' represents tyrosine or phenylalanine optionally substituted in the phenyl ring with halogen or hydroxy;

a and b are independently 0 or 1, $R_7$ represents OH, $NH_2$, $NHNH_2$, Asn-$NH_2$, or Gln-$NH_2$;

and retro forms thereof and salts thereof, and wherein, preferably, X represents Ac and all amino acid residues are L-forms, G' is glycine, Px is Pro, Y' is Tyr, $R_7$ is $NH_2$.

preferred are retro compounds of formula II having the formula : X-$(Y')_b$-$(PX)_2$-G'-A-$(G')_a$-$R_7$ wherein all amino acid residues are D-forms and wherein all symbols have the same meaning as defined above for formula II, a peptide compound of formula II wherein at least one Px residue is a D-amino acid and the rest are L-amino acids, and a cyclic sequence of formula II wherein X represents H, $R_7$ represents Asn or Gln having a covalent bond to Y' which represents Tyr, b is 1, and a is 1.

A compound of formula 2: H-GAG-$(Pa)_2$—$NH_2$ such as H-Gly-Ala-Gly-D-Hyp-Pro-Tyr-$NH_2$, H-Gly-Ala-Gly-D-Pro-Pro-Tyr-$NH_2$, H-Gly-Ala-Gly-D-Pro-Ala-Tyr-$NH_2$, H-Gly-Ala-Gly-Gly-D-Pro-Tyr-$NH_2$, H-Gly-Ala-Gly-D-Hyp-Ala-Tyr-$NH_2$, H-Gly-Ala-Gly-D-Hyp-D-Pro-Tyr-$NH_2$, or a salt thereof.

A compound of formula 3: H-GAG-$(Px)_2$-Y-$NH_2$, such as H-Gly-Ala-Gly-NCG-Pro-Tyr-$NH_2$, H-Gly-Ala-Gly-T4C-Pro-Tyr-$NH_2$, H-Gly-Ala-Gly-A2C-Pro-Tyr-$NH_2$, H-Gly-Ala-Gly-Pc-Pro-Tyr-$NH_2$, and pharmaceutically acceptable salts thereof.

A compound of formula 8: H-G'-A-G'-$(Px)2$-Y-$NH_2$ such as H-Sar-Ala-Sar-Hyp-Pro-Tyr-$NH_2$, H-Gly-Ala-Sar-Hyp-Pro-Tyr-$NH_2$ (SEQ ID NO: 96), and pharmaceutically acceptable salts thereof.

A compound of formula 6: X-D-Y-(D-PX)$_2$-G-D-A-G-$NH_2$ or the retro form thereof X-G-D-A-G-(D-PX)$_2$-D-Y-$NH_2$ or X-G-D-A-G-(D-PX)$_2$-D-Y-D-(Asn)-$NH_2$, such as H-Gly-D-Ala-Gly-D-Hyp-D-Pro-D-Tyr-$NH_2$, H-Gly-D-Ala-Gly-D-Hyp-D-Pro-D-Tyr-D-Asp-OH, Ac-D-Tyr-D-Pro-D-Hyp-Gly-D-Ala-Gly-$NH_2$, and pharmaceutically acceptable salts thereof.

A compound of formula 10: Cyclo(-GAG-$(Px)_2$-Y-N/Q-), such as cyclo(-Gly-Ala-Gly-Hyp-Pro-Tyr-Gln-) (SEQ ID NO: 97), cyclo(-Gly-Ala-Gly-Hyp-Pro-Tyr-Asn-) (SEQ ID NO: 98), cyclo(-Gly-Ala-Gly-Pro-Pro-Tyr-Asn-) (SEQ ID NO: 99), and pharmaceutically acceptable salts thereof.

as defined herein and salts thereof.

A compound of formula 11: Cyclo(-Y-$(Px)_2$-GA-$(G)_q$-N/Q-), such as cyclo(-Tyr-Pro-Hyp-Gly-Ala-Gly-Asn-) (SEQ ID NO: 59), cyclo(-Tyr-Pro-Hyp-Gly-Ala-Asn-) (SEQ ID NO: 57), cyclo(-Tyr(3-I, 5-I)-Pro-4Hyp-Gly-Ala-Gly-Asn) (SEQ ID NO: 100), and pharmaceutically acceptable salts thereof.

A compound of formula 12: X-Zd-G(N/Q)Y-$NH_2$, such as H-Gly-Ala-Gly-Asn-Tyr-$NH_2$ (SEQ ID NO: 84), Ac-Gly-Asn-Tyr-$NH_2$, H-Gly-Asn-Tyr-$NH_2$, Ac-Ala-Gly-Asn-Tyr-$NH_2$ (SEQ ID NO: 85), H-Ala-Gly-Asn-Tyr-$NH_2$ (SEQ ID NO: 85), and pharmaceutically acceptable salts thereof.

A cyclic peptide compound of formula I further characterised in having the general formula III:

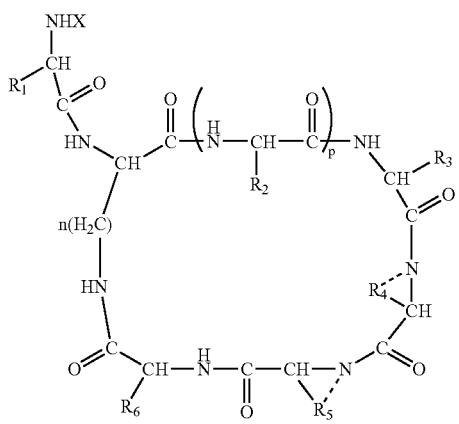

III wherein
X represents H or an N-terminal moiety such as a photoprobe capable of forming a covalent bond to the N terminal amino group or an acyl group ation with a C(2-22)alkyloyl carboxylic acid, such as aceyl, propinoyl, butanoyl and other fatty acid radicals such as behenoyl, being optionally substituted with one or more substituents selected from the group consisting of hydroxy, halogen, C(1-6)alkyl, nitro and cyano;
$R_1$ represents H or $CH_3$;
$R_2$ and $R_3$ are different or the same and represent any possible amino acid side chain;

---- represents an optional bond;
$R_5$ and $R_4$ represent any possible amino acid side chain or when the optional bond is present $R_5$ and $R_4$ represent together with the attached C and N atoms a proline ring which is optionally substituted with OH, preferably in the 4-position, or $R_5$ and $R_4$ represent together with the attached C and N atoms a moiety of formula Z or Za above;
$R_6$ represents an aromatic amino acid side chain optionally substituted in the aromatic ring with one or more substituents selected from halogen, nitro and hydroxy;
p is 0 or 1;
n is 1, 2, 3 or 4;
and salts thereof, and preferably wherein $R_1$ represents H, $R_2$ and $R_3$ are different or the same and represent H or $CH_3$, $R_5$ and $R_4$ represent together with the attached C and N atoms Pro or Hyp, $R_6$ represents Tyr, p is 1, and n is 1.
Exemplary compounds of formula III are H-Gly-Dapa-Gly-Hyp-Pro-Tyr⎤ (SEQ ID NO: 76)

H-Gly-Dab-Gly-Hyp-Pro-Tyr⎤ (SEQ ID NO: 77)

-continued

H-Gly-Dab-Ala-Gly-Hyp-Pro-Tyr⎤ (SEQ ID NO: 78)

H-Gly-Dapa-Ala-Gly-Hyp-Pro-Tyr⎤ (SEQ ID NO: 79)

H-Gly-D-Dapa-Gly-D-Hyp-D-Pro-D-Tyr⎤

H-Gly-D-Dab-Gly-D-Hyp-D-Pro-D-Tyr⎤

H-Gly-D-Dab-D-Ala-Gly-D-Hyp-D-Pro-D-Tyr⎤

H-Gly-D-Dapa-D-Ala-Gly-D-Hyp-D-Pro-D-Tyr⎤ and pharmaceutically acceptable salts thereof.
A preferred compound of formula I is further characterised by the general formula IV

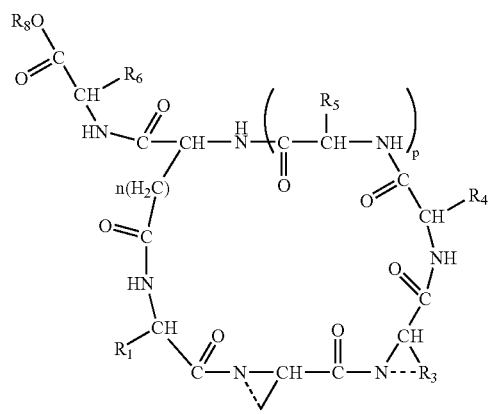

IV

Wherein $R_8$ represents H or a C(1-6)alkyl group;
$R_6$ represents H or $CH_3$;
$R_4$ and $R_5$ are different or the same and represent any possible amino acid side chain;

---- represents an optional bond;
$R_2$ and $R_3$ represent any possible amino acid side chain, or when the optional bond is present $R_2$ and $R_3$ represent together with the attached C and N atoms a proline ring which is optionally substituted with OH preferably in the 4-position or $R_2$ and $R_3$ represent a moiety of formula Z or Za;
$R_1$ represents an aromatic amino acid side chain;
p is 0 or 1;
n is 1, 2, 3 or 4;
and salts thereof, and preferably wherein $R_8$ represents H, $R_4$ and $R_5$ are different or the same and represent the amino acid side chain of Gly or Ala, $R_2$ and $R_3$ represent together with the attached C and N atoms Pro or Hyp, $R_1$ represents Tyr, p is 1, and n is 1.

Exemplary compounds of formula IV are

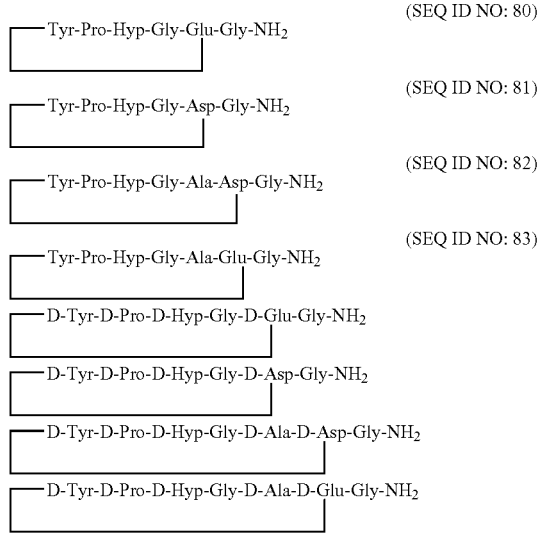

```
─── Tyr-Pro-Hyp-Gly-Glu-Gly-NH₂           (SEQ ID NO: 80)

─── Tyr-Pro-Hyp-Gly-Asp-Gly-NH₂           (SEQ ID NO: 81)

─── Tyr-Pro-Hyp-Gly-Ala-Asp-Gly-NH₂       (SEQ ID NO: 82)

─── Tyr-Pro-Hyp-Gly-Ala-Glu-Gly-NH₂       (SEQ ID NO: 83)

─── D-Tyr-D-Pro-D-Hyp-Gly-D-Glu-Gly-NH₂

─── D-Tyr-D-Pro-D-Hyp-Gly-D-Asp-Gly-NH₂

─── D-Tyr-D-Pro-D-Hyp-Gly-D-Ala-D-Asp-Gly-NH₂

─── D-Tyr-D-Pro-D-Hyp-Gly-D-Ala-D-Glu-Gly-NH₂
``` and pharmaceutically acceptable salts thereof.

Further preferred compounds are peptide compound wherein the amino acid residues may be L- and/or D-forms, and having the general formula V

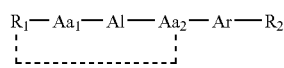

$$R_1 - Aa_1 - Al - Aa_2 - Ar - R_2 \quad\quad V$$

Wherein $R_1$ represents an optional amide bond between the N and the C terminal of the peptide, H or Ac;
$Aa_1$ represents a peptide sequence of between 0 and 4 amino acid residues;
Al represents an amino acid residue selected from the group consisting of Gly, beta Alanine and Sar;
$Aa_2$ represents an amino acid residue selected from the group consisting of Asn, Gln, Gly, Tyr, or a chemical unit, such as a hydroxy acid, an amino sulphonic acid, a phosphate group or a hydrocarbon chain connecting Al and Ar via 4 covalent bonds;
Ar represents an aromatic amino acid residue, such as a Tyr, Trp, Phe, His, or Nal, optionally substituted with one or more substituents selected from the group consisting of halogen, such as F, Cl, Br, or I, OH, $NO_2$, $NH_2$, COOH, and CONH;
$R_2$ REPRESENTS OH, $NH_2$ OR IS MISSING;
and retro analogues, retro all-D analogues (retro-inverse analogues) and salts thereof, and preferably wherein $Aa_1$ is selected from the group consisting of Ala, Gly-Ala, Gly-Asn-Tyr, and Gly-Asn-Tyr-Ala (SEQ ID NO: 103), wherein Al represents Gly or Sar, $Aa_2$ represents Asn or Gln, wherein Ar represents Tyr or Phe optionally substituted with one or more halogen, such as I, wherein $R_2$ represents $NH_2$ when the compound is non-cyclic or $R_2$ is missing when the compound is cyclic.
Exemplary compounds of formula V are
H-Gly-Ala-Gly-Asn-Tyr-$NH_2$ (SEQ ID NO: 84),
cyclo(-Tyr-Ala-Ser-Ala-Gly-Asn-) (SEQ ID NO: 65),
cyclo(-Tyr-Ala-Ser-Ala-Gly-Asn-) (SEQ ID NO: 65),
cyclo(-Tyr-Gly-Asn-Tyr-Ala-Gly-Asn-) (SEQ ID NO: 67),
cyclo(-Tyr-Val-Ser-Gly-Ala-Gly-Asn-) (SEQ ID NO: 68),
Ac-Gly-Asn-Tyr-$NH_2$,
H-Gly-Asn-Tyr-$NH_2$,
Ac-Ala-Gly-Asn-Tyr-$NH_2$ (SEQ ID NO: 85),
H-Ala-Gly-Asn-Tyr-$NH_2$ (SEQ ID NO: 85), and pharmaceutically acceptable salts thereof.

Other compounds which are useful in the method of the present invention include the antiarrhythmic peptides and their functional analogs, such as AAP, AAP10, [Pro⁴]AAP10-$NH_2$, HP5 and the novel peptide conjugates

```
H-Gly-Ala-Gly-Hyp-Pro-Tyr-Lys-Lys-   (SEQ ID NO: 104)
Lys-Lys-Lys-Lys-OH

H-Gly-Ala-Gly-Hyp-Pro-Tyr-Lys-Lys-   (SEQ ID NO: 104)
Lys-Lys-Lys-Lys-NH₂

3(4-hydroxyphenyl)propionyl-Pro-     (SEQ ID NO: 105)
Hyp-Gly-Ala-Gly-Lys-Lys-Lys-Lys-
Lys-Lys-OH
and 3(4-hydroxyphenyl)propionyl-Pro-     (SEQ ID NO: 105)
Hyp-Gly-Ala-Gly-Lys-Lys-Lys-Lys-
Lys-Lys-NH₂
```

Stability

Stability of the Compounds of the Invention

Furthermore, the compounds of the present invention are characterised in being stable towards enzymatic degradation, and/or being stable towards degradation in plasma, and/or having an improved in vivo half life. It is preferred that the compounds including the antiarrhythmic compounds of the present invention are stable towards enzymatic degradation and/or stable in plasma. The various derivatives and chemical modifications of the native peptide sequence of AAP as presented by the invention, e.g., the C-terminal amidation or esterification, the use of D-amino acids and derivatives of natural amino acids, the N-terminal modifications, and the cyclic analogues all represent modifications that are designed to enhance stability while retaining the essential antiarrhythmic and/or antithrombotic properties of native AAP.

Peptides are usually very easily degraded by proteolytic enzymes present in the gastro-intestinal system and living tissues and body fluids. Therefore, it is preferred herein to use peptides that have been modified to impart increased stability. It is preferred that the compounds including the antiarrhythmic compounds of the present invention are stable towards enzymatic degradation and/or stable in plasma. Preferred peptides for use in the method of the invention have a half life in solution as measured in a standard stability assay of more than 50 minutes and preferably more than 4 hours. As will appear in tables 7 and 8 below a number of peptides of the invention have a half-life of degradation of more than 5 hours in a standard stability assay. Stability is an important parameter for drug efficiency and a prolonged half-life, such as a T½ of more than 300 min, of the peptides herein is preferred. A standard stability assay as used herein refers to the in vitro plasma stability assay described below.

Method of Analysis of In Vitro Plasma Stability

The stability of peptides is analysed in serum and plasma. The peptides are incubated at 37° C. in plasma or serum and samples taken at approx. 9 regular intervals between t=0 and t=156 min are analysed by HPLC.

Appropriate conditions (column, solvent, gradient, and temp.) for the HPLC analyses are estimated to ensure that the drug peak and the plasma peaks do not have the same retention time. This is done by subsequent injections of the drug, plasma, and a co-injection with the drug and the plasma, followed by optimisation of the LC method parameters until a satisfactory separation is obtained. Three parallel experiments are performed for each plasma type. 100 ml of peptide is mixed with 900 ml plasma at t=0 and incubated at 37° C. (drug-plasma mixture conc. 0.1 mg/ml). Samples of 100 ml of the drug-plasma mixture are removed at appropriate intervals and the degradation stopped by precipitation of the sample with 10 ml MeCN:TFA 50:50 v/v. A control plasma sample without the drug treated in the same manner is also taken. The plasma samples are centrifuged for 15 min. at 12,000 rpm (Eppendorf centrifuge) at ambient temperature. The resulting supernatant solution is transferred to 300 ml HP autosamler vials and analyzed by HPLC. The samples are analyzed in the following order: blank, the peptide at 0.1 mg/mL, the plasma without the peptide, the three parallel samples for t=0, the three parallel samples for t=5 min. the three parallel samples for t=10 min. etc. And finally the three parallel samples for t=0 are repeated to make sure that there have been no degradation or other failure during the analyses. The sample concentrations (peak height in mAU) are plotted vs. time and fitted to a function describing a mono exponential decay (Excel). The half-lives of degradation (T½) (min.) of various compounds of the invention compared to AAP10, AAP and HP5 in human plasma are presented in Table 7 below as mean (n=3) ± standard deviation. the compounds 2, 3, 27, 48 and 49 of the invention are considerably more stable in plasma and serum than AAP10 which has a half life of less than 10 minutes, and HP5 which has a half life of less than 12 minutes.

The following Table 8 shows activity of the compounds in the calcium chloride induced arrythmia model and half lives.

TABLE 8

|  | $CaCl_2$ mice In vivo, % | $CaCl_2$ mice Score | Human plasma half life, min. |
|---|---|---|---|
| HPP-5-OH | 50 +/- 11 | 2 | 12 |
| HPP-PHypGAGKKKKKK-OH (SEQ ID NO: 105) | 80 +/- 17 | 3 | 2 |
| H-AAP-10-NH2 (H-GAG-4Hyp-PY-NH$_2$) (SEQ ID NO: 1) | 76 +/- 21 | 3 | 13 |
| H-AAP-10-K6-OH (SEQ ID NO: 104) | 64 +/- 10 | 3 | 87* |
| Cyclo(retro-AAP-10-Asn) (SEQ ID NO: 98) | 59 +/- 9 | 2 | >300 |
| Ac-Retro(AAP-10)-(all D)-NH2 | 65 +/- 7 | 3 | >300 |
| Ac-Retro(AAP-10)-OH (SEQ ID NO: 1) | 50 +/- 20 | 1 |  |
| $CF_3C(O)$-AAP10-NH2 (SEQ ID NO: 1) | 48 +/- 13 | 3 | 240 |

TABLE 7

Results of in vitro stability test in plasma and serum, T½ in min and hrs

| MEDIA AND COMPOUNDS | PLASMA, HEPARIN | | | SERUM | |
|---|---|---|---|---|---|
|  | RAT | RABBIT | HUMAN | RABBIT | HUMAN |
| AAP |  | 4.4 min ± 12% | 7.6 min ± 6% |  |  |
| AAP10 (SEQ ID NO: 1) | 8.2 min ± 13% | 9.5 min ± 12% | — | 2.7 min ± 4% | — |
| HP5 |  | 3.7 min ± 1% | 11.9 min ± 11% |  |  |
| Cyclo(retro-AAP-10-Asn) (SEQ ID NO: 98) | — | * >5 hrs | — | — | * >5 hrs |
| Ac-retro(AAP-10)-(aIID)-NH2 | — | * >5 hrs | * >5 hrs | — | * >5 hrs |
| $CF_3C(O)$-AAP10-NH2 (SEQ ID NO: 1) | — | 3.8 hrs ± 0.5% | — | — | 3.1 hrs ± 10% |
| Cyclo(GAG-Hyp-PYN) (SEQ ID NO: 98) | — | 30 hrs ± 8% | 9 hrs ± 1% | — | — |
| Cyclo(GAG-Hyp-PYQ) (SEQ ID NO: 97) | — | 14 hrs ± 2% | 15 hrs ± 1% | — | — |
| H-D-Y-D-N-G-NH2 (SEQ ID NO: 106) | — |  | 296 min ± 34% |  |  |

TABLE 8-continued

| | CaCl₂ mice In vivo, % | CaCl₂ mice Score | Human plasma half life, min. |
|---|---|---|---|
| HPP-PHypGAGKKKKKK-NH2 (SEQ ID NO: 105) | 21 +/- 17 | 1 | >300 |
| [Pro⁴]AAP10-NH2 (SEQ ID NO: 107) | 62 +/- 9 | 3 | 5 |
| AAP | 35 +/- 7 | 2 | 8 |
| H-[D-Hyp⁴]AAP-10-NH2 | 28 +/- 10 | 1 | |
| H-[D-Pro⁴, Ala⁵]AAP-10-NH2 | 29 +/- 12 | 1 | |
| AAP-10-K6-NH2 (SEQ ID NO: 104) | 33 +/- 17 | 2 | |
| H-C(Acm)GAGHypPYC(Acm)-NH2 (SEQ ID NO: 90) | 23 +/- 10 | 1 | |
| H-AAP-10-Asn-NH2 (SEQ ID NO: 98) | 31 +/- 6 | 2 | |
| Cyclo(GAGHypPYN) (SEQ ID NO: 98) | 57 +/- 8 | 2 | 780 |
| Cyclo(GAGHypPYQ) (SEQ ID NO: 97) | 48 +/- 14 | 2 | 900 |
| H-HypPYNGAG-NH2 (SEQ ID NO: 95) | 34 +/- 10 | 2 | |
| H-GAG-T4c-PY-NH2 | 32 +/- 6 | 2 | |
| H-GA-Sar-Hyp-PY-NH2 (SEQ ID NO: 96) | 46 +/- 11 | 2 | |
| H-Sar-A-Sar-Hyp-PY-NH2 | 24 +/- 7 | 1 | |
| H-GAG-Pc-PY-NH2 | 21 +/- 11 | 1 | |
| H-GAGGPY-NH2 (SEQ ID NO: 18) | 32 +/- 9 | 2 | |
| H-GAG-DHypAY-NH2 | 29 +/- 9 | 1 | |
| H-GAG-DHyp-DProY-NH2 | 49 +/- 6 | 2 | |
| des-Hyp⁴-[Asn⁵]AAP-10-NH2 (SEQ ID NO: 108) | 53 +/- 15 | 2 | 7 |
| AcGNY | 46 +/- 9 | 2 | 2140 |
| GNY | 58 +/- 10 | 2 | 63 |
| H-GANY-NH2 (SEQ ID NO: 109) | 21 +/- 7 | 1 | |
| H-DY-DN-G-NH2 (SEQ ID NO: 106) | 25 +/- 9 | 1 | 296 |
| H-YNG-NH2 | 34 +/- 9 | 2 | |
| H-GGY-NH2 | 39 +/- 9 | 2 | |
| H-G-DN-Y-NH2 (SEQ ID NO: 110) | 37 +/- 10 | 2 | |
| H-Y-DN-G-OH (SEQ ID NO: 111) | 39 +/- 9 | 2 | |
| Ac-Y-DN-G-OH (SEQ ID NO: 111) | 44 +/- 10 | 2 | |
| Ac-G-D-N-Y-NH2 (SEQ ID NO: 110) | 19 +/- 8 | 1 | |
| Ac-Y-D-N-G-NH2 (SEQ ID NO: 105) | 17 +/- 8 | 1 | |
| H-GK(DNP)Y-NH2 | 25 +/- 7 | 1 | |

* Half life in human plasma measured in EDTA plasma, HPP refers to 3(4-hydroxyphenyl)propionyl radical

TABLE 9

Analysis of in vitro Plasma Stability for AAP10 and Compound 2 under Sterile Conditions.
The aim of study is to estimate the in vitro half-life of test drugs (peptides) in plasma from different species.
The drugs are incubated under sterile conditions at 37° C. in plasma from various species and the degradation of the drugs is followed. Samples are analyzed by HPLC.

| Drug | Batch no. | MW (g/mol) | Peptide content | Solvent |
|---|---|---|---|---|
| | Bx. 24.53 B | 575.63 | 83.47 | MQW |
| Sequence: | H-GAG-4Hyp-PY-NH₂, H-AAP-10-NH₂ (SEQ ID NO: 1) | | | |

| | Plasma Conc. | Peptide conc. | Test time |
|---|---|---|---|
| Test media: Rat plasma, heparin | | | |
| Groups of study (n = 3/group): | 90% | 0.2 mM | t = 0, 1, 2, 3, 5, 7, 10, 15 and 20 min. |
| Test media: Human plasma, heparin, | | | |
| Groups of study (n = 3/group): | 90% | 0.2 mM | t = 0, 1, 2, 3, 5, 7, 10, 15 and 20 min. |

TABLE 9-continued

Analysis of in vitro Plasma Stability for AAP10 and Compound 2 under Sterile Conditions.
The aim of study is to estimate the in vitro half-life of test drugs (peptides) in plasma from different species.
The drugs are incubated under sterile conditions at 37° C. in plasma from various species and the degradation of the drugs is followed. Samples are analyzed by HPLC.

| | Drug | Batch no. | MW (g/mol) | Peptide content | Solvent |
|---|---|---|---|---|---|
| | Comp. 2 | Bx. 20.17B-2A | 617.66 | 100% | MQW |
| Sequence: | Ac-D-Tyr-D-Pro-D-Hyp-Gly-D-Ala-Gly-NH2 | | | | |
| | Plasma conc. | Peptide conc. | Test time | | |

| | Test media: Rat plasma, heparin | | |
|---|---|---|---|
| Groups of study (n = 3/group): | 90% | 0.2 mM | t = 0, 390, 1370, 1865, 2800, 3240, 4242, 4702 and 10007 min. |
| | Test media: Human plasma, heparin, | | |
| Groups of study (n = 3/group): | 90% | 0.2 mM | t = 0, 390, 1368, 1863, 2798, 3238, 4240, 4700 and 10005 min. |

| | |
|---|---|
| Method and Analyses: | Method: Appropriate conditions (column, solvent, gradient, and temp.) for the HPLC analyses are estimated to ensure that the drug peak and the plasma peaks do not have the same retention time. This is done by subsequent injections of the drug, plasma, and a co-injection with the drug and the plasma, followed by optimisation of the LC method parameters until a satisfactory separation is obtained. Three parallel experiments are performed for each plasma type under sterile conditions. 100 μl of the test peptides (2 mM in MQW) will be mixed with 900 μl plasma at t = 0 and incubated at 37° C. (drug-plasma mixture conc. 0.2 mM). Samples of 100 μl of the drug-plasma mixture are removed at appropriate intervals and the degradation stopped by precipitation of the sample with 10 μl MeCN:TFA 50:50 v/v. A control plasma sample without the drug treated in the same manner is also taken. The plasma samples are centrifuged for 15 min. at 12,000 rpm (Eppendorf centrifuge) at ambient temperature. The resulting supernatant solution is transferred to 300 μl HP autosamler vials and analyzed by HPLC. HPLC analysis are performed as follows: Detection: DAD1, 214.5 nm. Flow: 0.200 ml/min. Inj. vol. 10 μl. Temp. 30° C. AAP10: Column: Vydac 218MS52, #95, 000517, 250 mm × 2.1 mm. Solvents; A: 0.1% TFA in MQW B. 0.1% TFA in MQW:MeCN 10:90. Gradient (time; % B): 0; 0 2; 0 14; 25 15; 100 16, 100 17; 0 30; 0 Method file: TJE_63A.M Sequence file: 010712T1 (HPLC 2) Compound 2: Column: Luna 3u, C18(2), No. 296440, 150 × 2 mm. Solvents; A: 0.02% HFBA in MQW B. 0.02% HFBA in MQW:MeOH 10:90. Gradient (time; % B): 0; 0 5; 30 15; 30 16; 95 17; 95 18; 5 35; 5 Method file: TJE_123A.M Sequence file: 010723T2 (HPLC 2) The samples are analyzed in the following order: blank, the drug at 0.2 mM, the plasma without the drug, the three parallel samples for t = 0, the three parallel samples for t1 the three parallel samples for t2 etc. And finally the three parallel samples for t = 0 are repeated to make sure that there have been no degradation or other failure during the analyses. |
| Calculations and Statistics: | The sample concentrations (peak height in mAU) will be plotted vs. time and fitted to a function describing a mono exponential decay (Excel). The half-life of the test drug in the different types of plasma will be presented as mean +/− standard deviation. |
| Plasma stability H-AAP-10-NH$_2$ | 3.8 min +/− 0.1 min (rat); 1.8 min +/− 1.0 min (human); incubation 20 min |

TABLE 9-continued

Analysis of in vitro Plasma Stability for AAP10 and Compound 2
under Sterile Conditions.
The aim of study is to estimate the in vitro half-life of test drugs
(peptides) in plasma from different species.
The drugs are incubated under sterile conditions at 37° C. in
plasma from various species and the degradation of the drugs is
followed. Samples are analyzed by HPLC.

| | |
|---|---|
| Ac-Retro(APP-10)-(all D)-NH2 | 10.3 days +/− 1.2 days (rat); 14.1 days +/− 1.5 days (human); incub. 7 days |

Further preferred compounds that are useful in the method of the invention are non-peptide compounds that facilitate GJIC as reported in the literature, such as resveratrol (trans-3,5,4'-trihydroxystilbene and cis-3,5,4'-trihydroxystilbene) including the various dimers, trimers, tetramers and derivatives thereof and the structurally related compound caffeic acid phenethyl ester and derivatives thereof; and the aporphinoid alkaloids boldine and taspine. The effect of resveratrol on GJIC was examined in the in vivo model of CaCl2-induced AV block described herein. Resveratrol, 100 nmol/kg i.v. (n=6 mice) prevented the time until calcium-induced calcium block relative to animals treated with vehicle (n=7 mice), (136±9% versus 100±7%; p<0.01).

U.S. Pat. No. 6,008,260 relates to the use of resveratrol administered to mammals as a prophylactic against chemically induced cancers, and Nielsen M, Ruch R J, Vang O (Biochem Biophys Res Commun Sep. 7, 2000; 275(3):804-9) have shown that resveratrol which is a naturally occurring stilbene/alexin, and notably trans-resveratrol (trans-3,5,4'-trihydroxystilbene), reverses tumor-promoter-induced inhibition of gap-junctional intercellular communication and suggest its use as an agent for the prevention of cancer. The effect of resveratrol on gap-junctional intercellular communication (GJIC) in WB-F344 rat liver epithelial cells was investigated because inhibition of GJIC is an important mechanism of tumor promotion. Seventeen to 50 microM resveratrol increased GJIC significantly by a factor of 1.3 compared with solvent vehicle controls, when the WB-F344 cells were exposed to resveratrol for 6 h. Most tumor promoters, including the phorbol ester TPA and the insecticide DDT, block GJIC. Resveratrol at 17-50 microM also significantly prevented down-regulation of GJIC by TPA and DDT, by a factor of 2.7 and 1.8, respectively. This recovery of GJIC from TPA inhibition was partly correlated with hindered hyperphosphorylation of Cx43. In conclusion, resveratrol was found to enhance GJIC and counteract the effects of tumor promoters on GJIC, and this is likely a mechanism that contributes to the anticarcinogenic properties of resveratrol.

WO 0059466 (LVMH Recherche) discloses the use of a lipid extract of Skeletonema costatum which contains the alkaloid boldine in a cosmetic composition for the amelioration of the signs of skin ageing. Said lipid extract and the compound boldine improves the gap junctional intercellular communication in keratinocytes, fibroblasts and pre-adipocytes The inventors show that treatment with boldine increases the content of connexin 43 in keratinocytes of middel aged and elderly people to the content found in keratinocytes of young people in a dose dependent manner with a boldine concentration of 50 nM being optimal. Since an increase of the cellular content of connexin 43 must contribute to a facilitation of gap junctional intercellular communication the compound boldine can be useful in the present invention.

Thus, it is a purpose of the present invention to provide a method for the amelioration of skin aging, cellulite and wrinkles comprising administering to a patient in need of such treatment a therapeutically effective amount of at least one peptide of formulae I to VIII or tables 1 and 8 disclosed herein that facilitates intercellular communication.

Other compounds that share the structure of boldine include the aporphinoid alkaloids, such as taspine, which has been reported in U.S. Pat. No. 5,156,847 issued on Oct. 20, 1992 to be useful in the treatment of wounds.

Formulations and Compositions

Formulations containing a compound as described herein for the treatment of the above mentioned diseases and medical conditions may be in any suitable form that can be administered by medical personnel or by the patient as needed. Examples are injection formulations for i.v. administration, formulations for oral administration including tablets and capsules, and suppositories. The compounds of the present invention may be administered as an independent medicament or in a combination treatment with other medicaments suitable for treatment of the particular disease. The compounds described herein are peptides of relatively low molecular weight that may have relatively low oral bioavailability in which case non-oral formulations will be preferred, e.g. formulations for injection administration or for administration via the nasal or rectal epithelium or through the skin, e.g. aided by iontophoresis.

In the therapeutic methods of the invention, a treatment compound can be administered to a subject in any of several ways including intracorporeally or topically. Additionally, preferred compounds of the invention eg., Compound 3, Compound 2, Compound 40 can be administered as a prophylactic to prevent the onset of or reduce the severity of a targeted condition. Alternatively, such preferred compounds can be administered during the course of a targeted condition e.g., to help alleviate symptoms.

A treatment compound can be administered to a subject, either alone or in combination with one or more therapeutic agents, as a pharmaceutical composition in mixture with conventional excipient, i.e. pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, particularly in the form of liquid solutions or suspensions; for oral administration, particularly in the form of tablets or capsules; intranasally, particularly in the form of powders, nasal drops, or aerosols; vaginally; topically e.g. in the form of a cream; rectally e.g. as a suppository; etc.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain compounds of the invention and particularly Compound 3, Compound 2, Compound 40 etc.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapeutic agent(s) directly at a surgical site, e.g. administration by use of stents.

The concentration of one or more treatment compounds in a therapeutic composition will vary depending upon a number of factors, including the dosage of the invention compound to be administered, the chemical characteristics (e.g., hydrophobicity) of the composition employed, and the intended mode and route of administration. In general terms, one or more than one of the invention compounds and preferably at least one of Compound 3, Compound 2, Compound 40 may be provided in an aqueous physiological buffer solution containing about 0.1 to 10% w/v of a compound for parenteral administration.

It will be appreciated that the actual preferred amounts of active compounds used in a given therapy will vary according to e.g. the specific compound being utilized, the particular composition formulated, the mode of administration and characteristics of the subject, e.g. the species, sex, weight, general health and age of the subject. Optimal administration rates for a given protocol of administration can be readily ascertained by those skilled in the art using conventional dosage determination tests conducted with regard to the foregoing guidelines. Suitable dose ranges may include from about 1 mg/kg to about 100 mg/kg of body weight per day.

Therapeutic compounds of the invention are suitably administered in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the invention also can include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt.

Compositions

The invention also concerns a composition comprising a pharmacologically active antiarrhythmic peptide as defined herein in combination with a pharmaceutically acceptable carrier and/or diluent. Such compositions may be in a form adapted to oral, subcutaneous, parenteral (intravenous, intraperitoneal), intramuscular, rectal, epidural, intratracheal, intranasal, dermal, vaginal, buccal, ocularly, direct brain or pulmonary administration, preferably in a form adapted to subcutaneous, intravenous or oral administration, and such compositions may be prepared in a manner well-known to the person skilled in the art, e.g., as generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker. The compositions may appear in conventional forms, for example, solutions and suspensions for injection including i.v. infusion concentrates, capsules and tablets, preferably in the form of enteric formulations, e.g. as disclosed in U.S. Pat. No. 5,350,741, for oral administration.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene and water.

Similarly, the carrier or diluent may include any sustained release material known in the art, such as glyceryl monostearate or glyceryl distearate, alone or mixed with a wax.

If a solid carrier isused for oral administration, the preparation may be tabletted, placed in a hard gelatin capsule in powder or pellet form or it can be in the form of a troche or lozenge. The amount of solid carrier will vary widely but will usually be from about about 25 mg to about 1 g.

A typical tablet which may be prepared by conventional tabletting techniques may contain: Core: active compound (as free compound or salt thereof) 100 mg; colloidal silicon dioxide (Aerosil) 1.5 mg; cellulose, microcryst. (Avicel) 70 mg; modified cellulose gum (Ac-Di-Sol) 7.5 mg; magnesium stearate.

Coating: HPMC approx. 9 mg; *Mywacett 9-40T approx. 0.9 mg; *acylated monoglyceride used as plasticizer for film coating.

If a liquid carrier is used, the preparation may be in the form of a syrup, emulsion, soft gelatin capsule or sterile injectable liquid such as an aqueous or non-aqueous liquid suspension or solution.

The composition may also be in a form suited for local or systemic injection or infusion and may, as such, be formulated with sterile water or an isotonic saline or glucose solution. The compositions may be sterilized by conventional sterilization techniques which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

Formulation of peptide for intravenous injection

Multi-dose formulations may be prepared as a solution of a compound of the invention in sterile, isotonic saline, stored in capped vials, and if necessary a preservative is added (e.g. benzoates). Fixed dose formulations may be prepared as a solution of the compound in sterile, isotonic saline, stored in glass ampoules, and if necessary filled with an inert gas. Each dose of the compound is stored dry in ampoules or capped vials, if necessary filled with inert gas. The multi-dose formulation demands the highest degree of stability of the compound. When the stability of the compound is low fixed dose formulations can be used. The peptide may also be formulated as an i.v. infusion concentrate.

For nasal administration, the preparation may contain a compound of the present invention dissolved or suspended in a liquid carrier, in particular, an aqueous carrier, for aerosol application. The carrier may contain additives such as solubilizing agents, e.g., propylene glycol, surfactants such as bile acid salts or polyoxyethylene higher alcohol ethers, absorption enhancers such as lecithin (phosphatidylcholine) or cyclodextrin, or preservatives such as parabines.

Moreover, the small size of the peptide compounds of the invention may be an advantage for oral and nasal administration, since the relatively fast absorption via mucosal membranes compared to larger peptides minimises enzymatic degradation, especially in the duodenum and the ileum.

Preparation of enteric tablets containing Compound 2

400 mg L-tartaric acid and 40 mg polyethylene glycol-hydrogenated castor oil is dissolved in 5 ml methanol. The solution is placed in a mortar previously warmed to 30° C. To the solution is added 1.5 mg of Compound 2. Immediately after the addition of Compound 2 the mixture is stirred with a pestle under a hot air current of 40° C. and then placed in a dessicator under vacuum overnight to remove the solvent. The resulting solid mass is pulverised with the pestle and kneaded with 30 mg of sodium bicarbonate and a small amount of 70% ethanol. the mixture is then divided and shaped into tablets and dried. The dried tablets are given a coating of hydroxypropylmethylcellulose phthalat to obtain an enteric tablet.

The invention also concerns a pharmacologically active antiarrhythmic peptide or peptide derivative or a functional analogue thereof as disclosed herein for use in therapy, and the use thereof as defined herein for the manufacture of a pharmaceutical composition for use in therapy, e.g., in the treatment of arrhythmias and thrombotic complication during cardiovascular disorders, such as acute ischemic heart disease (e.g., stable angina pectoris, unstable angina pectoris, acute myocardial infaction), congestive heart failure (e.g., systolic, diastolic, high-output, low-output, right or left sided heart failure), congenital heart diseases, cor pulmonale, cardiomyopathies, myocarditides, hypertensive heart disease, and during coronary revascularization.

In specific embodiments, an antiarrhythmic peptide according to the present invention may be used to treat and/or prevent bradyarrhythmias (e.g., due to disease in sinus node, AV node, bundle of His, right or left bundle branch), and tachyarrhythmias associated with reentry (e.g., atrial premature complexes, AV junctional complexes, ventricular premature complexes, atrial fibrillation, atrial flutter, paroxymal supraventricular tachycardia, sinus node reentrant tachycardia, AV nodal reentrant tachycardia, and non-sustained ventricular tachycardia) either alone or in combination with other antiarrhythmic compounds, such as class I agents (e.g., lidocaine), class II agents (e.g., metoprolol or propranolol), class III agents (e.g., amiodarone or sotalol) or class IV agents (e.g., verapamil).

In specific embodiments, an antiarrhythmic peptide according to the present invention may be used to prevent thrombotic events in patients with diseases in the vessel wall (e.g., atherosclerosis), increased platelet production (universal polycytemia), and/or decreased flow (heart disease, vascular disease) either alone or in combination with either alone or in combination with GP IIb/IIIa inhibitors (e.g., c7E3 Fab; abciximab), cyclooxygenaseinhibitors (e.g., aspirin), thromboxane A2 antagonists, coumadine derivatives (e.g., warfarin), or the synthetic peptide, integrilin.

In specific embodiments, an antiarrhythmic peptide according to the present invention may, due to the effect on the intercellular gap junction channels, be used to treat and/or prevent bone loss and increase the healing of bone fractures[93]; treat and/or prevent disease in poorly vascularized cartilage and joints[94]; treat and/or prevent cataract[81]; treat and/or prevent vascularization of the cornea in disease states with poor nutrition of the cornea and increase the healing of corneal lesions[95]; treat and/or prevent growth and spreading of cancer cells, such as cancer cells derived from epithelial cell lines[96]; treat and/or prevent hypertension by increasing vasomotion[74]; prevent ejection of implantates, such as cell and organs, in an organism.

Peptide Synthesis

A preferred general procedure is described below. However, more detailed descriptions of solid phase peptide syntheses are found in WO98/11125 hereby incorporated in its entirety.

Apparatus and Synthetic Strategy

Peptides were synthesized batchwise in a polyethylene vessel equipped with a polypropylene filter for filtration using 9-fluorenylmethyloxycarbonyl (Fmoc) as N-a-amino protecting group and suitable common protection groups for side-chain functionalities.

Solvents

Solvent DMF (N,N-dimethylformamide, Riedel de-Häen, Germany) was purified by passing through a column packed with a strong cation exchange resin (Lewatit S 100 MB/H strong acid, Bayer A G Leverkusen, Germany) and analyzed for free amines prior to use by addition of 3,4-dihydro-3-hydroxy-4-oxo-1,2,3-benzotriazine (Dhbt-OH) giving rise to a yellow color (Dhbt-O⁻ anion) if free amines are present. Solvent DCM (dichloromethane, analytical grade, Riedel de-Häen, Germany) was used directly without purification. Acetonitril ( HPLC-grade, Lab-Scan, Dublin Ireland) was used directly without purification.

Amino Acids

Fmoc-protected amino acids were purchased from Advanced ChemTech (ACT) in suitabel side-chain protected forms. Otherwise protected amino acids (Fmoc-Glu(OH)-OAllyl; Fmoc-Asp(OH)-OAllyl from NovaBiochem (Switzerland), Fmoc-4-Hyp(OtBu)-OH; from Bachem (Switzerland).

Coupling Reagents

Coupling reagent diisopropylcarbodiimide (DIC) was purchased from (Riedel de-Häen, Germany), PyBop from Advanced ChemTech.

Linkers (4-hydroxymethylphenoxy)acetic acid (HMPA), was purchased from Novabiochem, Switzerland; and was coupled to the resin as a preformed 1-hydroxybenzotriazole (HOBt) ester generated by means of DIC.

Solid Supports

Peptides synthesized according to the Fmoc-strategy on TentaGel S resins 0,22-0,31 mmol/g (TentaGel-S-$NH_2$; TentaGel S-Ram, TentaGel S RAM-Lys(Boc)Fmoc; Rapp polymere, Germany);

Catalysts and Other Reagents

Diisopropylethylamine (DIEA) was purchased from Aldrich, Germany, and ethylenediamine from Fluka, piperidine and pyridine from Riedel-de Häen, Frankfurt, Germany. 4-(N,N-dimethylamino)pyridine (DMAP) was purchased from Fluka, Switzerland and used as a catalyst in coupling reactions involving symmetrical anhydrides. Ethandithiol was purchased from Riedel-de Häen, Frankfurt, Germany. 3,4-dihydro-3-hydroxy-4-oxo-1,2,3-benzotriazine (Dhbt-OH), 1-hydroxybenzotriazole (HOBt) (HOAt) were obtained from Fluka, Switzerland.

Coupling Procedures

The first amino acid was coupled as a symmetrical anhydride in DMF generated from the appropriate N-α-protected amino acid and DIC. The following amino acids were coupled as in situ generated HOBt or HOAt esters made from appropriate N-α-protected amino acids and HOBt or HOAt by means of DIC in DMF. Acylations were checked by the ninhydrin test performed at 80° C. in order to prevent Fmoc deprotection during the test[97].

Deprotection of the N-α-Amino Protecting Group (Fmoc).

Deprotection of the Fmoc group was performed by treatment with 20% piperidine in DMF (1×5 and 1×10 min.), followed by wash with DMF (5×15 ml, 5 min. each) until no yellow color could be detected after addition of Dhbt-OH to the drained DMF.

Deprotection of Allyl

A solution of 3 eq. Pd(PPh$_3$)$_4$ dissolved in 15-20 ml CHCl$_3$, AcOH, NMM (37:2:1) was added to the peptid resin. The treatment was continued for three hours at room temperature accompanied by bubbling a stream of $N_2$ through the mixture.

Coupling of HOBt-Esters 3 eq. N-α-amino protected amino acid was dissolved in DMF together with 3 eq. HOBt and 3 eq. DIC and then added to the resin.

Preformed Symmetrical Anhydride 6 eq. N-α-amino protected amino acid was dissolved in DCM and cooled to 0° C. DIC (3 eq.) was added and the reaction continued for 10 min. The solvent was removed in vacuo and the remanence dissolved in DMF. The solution was immediately added to the resin followed by 0.1 eq. of DMAP.

Cyclization of the Peptide on the Resin 1,5 eq. PyBop was dissolved in DMF together with 1,5 eq. HOBt and 3 eq. NMM was added to the peptide resin. The reaction was continued over night.

Cleavage of Peptide from Resin with Acid

Peptides were cleaved from the resins by treatment with 95% triflouroacetic acid (TFA, Riedel-de Häen, Frankfurt, Germany)-water v/v or with 95% TFA and 5% ethandithiol v/v at r.t. for 2 h. The filtered resins were washed with 95% TFA-water and filtrates and washings evaporated under reduced pressure. The residue was washed with ether and freeze dried from acetic acid-water. The crude freeze dried product was analyzed by high-performance liquid chromatography (HPLC) and identified by electrospray ionisation mass spectrometry (ESMS).

Batchwise Peptide Synthesis on TentaGel Resin (PEG-PS)

TentaGel resin (1 g, 0.22-0.31 mmol/g) was placed in a polyethylene vessel equipped with a polypropylene filter for filtration. The resin was swelled in DMF (15 ml), and treated with 20% piperidine in DMF to secure the presence of non-protonated amino groups on the resin. The resin was drained and washed with DMF until no yellow color could be detected after addition of Dhbt-OH to the drained DMF. HMPA (3 eq.) was coupled as a preformed HOBt-ester as described above and the coupling was continued for 24 h. The resin was drained and washed with DMF (5×5 ml, 5 min each) and the acylation checked by the ninhydrin test. The first amino acid was coupled as a preformed symmetrical anhydride as described above. The following amino acids according to the sequence were coupled as preformed Fmoc-protected HOBt esters (3 eq.) as described above. The couplings were continued for 2 h, unless otherwise specified. The resin was drained and washed with DMF (5×15 ml, 5 min each) in order to remove excess reagent. All acylations were checked by the ninhydrin test performed at 80° C. After completed synthesis the peptide-resin was washed with DMF (3×15 ml, 5 min each), DCM (3×15 ml, 1 min each) and finally diethyl ether (3×15 ml, 1 min each) and dried in vacuo.

HPLC Conditions

Gradient HPLC analysis was done using a Hewlett Packard HP 1100 HPLC system consisting of a HP 1100 Quaternary Pump, a HP 1100 Autosampler a HP 1100 Column Thermostat and HP 1100 Multiple Wavelength Detector. Hewlett Packard Chemstation for LC software (rev. A.06.01) was used for instrument control and data acquisition. The following columns and HPLC buffer system was used:

Column

Kromasil, Phenomenex 00F-3033-E0, 329889 (new); 5 μm C-18, 100 Å 150×4,6 mm; Batch nr. 5243-10.

Buffer system: A: 0,1% TFA in MQV; B: 0,085% TFA, 10% MQV, 90% MeCN.

Gradient:
1-1,5 min. 25% B
1,5-13,5 min 25-50% B
13,5-14,5 min 50-100% B
14,5-15,5 min 100% B
15,5-17,5 min 100-25% B
17,5-20 min 25% B Flow 1,5 ml/min Oven temperature 40° C.

UV detection: λ=215 nm

Mass spectra were obtained on a Micro-mass LCT instrument.

The foregoing Detailed Description of the Invention has been disclosed in the U.S. Ser. No. 09/792,286 application as filed on Feb. 22, 2001.

Turning to the present invention, it is generally applicable for the treatment or prevention of diseases associated with decreased or impaired intercellular communication. Gap junctional intercellular communication (GJIC) is vital for the normal functioning of mammalian cells and tissues, and closing or gating of gap junctions is often correlated with disease states. Several instances of decreased intercellular gap junctional communication associated with disease states have been reported in the literature. While substances that block gap junctions are known, the reports on the use of compounds that facilitate or mediate gap junction communication or increase GJIC in the treatment of non-proliferative diseases are limited to the use of the compound irsogladine (6-(2,5-dichlorophenyl)-2,4-diamino-1,3,5-triazine) which is reported to activate gap-junctional intercellular communication through M1 muscarinic acetylcholine receptor where GJIC has been inhibited, but 10(−10) to 10(−6) M irsogladine alone did not affect GJIC (Ueda, F. et al. J Pharmacol Exp Ther August 1995; 274(2):815-9).

Accordingly, the invention further relates to the use of an intercellular communication facilitating compound, and in particular an AAP receptor agonist preferably of formulae I-VI herein, for the preparation of a medicament. Additional ingredients of the medicament include a pharmaceutically acceptable carrier or excipient, e.g. selected from those mentioned above.

Peptide Synthesis of Individual Peptides.

Synthesis Example 1. Peptide synthesis of Ac-Tyr-Pro-4Hyp-Gly-Ala-Gly-OH (SEQ ID NO: 19) (Compound 1) on TentaGel-S—NH—$_2$; Rapp polymere, Germany.

First batch: Dry TentaGel-S—NH$_2$ (0.27 mmol/g, 1 g) was placed in a polyethylene vessel equipped with a polypropylene filter for filtration and treated as described under "batchwise peptide synthesis on TentaGel resin" until finishing the coupling of the N-terminal Tyrosine. All couplings were continued over night. After deprotection of the Fmoc group the N-terminal amino group was acetylated with acetic acid anhydride (1 ml, 10.5 mmol) together with 100 µl pyridine disolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. The crude freeze dried product was analyzed by HPLC and the purity was found to be better than 70% and the identity of the peptide was confirmed by ES-MS (found MH$^+$ 619.24, calculated MH$^+$ 619.26). Yield of crude material 137.7 mg. After purification using preparative HPLC as described above, 58 mg peptide product was collected with a purity better than 95%. Total yield of purified peptide product was 35%.

Second batch: Dry TentaGel-S—NH—$_2$ (0.27 mmol/g, 1 g) was placed in a polyethylene vessel equipped with a polypropylene filter for filtration and treated as described under "batchwise peptide synthesis on TentaGel resin" until finishing the coupling of the N-terminal Tyrosine. All couplings were continued over night. After deprotection of the Fmoc group the N-terminal amino group was acetylated with acetic acid anhydride (1 ml, 10.5 mmol) together with 100 µl pyridine disolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. The crude freeze dried product was analyzed by HPLC and the purity was found to be better than 70% and the identity of the peptide was confirmed by ES-MS (found MH$^+$ 619.25, calculated MH$^+$ 619.26). Yield of crude material 137.3 mg. After purification using preparative HPLC as described above, 27.9 mg peptide product was collected with a purity better than 91%. Total yield of purified peptide product was 15.5%.

Synth. Ex. 2. Peptide synthesis of Ac-D-Tyr-D-Pro-D-4Hyp-Gly-D-Ala-Gly-NH$_2$ (Compound 2) on TentaGel-S-Ram; Rapp polymere, Germany First batch: Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal D-Tyrosine. All couplings were continued over night. After deprotection of the Fmoc group the N-terminal amino group was acetylated with acetic acid anhydride (1 ml, 10.5 mmol) together with 100 µl pyridine disolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above freeze and dried from acetic acid. The yield of crude freeze dried product was 119.7 mg. The identity of the peptide was confirmed by ES-MS (found MH$^+$ 618.25, calculated MH$^+$ 618.28). After purification using preparative HPLC as described above, 42 mg peptide product was collected with a purity better than 95%. Total yield of purified peptide product was 30%.

Second batch: Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal D-Tyrosine. All couplings were continued over night. After deprotection of the Fmoc group the N-terminal amino group was acetylated with acetic acid anhydride (1 ml, 10.5 mmol) together with 100 µl pyridine disolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above freeze and dried from acetic acid. The yield of crude freeze dried product was 119.7 mg. The identity of the peptide was confirmed by ES-MS (found MH$^+$ 618.29, calculated MH$^+$ 618.28). After purification using preparative HPLC as described above, 100 mg peptide product was collected with a purity better than 99%. Total yield of purified peptide product was 71%.

Synth. Ex.3. Peptide synthesis of Cyclo(Tyr-Pro-4Hyp-Gly-Ala-Gly-Asn) (SEQ ID NO: 59) (Compound 3) on TentaGel-S-Ram; Rapp polymere, Germany.

First batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid, yield 57 mg crude product. After purification using preparative HPLC as described above, 2.7 mg cyclic peptide product was collected with a purity better than 95%. Total yield of purified peptide product was 1.3%. The identity of the peptide was confirmed by ES-MS (found MH$^+$ 673.32, calculated MH$^+$ 673.28).

Second batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid, yield 57 mg crude product. After purification using preparative HPLC as described above, 10 mg cyclic peptide product was collected with a purity better than 99%. Total yield of purified peptide product was 7%. The identity of the peptide was confirmed by ES-MS (found MH$^+$ 673.30, calculated MH$^+$ 673.29).

Synth. Ex. 4. Peptide synthesis of Cyclo(Tyr-Pro-4Hyp-Gly-Ala-Asn) (SEQ ID NO: 57) (Compound 4) on TentaGel-S-Ram; Rapp polymere, Germany.

First batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid to yield the crude product. After purification using preparative HPLC as described above, a cyclic peptide product was collected.

Second batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAll was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid to yield the crude product 58.6 mg.

After purification using preparative HPLC as described above, 5.7 mg cyclic peptide product was collected with a purity better than 98%. Total yield of purified peptide product was 4.4%. The identity of the peptide was confirmed by ES-MS (found MH$^+$ 616.25, calculated MH$^+$ 616.27).

Synth. Ex. 5. Peptide synthesis of H-Gly-Ala-Gly-D-Hyp-Pro-Tyr-NH$_2$ (Compound 5) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 46.6 mg peptide product was collected with a purity better than 99%. Total yield of purified peptide product was 28.6%.

The identity of the peptide was confirmed by ES-MS (found MH$^+$ 576.27, calculated MH$^+$ 576.26).

Synth. Ex. 6. Peptide synthesis of H-Gly-Ala-Gly-D-Pro-Pro-Tyr-NH$_2$ (Compound 6) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 26 mg peptide product was collected with a purity better than 98%. Total yield of purified peptide product was 16.3%.

The identity of the peptide was confirmed by ES-MS (found MH$^+$ 560.25, calculated MH$^+$ 560.28).

Synth. Ex. 7. Peptide synthesis of H-Gly-Ala-Gly-D-Pro-Ala-Tyr-NH$_2$ (Compound 7) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 18.9 mg peptide product was collected with a purity better than 98%. Total yield of purified peptide product was 12.2%.

The identity of the peptide was confirmed by ES-MS (found MH$^+$ 534.25, calculated MH$^+$ 534.26).

Synth. Ex. 8. Peptide synthesis of H-Gly-Ala-Gly-Gly-D-Pro-Tyr-NH$_2$ (Compound 8) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 130 mg. After purification using preparative HPLC as described above, 70.1 mg peptide product was collected with a purity better than 94%. Total yield of purified peptide product was 48.2%.

The identity of the peptide was confirmed by ES-MS (found MH$^+$ 520,25, calculated MH$^+$ 520.56).

Synth. Ex. 9. Peptide synthesis of H-Gly-Ala-Gly-D-Hyp-Ala-Tyr-NH$_2$ (Compound 9) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 131 mg. After purification using preparative HPLC as described above, 72.4 mg peptide product was collected with a purity better than 92%. Total yield of purified peptide product was 49%.

The identity of the peptide was confirmed by ES-MS (found MH$^+$ 550,28, calculated MH$^+$ 550.59).

Synth. Ex. 10. Peptide synthesis of H-Gly-Ala-Gly-D-Hyp-D-Pro-Tyr-NH$_2$ (Compound 10) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 150.8 mg. After purification using preparative HPLC as described above, 93.1 mg peptide product was collected with a purity better than 99%. Total yield of purified peptide product was 58%.

The identity of the peptide was confirmed by ES-MS (found MH$^+$ 576.63, calculated MH$^+$ 576.63).

Synth. Ex. 11. Peptide synthesis of H-Gly-Ala-Gly-NCG-Pro-Tyr-NH$_2$ (Compound 11) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 24.3 mg. After purification using preparative HPLC as described above, 10.2 mg peptide product was collected with a purity better than 91%. Total yield of purified peptide product was 4%.

The identity of the peptide was confirmed by ES-MS (found MH$^+$ 602,23, calculated MH$^+$ 602.32).

Synth. Ex. 12. Peptide synthesis of H-Gly-Ala-Gly-T4C-Pro-Tyr-NH$_2$ (Compound 12) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 29.9 mg. After purification using preparative HPLC as described above, 19 mg peptide product was collected with a purity better than 97%. Total yield of purified peptide product was 50%.

The identity of the peptide was confirmed by ES-MS (found MH$^+$ 578,18, calculated MH$^+$ 578.23).

Synth. Ex. 13. Peptide synthesis of H-Gly-Ala-Gly-A2C-Pro-Tyr-NH$_2$ (Compound 13) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 27.3 mg. After purification using preparative HPLC as described above, 12.7 mg peptide product was collected with a purity better than 97%. Total yield of purified peptide product was 34%.

The identity of the peptide was confirmed by ES-MS (found MH$^+$ 546,28, calculated MH$^+$ 546.55).

Synth. Ex. 14. Peptide synthesis of H-Gly-Ala-Gly-PC-Pro-Tyr-NH$_2$ (Compound 14) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 23.4 mg. After purification using preparative HPLC as described above, 13.5 mg peptide product was collected with a purity better than 97%. Total yield of purified peptide product was 34.6%.

The identity of the peptide was confirmed by ES-MS (found MH$^+$ 574,32, calculated MH$^+$ 574.29).

Synth. Ex. 15. Peptide synthesis of Ac-Tyr-Pro-Hyp-Gly-Ala-Gly-NH2 (SEQ ID NO: 19) (Compound 15) on Tenta-Gel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Tyrosine. All couplings were continued over night. After deprotection of the Fmoc group the N-terminal amino group was acetylated with acetic acid anhydride (1 ml, 10.5 mmol) together with 100 µl pyridine disolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 89.9 mg. After purification using preparative HPLC as described above, 80.1 mg peptide product was collected with a purity better than 99%. Total yield of purified peptide product was 58.9%.

The identity of the peptide was confirmed by ES-MS (found MH$^+$ 618.30, calculated MH$^+$ 618.28).

Synth. Ex. 16. Peptide synthesis of H-Cys(Acm)-Gly-Ala-Gly-Hyp-Pro-Tyr-Cys(Acm)-NH$_2$ (SEQ ID NO: 90) (Compound 16) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Cystine(Acm). All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 47.3 mg. After purification using preparative HPLC as described above, 29.1 mg peptide product was collected with a purity better than 97%. Total yield of purified peptide product was 12.9%.

The identity of the peptide was confirmed by ES-MS (found MH$^+$ 924.50, calculated MH$^+$ 924.36).

Synth. Ex. 17. Peptide synthesis of H-Cys(Acm)-Gly-Hyp-Pro-Tyr-Cys(Acm)-NH$_2$ (SEQ ID NO: 91) (Compound 17) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Cystine(Acm). All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 45.67 mg. After purification using preparative HPLC as described above, 29.15 mg peptide product was collected with a purity better than 94%. Total yield of purified peptide product was 14.9%.

The identity of the peptide was confirmed by ES-MS (found MH$^+$ 796.25, calculated MH$^+$ 796.30).

Synth. Ex. 18. Peptide synthesis of H-Cys(Acm)-Tyr-Pro-Hyp-Gly-Ala-Gly-Cys(Acm)-NH$_2$ (SEQ ID NO: 92) (Compound 18) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Cystine(Acm). All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. The crude freeze dried product was analyzed by HPLC and purified and characterized in a similar manner as compound 17 Synth. Ex. 19. Peptide synthesis of H-Cys(Acm)-Tyr-Pro-Hyp-Gly-Cys(Acm)-NH$_2$ (SEQ ID NO: 93) (Compound 19) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Cystine(Acm). All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 2.76 mg peptide product was collected with a purity better than 94%. Total yield of purified peptide product was 17.9%.

The identity of the peptide was confirmed by ES-MS (found MH$^+$ 796.25, calculated MH$^+$ 796.30).

Synth. Ex. 20.

Synthesis of H-Cys-Tyr-Pro-Hyp-Gly-Cys-NH$_2$ (Compound 20)

(SEQ ID NO: 74)

19 mg of the peptide H-Cys-Tyr-Pro-Hyp-Gly-Cys-NH$_2$ (SEQ ID NO: 74) is oxidised by dissolving the peptide in 1.5 ml (5% acetic acid in water and DMSO 4:1 v/v pH ~6). The mixture is placed in the freezer for 6 days.

After purification using preparative HPLC as described above, 91 mg peptide product was collected with a purity better than 97%. Total yield of purified peptide product was 47%. The identity of the peptide was confirmed by ES-MS (found MH$^+$ 652.29, calculated MH$^+$ 652.21

Synth. Ex. 21.

Synthesis of H-Cys-Gly-Hyp Pro-Tyr-Cys-NH$_2$ (Compound 21)

(SEQ ID NO: 71)

32 mg of the peptide H-Cys-Gly-4Hyp-Pro-Tyr-Cys-NH$_2$ (SEQ ID NO: 71) is oxidised by dissolving the peptide in 1.5 ml (5% acetic acid in water and DMSO 4:1 v/v pH ~6). The mixture is placed in the freezer for 6 days.

After purification using preparative HPLC as described above, 6.13 mg peptide product was collected with a purity better than 99%. Total yield of purified peptide product was 3%.

The identity of the peptide was confirmed by ES-MS (found MH$^+$ 652.23, calculated MH$^+$ 652.21

Synth. Ex. 22. Peptide synthesis of H-Gly-D-Ala-Gly-D-Hyp-D-Pro-D-Tyr-NH$_2$ (Compound 22) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 47 mg peptide product was collected with a purity better than 94%. Total yield of purified peptide product was 30%.

The identity of the peptide was confirmed by ES-MS (found MH$^+$ 576,26, calculated MH$^+$ 576.26).

Synth. Ex. 23. Peptide synthesis of H-Gly-D-Ala-Gly-D-Hyp-D-Pro-D-Tyr-D-Asn-OH (Compound 23) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 93.7 mg. After purification using preparative HPLC as described above, 60.7 mg peptide product was collected with a purity better than 93%. Total yield of purified peptide product was 47.5%.

The identity of the peptide was confirmed by ES-MS (found MH$^+$ 690.32, calculated MH$^+$ 690.30).

Synth. Ex. 24. Synthesis of Ac-D-Tyr(3,5-di-I)-D-Pro-D-Hyp-Gly-D-Ala-Gly-NH2 (Compound 24).

40.6 mg (64 μmol) of the peptide (compound 2) is dissolved in 10 ml 0.1M phosphate buffer pH 6.5 (solution A).

75.6 mg KI (400 μmol) is dissolved in 10 ml phosphate buffer pH 6.5 and 120 Iodobeads (IODO-BEADS, N-chlorobenzensulfonamide, Oxidative capacity 0.55 μmol/bead; PIERCE, 28665ZZ) are added and the solution is left at r.t. for 10 min (solution B).

Solution A and B are combined and gently agitated for 15 min. The Iodinated peptide was isolated and purified using preparative HPLC as described above, 39.5 mg peptide product was collected with a purity better than 90%. The identity of the peptide was confirmed by ES-MS (found MH$^+$ 870.09, calculated MH$^+$ 870.08).

Synth. Ex. 25. Synthesis of Ac-D-Tyr(mono-Iodo)-D-Pro-D-Hyp-Gly-D-Ala-Gly-NH2 (Compound 25).

40.6 mg (64 μmol) of the peptide (compound 2) is dissolved in 10 ml 0.1M phosphate buffer pH 6.5 (solution A). 75.6 mg KI (400 μmol) is dissolved in 10 ml phosphate buffer pH 6.5 and 120 Iodobeads (IODO-BEADS, N-chloro-benzensulfonamide, Oxidative capacity 0.55 μmol/bead; PIERCE, 28665ZZ) are added and the solution is left at r.t. for 10 min (solution B).

Solution A and B are combined and gently agitated for 15 min. The iodinated peptide was isolated and purified using preparative HPLC as described above, 3.3 mg peptide product was collected with a purity better than 90%. The identity of the peptide was confirmed by ES-MS (found MH$^+$ 744.19, calculated MH$^+$ 744.18).

Synth. Ex. 26. Peptide synthesis of Ac-D-Tyr-D-Pro-D-4Hyp-(1,2$^{13}$C,$^{15}$N-Gly)-D-Ala-(1,2$^{13}$C,$^{15}$N-Gly)-NH$_2$ (Compound 26) on TentaGel-S-Ram; Rapp polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal D-Tyrosine. All couplings were continued over night. After deprotection of the Fmoc group the N-terminal amino group was acetylated with acetic acid anhydride (1 ml, 10.5 mmol) together with 100 µl pyridine disolved in 2 ml DMF. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 142.4 mg. After purification using preparative HPLC as described above, 79.7 mg peptide product was collected with a purity better than 99%. Total yield of purified peptide product was 50%.

The identity of the peptide was confirmed by ES-MS (found MH$^+$ 624.25, calculated MH$^+$ 624.26).

Synth. Ex. 27. Peptide synthesis of H-Pro-Tyr-Asn-Gly-Ala-Gly-Hyp-NH2 (SEQ ID NO: 94) (Compound 27) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Proline. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 135.7 mg peptide product was collected with a purity better than 98%. Total yield of purified peptide product was 82.7%.

The identity of the peptide was confirmed by ES-MS (found MH$^+$ 690.38, calculated MH$^+$ 690.31).

Synth. Ex. 28. Peptide synthesis of H-Hyp-Pro-Tyr-Asn-Gly-Ala-Gly-NH2 (SEQ ID NO: 95) (Compound 28) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal 4-hydroxy-Proline. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 127 mg peptide product was collected with a purity better than 98%. Total yield of purified peptide product was 69.8%.

The identity of the peptide was confirmed by ES-MS (found MH$^+$ 690.25, calculated MH$^+$ 690.31).

Synth. Ex. 29. Peptide synthesis of H-Sar-Ala-Sar-Hyp-Pro-Tyr-NH$_2$ (Compound 29) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Sarcosine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 150 mg. After purification using preparative HPLC as described above, 85.5 mg peptide product was collected with a purity better than 93%. Total yield of purified peptide product was 57%.

The identity of the peptide was confirmed by ES-MS (found MH$^+$ 604.33, calculated MH$^+$ 604.30).

Synth. Ex. 30. Peptide synthesis of H-Gly-Ala-Sar-Hyp-Pro-Tyr-NH$_2$ (SEQ ID NO: 96) (Compound 30) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 124 mg. After purification using preparative HPLC as described above, 64.8 mg peptide product was collected with a purity better than 96%. Total yield of purified peptide product was 41.6%.

The identity of the peptide was confirmed by ES-MS (found MH$^+$ 590.19, calculated MH$^+$ 590.29).

Synth. Ex. 31. Peptide synthesis of ASAL-Pro-Hyp-Gly-Ala-Gly-NH2 (SEQ ID NO: 89) (Compound 31) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Proline. All couplings were continued over night. After deprotection of the Fmoc group the N-terminal amino group was acetylated with Azido salicylic acid using standard coupling procedure as described above. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 15.9 mg peptide product was collected with a purity better than 94%.

The identity of the peptide was confirmed by ES-MS (found MH$^+$ 575.23, calculated MH$^+$ 575.56).

Synth. Ex. 32. Peptide synthesis of ASAL(mono-iodo)-Pro-Hyp-Gly-Ala-Gly-NH2 (SEQ ID NO: 89) (Compound 32)

10.3 mg of the peptide (compound 31) is dissolved in 2.5 ml 0.1M phosphate buffer pH 6.5 (solution A).

18.9 mg KI (100 µmol) is dissolved in 2.5 ml phosphate buffer pH 6.5 and 30 Iodobeads (IODO-BEADS, N-chlorobenzensulfonamide, Oxidative capacity 0.55 µmol/bead; PIERCE, 28665ZZ) are added and the solution is left at r.t. for 10 min (solution B).

Solution A and B are combined and gently agitated for 1 hours. The Iodinated peptide was isolated and purified using preparative HPLC as described above, 4.4 mg peptide product was collected with a purity better than 99%. The identity of the peptide was confirmed by ES-MS (found $MH^+$ 701.13, calculated $MH^+$ 701.46).

Synth. Ex. 33. Peptide synthesis of AB-Tyr-Pro-Hyp-Gly-Ala-Gly-NH2 (SEQ ID NO: 19) (Compound 33) on Tenta-Gel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Tyrosine. All couplings were continued over night. After deprotection of the Fmoc group the N-terminal amino group was acetylated with Azido Benzoicic acid using standard coupling procedure as described above. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 20.5 mg peptide product was collected with a purity better than 90%.

The identity of the peptide was confirmed by ES-MS (found $MH^+$ 721.28, calculated $MH^+$ 721.26).

Synth. Ex. 34. Peptide synthesis of AB-Tyr(3,5-di-iodo)-Pro-Hyp-Gly-Ala-Gly-NH2 (SEQ ID NO: 112) (Compound 34) 10.3 mg of the peptide (compound 34) is dissolved in 2.5 ml 0.1M phosphate buffer pH 6.5 (solution A).

18.9 mg KI (100 µmol) is dissolved in 2.5 ml phosphate buffer pH 6.5 and 30 Iodobeads (IODO-BEADS, N-chlorobenzensulfonamide, Oxidative capacity 0.55 µmol/bead; PIERCE, 28665ZZ) are added and the solution is left at r.t. for 10 min (solution B).

Solution A and B are combined and gently agitated for 1 hours. The Iodinated peptide was isolated and purified using preparative HPLC as described above, 1.2 mg peptide product was collected with a purity better than 90%. The identity of the peptide was confirmed by ES-MS (found $MH^+$ 973.08, calculated $MH^+$ 973.46).

Synth. Ex.35. Peptide synthesis cyclo(-Gly-Ala-Gly-Hyp-Pro-Tyr-Gln-) (SEQ ID NO: 97) (Compound 35) on Tenta-Gel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Glu (OH)—OAII was connected to the TentaGel-S-Ram resin via the side-chain carboxylic acid, which finally after cleavage will end up amidated (Gln). The procedure described under "batchwise peptide synthesis on TentaGel resin" was followed until finishing the coupling of the N-terminal Glycine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 135.3 mg. After purification using preparative HPLC as described above, 19.1 mg peptide product was collected with a purity better than 98%. Total yield of purified peptide product was 6.6%.

The identity of the peptide was confirmed by ES-MS (found $MH^+$ 687.38, calculated $MH^+$ 687.32).

Synth. Ex.36. Peptide synthesis cyclo(-Gly-Ala-Gly-Hyp-Pro-Tyr-Asn-) (SEQ ID NO: 98) (Compound 36) on Tenta-Gel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Glycine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 63.4 mg. After purification using preparative HPLC as described above, 13.2 mg peptide product was collected with a purity better than 97%. Total yield of purified peptide product was 6.2%.

The identity of the peptide was confirmed by ES-MS (found $MH^+$ 673.38, calculated $MH^+$ 673.30).

Synth. Ex.37. Peptide synthesis cyclo(-Gly-Ala-Gly-Pro-Pro-Tyr-Asn-) (SEQ ID NO: 99) (Compound 37) on Tenta-Gel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Glycine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 85.1 mg. After purification using preparative HPLC as described above, 9.8 mg peptide product was collected with a purity better than 98%. Total yield of purified peptide product was 3.5%.

The identity of the peptide was confirmed by ES-MS (found $MH^+$ 657.38, calculated $MH^+$ 657.31).

Synth. Ex. 38. Synthesis of Cyclo(Tyr(3,5-diiodo)-Pro-4Hyp-Gly-Ala-Gly-Asn) (SEQ ID NO: 113) (Compound 38).

10.8 mg of the peptide (compound 3) is dissolved in 2.5 ml 0.1M phosphate buffer pH 6.5 (solution A).

18.9 mg KI (400 μmol) is dissolved in 2.5 ml phosphate buffer pH 6.5 and 30 Iodobeads (IODO-BEADS, N-chlorobenzensulfonamide, Oxidative capacity 0.55 μmol/bead; PIERCE, 28665ZZ) are added and the solution is left at r.t. for 10 min (solution B). Solution A and B are combined and gently agitated for 2 hours. The Iodinated peptide was isolated and purified using preparative HPLC as described above, 9.8 mg peptide product was collected with a purity better than 95%. The identity of the peptide was confirmed by ES-MS (found $MH^+$ 925.10, calculated $MH^+$ 925.30).

Synth. Ex. 39. Peptide synthesis of H-Gly-Ala-Gly-Asn-Tyr-$NH_2$ (SEQ ID NO: 84) (Compound 39) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 124 mg. After purification using preparative HPLC as described above, 26.5 mg peptide product was collected with a purity better than 96%. Total yield of purified peptide product was 20.5%.

The identity of the peptide was confirmed by ES-MS (found $MH^+$ 480.24, calculated $MH^+$ 480.50).

Synth. Ex. 40. Peptide synthesis of Ac-Gly-Asn-Tyr-$NH_2$ (Compound 40) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. After deprotection of the Fmoc group the N-terminal amino group was acetylated with acetic acid anhydride (1 ml, 10.5 mmol) together with 100 μl pyridine disolved in 2 ml DMF. The coupling was continued over night. The acylations were checked by the ninhydrin test performed at 80° C. as earlier described. After acylation of the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 90.4 mg. After purification using preparative HPLC as described above, 63.4 mg peptide product was collected with a purity better than 99%. Total yield of purified peptide product was 65.1%.

The identity of the peptide was confirmed by ES-MS (found $MH^+$ 394.16, calculated $MH^+$ 394.20).

Synth. Ex. 41. Peptide synthesis of H-Gly-Asn-Tyr-$NH_2$ (Compound 41) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 91.4 mg. After purification using preparative HPLC as described above, 62.1 mg peptide product was collected with a purity better than 95%. Total yield of purified peptide product was 54.5%.

The identity of the peptide was confirmed by ES-MS (found $MH^+$ 352.16, calculated $MH^+$ 352.18).

Synth. Ex. 42. Peptide synthesis of Ac-Ala-Gly-Asn-Tyr-$NH_2$ (SEQ ID NO: 85) (Compound 42) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Alanine. After deprotection of the Fmoc group the N-terminal amino group was acetylated with acetic acid anhydride (1 ml, 10.5 mmol) together with 100 μl pyridine disolved in 2 ml DMF. The coupling was continued over night. The acylations were checked by the ninhydrin test performed at 80° C. as earlier described. After acylation of the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 105 mg. After purification using preparative HPLC as described above, 52 mg peptide product was collected with a purity better than 98%. Total yield of purified peptide product was 45%.

The identity of the peptide was confirmed by ES-MS (found $MH^+$ 465.22, calculated $MH^+$ 465.30).

Synth. Ex. 43. Peptide synthesis of H-Ala-Gly-Asn-Tyr-$NH_2$ (SEQ ID NO: 85) (Compound 43) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Alanine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 104.5 mg. After purification using preparative HPLC as described above, 77.8 mg peptide product was collected with a purity better than 96%. Total yield of purified peptide product was 58.8%.

The identity of the peptide was confirmed by ES-MS (found MH+ 423.19, calculated MH+ 423.28).

Synth. Ex.44. Peptide synthesis cyclo(-Tyr-Ala-Ser-Ala-Gly-Asn-) (SEQ ID NO: 65) (Compound 44) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 60.2 mg. After purification using preparative HPLC as described above, 5.0 mg peptide product was collected with a purity better than 87%. Total yield of purified peptide product was 4.3%.

The identity of the peptide was confirmed by ES-MS (found MH+ 564.25, calculated MH+ 564.57).

Synth. Ex.45. Peptide synthesis cyclo(-Tyr-Gly-Asn-Tyr-Gly-Asn-) (SEQ ID NO: 66) (Compound 45) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 79.1 mg. After purification using preparative HPLC as described above, 20 mg peptide product was collected with a purity better than 90%. Total yield of purified peptide product was 14.0%.

The identity of the peptide was confirmed by ES-MS (found MH+ 569.25, calculated MH+ 569.67).

Synth. Ex.46. Peptide synthesis cyclo(-Tyr-Gly-Asn-Tyr-Ala-Gly-Asn-) (SEQ ID NO: 67) (Compound 46) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 58.9 mg. After purification using preparative HPLC as described above, 15.9 mg peptide product was collected with a purity better than 98%. Total yield of purified peptide product was 11%.

The identity of the peptide was confirmed by ES-MS (found MH+ 740.31, calculated MH+ 740.75).

Synth. Ex.47. Peptide synthesis cyclo(-Tyr-Val-Ser-Gly-Ala-Gly-Asn-) (SEQ ID NO: 68) (Compound 47) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp (OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 54.1 mg. After purification using preparative HPLC as described above, 19.6 mg peptide product was collected with a purity better than 95%. Total yield of purified peptide product was 15%.

The identity of the peptide was confirmed by ES-MS (found MH+ 649.10, calculated MH+ 649.68).

Synth. Ex. 48. Peptide synthesis of H-Gly-Pro-Hyp-Gly-Ala-Gly-OH (SEQ ID NO: 88) (Compound CE-1) on TentaGel-S—NH—$_2$; Rapp polymere, Germany.

Dry TentaGel-S—NH—$_2$ (0.27 mmol/g, 1 g) was placed in a polyethylene vessel equipped with a polypropylene filter for filtration and treated as described under "batchwise peptide synthesis on TentaGel resin" until finishing the coupling of the N-terminal Glycine. All couplings were continued over night. All couplings were continued over night. The acylations were checked by the ninhydrin test performed at 80° C as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. After purification using preparative HPLC as described above, 16.9 mg peptide product was collected with a purity better than 92%. Total yield of purified peptide product was 10.1%.

The identity of the peptide was confirmed by ES-MS (found MH+ 471.22, calculated MH+ 471.21).

Synth. Ex. 49. Peptide synthesis of H-Gly-Ala-Gly-Hyp-Pro-Tyr-NH$_2$ (SEQ ID NO: 1) (Compound CE-2) on Tenta-Gel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 159 mg. After purification using preparative HPLC as described above, 101 mg peptide product was collected with a purity better than 98%. Total yield of purified peptide product was 60%.

The identity of the peptide was confirmed by ES-MS (found MH+ 576,26, calculated MH+ 576.26).

Synth. Ex. 50. Peptide synthesis of 3-(4-hydroxyphenyl)propionyl-Pro-Hyp-Gly-Ala-Gly-NH2 (SEQ ID NO: 2) (Compound CE-3) on TentaGel-S-Ram; Rapp polymere, Germany.

Dry TentaGel-S-Ram (0.23 mmol/g, 1 g) was placed in a polyethylene vessel equipped with a polypropylene filter for filtration.and treated as described under "batchwise peptide synthesis on TentaGel resin" until finishing the coupling of the N-terminal Proline. All couplings were continued over night. After deprotection of the Fmoc group the N-terminal amino group was acetylated with 3-(4-hydroxyphenyl)propionic acid using standard coupling procedure as described above. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. Yield of crude material 143 mg. After purification using preparative HPLC as described above, 73.7 mg peptide product was collected with a purity better than 95%. Total yield of purified peptide product was 50%.

The identity of the peptide was confirmed by ES-MS (found MH+ 561.30, calculated MH+ 561.24).

SYNTHESIS OF COMPOUNDS OF THE PRESENT INVENTION

EXAMPLE 51

Synthesis of K6 Extended Peptides

Peptide synthesis of H-Gly-Ala-Gly-Hyp-Pro-Tyr-Lys-Lys-Lys-Lys-Lys-Lys-OH (SEQ ID NO: 104) (Compound 48) on TentaGel-S—NH2; Rapp polymere, Germany.

Dry TentaGel-S—NH2 (0.27 mmol/g, 1 g) was placed in a polyethylene vessel equipped with a polypropylene filter for filtration and treated as described under "batchwise peptide synthesis on TentaGel resin" until finishing the coupling of the N-terminal Glycine. All couplings were continued over night and checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid. The identity of the peptide was confirmed by ES-MS (found MH+ 1344.7, calculated MH+ 1344.82). After purification using preparative HPLC as described above, 121 mg peptide product was collected with a purity better than 99%.

Peptide synthesis of 3(4-hydroxyphenyl)propionyl-Pro-Hyp-Gly-Ala-Gly-Lys-Lys-Lys-Lys-Lys-Lys-OH (SEQ ID NO: 105) (Compound 49) on TentaGel-S—NH2; Rapp polymere, Germany.

Dry TentaGel-S—NH2 (0.27 mmol/g, 1 g) was placed in a polyethylene vessel equipped with a polypropylene filter for filtration and treated as described under "batchwise peptide synthesis on TentaGel resin" until finishing the coupling of the N-terminal Proline. All couplings were continued over night. After deprotection of the Fmoc group the N-terminal amino group was acetylated with 3(4-hydroxyphenyl)propionic acid using standard procedure as described above. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above freeze and dried from acetic acid. The identity of the peptide was confirmed by ES-MS (found MH+ 1329.88, calculated MH+ 1329.81). After purification using preparative HPLC as described above, 99.7 mg peptide product was collected with a purity better than 98%.

Peptide synthesis of H-Gly-Ala-Gly-Hyp-Pro-Tyr-Lys-Lys-Lys-Lys-Lys-Lys-NH2 (SEQ ID NO: 104) (Compound 50) on TentaGel-S-Ram; Rapp polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above freeze and dried from acetic acid. The identity of the peptide was confirmed by ES-MS (found MH+ 1343.6, calculated MH+ 1343.84). After purification using preparative HPLC as described above, 84.7 mg peptide product was collected with a purity better than 98%.

Peptide synthesis of 3(4-hydroxyphenyl)propionyl-Pro-Hyp-Gly-Ala-Gly-Lys-Lys-Lys-Lys-Lys-Lys-NH2 (SEQ ID NO: 105) (Compound 51) on TentaGel-S-Ram; Rapp polymere, Germany Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal Proline. All couplings were continued over night. After deprotection of the Fmoc group the N-terminal amino group was acetylated with 3(4-hydroxyphenyl)-propionic acid using standard procedure as described above. The coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above freeze and dried from acetic acid. The yield of crude freeze dried product was 299 mg. The identity of the peptide was confirmed by ES-MS (found MH+ 1328.9, calculated MH+ 1329.1). After purification using preparative HPLC as described above, 155 mg peptide product was collected with a purity better than 94%.

EXAMPLE 52

Synthesis of H-Gly-ψ(CH2-NH)-Asn-Tyr-OH ×TFA (Compound 52)

1) Boc-Asn-Tyr(tBu)-OtBu

Boc-Asn-OH (3.5 g 15 mmol) is dissolved in dichloromethane (100 ml amylene stabilised free of alcohol) and HOBt (2.24 g dry 16.5 mmol) is added. The mixture is cooled in an ice/water bath and DIC (2.45 ml 16 mmol) is added. The mixture will be allowed to react for 20 min. The HOBt on the bottom will react and a precipitate of DIU (on top) will form. H-Tyr(tBu)-OtBu×HCl (5.1 g 15.4 mmol) is dissolved in DMF (30 ml dry). The dichloromethane mixture containing the activated ester is filtered from the DIU directly into the DMF solution. The combined mixture is cooled in ice/water and NMM (1.75 ml 15.8 mmol) is added. The mixture is allowed to react over night. The solvents will be removed in vacuo. Ethyl acetate 200 ml is added and a precipitate is removed and the solution is washed with citric acid (2×50 ml 10%), sodium hydrogen carbonate (2×50 ml saturated) and brine (2×50 ml). The solution is dried with magnesium sulfate and the solvent removed in vacuo ending at 0.2 mBar for 30 min. The raw product will be suspended in pentane (40 ml) and filtered from a precipitate of DIU. The pentane will be removed in vacuo yielding the title compound.

2) Asn-Tyr×TFA

Boc-Asn-Tyr(tBu)-OtBu (7.1 g 14 mmol) is dissolved in TFA/EDT 19/1 (30 ml) and allowed to stand for 2 h. The TFA is removed in vacuo and ether (200 ml) added to precipitate the product. The ether is decanted from the product that is washed with ether (3×100 ml). The product will be dried in vacuo to yield the product that can be used without further purification.

3) Boc-Gly-ψ(CH2-NH)-Asn-Tyr-OH

Asn-Tyr×TFA (5.6 g 13.7 mmol) and acetic acid (1 ml) are dissolved in methanol (100 ml dry) and Boc-glycinal (2.72 g 17 mmol) is added. The mixture is stirred for 10 min. then Sodium cyanoborohydride (2.15 g) is added potion wise over 30 min. The mixture is stirred for a further 2 h. Most of the methanol is removed in vacuo. Ethyl acetate (200 ml) is added and the boron complex hydrolysed by shaking with saturated Sodium bicarbonate (100 ml) for 15 min. The ethyl acetate is washed with further saturated Sodium bicarbonate (100 ml). The combined water phases will be extracted with ethyl acetate (100 ml) The combined organic phases will be washed with brine (2×50 ml) and dried over magnesium sulfate. The ethyl acetate is removed in vacuo yielding the desired product.

4) H-Gly-ψ(CH2-NH)-Asn-Tyr-OH×TFA

Analogous to 2) Starting from Boc-Gly-ψ(CH2-NH)-Asn-Tyr-OH (5.20 g 11.9 mmol) Yielding (expected) around 5.37 g (100%). An analytical pure sample will be obtained by purifying 1 g by RP HPLC. Expected yield around 90%. Purity >98%.

EXAMPLE 53

Solid Phase Synthesis of Ac-Gly-Asn-Tyr-NH2 (SEQ ID NO: 59) (Compound 53), Cyclo(Tyr-Pro-4Hyp-Gly-Ala-Gly-Asn) (Compound 54), Ac-D-Tyr-D-Pro-D-4Hyp-Gly-D-Ala-Gly-NH2 (Compound 55), Ac-Asn-Tyr-NH2 (Compound 56), Ac-Gly-Tyr-NH2 (Compound 57), Hydroxyacetyl-Asn-Tyr-NH2 (Compound 58), H-Gly (YCH2NH)-Gly-Tyr-NH2 (Compound 59) and H-Gly-Asn-Phe(pNO2)—NH2 (Compound 60).

General methods of solid phase synthesis have been reported in PCT application PCT/US01/19113 entitled Novel Peptide Conjugates by Larsen, B. D et al.

Peptide synthesis of Cyclo(Tyr-Pro-4Hyp-Gly-Ala-Gly-Asn) (SEQ ID NO: 59) (Compound 54) on TentaGel-S-Ram; Rapp polymere, Germany.

First batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid, yield 57 mg crude product. After purification using preparative HPLC as described above, 2.7 mg cyclic peptide product was collected with a purity better than 95%. Total yield of purified peptide product was 1.3%. The identity of the peptide was confirmed by ES-MS (found MH+ 673.32, calculated MH+ 673.28).

Second batch: Dry TentaGel-S-Ram (0.23 mmol/g, 1 g) was placed in a polyethylene vessel equipped with a polypropylene filter for filtration and treated as described under "batchwise peptide synthesis on TentaGel resin". The first amino acid Fmoc-Asp(OH)—OAII was connected to the TentaGel-S-Ram resin via the side-chain carboxylic acid, which finally after cleavage will end up amidated (Asn). The procedure described under "batchwise peptide synthesis on TentaGel resin" was followed until finishing the coupling of the N-terminal Tyrosine. All couplings were continued over night. After deprotection of the Fmoc group and the Allyl group (according to the procedure described above) the resin bound peptide was cyclized using PyBop as coupling reagent as described above and the coupling was continued over night. The acylations were checked by the ninhydrin test performed at 80° C. as earlier described. After completed synthesis the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid, yield 57 mg crude product. After purification using preparative HPLC as described above, 10 mg cyclic peptide product was collected with a purity better than 99%. Total yield of purified peptide product was 7%. The identity of the peptide was confirmed by ES-MS (found MH+ 673.30, calculated MH+ 673.29).

Peptide synthesis of Ac-Asn-Tyr-NH2 (Compound 56) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batch wise peptide synthesis on TentaGel resin" until finishing the coupling of the N-terminal Asparagine. After deprotection of the Fmoc group the N-terminal amino group was acetylated with acetic acid anhydride (1 ml, 10.5 mmol) together with 100 ml pyridine disolved in 2 ml DMF. The coupling was continued over night. The acylations were checked by the ninhydrin test performed at 80° C. as earlier described. After acylation of the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid.

Peptide synthesis of Ac-Gly-Tyr-NH2 (Compound 57) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batchwise peptide synthesis on TentaGel resin" until finishing the coupling of the N-terminal Glycine. After deprotection of the Fmoc group the N-terminal amino group was acetylated with acetic acid anhydride (1 ml, 10.5 mmol) together with 100 ml pyridine disolved in 2 ml DMF. The coupling was continued over night. The acylations were checked by the ninhydrin test performed at 80° C. as earlier described. After acylation of the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid.

Peptide synthesis of Hydroxyacetyl-Asn-Tyr-NH2 (Compound 58) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batch wise peptide synthesis on TentaGel resin" until finishing the coupling of the N-terminal Asparagine. After deprotection of the Fmoc group the N-terminal amino group was acetylated with hydroxyacetic acid using standard coupling procedure described above. The coupling was continued over night. The acylations were checked by the ninhydrin test performed at 80° C. as earlier described. After acylation of the N-terminal amino group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid.

Peptide synthesis of H-Gly(YCH2NH)-Gly-Tyr-NH2 (Compound 59) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batch wise peptide synthesis on TentaGel resin" until finishing the coupling of the C-terminal Tyrosine. After deprotection of the Fmoc group the N-terminal amino group was acetylated with Bromoacetic acid using standard coupling procedure described above. The coupling was continued over night. The acylations were checked by the ninhydrin test performed at 80° C. as earlier described. After acylation of the N-terminal amino group the peptide-resin was treated with a large excess of ethylenediamine dissolved in DMF. The reaction was continued over night. The peptide resin was then washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid.

Peptide synthesis of H-Gly-Asn-Phe(pNO2)—NH2 (Compound 60) on TentaGel-S-Ram; Rapp polymere, Germany.

Dry TentaGel-S-Ram (0.23 mmol/g, 1 g) was placed in a polyethylene vessel equipped with a polypropylene filter for filtration and treated as described under "batch wise peptide synthesis on TentaGel resin" until finishing the coupling of the N-terminal Glycine. All couplings were continued over night. The acylations were checked by the ninhydrin test performed at 80° C. as earlier described. After deprotection of the Fmoc group the peptide-resin was washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid.

EXAMPLE 54

Synthesis of Gly-(DBF)-Tyr-NH$_2$×TFA (Compound 61)

General methods of solid phase synthesis have been reported in PCT application PCT/US01/19113 entitled *Novel Peptide Conjugates* by Larsen, B. D et al. with the following changes.

Batch Wise Peptide Synthesis on TentaGel-S-RAM Resin (PEG-PS).

TentaGel resin (1 g, 0.22-0.31 mmol/g) was placed in a polyethylene vessel equipped with a polypropylene filter for filtration. The resin was swelled in DMF (15 ml), and the Fmoc group removed see Deprotection of the N-α-amino protecting group (Fmoc). The amino acids according to the sequence were coupled as preformed Fmoc-protected HOBt esters (3 eq.) as described above. The couplings were continued for 2 h, unless otherwise specified. The resin was drained and washed with DMF (5×15 ml, 5 min each) in order to remove excess reagent. All acylations were checked by the ninhydrin test performed at 80° C. After completed synthesis the peptide-resin was washed with DMF (3×15 ml, 5 min each), DCM (3×15 ml, 1 min each) and finally diethyl ether (3×15 ml, 1 min each) and dried in vacuo.

Amino Acids 4-(Fmoc-2-aminoethyl)-6-dibenzofuranpropionic acid (Fmoc-DBF—OH) was purchased from Neosystem, Strassbourg France.

Analytical HPLC

Column: VYDAC 238TP5415 150×4.6 mm monomeric RP C18 5 µm 300 Å

Flow: 1.00 ml/min

Temperature: 40° C.

Detection: 215 nm

| Gradient 1: | 0-1.5 min | A |
|---|---|---|
| | 1.5-25 min | Linear gradient to 50% B |
| | 25-30 min | Linear gradient to 100% B |
| | 30-35 min | B |
| | 35-40 min | Linear gradient to A |
| | 40-45 min | A |

Cleavage of Peptide from Resin With Acid.

Peptides were cleaved from the resins by treatment with 95% triflouroacetic acid (TFA, Riedel-de Häen, Frankfurt, Germany and 5% ethandithiol v/v at r.t. for 2 h. The filtered resins were washed with TFA. Filtrates and washings reduced to 5-10% at reduced pressure. Tenfold ether was added to the residue to precipitate the peptide, which was washed filtered on a sintered glass filter, washed with ether and dried in vacuo in an excicator over $P_2O_5$. The crude product was analysed by high-performance liquid chromatography (HPLC) and identified by electro spray ionisation mass spectrometry (ESMS).

Synthesis of Gly-(DBF)-Tyr-$NH_2$×TFA (Compound 61)

TentaGel-S-RAM-FMOC (0.23 mmol/g, 1.02 g) was placed in a polyethylene vessel equipped with a polypropylene filter for filtration and The resin was swelled in DMF and treated as described under "Batch wise peptide synthesis on TentaGel-S-RAM resin" until finishing the coupling of the N-terminal glycine. All couplings were continued over night. Fmoc-DBF—OH is not very soluble in DMF and the suspension of this protected amino acid and HOBt in DMF is heated to 50° C. and 10% NMP added before reaction with DIC. The peptide was cleaved from the resin as described above yielding 101.3 mg (70%). HPLC showed a 93% purity.

Purification was performed using RP-HPLC on a Biocad with automated fraction collecting.

Column: Kromasil RP C8; K 100-10-C8 250×50.8 mm.

Temperature: Ambient aprox. 20° C.

Flow 35 ml/min.

Detection UV at 215 nm and 280 nm.

Buffer A: 0.10% TFA in water. Buffer B: 0.10% TFA, 9.9% water 90% acetonitrile.

Gradient: Start pure A. Steep gradient to 20% B over 5 min then gradient to 60% B over 50 min. The fractions containing the pure product were pooled and freeze dried to yield 79.4 mg (55% of resin load) of white material 99% pure according to HPLC. Retention time 10.2 min (Analytical gradient 1). MS showed the expected monoisotopic mass of 502.21.

The compound is represented by the following formula:

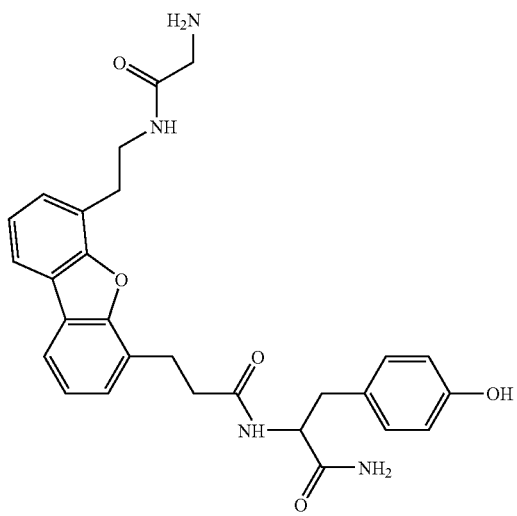

The disclosure of the PCT/US01/19113 application is incorporated herein by reference.

EXAMPLE 55

Peptide synthesis of Gly-Dapa-Gly-Hyp-Pro-Tyr (SEQ ID NO: 76) (Compound 62) on TentaGel-S—NH2; Rapp polymere, Germany.

Dry TentaGel-S—NH2 (0.27 mmol/g, 1 g) is placed in a polyethylene vessel equipped with a polypropylene filter for filtration and treated as described under "batchwise peptide synthesis on TentaGel resin" until finishing the coupling of the N-terminal Fmoc-Glycine. All couplings are continued over night. The acylations are checked by the ninhydrin test performed at 80° C. as earlier described. After completed synthesis the peptide-resin is washed with DMF (3×15 ml, 1 min each), DCM (3×15 ml, 1 min each), diethyl ether (3×15 ml, 1 min each) and dried in vacuo.

The peptide was cleaved from the resin as described above and freeze dried from acetic acid.

The Fmoc-protected peptide isdissolved in DMF and cyclized using PyBOP® (benzotriazole-1-yloxy-trisphosphonium hexafluorophosphate) as coupling reagent as described above. The cyclisation reaction is continued over night. The cyclised peptide is precipitated after addition of ether and isolated by filtration. The crude cyclised peptide is washed with ether (×3) and then dissolved in 20% piperidine in DMF v/v in order to remove the N-terminal Fmoc-group. The crude deprotected peptide is isolated by filtration after addition of ether. The precipitate is dissolved in acetic acid and freeze dried. The crude peptide is purified using preparative HPLC as described above.

REFERENCE LIST

[1.] A. L. Waldo, A. J. Camm, H. deRuyter, P. L. Friedman, D. J. MacNeil, J. F. Pauls, B. Pitt, C. M. Pratt, P. J. Schwartz, E. P. Veltri, *Lancet* 1996, 348 7-12.

[2.] P. A. Guerrero, R. B. Schuessler, L. M. Davis, E. C. Beyer, C. M. Johnson, K. A. Yamada, J. E. Saffitz, *J. Clin Invest* 1997, 99 1991-1998.

[3.] D. L. Lerner, K. A. Yamada, R. B. Schuessler, J. E. Saffitz, *Circulation* 2000, 101 547-552.

[4.] A. Hagendorff, B. Schumacher, S. Kirchhoff, B. Luderitz, K. Willecke, *Circulation* 1999, 99 1508-1515.
[5.] S. Kirchhoff, E. Nelles, A. Hagendorff, O. Kruger, O. Traub, K. Willecke, *Curr Biol* 1998, 8 299-302.
[6.] A. M. Simon, D. A. Goodenough, D. L. Paul, *Curr Biol* 1998, 8 295-298.
[7.] A. C. de Carvalho, M. O. Masuda, H. B. Tanowitz, M. Wittner, R. C. Goldenberg, D. C. Spray, *J Cardiovasc Electrophysiol* 1994, 5 686-698.
[8.] R. R. Kaprielian, M. Gunning, E. Dupont, M. N. Sheppard, S. M. Rothery, R. Underwood, D. J. Pennell, K. Fox, J. Pepper, P. A. Poole-Wilson, N. J. Severs, *Circulation* 1998, 97 651-660.
[9.] N. S. Peters, C. R. Green, P. A. Poole-Wilson, N. J. Severs, *Circulation* 1993, 88 864-875.
[10.] J. E. Saffitz, R. B. Schuessler, K. A. Yamada, *Cardiovasc Res* 1999, 42 309-317.
[11.] S. Aonuma, Y. Kohama, K. Akai, Y. Komiyama, S. Nakajima, M. Wakabayashi, T. Makino, *Chem Pharm Bull (Tokyo)* 1980, 28 3332-3339.
[12.] S. Aonuma, Y. Kohama, K. Akai, S. Iwasaki, *Chem Pharm Bull (Tokyo)* 1980, 28 3340-3346.
[13.] S. Aonuma, Y. Kohama, T. Makino, Y. Fujisawa, *J Pharmacobiodyn* 1982, 5 40-48.
[14.] M. A. Ronsberg, T. K. Saunders, P. S. Chan, P. Cervoni, *Med Sci 86 A.D.*, 14 350-351.
[15.] M. Dikshit, R. Srivastava, B. Kundu, K. B. Mathur, K. Kar, *Indian J Exp Biol* 1988, 26 874-876.
[16.] Y. Kohama, N. Okimoto, T. Mimura, C. Fukaya, M. Watanabe, K. Yokoyama, *Chem Pharm Bull (Tokyo)* 1987, 35 3928-3930.
[17.] Y. Kohama, S. Kuwahara, K. Yamamoto, M. Okabe, T. Mimura, C. Fukaya, M. Watanabe, K. Yokoyama, *Chem Pharm Bull (Tokyo)* 1988, 36 4597-4599.
[18.] S. Dhein, N. Manicone, A. Muller, R. Gerwin, U. Ziskoven, A. Irankhahi, C. Minke, W. Klaus, *Naunyn Schmiedebergs Arch Pharmacol* 1994, 350 174-184.
[19.] T. Argentieri, E. Cantor, I. R. Wiggins, *Experientia* 1989, 45 737-738.
[20.] A. Muller, M. Gottwald, T. Tudyka, W. Linke, W. Klaus, S. Dhein, *Eur J Pharmacol* 1997, 327 65-72.
[21.] R. Grover, S. Dhein, *Peptides* 1998, 19 1725-1729.
[22.] S. Dhein, T. Tudyka, *Drugs* 1995, 49 851-855.
[23.] C. S. Kuo, K. Munakata, C. P. Reddy, B. Surawicz, *Circulation* 1983, 67 1356-1367.
[24.] S. Dhein, K. Krusemann, T. Schaefer, *Br J Pharmacol* 1999, 128 1375-1384.
[25.] N. S. Peters, J. Coromilas, N. J. Severs, A. L. Wit, *Circulation* 1997, 95 988-996.
[26.] D. W. Liu, C. Antzelevitch, *Circ Res* 1995, 76 351-365.
[27.] Kanagaratnam, P., Severs, N. J., and Peters, N. S. The Relationship between Conduction, Activation pattern and Quantity of Immunoreactive Connexin in Chronic Human Atrial Fibrillation. Circulation 102[18], II-485. 2000. Ref Type: Abstract
[28.] J. M. Pastore, D. S. Rosenbaum, *Circulation Research* 2000, 87 1157-1163.
[29.] R. D. Berger, *Circulation Research* 2000, 87 1083-1084.
[30.] J. E. Saffitz, K. A. Yamada, *Circulation* 1998, 97 630-632.
[31.] Gutstein, D. E., Morley, G. E., Tamaddon, Houman S., Vaidya, D., Schneider, M. D., Chen, J., Chien, K. R., Stuhlmann, H., and Fishman, G. I. Genetic Manipulation of Connexin43 Expression in the Heart: Establishing a Role for Gap Junction Remodeling in Arrhythmogenesis and Ventricular Dysfunction. Circulation 102[18], II-15. 2001. Ref Type: Abstract
[32.] A. Muller, T. Schaefer, W. Linke, T. Tudyka, M. Gottwald, W. Klaus, S. Dhein, *Naunyn Schmiedebergs Arch. Pharmacol.* 1997, 356 76-82.
[33.] S. Dhein, R. Grover, A. Müller, M. Lauven, P. Poeppel, T. Schaefer, *Circulation* 1999, 100 I-426.
[34.] Koenig, J. I. Radioligand binding in intact cells. Keen, M. [106], 89-98. 1999. Totowa, NJ, Humana Press Inc. Methods in Molecular Biology. Ref Type: Serial (Book, Monograph)
[35.] K. Wassermann, K. Mølgaard, E. Steiness, *Cancer Chemother.Pharmacol.* 1985, 15 244-252.
[36.] E. Meier, K. Frederiksen, M. Nielsen, H. L. Lembøl, H. Pedersen, J. Hyttel, *Drug Development Research* 1997, 40 1-16.
[37.] J. J. Lynch, R. G. Rahwan, D. T. Witiak, *J Cardiovasc.Pharmacol.* 1981, 3 49-60.
[38.] M. Zabel, S. H. Hohnloser, S. Behrens, R. L. Woosley, M. R. Franz, *J Cardiovasc Electrophysiol* 1997, 8 1239-1245.
[39.] S. Dhein, N. Manicone, A. Muller, R. Gerwin, U. Ziskoven, A. Irankhahi, C. Minke, W. Klaus, *Naunyn Schmiedebergs Arch Pharmacol* 1994, 350 174-184.
[40.] X. D. Huang, G. E. Sandusky, D. P. Zipes, *J Cardiovasc.Electrophysiol.* 1999, 10 79-91.
[41.] D. Xing, J. B. Martins, *Am J Physiol Heart Circ.Physiol* 2001, 280 H684-H692.
[42.] F. Shapiro, *Calcif Tissue Int* 1997, 61 285-293.
[43.] R. Civitelli, E. C. Beyer, P. M. Warlow, A. J. Robertson, S. T. Geist, T. H. Steinberg, *J.Clin.Invest.* 1993, 91 1888-1896.
[44.] T. H. Steinberg, R. Civitelli, S. T. Geist, A. J. Robertson, E. Hick, R. D. Veenstra, H. Z. Wang, P. M. Warlow, E. M. Westphale, J. G. Laing, a. et, *EMBO J.* 1994, 13 744-750.
[45.] H. Chiba, N. Sawada, M. Oyamada, T. Kojima, S. Nomura, S. Ishii, M. Mori, *Cell Struct.Funct.* 1993, 18 419-426.
[46.] F. Lecanda, D. A. Towler, K. Ziambaras, S. L. Cheng, M. Koval, T. H. Steinberg, R. Civitelli, *Mol Biol Cell* 1998, 9 2249-2258.
[47.] F. Lecanda, P. M. Warlow, S. Sheikh, F. Furlan, T. H. Steinberg, R. Civitelli, *J.Cell Biol.* 2000, 151 931-943.
[48.] N. R. Jorgensen, S. T. Geist, R. Civitelli, T. H. Steinberg, *J.Cell Biol.* 1997, 139 497-506.
[49.] N. R. Jorgensen, Z. Henriksen, C. Brot, E. F. Eriksen, O. H. Sorensen, R. Civitelli, T. H. Steinberg, *J Bone Miner.Res.* 2000, 15 1024-1032.
[50.] A. Clairmont, D. Tessman, A. Stock, S. Nicolai, W. Stahl, H. Sies, *Carcinogenesis* 1996, 17 1389-1391.
[51.] M. A. Van der Molen, C. T. Rubin, K. J. McLeod, L. K. McCauley, H. J. Donahue, *J.Biol.Chem.* 1996, 271 12165-12171.
[52.] R. Civitelli, K. Ziambaras, P. M. Warlow, F. Lecanda, T. Nelson, J. Harley, N. Atal, E. C. Beyer, T. H. Steinberg, *J.Cell Biochem.* 1998, 68 8-21.
[53.] P. D'Andrea, A. Calabrese, I. Capozzi, M. Grandolfo, R. Tonon, F. Vittur, *Biorheology* 2000, 37 75-83.
[54.] P. D'Andrea, F. Vittur, *Cell Calcium* 1996, 20 389-397.
[55.] S. Loty, C. Foil, N. Forest, J. Sautier, *Arch.Oral Biol.* 2000, 45 843-856.
[56.] N. Cirenei, B. M. Colombo, M. Mesnil, S. Benedetti, H. Yamasaki, G. Finocchiaro, *Gene Ther.* 1998, 5 1221-1226.
[57.] O. Moennikes, A. Buchmann, K. Willecke, O. Traub, M. Schwarz, *Hepatology* 2000, 32 501-506.
[58.] O. Moennikes, A. Buchmann, A. Romualdi, T. Ott, J. Werringloer, K. Willecke, M. Schwarz, *Cancer Res.* 2000, 60 5087-5091.

[59.] L. Zhou, E. M. Kasperek, B. J. Nicholson, *J Cell Biol.* 1999, 144 1033-1045.

[60.] D. W. Laird, P. Fistouris, G. Batist, L. Alpert, H. T. Huynh, G. D. Carystinos, M. A. Alaoui-Jamali, *Cancer Res.* 1999, 59 4104-4110.

[61.] T. Shibata, H. Nagayasu, J. Hamada, S. Konaka, M. Hosokawa, T. Kawano, H. Kitajo, M. Arisue, *Tumour.Biol.* 2000, 21 299-308.

[62.] X. Guan, R. J. Ruch, *Carcinogenesis* 1996, 17 1791-1798.

[63.] R. J. Ruch, W. J. Bonney, K. Sigler, X. Guan, D. Matesic, L. D. Schafer, E. Dupont, J. E. Trosko, *Carcinogenesis* 1994, 15 301-306.

[64.] B. V. Madhukar, H. L. Feijter-Rupp, J.E. Trosko, *Cancer Lett.* 1996, 106 117-123.

[65.] W. K. Hong, M. B. Sporn, *Science* 1997, 278 1073-1077.

[66.] K. M. Abdullah, G. Luthra, J. J. Bilski, S. A. Abdullah, L. P. Reynolds, D. A. Redmer, A. T. Grazul-Bilska, *Endocrine.* 1999, 10 35-41.

[67.] M. Saitoh, M. Oyamada, Y. Oyamada, T. Kaku, M. Mori, *Carcinogenesis* 1997, 18 1319-1328.

[68.] J. A. Goliger, D. L. Paul, *Mol.Biol.Cell* 1995, 6 1491-1501.

[69.] T. Mine, R. Kushima, T. Fujita, *J Clin.Gastroenterol.* 1997, 25 Suppl 1 S111-S115.

[70.] T. Mine, H. Yusuda, A. Kataoka, A. Tajima, J. Nagasawa, T. Takano, *J Clin.Gastroenterol.* 1995, 21 Suppl 1 S104-S107.

[71.] G. J. Christ, P. R. Brink, *Braz.J Med Biol.Res.* 2000, 33 423-429.

[72.] B. R. Berg, K. D. Cohen, I. H. Sarelius, *Am J Physiol* 1997, 272 H2693-H2700.

[73.] C. de Wit, F. Roos, S. S. Bolz, S. Kirchhoff, O. Kruger, K. Willecke, U. Pohl, *Circulation Research* 2000, 86 649-655.

[74.] B. Nafz, J. Stegemann, M. H. Bestle, N. Richter, E. Seeliger, I. Schimke, H. W. Reinhardt, P. B. Persson, *Circulation* 2000, 101 553-557.

[75.] H. Q. Xie, V. W. Hu, *Exp.Cell Res.* 1994, 214 172-176.

[76.] R. Dermietzel, *Brain Res Brain Res Rev* 1998, 26 176-183.

[77.] R. Rozental, M. Srinivas, S. Gokhan, M. Urban, R. Dermietzel, J. A. Kessler, D. C. Spray, M. F. Mehler, *Brain Res.Brain Res.Rev.* 2000, 32 57-71.

[78.] H. Aldskogius, E. N. Koziova, *Prog.Neurobiol.* 1998, 55 1-26.

[79.] J. D. Pal, X. Liu, D. Mackay, A. Shiels, V. M. Berthoud, E. C. Beyer, L. Ebihara, *Am J Physiol Cell Physiol* 2000, 279 C596-C602.

[80.] V. Krutovskikh, H. Yamasaki, *Mutat.Res.* 2000, 462 197-207.

[81.] D. Mackay, A. Ionides, Z. Kibar, G. Rouleau, V. Berry, A. Moore, A. Shiels, S. Bhattacharya, *Am J Hum.Genet.* 1999, 64 1357-1364.

[82.] K. Nakamura, Y. Shibata, *Cells Tissues.Organs* 1999, 165 16-21.

[83.] L. Nemeth, S. Maddur, P. Puri, *J Pediatr.Surg.* 2000, 35 823-828.

[84.] A. M. Simon, D. A. Goodenough, E. Li, D. L. Paul, *Nature* 1997, 385 525-529.

[85.] B. Sommersberg, A. Bulling, U. Salzer, U. Frohlich, R. E. Garfield, A. Amsterdam, A. Mayerhofer, *Biol.Reprod.* 2000, 63 1661-1668.

[86.] I. Granot, N. Dekel, *Hum.Reprod.* 1998, 13 Suppl 4 85-97.

[87.] W. M. Kilarski, E. Dupont, S. Coppen, H. I. Yeh, C. Vozzi, R. G. Gourdie, M. Rezapour, U. Ulmsten, G. M. Roomans, N. J. Severs, *Eur.J Cell Biol.* 1998, 75 1-8.

[88.] H. N. Ciray, X. Fu, M. Olovsson, G. Ahlsen, C. Shuman, B. Lindblom, U. Ulmsten, *Am J Obstet.Gynecol.* 2000, 182 926-930.

[89.] C. Batias, N. Defamie, A. Lablack, D. Thepot, P. Fenichel, D. Segretain, G. Pointis, *Cell Tissue Res.* 1999, 298 113-121.

[90.] E. Schleiermacher, *Hum.Genet.* 1980, 54 391-404.

[91.] C. Vozzi, S. Ulirich, A. Charollais, I. Philippe, L. Orci, P. Meda, *J Cell Biol.* 1995, 131 1561-1572.

[92.] P. Meda, M. Chanson, M. Pepper, E. Giordano, D. Bosco, O. Traub, K. Willecke, A. el Aoumari, D. Gros, E. C. Beyer, *Exp.Cell Res.* 1991, 192 469-480.

[93.] K. Ziambaras, F. Lecanda, T. H. Steinberg, R. Civitelli, *J.Bone Miner.Res.* 1998, 13 218-228.

[94.] I. Capozzi, R. Tonon, P. D'Andrea, *Biochem J* 1999, 344 Pt 2 545-553.

[95.] S. G. Spanakis, S. Petridou, S. K. Masur, *Invest Ophthalmol.Vis.Sci.* 1998, 39 1320-1328.

[96.] H. Yamasaki, V. Krutovskikh, M. Mesnil, T. Tanaka, D. M. Zaidan, Y. Omori, *C.R.Acad.Sci.III.* 1999, 322 151-159.

[97.] B. D. Larsen, A. Holm, *Int.J Pept.Protein Res.* 1994, 43 1-9.

The invention has been described with reference to preferred embodiments thereof. However, it will be appreciated that those skilled in the art, upon consideration of this disclosure, may make modifications and improvements within the spirit and scope of the invention. All references disclosed herein are incorporated by reference including the following Danish patent applications: DK PA 2000 00288 as filed on 23 Feb. 2000 and DK PA 2000 00738 as filed on 4 May 2000.

The invention claimed is:

1. A compound selected from the group consisting of hydroxyacetyl-Asn-Tyr-NH$_2$, hydroxyacetyl-Asn-Tyr-OH, hydroxyacetyl-Gly-Tyr-NH$_2$, and hydroxyacetyl-Gly-Tyr-OH; or a pharmaceutically acceptable salt thereof.

2. A phamaceutical composition comprising:
   (a) a compound of claim 1 or a pharmaceutically acceptable salt thereof; and
   (b) a pharmaceutically acceptable carrier or diluent.

3. The pharmaceutical composition of claim 2, wherein said composition is in a form suitable for oral or parenteral administration.

4. The pharmaceutical composition of claim 3, wherein said form suitable for oral administration is an enteric tablet.

5. Hydroxyacetyl-Asn-Tyr-NH$_2$, or a pharmaceutically acceptable salt thereof.

6. A pharmaceutical composition comprising:
   (a) the compound of claim 5, or a pharmaceutically acceptable salt thereof; and
   (b) a pharmaceutically acceptable carrier or diluent.

7. The pharmaceutical composition of claim 6, wherein said composition is in a form suitable for oral or parenteral administration.

8. The pharmaceutical composition of claim 7, wherein said form suitable for oral administration is an enteric tablet.

9. Hydroxyacetyl-Asn-Tyr-OH, or a pharmaceutically acceptable salt thereof.

10. A pharmaceutical composition comprising:
    (a) the compound of claim 9, or a pharmaceutically acceptable salt thereof; and
    (b) a pharmaceutically acceptable carrier or diluent.

11. The pharmaceutical composition of claim 10, wherein said composition is in a form suitable for oral or parenteral administration.

12. The pharmaceutical composition of claim 11, wherein said form suitable for oral administration is an enteric tablet.

13. Hydroxyacetyl-Gly-Tyr-NH$_2$, or a pharmaceutically acceptable salt thereof.

14. A pharmaceutical composition comprising:
(a) the compound of claim 13, or a pharmaceutically acceptable salt thereof; and
(b) a pharmaceutically acceptable carrier or diluent.

15. The pharmaceutical composition of claim 14, wherein said composition is in a form suitable for oral or parenteral administration.

16. The pharmaceutical composition of claim 15, wherein said form suitable for oral administration is an enteric tablet.

17. Hydroxyacetyl-Gly-Tyr-OH, or a pharmaceutically acceptable salt thereof.

18. A pharmaceutical composition comprising:
(a) the compound of claim 17, or a pharmaceutically acceptable salt thereof; and
(b) a pharmaceutically acceptable carrier or diluent.

19. The pharmaceutical composition of claim 18, wherein said composition is in a form suitable for oral or parenteral administration.

20. The pharmaceutical composition of claim 19, wherein said form suitable for oral administration is an enteric tablet.

* * * * *

UNITED STATES PATENT AND TRADEMARK OFFICE
CERTIFICATE OF CORRECTION

PATENT NO. : 7,585,839 B2  Page 1 of 1
APPLICATION NO. : 10/646294
DATED : September 8, 2009
INVENTOR(S) : Larsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1159 days.

Signed and Sealed this

Fourteenth Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,585,839 B2  
APPLICATION NO. : 10/646294  
DATED : September 8, 2009  
INVENTOR(S) : Bjarne D. Larsen et al.

Page 1 of 1

It is certified that error appears in the above-identified patent and that said Letters Patent is hereby corrected as shown below:

In the Specifications:

Column 3, lines 11-12 replace "interacting proteins. understanding" with --interacting proteins. Understanding--;

Line 16 replace "GJIC and connexins. Changes in the phosphorylation" with --GJIC and connexins. Changes in the phosphorylation--.

Column 6, line 50 replace "APP10" with --AAP10--.

Column 51, line 30 replace "repesenting" with --representing--.

Column 53, line 18 replace "Gin" with --Gln--.

Column 166, line 59 replace "C. Foil" with --C. Foll--.

Column 167, line 46 replace "E.N. Koziova" with --E.N. Kozlova--.

Column 168, line 27 replace "Ulirich" with --Ullrich--.

Signed and Sealed this  
Thirtieth Day of April, 2013

Teresa Stanek Rea  
*Acting Director of the United States Patent and Trademark Office*